US009206482B2

(12) United States Patent
Davicioni et al.

(10) Patent No.: US 9,206,482 B2
(45) Date of Patent: Dec. 8, 2015

(54) SYSTEMS AND METHODS FOR EXPRESSION-BASED CLASSIFICATION OF THYROID TISSUE

(75) Inventors: Elai Davicioni, Vancouver (CA); Sam Michael Wiseman, Vancouver (CA)

(73) Assignee: GenomeDx Biosciences Inc., Vancouver, British Columbia (CA)

( * ) Notice: Subject to any disclaimer, the term of this patent is extended or adjusted under 35 U.S.C. 154(b) by 0 days.

(21) Appl. No.: 13/258,429

(22) PCT Filed: Apr. 29, 2010

(86) PCT No.: PCT/CA2010/000621
§ 371 (c)(1), (2), (4) Date: Sep. 21, 2011

(87) PCT Pub. No.: WO2010/124372
PCT Pub. Date: Nov. 4, 2010

(65) Prior Publication Data

US 2012/0172243 A1 Jul. 5, 2012

Related U.S. Application Data

(60) Provisional application No. 61/173,738, filed on Apr. 29, 2009.

(51) Int. Cl.
*C12Q 1/68* (2006.01)
*C07H 21/04* (2006.01)

(52) U.S. Cl.
CPC ........ *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 5,143,854 | A | 9/1992 | Pirrung et al. |
| 5,288,514 | A | 2/1994 | Ellman et al. |
| 5,384,261 | A | 1/1995 | Winkler et al. |
| 5,538,848 | A | 7/1996 | Livak et al. |
| 5,677,195 | A | 10/1997 | Winkler et al. |
| 5,846,717 | A | 12/1998 | Brow et al. |
| 5,985,557 | A | 11/1999 | Prudent et al. |
| 5,994,069 | A | 11/1999 | Hall et al. |
| 6,001,567 | A | 12/1999 | Brow et al. |
| 6,090,543 | A | 7/2000 | Prudent et al. |
| 6,136,182 | A | 10/2000 | Dolan et al. |
| 7,319,011 | B2 | 1/2008 | Riggins et al. |
| 2003/0194734 | A1 | 10/2003 | Jatkoe |
| 2005/0042222 | A1 | 2/2005 | Yamamoto et al. |
| 2007/0031873 | A1 | 2/2007 | Wang et al. |
| 2007/0037186 | A1 | 2/2007 | Jiang et al. |
| 2008/0044824 | A1 | 2/2008 | Giordano et al. |
| 2008/0145841 | A1 | 6/2008 | Libutti et al. |
| 2012/0115743 | A1 | 5/2012 | Davicioni et al. |

FOREIGN PATENT DOCUMENTS

| | | | |
|---|---|---|---|
| WO | WO 90/15070 | A1 | 12/1990 |
| WO | WO 92/10092 | A1 | 6/1992 |
| WO | WO 93/09668 | A1 | 5/1993 |
| WO | WO 93/22684 | A1 | 11/1993 |
| WO | 2005085471 | A2 | 9/2005 |
| WO | 2005100608 | A2 | 10/2005 |
| WO | 2006047484 | A2 | 5/2006 |
| WO | 2006127537 | A2 | 11/2006 |
| WO | 2009143603 | A1 | 12/2009 |
| WO | 2010/056374 | A2 | 5/2010 |
| WO | 2010099598 | A1 | 9/2010 |

OTHER PUBLICATIONS

Dougherty, Pattern Recognition 38:2226-2228, 2005.*
Kasraeian et al. Clin. Orthop. Relat. Res. 468:2992-3002, 2010, publ. online May 29, 2010.*
Cerutti, et al., Clin Cancer Res., vol. 12, No. 11, Pt. 1, pp. 3311-3318 (2006).
Finley, et al., Ann Surg., vol. 240, No. 3:, pp. 25-36; discussion 436-7 (2004).
Finley, et al., Thyroid. vol. 15, No. 6, pp. 562-568 (2005).
Fontaine et al., PLoS ONE, vol. 4, No. 10, e7632 (2009).
Fryknäs, et al., Tumour Biol., vol. 27, No. 4, pp. 211-220 (2006).
Griffiths, et al., Expert Rev. Anticancer Therapy, vol. 8, No. 9, pp. 1399-1413 (2008).
Hamada, et al., Cancer Lett, vol. 224, No. 2, pp. 289-301 (2005).
Kebebew, et al., Cancer, vol. 106, No. 12, pp. 2592-2597 (2006).
Mazzanti, et al., Cancer Res., vol. 64, No. 8, pp. 2898-2903 (2004); Erratum in: Cancer Res., vol. 64, No. 14, p. 5028 (2004).
Mineva et al., Cell Stress & Chaperones, vol. 10, No. 3, pp. 171-184 (2005).
Shibru, et al., Cancer. vol. 3, No. 5, pp. 930-935 (2008).
Yukinawa, et al., BMC Genomics, vol. 27, No. 7, pp. 190 (2006).
Micheala A. Aldred et al., Journal of Clinical Oncology, vol. 22, No. 17, pp. 3531-3539.
Krzysztof Fujarewicz et al., Endocrine-Related Cancer, vol. 14, pp. 809-826 (2007).
Obi L. Griffith et al., J. of Clinical Oncology, vol. 24, No. 31, pp. 5043-5051 (2006).
Nijaguna B. Prasad, Clin. Cancer Res., vol. 14, No. 11, pp. 3327-3337 (2008).
Mark D. Robinson, BMC Bioinformatics, vol. 8, pp. 449-464 (2007).
Intarnational Search Report for PCT/CA2010/000621, completed Jul. 14, 2010.

(Continued)

*Primary Examiner* — Nancy T Vogel
(74) *Attorney, Agent, or Firm* — Wilson Sonsini Goodrich & Rosati

(57) ABSTRACT

A system for classifying thyroid nodule tissue as malignant or benign is provided that is based on the identification of sets of gene transcripts, which are characterized in that changes in expression of each gene transcript within a set of gene transcripts can be correlated to with either malignant or benign thyroid nodule disease. The thyroid classification system provides for sets of "thyroid classifying" target sequences and further provides for combinations of polynucleotide probes and primers derived there from. These combinations of polynucleotide probes can be provided in solution or as an array. The combination of probes and the arrays can be used for diagnosis. The invention further provides further methods of classifying thyroid nodule tissue.

14 Claims, 6 Drawing Sheets

(56) References Cited

OTHER PUBLICATIONS

Written Opinion of the International Searching Authority for PCT/CA2010/000621, mailed Aug. 11, 2010.
International Search Report for PCT/CA2010/000266, mailed Jul. 12, 2010.
US 5,962,233, Oct. 1999, Livak et al. (withdrawn).
Englisch, et al. Chemically Modified Oligonucleotides as Probes and Inhibitors. Angew. Chem. Int. Ed. Eng. 1991; 30:613-629.
Fodor, et al. Light-directed, spatially addressable parallel chemical synthesis. Science. Feb. 15, 1991;251(4995):767-73.
Gait. Oligoribonucleotides. In Antisense Research and Applications. Crooke, S. T. and Lebleu, B., ed., CRC Press. 1993; Ch 16 289-302.
Kanehisa. Use of statistical criteria for screening potential homologies in nucleic acid sequences. Nucleic Acids Res. Jan. 11, 1984;12(1 Pt 1):203-13.
Kebebew, et al. Diagnostic and extent of disease multigene assay for malignant thyroid neoplasms. Cancer. Jun. 15, 2006;106(12):2592-7.
Koshkin, et al. LNA (locked nucleic acids): An RNA mimic forming exceedingly stable LNA: LNA duplexes. J. Am. Chem. Soc. 1998; 120:13252-13253.
Koshkin, et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron. 1998; 54(14):3607-3630.
Kroschwitz. The Concise Encyclopedia of Polymer Science and Engineering, (1990) pp. 858-859. John Wiley & Sons.
Kumar, et al. The first analogues of LNA (locked nucleic acids): phosphorothioate-LNA and 2'-thio-LNA. Bioorg Med Chem Lett. Aug. 18, 1998;8(16):2219-22.
Martin. A New Access to 2'-O-Alkylated Ribonucleosides and Properties of 2'-O-Alkylated Oligoribonucleotides. Helv. Chim. Acta. 1995; 78:486-504. (in German with English abstract).
Nielsen, et al. Sequence-selective recognition of DNA by strand displacement with a thymine-substituted polyamide. Science. Dec. 6, 1991;254(5037):1497-500.
Office action dated Mar. 11, 2014 for U.S. Appl. No. 13/254,571.
Puskas, et al. Gene profiling identifies genes specific for well-differentiated epithelial. thyroid tumors. Cell Mol Biol (Noisy-le-grand). Sep. 5, 2005;51(2):177-86.
Sanghvi. Heterocyclic base modifications in nucleic acids and their applications in antisense oligonucleotides. In Antisense Research and Applications. Crooke, S. T. and Lebleu, B., ed., CRC Press. 1993; Ch 15 274-285.
Singh, et al. LNA (locked nucleic acids): synthesis and high-affinity nucleic acid recognition. Chem. Commun. 1998; 4:455-456.
Singh, et al. Synthesis of 2'-amino-LNA: A novel conformationally restricted high-affinity oligonucleotide analogues with a handle. J. Bio. Chem. 1998; 63:10035-10039.
Office action dated Dec. 4, 2014 for U.S. Appl. No. 13/254,571.
Cibas, et al. The Bethesda System for Reporting Thyroid Cytopathology. Am J Clin Pathol. Nov. 2009;132(5):658-65. doi: 10.1309/AJCPPHLWMI3JV4LA.
Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.
Notice of allowance dated Mar. 27, 2015 for U.S. Appl. No. 13/254,571.

* cited by examiner

SYSTEMS AND METHODS FOR EXPRESSION-BASED CLASSIFICATION OF THYROID TISSUE

This application is the U.S. National Stage of International Application No. PCT/CA2010/000621, filed Apr. 29, 2010, which claims the benefit of U.S. Provisional Application No. 61/173,738, filed Apr. 29, 2009, both of which are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 2, 2011, is named 142US371.txt and is 333,751 bytes in size.

FIELD OF THE INVENTION

This invention relates to the field of diagnostics and in particular to systems and methods for diagnosis of thyroid cancer.

BACKGROUND

Thyroid nodule disease is a common clinical problem, found in 4-7% of the living adult population in North America. The occurrence of thyroid nodules increases with age; autopsies reveal the presence of thyroid nodules in 50% of the population. It is estimated that, at 80 years old, 90% of the population will have at least one thyroid nodule. However, the vast majority of solitary thyroid nodules are benign in nature, and would require no further treatment if a correct diagnosis could be obtained without surgery.

A number of techniques can be used to diagnose thyroid conditions, including radioactive thyroid scans, ultrasound, thyroid hormone level and thyroglobulin measurements, and fine needle aspiration biopsy (FNAB). Thyroid scans do not effectively distinguish benign and malignant conditions, however, and are typically used in conjunction with other techniques. Similarly, ultrasound may provide information suggestive of either benign or malignant conditions, but cannot definitively diagnose thyroid status. Measurements of thyroid hormone level and thyroglobulin can be informative, but are nondiagnostic by themselves.

Thyroid FNAB is the only non-surgical method which can by itself differentiate malignant and benign nodules. More than 300,000 fine needle aspiration biopsies (FNAB) of the thyroid are performed annually in the US and evaluated using cytology. The primary purpose of FNAB is to distinguish thyroid nodules that require immediate surgical intervention (e.g., total thyroidectomy in the case of a diagnosis of malignant disease) from nodules that can be treated effectively with less aggressive clinical approaches.

In FNAB, samples of thyroid cells are obtained by inserting a needle into the thyroid and aspirating cells into a syringe. Usually, 2 to 4 aspirations are made from different sites in each nodule. The cells are mounted on a slide (for each aspiration, 2 to 4 slides are prepared), stained, and examined. The sample is then classified as nondiagnostic (indeterminate), benign, suspicious or malignant. Most samples are categorized as benign.

FNAB can be used to successfully diagnose papillary carcinoma, medullary carcinoma, anaplastic carcinoma, thyroid lymphoma and metastases to the thyroid from other sites. Papillary carcinoma accounts for ~60-70% and the follicular variant of papillary carcinoma accounts for ~6% of thyroid cancers. These well differentiated thyroid cancers are usually curable, but they must be found first.

Especially problematic are cases considered ‘suspicious’, ‘inadequate’ or ‘indeterminate’ by cytological diagnosis of FNAB samples. These patients are invariably triaged by invasive surgery, which has a significant morbidity. Overtreatment with total-thyroidectomy frequently occurs as a result; it is estimated that less than 25% of patients with such diagnoses in fact have cancer that warrants removal of the thyroid gland. Approximately 5-10% of samples are classified as nondiagnostic by FNAB. In those cases, FNAB can be repeated; however, only half of repeat biopsies yield a diagnostic result. For the remaining patients, further testing and surgery may be required. Due to the fear of cancer, invasive surgery is chosen, but in most cases is unnecessary. Approximately 10-20% of samples are classified as suspicious by FNAB. Of these, approximately 25% will ultimately prove to be malignant after surgery, typically exhibiting follicular or Hurthle cell cancers, which cannot be diagnosed by FNAB. Follicular carcinoma, which accounts for ~12-15% of all thyroid cancers and the less prevalent Hurthle cell carcinoma cannot be distinguished cytologically from benign follicular or Hurthle cell adenomas. Therefore, most patients with suspicious biopsies are typically subjected to surgery, when in fact ~75% of these patients do not have malignant disease.

A contributing factor to the difficulties with current FNAB cytology-based diagnoses is the variability between different pathologists and cytopathologists in diagnostic agreement between cytological analysis and final histological review, ranging from 40%-90%. The overall accuracy of diagnoses using only FNAB ranges from 60% to >90%, and is dependent on the expertise of the cytologist and whether or not ‘suspicious’ or ‘indeterminate’ diagnostic categories are included in the reported accuracy of the study (see http://www.endocrineweb.com/noduleus.html). When factoring the cytology diagnostic categories of ‘suspicious’ or ‘indeterminate’, the literature shows that the overall specificity of FNAB cytology for diagnosis of malignant disease decreases dramatically to <60% with false-positive rates of ~40%. Patients with malignant thyroid disease are invariably treated by total removal of the tumor and all of the thyroid gland followed by radioactive iodine treatment, whereas benign thyroid disease can be treated less aggressively with a near-total thyroidectomy, partial thyroidectomy (e.g., ‘lobectomy’) or a watchful-waiting approach (e.g., observation without surgical intervention). As FNAB and cytology cannot reliably distinguish malignant from benign disease in cases with ‘suspicious’ cytological findings, such as occurs in the case of follicular and Hurthle cell lesions, these patients are typically all treated as if they were diagnosed with malignant disease (i.e., with aggressive surgery). Since only a small fraction of these patients in fact have malignant disease, overtreatment of thyroid nodule disease patients occurs frequently, with significant consequences for patients. As such, many unnecessary thyroidectomies are therefore performed in patients with what ultimately proves to be benign or non-neoplastic thyroid nodule disease when an FNAB sample is deemed as ‘suspicious’ or ‘indeterminate.’ These deficiencies negatively impact patient outcomes, long-term well-being and healthcare efficiencies.

Use of molecular analyses has the potential to increase the sensitivity, specificity and/or overall accuracy of thyroid diagnoses as compared to FNAB cytology alone. Such a result would reduce the number of unnecessary surgeries for patients without malignant disease and avoid inadvertent undertreatment of highly curable thyroid cancers resulting from misdiagnoses. However, prior attempts at using gene expression profiling to develop diagnostic gene expression signatures and identify mRNA biomarkers useful for the differential diagnosis of thyroid nodule disease have not yet yielded new clinical tools to improve the diagnosis of malignant from benign thyroid nodule disease from clinical specimens. Most of these efforts and those of protein immunohistochemistry studies focused on the protein-encoding genome. However, the transcriptome is inherently more complex than this, given that <2% of the genome encodes for protein and recent studies that have shown that more than 90% of the genome undergoes transcription yielding millions of non-coding RNA transcripts that serve regulatory roles over the protein-endcoding transcriptome. So, gene-level analysis may provide only a rough estimate of diagnosis as it cannot capture the full differences between the genomes of malignant and benign thyroid nodule disease (e.g., alternative gene splicing, non-coding and functional RNA expression). Recent efforts to validate a 3-gene signature for diagnosis of thyroid nodule disease FNAB with a QRT-PCR approach report a low diagnostic accuracy in a large validation study (see Sibru et al., citation #14). Other prior attempts using gene-biased microarrays showed similar performance characteristics with low diagnostic accuracy for gene-based signatures (see Jiang et al., US 2007/0037186 A1). For example, Jiang et al., (US 2007/0037186 A1) disclosed a 4-gene QRT-PCR panel with a sensitivity of 92% but a specificity of just 61%. In addition, since these signatures were developed and validated from fresh or fresh frozen tissue specimens their applicability to more routine tissues specimens commonly available in the clinic such as formalin-fixed paraffin embedded fine-needle aspirate cell blocks and surgical resections is not assured because of the impact of sample processing on nucleic acid integrity. As a result, diagnoses using these provide results little better than currently available FNAB cytology in widespread clinical use.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide systems and methods for expression-based classification of thyroid tissue. In accordance with one aspect of the present invention, there is provided a system for expression-based classification of thyroid tissue as malignant or benign, said system comprising one or more polynucleotides, each of said polynucleotides capable of specifically hybridizing to a RNA transcript of a gene selected from the group of genes set forth in Table 1.

In accordance with another aspect of the present invention, there is provided a system for expression-based classification of thyroid tissue as malignant or benign, said system comprising a set of polynucleotides for detecting a set of target sequences selected from the group consisting of SEQ ID NOs: 1-7; SEQ ID NOs: 1-12 and 283-306; and SEQ ID NOs: 261, 657, 658, and 659.

In accordance with another aspect of the present invention, there is provided a nucleic acid array for expression-based classification of thyroid tissue as malignant or benign, said array comprising at least ten probes immobilized on a solid support, each of said probes being between about 15 and about 500 nucleotides in length, each of said probes being derived from a sequence corresponding to, or complementary to, a transcript of a gene selected from the group of genes set forth in Table 1, or a portion of said transcript.

In accordance with another aspect of the present invention, there is provided a method of classifying a thyroid nodule in a subject as malignant or benign, said method comprising: (a) determining the expression level of one or more transcripts of one or more genes in a test sample obtained from said subject to provide an expression pattern profile, said one or more genes selected from the group of genes set forth in Table 1, and (c) comparing said expression pattern profile with a reference expression pattern profile.

In accordance with another aspect of the present invention, there is provided a kit for characterizing the expression of one or more nucleic acid sequences depicted in SEQ ID NOs: 1-659 comprising one or more nucleic acids selected from:

(a) a nucleic acid depicted in any of SEQ ID NOs: 1-659;
(b) an RNA form of any of the nucleic acids depicted in SEQ ID NOs: 1-659;
(c) a peptide nucleic acid form of any of the nucleic acids depicted in SEQ ID NOs: 1-659;
(d) a nucleic acid comprising at least 20 consecutive bases of any of (a-c);
(e) a nucleic acid comprising at least 25 consecutive bases having at least 90% sequence identity to any of (a-c); or
(f) a complement to any of (a-e); and optionally instructions for correlating the expression level of said one or more nucleic acid sequences with the disease state of thyroid tissue.

In accordance with another aspect of the present invention, there is provided an array of probe nucleic acids certified for use in classifying thyroid disease status, wherein said array comprises at least two different probe nucleic acids that specifically hybridize to corresponding different target nucleic acids depicted in one of SEQ ID NOs: 1-659, an RNA form thereof, or a complement to either thereof.

In accordance with another aspect of the present invention, there is provided a device for classifying a biological sample from a thyroid gland as malignant or benign, the device comprising means for measuring the expression level of one or more transcripts of one or more genes selected from the group of genes set forth in Table 1; means for correlating the expression level with a classification of thyroid disease status; and means for outputting the thyroid disease status.

In accordance with another aspect of the present invention, there is provided a computer-readable medium comprising one or more digitally-encoded expression pattern profiles representative of the level of expression of one or more transcripts of one or more genes selected from the group of genes set forth in Table 1, each of said one or more expression pattern profiles being associated with a value wherein each of said values is correlated with the presence of malignant or benign tissue in a thyroid gland sample.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
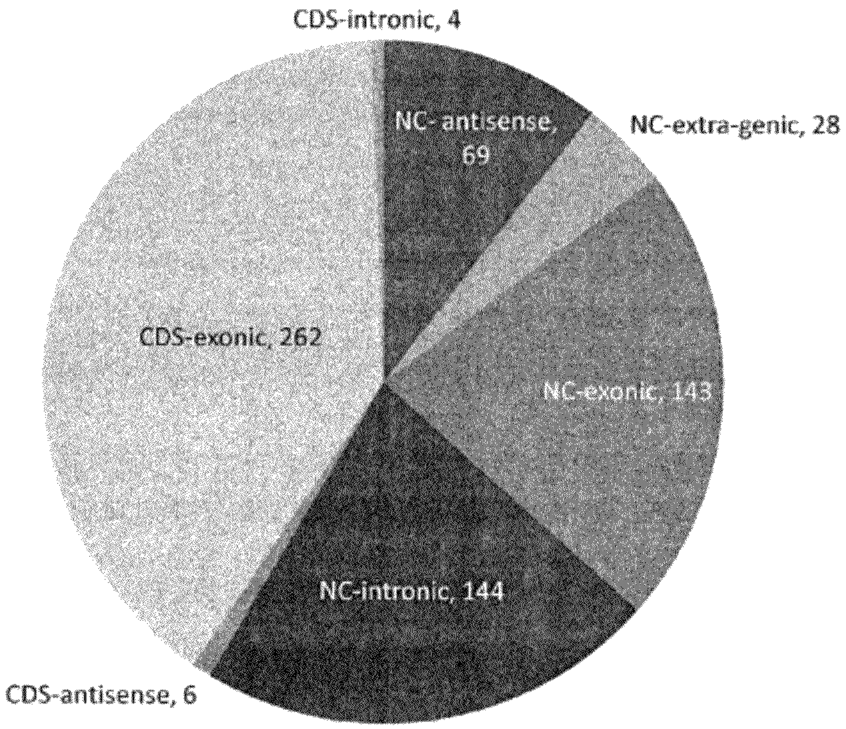
FIG. 1 is a pie chart that depicts the annotations of the 656 selected RNAs from genes previously described in the literature that were identified as differentially expressed in the training subset. Note that more than 60% correspond to non-canonical expressed transcripts (i.e., intronic, antisense and extra-genic) while only a small portion are actually from exonic sequences of protein-encoding genes. The labels in the pie chart indicate the position of the differentially expressed probes relative to the nearest annotated gene. CDS-RNA overlaps with the coding sequence translations of mRNAs in RefSeq or GenBank databases, NC—'non-coding' RNA does not overlap with the CDS.

The present invention provides a system and methods for classifying thyroid tissue from a subject as malignant or benign, which allows for the diagnosis of thyroid cancer in the subject. The system and methods are based on the identification of gene transcripts that are differentially expressed in thyroid cancer relative to benign thyroid nodule disease. These gene transcripts can be considered as a library which can be used as a resource for the identification of sets of specific target sequences ("thyroid classification sets"), which may represent the entire library of gene transcripts or a subset of the library and the detection of which is indicative of the status of the thyroid tissue (for example, malignant or benign). The invention further provides for probes capable of detecting these target sequences and primers that are capable of amplifying the target sequences.

In accordance with one embodiment of the invention, the target sequences comprised by the thyroid classification set are sequences based on or derived from the gene transcripts from the library, or a subset thereof. Such sequences are occasionally referred to herein as "probe selection regions" or "PSRs." In another embodiment of the invention, the target sequences comprised by the thyroid classification set are sequences based on the gene transcripts from the library, or a subset thereof, and include both coding and non-coding sequences.

In one embodiment, the systems and methods provide for the molecular analysis of the expression levels of one or more of the target sequences as set forth in SEQ ID NOs: 1-659 (Table 3). Increased relative expression of one or more target sequences in Group I corresponding to the sequences as set forth in SEQ ID NOs: 1-4, and 8-282, and/or decreased relative expression of one or more target sequences in Group II corresponding to the sequences as set forth in SEQ ID NOs: 5-7, and 283-659, can be correlated with increased likelihood of malignant thyroid nodule disease. Conversely, increased relative expression of one or more target sequences in Group II and/or decreased relative expression of one or more target sequences in Group I can be correlated with an increased likelihood of benign thyroid nodule disease. Subsets and combinations of these target sequences or probes complementary thereto may be used as described herein.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Definitions

Unless defined otherwise or the context clearly dictates otherwise, all technical and scientific terms used herein have the same meaning as commonly understood by one of ordinary skill in the art to which this invention belongs. In describing the present invention, the following terms will be employed, and are intended to be defined as indicated below.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide will hybridize under selective hybridization conditions to its complement. Typically, selective hybridization will occur when there is at least about 65% complementarity over a stretch of at least 14 to 25 bases, for example at least about 75%, or at least about 90% complementarity. See, M. Kanehisa Nucleic Acids Res. 12:203 (1984).

"Preferential binding" or "preferential hybridization" refers to the increased propensity of one polynucleotide to bind to its complement in a sample as compared to a non-complementary polymer in the sample.

Hybridization conditions will typically include salt concentrations of less than about 1M, more usually less than about 500 mM, for example less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

A "target sequence" as used herein (also occasionally referred to as a "PSR" or "probe selection region") refers to a region of the genome against which one or more probes can be designed. As used herein, a probe is any polynucleotide capable of selectively hybridizing to a target sequence or its complement, or to an RNA version of either. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers.

"Having" is an open ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

The term "suspected of comprising thyroid cancer," as used in reference to biological samples or purified fractions or components thereof or products derived therefrom, refers to any sample or product that is to analyzed for the expression of the target sequences described herein, and includes samples comprising normal thyroid tissue, as well as samples comprising thyroid tumors, whether benign or malignant. Such tissue may be obtained from the thyroid itself, from another location within a patient that is a suspected metastases, or from a known sample of malignant thyroid cancer or from a known thyroid cancer cell line. Samples known to be malignant can function as positive controls, while samples known to be noncancerous (or of nonthyroid origin) can function as negative controls, but are "suspected" of comprising thyroid cancer in that they are tested to determine whether the assay being performed produces false positives or other abnormal results, indicating a problem with a given assay.

As used herein, the term "about" refers to approximately a +/−10% variation from a given value. It is to be understood that such a variation is always included in any given value provided herein, whether or not it is specifically referred to.

Use of the singular forms "a," "an," and "the" include plural references unless the context clearly dictates otherwise. Thus, for example, reference to "a polynucleotide" includes a plurality of polynucleotides, reference to "a target" includes a plurality of such targets, reference to "a normalization method" includes a plurality of such methods, and the like. Additionally, use of specific plural references, such as "two," "three," etc., read on larger numbers of the same subject, unless the context clearly dictates otherwise.

Terms such as "connected," "attached," "linked" and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

THYROID CLASSIFICATION SYSTEM

The system of the present invention is based on the identification of a library of gene transcripts that are differentially expressed in thyroid cancer relative to benign thyroid nodule disease and thus may be diagnostic for thyroid cancer. For example, relative over and/or under expression of one or more of the gene transcripts in a thyroid nodule sample compared to a reference sample or expression profile or signature there from may be indicative of a malignant condition. The reference sample can be, for example, from one or more benign thyroid nodules from one or more references subject(s). The reference expression profile or signature may optionally be normalized to one or more appropriate reference gene transcripts. Alternatively or in addition to, expression of one or more of the gene transcripts in a thyroid nodule sample may be compared to an expression profile or signature from one or more known thyroid cancer samples such that a substantially similar expression profile or signature may be used to validate a finding of cancer or may be compared to the expression profile or signature from normal thyroid tissue.

Expression profiles or signatures from diagnostic samples may be normalized to one or more house keeping gene transcripts such that normalized over and/or under expression of one or more of the gene transcripts in a thyroid nodule sample may be indicative of a malignant condition.

Thyroid Classification Library

The Thyroid Classification Library in accordance with the present invention comprises one or more gene transcripts whose relative and/or normalized expression is indicative of a thyroid malignancy or of benign thyroid nodule disease. Exemplary genes from which a transcribed RNA or encoded protein shows differential expression in benign and/or malignant thyroid tissue are shown in Table 1. A single gene may give rise to more than one gene transcript. Not all transcripts of a given gene are necessarily indicative of a thyroid malignancy or of benign thyroid nodule disease. A single gene may also give rise to two or more transcripts, where at least one of the two or more transcripts is indicative of a thyroid malignancy while at least one different transcript is indicative of benign thyroid disease. In one embodiment, the library comprises one or more of the gene transcripts of the genes shown in Table 1.

In one embodiment, the library comprises at least one transcript from at least one gene selected from those listed in Table 1. In one embodiment, the library comprises at least one transcript from each of at least 5 genes selected from those listed in Table 1. In another embodiment, the library comprises at least one transcript from each of at least 10 genes selected from those listed in Table 1. In a further embodiment, the library comprises at least one transcript from each of at least 15 genes selected from those listed in Table 1. In other embodiments, the library comprises at least one transcript from each of at least 20, at least 25, at least 30, at least 35, at least 40, at least 45, at least 50, at least 55, at least 60 and at least 65 genes selected from those listed in Table 1. In a further embodiment, the library comprises at least one transcript from all of the genes listed in Table 1. In a further embodiment, the library comprises at all transcripts from all of the genes listed in Table 1.

In one embodiment, the library comprises at least one transcript from at least one gene selected from the group consisting of ABCA8 (ATP-binding cassette, sub-family A (ABC1), member 8); ADORA1 (Adenosine A1 receptor); ALOX5 (Arachidonate 5-lipoxygenase); AMIGO2 (Adhesion molecule with Ig-like domain 2); ANK2 (Ankyrin 2, neuronal); APOE (Apolipoprotein E); ARG2 (Arginase, type II); ARHGAP11A (Rho GTPase activating protein 11A); ARMCX3 (Armadillo repeat containing, X-linked 3); BCL2 (B-cell CLL/lymphoma 2); BEX1 (Brain expressed, X-linked 1); BMP8A (Bone morphogenetic protein 8a); C1 orf212 (Chromosome 1 open reading frame 212); C7orf24 (Chromosome 7 open reading frame 24); CA4 (Carbonic anhydrase IV); CAMK2N1 (Calcium/calmodulin-dependent protein kinase II inhibitor 1); CCL14 (Chemokine (C—C motif) ligand 14); CCL21 (Chemokine (C—C motif) ligand 21); CCND1 (Cyclin D1); CD44 (CD44 molecule (Indian blood group)); CD55 (CD55 molecule, decay accelerating factor for complement (Cromer blood group)); CDH16 (Cadherin 16, KSP-cadherin); CDH3 (Cadherin 3, type 1, P-cadherin (placental)); CDKN2A (Cyclin-dependent kinase inhibitor 2A (melanoma, p16, inhibits CDK4)); CFD (Complement factor D (adipsin)); ChGn (Chondroitin beta-1,4 N-acetylgalactosaminyltransferase); CHI3L1 (Chitinase 3-like 1 (cartilage glycoprotein-39)); CHRDL1 (Chordin-like 1); CHST2 (Carbohydrate (N-acetylglucosamine-6-O) sulfotransferase 2); CITED1 (Cbp/p300-interacting transactivator, with Glu/Asp-rich carboxy-terminal domain, 1); CKS2 (CDC28 protein kinase regulatory subunit 2); COL9A3 (Collagen, type IX, alpha 3); CRABP1 (Cellular retinoic acid binding protein 1); CSNK1G2 (Casein kinase 1, gamma 2); CST6 (Cystatin E/M); CTSC (Cathepsin C); CTSH (Cathepsin H); CTSS (Cathepsin S); DDIT3 (DNA-damage-inducible transcript 3); DIO1 (Deiodinase, iodothyronine, type I); DIO2 (Deiodinase, iodothyronine, type II); DLG7 (Discs, large homolog 7 (Drosophila)); DPP4 (Dipeptidyl-peptidase 4 (CD26, adenosine deaminase complexing protein 2)); DUSP5 (Dual specificity phosphatase 5); DUSP6 (Dual specificity phosphatase 6); EFEMP1 (EGF-containing fibulin-like extracellular matrix protein 1); ELMO1 (Engulfment and cell motility 1); ENDOD1 (Endonuclease domain containing 1); ENPP1 (Ectonucleotide pyrophosphatase/phosphodiesterase 1); EPS8 (Epidermal growth factor receptor pathway substrate 8); ETHE1 (Ethylmalonic encephalopathy 1); ETV5 (Ets variant gene 5 (ets-related molecule)); FABP4 (Fatty acid binding protein 4, adipocyte); FAM129A (Family with sequence similarity 129, member A); FAM129B (Family with sequence similarity 129, member B); FAM129C (Family with sequence similarity 129, member C); FBLN1 (Fibulin 1); FCGBP (Fc fragment of IgG binding protein); FHL1 (Four and a half LIM domains 1); FN1 (Fibronectin 1); FZD4 (Frizzled homolog 4 (Drosophila)); GABBR2 (Gamma-aminobutyric acid (GABA) B receptor, 2); GALE (UDP-galactose-4-epimerase); GALNT7 (UDP-N-acetyl-alpha-D-galactosamine: polypeptide N-acetylgalactosaminyltransferase 7 (Ga1NAc-T7)); GDF15 (Growth differentiation factor 15); GJB3 (Gap junction protein, beta 3, 31 kDa); GPM6A (Glycoprotein M6A); HBA2 (Hemoglobin, alpha 2); HBD (Hemoglobin, delta); HLA-DMB (Major histocompatibility complex, class II, DM beta); HLA-DQA1 (Major histocompatibility complex, class II, DQ alpha 1); HLA-DRA (Major histocompatibility complex, class II, DR alpha); HLF (Hepatic leukemia factor); HMGA2 (High mobility group AT-hook 2); ICAM1 (Intercellular adhesion molecule 1 (CD54), human rhinovirus receptor); ICAM4 (Intercellular adhesion molecule 4 (Landsteiner-Wiener blood group)); ID4 (Inhibitor of DNA binding 4, dominant negative helix-loop-helix protein); IGFBP6 (Insulin-like growth factor binding protein 6); IGSF1 (Immunoglobulin superfamily, member 1); ITM2A (Integral membrane protein 2A); ITPR1 (Inositol 1,4,5-triphosphate receptor, type 1); KCNAB1 (Potassium voltage-gated channel, shaker-related subfamily, beta member 1); KCNJ2 (Potassium inwardly-rectifying channel, subfamily J, member 2); KIAA0746 (KIAA0746 protein); KIT (V-kit Hardy-Zuckerman 4 feline sarcoma viral oncogene homolog); KLK10 (Kallikrein-related peptidase 10); KRT15 (Keratin 15); KRT19 (Keratin 19); LAMB3 (Laminin, beta 3); LCN2 (Lipocalin 2); LGALS3 (Lectin, galactoside-binding, soluble, 3); LIPG (Lipase, endothelial); LPL (Lipoprotein lipase); LRP2 (Low density lipoprotein-related protein 2); LRP4 (Low density lipoprotein receptor-related protein 4); MATN2 (Matrilin 2); MET (Met proto-oncogene (hepatocyte growth factor receptor)); MPPED2 (Metallophosphoesterase domain containing 2); MPZL2 (Myelin protein zero-like 2); MPZL3 (Myelin protein zero-like 3); MRC2 (Mannose receptor, C type 2); MT1F (Metallothionein 1F); MT1G (Metallothionein 1G); MT1H (Metallothionein 1H); MT1M (Metallothionein 1M); MT1X (Metallothionein 1×); MT2A (Metallothionein 2A); MTF1 (Metal-regulatory transcription factor 1); MUC1 (Mucin 1, cell surface associated); MYBPH (Myosin binding protein H); NELL2 (NEL-like 2 (chicken)); NMU (Neuromedin U); NRCAM (Neuronal cell adhesion molecule); NRIP 1 (Nuclear receptor interacting protein 1); OPRM1 (Opioid receptor, mu 1); P4HA2 (Procollagen-proline, 2-oxoglutarate 4-dioxygenase (proline 4-hydroxylase), alpha polypeptide II); PDLIM4 (PDZ and LIM domain 4); PDZK 1 IP1 (PDZK1 interacting protein 1); PIP3-E (Phosphoinositide-binding protein PIP3-E); PLAU (Plasminogen activator, urokinase); PLXNC 1 (Plexin C1); PPARGC1A (Peroxisome proliferator-activated receptor gamma, coactivator 1 alpha); PRIM2 (Primase, DNA, polypeptide 2 (58 kDa)); PRMT8 (Protein arginine methyltransferase 8); PROS1 (Protein S (alpha)); PRSS23 (Protease, serine, 23); PSD3 (Pleckstrin and Sec7 domain containing 3); PTPRE (Protein tyrosine phosphatase, receptor type, E); QPCT (Glutaminyl-peptide cyclotransferase (glutaminyl cyclase)); RAB23 (RAB23, member RAS oncogene family); RCN3 (Reticulocalbin 3, EF-hand calcium binding domain); RET (Ret proto-oncogene); RGS16 (Regulator of G-protein signaling 16); RHOBTB3 (Rho-related BTB domain containing 3); RXRG (Retinoid X receptor, gamma); S100A10 (S100 calcium binding protein A10; SCG5 (Secretogranin V (7B2 protein)); SDC4 (Syndecan 4); SERPINA1 (Serpin peptidase inhibitor, Glade A (alpha-1 antiproteinase, antitrypsin), member 1); SFTPB (Surfactant, pulmonary-associated protein B); SLC1A1 (Solute carrier family 1 (neuronal/epithelial high affinity glutamate transporter, system Xag), member 1); SLC26A4 (Solute carrier family 26, member 4); SLC27A6 (Solute carrier family 27 (fatty acid transporter), member 6); SLC34A2 (Solute carrier family 34 (sodium phosphate), member 2); SLC5A5 (Solute carrier family 5 (sodium iodide symporter), member 5); SLPI (Secretory leukocyte peptidase inhibitor); SOD3 (Superoxide dismutase 3, extracellular); SOX4 ($SR^{y}$ (sex determining region Y)-box 4); SPOCK1 (Sparc/osteonectin, cwcv and kazal-like domains proteoglycan (testican) 1); SPP1 (Secreted phosphoprotein 1 (osteopontin, bone sialoprotein I, early T-lymphocyte activation 1)); ST14 (Suppression of tumorigenicity 14 (colon carcinoma)); STT3A (STT3, subunit of the oligosaccharyltransferase complex, homolog A (*S. cerevisiae*)); STT3B (STT3, subunit of the oligosaccharyltransferase complex, homolog B (*S. cerevisiae*)); SYN1 (Synapsin I); TACSTD2 (Tumor-associated calcium signal transducer 2); TCEAL2 (Transcription elongation factor A (SII)-like 2); TFF3 (Trefoil factor 3 (intestinal)); TGFα (Transforming growth factor, alpha); TIAM1 (T-cell lymphoma invasion and metastasis 1); TIMP1 (TIMP metallopeptidase inhibitor 1); TM7SF4 (Transmembrane 7 superfamily member 4); TNC (Tenascin C (hexabrachion)); TPD52L1 (Tumor protein D52-like 1); TPO (Thyroid peroxidase); TRIM14 (Tripartite motif-containing 14); TUSC3 (Tumor suppressor candidate 3); VEGFA (Vascular endothelial growth factor A) and ZMAT4 (Zinc finger, matrin type 4).

In one embodiment, the library comprises at least one transcript from at least one gene selected from the group consisting of HMGA2 (High mobility group AT-hook 2); CDH3 (Cadherin 3, type 1, P-cadherin (placental)); SERPINA1 (Serpin peptidase inhibitor, Glade A (alpha-1 antiproteinase, antitrypsin), member 1); IGFBP6 (Insulin-like growth factor binding protein 6); TPO (Thyroid peroxidase); KIT (V-kit Hardy-Zuckerman 4 feline sarcoma viral oncogene homolog) and MPPED2 (Metallophosphoesterase domain containing 2).

In one embodiment, the library comprises at least one transcript from at least one gene selected from the group consisting of HMGA2 (High mobility group AT-hook 2); CDH3 (Cadherin 3, type 1, P-cadherin (placental)); SERPINA1 (Serpin peptidase inhibitor, Glade A (alpha-1 antiproteinase, antitrypsin), member 1); IGFBP6 (Insulin-like growth factor binding protein 6); TPO (Thyroid peroxidase); KIT (V-kit Hardy-Zuckerman 4 feline sarcoma viral oncogene homolog), FN1 (fibronectin 1), HLF (Hepatic leukemia factor), MT1F (Metallothionein 1F), MT1G (Metallothionein 1G), PDLIM4 (PDZ and LIM domain 4), PPARGC1A (Peroxisome proliferator-activated receptor gamma, coactivator 1 alpha), SLC26A4 (Solute carrier family 26, member 4), TFF3 (Trefoil factor 3 (intestinal)), TACSTD2 (Tumor-associated calcium signal transducer 2), ZMAT4 (Zinc finger, matrin type 4) and MPPED2 (Metallophosphoesterase domain containing 2).

In one embodiment, the library comprises at least one transcript from Sparc/osteonectin, cwcv and kazal-like domains proteoglycan (testican) 1.

The invention also contemplates that alternative libraries may be designed that include transcripts of one or more of the genes in Table 1, together with additional gene transcripts that are identified as having differential expression in benign and/or malignant thyroid tissue. As is known in the art, the publication and sequence databases can be mined using a variety of search strategies to identify appropriate candidates for inclusion in the library. For example, currently available scientific and medical publication databases such as Medline, Current Contents, OMIM (online Mendelian inheritance in man), various Biological and Chemical Abstracts, Journal indexes, and the like can be searched using term or key-word searches, or by author, title, or other relevant search parameters. Many such databases are publicly available, and strategies and procedures for identifying publications and their contents, for example, genes, other nucleotide sequences, descriptions, indications, expression pattern, etc, are well known to those skilled in the art. Numerous databases are available through the internet for free or by subscription, see, for example, the National Center Biotechnology Information (NCBI), Infotrieve, Thomson ISI, and Science Magazine (published by the AAAS) websites. Additional or alternative publication or citation databases are also available that provide identical or similar types of information, any of which can be employed in the context of the invention. These databases can be searched for publications describing altered gene expression between malignant thyroid nodule disease and benign thyroid nodule disease. Additional potential candidate genes may be identified by searching the above described databases for differentially expressed proteins and by identifying the nucleotide sequence encoding the differentially expressed proteins.

Thyroid Classification Sets

A Thyroid Classification Set comprises one or more target sequences identified within the gene transcripts in the thyroid classification library, or a subset of these gene transcripts. The target sequences may be within the coding and/or non-coding regions of the gene transcripts. The set can comprise one or a plurality of target sequences from each gene transcript in the library, or subset thereof. The relative and/or normalized level of these target sequences in a sample is indicative of the level of expression of the particular gene transcript and thus of a thyroid malignancy or of benign thyroid nodule disease. For example, the relative and/or normalized expression level of one or more of the target sequences may be indicative of a thyroid malignancy while the relative and/or normalized expression level of one or more other target sequences may be indicative of benign thyroid nodule disease.

Accordingly, one embodiment of the present invention provides for a library or catalog of candidate target sequences derived from the transcripts (both coding and non-coding regions) of at least one gene suitable for classifying thyroid nodules as being malignant or benign. In a further embodiment, the library or catalog of candidate target sequences comprises target sequences derived from the transcripts of one or more of the genes set forth in Table 1. The library or catalog in affect provides a resource list of transcripts from which target sequences appropriate for inclusion in a thyroid classification set can be derived. In one embodiment, an individual thyroid classification set may comprise target sequences derived from the transcripts of one or more genes exhibiting a positive correlation with thyroid cancer. In one embodiment, an individual thyroid classification set may comprise target sequences derived from the transcripts of one or more genes exhibiting a negative correlation with thyroid cancer. In one embodiment, an individual Thyroid Classification Set may comprise target sequences derived from the transcripts of from two or more genes, wherein at least one gene has a transcript that exhibits a positive correlation with thyroid cancer and at least one gene has a transcript that exhibits a negative correlation.

In one embodiment, the Thyroid Classification Set comprises target sequences derived from the transcripts of at least one gene. In one embodiment, the Thyroid Classification set comprises target sequences derived from the transcripts of at least 5 genes. In another embodiment, the Thyroid Classification set comprises target sequences derived from the transcripts of at least 10 genes. In a further embodiment, the Thyroid Classification set comprises target sequences derived from the transcripts of at least 15 genes. In other embodiments, the Thyroid Classification set comprises target sequences derived from the transcripts of at least 20, at least 25, at least 30, at least 35, at least 40, at least 45, at least 50, at least 55, at least 60 and at least 65 genes.

Following the identification of candidate gene transcripts, appropriate target sequences can be identified by screening for target sequences that have been annotated to be associated with each specific gene locus from a number of annotation sources including GenBank, RefSeq, Ensembl, dbEST, GENSCAN, TWINSCAN, Exoniphy, Vega, microRNAs registry and others (see Affymetrix Exon Array design note).

As part of the target sequence selection process, target sequences can be optionally further evaluated for potential cross-hybridization against other putative transcribed sequences in the design (but not the entire genome) to identify only those target sequences that are predicted to uniquely hybridize to a single target.

The set of target sequences that are predicted to uniquely hybridize to a single target can be further filtered using a variety of criteria including, for example, sequence length, for their mean expression levels across a wide selection of human tissues, as being representative of transcripts expressed either as novel alternative (i.e., non-consensus) exons, alternative retained introns, novel exons 5' or 3' of the gene's transcriptional start site or representing transcripts expressed in a manner antisense to the gene, amongst others. Representative, non-limiting examples of filtered candidate target sequences in accordance with the present invention are shown in Table 3.

In one embodiment, the Thyroid Classification Set comprises target sequences derived from intron #3 of High mobility group AT-hook 2; exon #16 of Cadherin 3, type 1, P-cadherin (placental); exon #5 of Serpin peptidase inhibitor, Glade A (alpha-1 antiproteinase, antitrypsin), member 1; exon #4 of Insulin-like growth factor binding protein 6; exon #17 of Thyroid peroxidase; exon #22 of V-kit Hardy-Zuckerman 4 feline sarcoma viral oncogene homolog and intron #3 of Metallophosphoesterase domain containing 2.

In one embodiment, the Thyroid Classification Set comprises target sequences derived from exon #16 of Cadherin 3, type 1, P-cadherin (placental); intron #25 of Fibronectin 1; intron #31 of Fibronectin 1; intron #40 of Fibronectin 1; exon #1 of Hepatic leukemia factor; intron #3 of High mobility group AT-hook 2; exon #4 of Insulin-like growth factor binding protein 6; 25 base pairs 3' of Metallophosphoesterase domain containing 2; exon #6 of Metallophosphoesterase domain containing 2; intron #1 of Metallophosphoesterase domain containing 2; intron #3 of Metallophosphoesterase domain containing 2; intron #3 of Metallophosphoesterase domain containing 2; intron #3 of Metallophosphoesterase domain containing 2; exon #3 of Metallothionein 1F; exon #3 of Metallothionein 1G; exon #7 of PDZ and LIM domain 4; exon #5 of Peroxisome proliferator-activated receptor gamma, coactivator 1 alpha; exon #5 of Serpin peptidase inhibitor, Glade A (alpha-1 antiproteinase, antitrypsin), member 1; exon #13 of Solute carrier family 26, member 4; exon #17 of Solute carrier family 26, member 4; exon #5 of Solute carrier family 26, member 4; exon #6 of Solute carrier family 26, member 4; 185 base pairs 3' of Thyroid peroxidase; exon #1 of Thyroid peroxidase; exon #13 of Thyroid peroxidase; exon #17 otThyroid peroxidase; exon #5 of Thyroid peroxidase; exon #5 of Thyroid peroxidase; exon #7 of Thyroid peroxidase; intron #15 of Thyroid peroxidase; intron #8 of Thyroid peroxidase; exon #3 of Trefoil factor 3 (intestinal); exon #1 of Tumor-associated calcium signal transducer 2; exon #22 of V-kit Hardy-Zuckerman 4 feline sarcoma viral oncogene homolog; exon #6 of Zinc finger, matrin type 4 and exon #7 of Zinc finger, matrin type 4.

In one embodiment, the Thyroid Classification Set comprises target sequences derived from exon #11, intron's #2, 3, and 6 of Sparc/osteonectin, cwcv and kazal-like domains proteoglycan (testican) 1.

In one embodiment, the potential set of target sequences can be filtered for their expression levels using the multi-tissue expression data made publicly available by Affymetrix at (http://www.affinetrix.com/support/technical/sample data/exon array data.affx) such that probes with, for example, expression across numerous tissues or no expression in thyroid tissue can be excluded.

In one embodiment, the thyroid classification set can be specifically designed to be indicative of malignant thyroid cancer in general or alternatively be indicative of one or more individual types of thyroid cancer.

Validation of Target Sequences

Following in silico selection of target sequences or review of the literature for published target sequences, each target sequence suitable for use in the thyroid classification set may be validated to confirm differential relative or normalized expression in thyroid cancer or benign thyroid nodule disease. Validation methods are known in the art and include hybridization techniques such as microarray analysis or Northern blotting using appropriate controls, and may include one or more additional steps, such as reverse transcription, transcription, PCR, RT-PCR and the like. The validation of the target sequences using these methods is well within the abilities of a worker skilled in the art.

Minimal Expression Signature

In one embodiment, individual thyroid classification sets provide for at least a determination of a minimal expression signature, capable of distinguishing malignant from benign thyroid nodule disease. Means for determining the appropriate number of target sequences necessary to obtain a minimal expression signature are known in the art and include the Nearest Shrunken Centroids (NSC) method.

In this method (see US 20070031873), a standardized centroid is computed for each class. This is the average gene expression for each gene in each class divided by the within-class standard deviation for that gene. Nearest centroid classification takes the gene expression profile of a new sample, and compares it to each of these class centroids. The class whose centroid that it is closest to, in squared distance, is the predicted class for that new sample. Nearest shrunken centroid classification "shrinks" each of the class centroids toward the overall centroid for all classes by an amount called the threshold. This shrinkage consists of moving the centroid towards zero by threshold, setting it equal to zero if it hits zero. For example if threshold was 2.0, a centroid of 3.2 would be shrunk to 1.2, a centroid of −3.4 would be shrunk to −1.4, and a centroid of 1.2 would be shrunk to zero. After shrinking the centroids, the new sample is classified by the usual nearest centroid rule, but using the shrunken class centroids. This shrinkage can make the classifier more accurate by reducing the effect of noisy genes and provides an automatic gene selection. In particular, if a gene is shrunk to zero for all classes, then it is eliminated from the prediction rule. Alternatively, it may be set to zero for all classes except one, and it can be learned that the high or low expression for that gene characterizes that class. The user decides on the value to use for threshold. Typically one examines a number of different choices. To guide in this choice, PAM does K-fold cross-validation for a range of threshold values. The samples are divided up at random into K roughly equally sized parts. For each part in turn, the classifier is built on the other K-1 parts then tested on the remaining part. This is done for a range of threshold values, and the cross-validated misclassification error rate is reported for each threshold value. Typically, the user would choose the threshold value giving the minimum cross-validated misclassification error rate.

Alternatively, minimal expression signatures can be established through the use of optimization algorithms such as the mean variance algorithm widely used in establishing stock portfolios. This method is described in detail in US patent publication number 20030194734. Essentially, the method calls for the establishment of a set of inputs (stocks in financial applications, expression as measured by intensity here) that will optimize the return (e.g., signal that is generated) one receives for using it while minimizing the variability of the return. In other words, the method calls for the establishment of a set of inputs (e.g., expression as measured by intensity) that will optimize the signal while minimizing variability. Many commercial software programs are available to conduct such operations. “Wagner Associates Mean-Variance Optimization Application,” referred to as “Wagner Software” throughout this specification, is preferred. This software uses functions from the “Wagner Associates Mean-Variance Optimization Library” to determine an efficient frontier and optimal portfolios in the Markowitz sense is preferred. Use of this type of software requires that microarray data be transformed so that it can be treated as an input in the way stock return and risk measurements are used when the software is used for its intended financial analysis purposes.

The process of selecting a minimal expression signature can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with cancer. Output from the method would be an optimized set of genes that could include some genes that are expressed in peripheral blood as well as in diseased tissue.

Other heuristic rules can be applied that are not necessarily related to the biology in question. For example, one can apply a rule that only a prescribed percentage of the portfolio can be represented by a particular gene or group of genes. Commercially available software such as the Wagner Software readily accommodates these types of heuristics. This can be useful, for example, when factors other than accuracy and precision (e.g., anticipated licensing fees) have an impact on the desirability of including one or more genes.

In one embodiment, the thyroid classification set for obtaining a minimal expression signature comprises at least one, two, three, four, five, six, eight, 10, 15, 20, 25 or more of target sequences shown to have a positive correlation with malignant thyroid disease, for example those depicted in SEQ ID NOs:1-4, and 8-282 or a subset thereof. In another embodiment, the thyroid classification set for obtaining a minimal expression signature comprises at least one, two, three, four, five, six, eight, 10, 15, 20, 25 or more of those target sequences shown to have a positive correlation with benign thyroid disease, for example those depicted in of SEQ ID NOs:5-7, and 283-659, or a subset thereof. In yet another embodiment, the thyroid classification set for obtaining a minimal expression signature comprises at least one, two, three, four, five, six, eight, 10, 15, 20, 25 or more of target sequences shown to have a positive or negative correlation with malignant thyroid disease, for example those depicted in SEQ ID NOs:1-659 or a subset thereof.

In some embodiments, the thyroid classification set comprises target sequences for detecting expression products of SEQ IDs:1-659. In some embodiments, the thyroid classification set comprises probes for detecting expression levels of sequences exhibiting positive and negative correlation with a disease status of interest are employed. For example, a combination useful for identifying a sample as exhibiting malignant or benign disease comprises at least one, two, three, four, five, six, eight, 10, 15, 20, 25 or more of those target sequences shown to have a positive correlation with malignant thyroid disease, for example those depicted in SEQ ID NOs:1-4, and 8-282 or a subset thereof; and at least one, two, three, four, five, six, eight, 10, 15, 20, or more of those target sequences shown to have a positive correlation with benign thyroid disease, for example those depicted in of SEQ ID NOs: 5-7, and 283-659, or a subset thereof.

Exemplary subsets and combinations of interest also include the target sequences as set forth in SEQ ID NOs: 1-7; SEQ ID NOs: 1-12 and 283-306; and SEQ ID NOs: 261, 657, 658, and 659.

Exemplary subsets of interest include those described herein, including in the examples. Exemplary combinations of interest include those utilizing one or more of the sequences listed in Tables 3, 4 and 5. Of particular interest are those combinations utilizing at least one sequence exhibiting positive correlation with the trait of interest, as well as those combinations utilizing at least one sequence exhibiting negative correlation with the trait of interest. Also of interest are those combinations utilizing at least two, at least three, at least four, at least five or at least six of those sequences exhibiting such a positive correlation, in combination with at least two, at least three, at least four, at least five, or at least six of those sequences exhibiting such a negative correlation. Exemplary combinations include those utilizing at least one, two, three, four, five or six of the target sequences depicted in Tables 3, 4 and 5.

It is to be recognized that those sequences shown as having a positive correlation with malignant disease conversely also possess a negative correlation with benign disease. Correspondingly, those sequences shown as having a positive correlation with benign disease also possess a negative correlation with malignant disease.

The thyroid classification set can optionally include one or more target sequences specifically derived from the transcripts of one or more housekeeping genes and/or one or more internal control target sequences and/or one or more negative control target sequences. In one embodiment, these target sequences can, for example, be used to normalize expression data. Housekeeping genes from which target sequences for inclusion in a Thyroid Classification Set can be derived from are known in the art and include those genes in which are expressed at a constant level in normal, benign and malignant thyroid tissue.

The target sequences described herein may be used alone or in combination with each other or with other known or later identified disease markers.

Thyroid Classification Probes/Primers

The system of the present invention provides for combinations of polynucleotide probes that are capable of detecting the target sequences of the Thyroid classification sets. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a PSR in the thyroid classification set. Computer programs can also be employed to select probe sequences that will not cross hybridize or will not hybridize non-specifically.

One skilled in the art will understand that the nucleotide sequence of the polynucleotide probe need not be identical to its target sequence in order to specifically hybridise thereto. The polynucleotide probes of the present invention, therefore, comprise a nucleotide sequence that is at least about 75% identical to a region of the target gene or mRNA. In another embodiment, the nucleotide sequence of the polynucleotide probe is at least about 90% identical a region of the target gene or mRNA. In a further embodiment, the nucleotide sequence of the polynucleotide probe is at least about 95% identical to a region of the target gene or mRNA. Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the target gene.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection. Hybridization under particular pH, salt, and temperature conditions can be optimized by taking into account melting temperatures and by using empirical rules that correlate with desired hybridization behaviours. Computer models may be used for predicting the intensity and concentration-dependence of probe hybridization.

As is known in the art, in order to represent a unique sequence in the human genome, a probe should be at least 15 nucleotides in length. Accordingly, the polynucleotide probes of the present invention range in length from about 15 nucleotides to the full length of the PSR or target mRNA. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides in length.

The polynucleotide probes of a thyroid classification set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability.

The system of the present invention further provides for primers and primer pairs capable of amplifying target sequences defined by the thyroid classification set, or fragments or subsequences or complements thereof. The nucleotide sequences of the thyroid classifying set may be provided in computer-readable media for in silky) applications and as a basis for the design of appropriate primers for amplification of one or more target sequences of the thyroid classifying set.

Primers based on the nucleotide sequences of target sequences can be designed for use in amplification of the target sequences. For use in amplification reactions such as PCR, a pair of primers will be used. The exact composition of the primer sequences is not critical to the invention, but for most applications the primers will hybridize to specific sequences of the thyroid classification set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the thyroid classification set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid depicted in one of SEQ ID NOs: 1-659, an RNA form thereof, or a complement to either thereof. Optionally, when amplified, either stand produced by amplification may be provided in purified and/or isolated form.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3' amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, O, S and $CH_2$ component parts.

The present invention also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic, which has been shown to have excellent hybridization properties, is a peptide nucleic acid (PNA) [Nielsen et al., *Science,* 254:1497-1500 (1991)]. In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present invention also contemplates polynucleotide probes or primers comprising "locked nucleic acids" (LNAs), which are novel conformationally restricted oligonucleotide analogues containing a methylene bridge that connects the 2'-O of ribose with the 4'-C (see, Singh et al., *Chem. Commun.,* 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron,* 1998, 54:3607-3630). Studies of mismatched sequences show that LNA obey the Watson-Crick base pairing rules with generally improved selectivity compared to the corresponding unmodified reference strands.

LNAs form duplexes with complementary DNA or RNA or with complementary LNA, with high thermal affinities. The universality of LNA-mediated hybridization has been emphasized by the formation of exceedingly stable LNA:LNA duplexes (Koshkin et al., *J. Am. Chem. Soc.,* 1998, 120: 13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.,* 1998, 8:2219-2222).

Modified polynucleotide probes or primers may also contain one or more substituted sugar moieties. For example, oligonucleotides may comprise sugars with one of the following substituents at the 2' position: OH; F; O-, S-, or N-alkyl; O-, S-, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[(CH_2)_nO]_m CH_3$, $O(CH_2)_n OCH$;, $O(CH_2)_n NH_2$, $O(CH_2)_n CH_3$, $O(CH_2)_n ONH_2$, and $O(CH_2)_n ON[(CH_2)_n CH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_{13}$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—$CH_2 CH_2 OCH_3$, also known as 2'-O-(2-methoxyethyl) or 2'-MOE) [Martin et al., *Helv. Chirp. Acta,* 78:486-504 (1995)], 2'-dimethylaminooxyethoxy ($O(CH_2)_2 ON(CH_3)_2$ group, also known as 2'-DMAOE), 2'-methoxy (2'-O—$CH_3$), 2'-aminopropoxy (2'-$OCH_2 CH_2 CH_2 NH_2$) and 2'-fluoro (2'-F).

Similar modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte Chemie, Int. Ed.,* 30:613 (1991); and Sanghvi, Y. S., (1993) *Antisense Research and Applications, pp* 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications*, pp 276-278, Crooke, S. T. and Lebleu, B., ed., CRC Press, Boca Raton].

One skilled in the art will recognize that it is not necessary for all positions in a given polynucleotide probe or primer to be uniformly modified. The present invention, therefore, contemplates the incorporation of more than one of the aforementioned modifications into a single polynucleotide probe or even at a single nucleoside within the probe or primer.

One skilled in the art will also appreciate that the nucleotide sequence of the entire length of the polynucleotide probe or primer does not need to be derived from the target sequence. Thus, for example, the polynucleotide probe may comprise nucleotide sequences at the 5' and/or 3' to the transcription start and stop sites, respectively that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilisation onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilisation, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

In one embodiment, polynucleotides of the invention include a nucleic acid depicted in (a) any of SEQ ID NOs: 1-659; (b) an RNA form of any of the nucleic acids depicted in SEQ ID NOs: 1-659; (c) a peptide nucleic acid form of any of the nucleic acids depicted in SEQ ID NOs: 1-659; (d) a nucleic acid comprising at least 20 consecutive bases of any of (a-c); (e) a nucleic acid comprising at least 25 consecutive bases having at least 90% sequence identity to any of (a-c); and a complement to any of (a-e).

Complements may take any polymeric form capable of base pairing to the species recited in (a)-(e), including nucleic acid such as RNA or DNA, or may be a neutral polymer such as a peptide nucleic acid. Polynucleotides of the invention can be selected from the subsets of the recited nucleic acids described herein, as well as their complements.

In some embodiments, polynucleotides of the invention comprise at least 20 consecutive bases as depicted in SEQ ID NOs:1-659, or a complement thereto. The polynucleotides may comprise at least 21, 22, 23, 24, 25, 27, 30, 32, 35 or more consecutive bases as depicted in SEQ ID NOs:1-659.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly (ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Preparation of Probes and Primers

The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624, 120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288, 514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

THYROID CLASSIFICATION METHODS

The present invention further provides methods for characterizing thyroid samples for the presence of malignant or benign thyroid nodule disease. The methods use the thyroid classification sets, probes and primers described herein to provide expression signatures or profiles from a test sample derived from a subject having or suspected of having thyroid cancer. In some embodiments, such methods involve contacting a test sample with thyroid classifying probes (either in solution or immobilized) under conditions that permit hybridization of the probe(s) to any target nucleic acid(s) present in the test sample and then detecting any probe:target duplexes formed as an indication of the presence of the target nucleic acid in the sample. Expression patterns thus determined are then compared to one or more reference profiles or signatures.

Optionally, the expression pattern can be normalized. The methods use the thyroid classification sets, probes and primers described herein to provide expression signatures or profiles from a test sample derived from a subject to classify thyroid nodule tissue as malignant or benign.

In some embodiments, such methods involve the specific amplification of target sequences nucleic acid(s) present in the test sample using methods known in the art to generate an expression profile or signature which is then compared to a reference profile or signature.

In some embodiments, the invention further provides for diagnosing thyroid cancer, for prognosing patient outcome, and/or for designating treatment modalities.

In one embodiment, the methods generate expression profiles or signatures detailing the expression of the 659 target sequences having altered relative expression in malignant and benign thyroid disease disclosed herein. In one embodiment, the methods generate expression profiles or signatures detailing the expression of the subsets of these target sequences having 7 or 36 target sequences as described in the examples.

In one embodiment, the methods generate expression profiles or signatures detailing the expression of the target sequences as set forth in SEQ ID NOs: 1-7; the target sequences as set forth in SEQ ID NOs: 1-12 and 283-306; or the target sequences as set forth in SEQ ID NOs: 261, 657, 658, and 659.

In some embodiments, the methods detect increased relative expression of one or more target sequences in Group I corresponding to the expression products of SEQ IDs:1-4 and 8-282, and/or decreased relative expression of one or more target sequences in Group II corresponding to the expression products of SEQ ID NOs: 5-7, and 283-659, and thereby designate a sample as comprising malignant thyroid nodule disease. In some embodiments, increased relative expression of one or more target sequences in Group II and/or decreased relative expression of one or more target sequences in Group I and thereby designate a sample as comprising benign thyroid nodule disease.

In some embodiments, the methods detect combinations of expression levels of sequences exhibiting positive and negative correlation with a disease status. In one embodiment, the methods detect a minimal expression signature.

Any method of detecting and/or quantitating the expression of the encoded target sequences can in principle be used in the invention. Such methods can include Northern blotting, array or microarray hybridization, by enzymatic cleavage of specific structures (e.g., an Invader® assay, Third Wave Technologies, e.g. as described in U.S. Pat. Nos. 5,846,717, 6,090, 543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis. Single-molecule sequencing (e.g., Illumina, Helicos, PacBio, ABI SOLID), in situ hybridization, bead-array technologies (e.g., Luminex xMAP, Illumina BeadChips), branched DNA technology (e.g., Panomics, Genisphere).

The expressed target sequences can be directly detected and/or quantitated, or may be copied and/or amplified to allow detection of amplified copies of the expressed target sequences or its complement. In some embodiments, degraded and/or fragmented RNA can be usefully analyzed for expression levels of target sequences, for example RNA having an RNA integrity number of less than 8.

In some embodiments, quantitative RT-PCR assays are used to measure the expression level of target sequences depicted in SEQ IDs: 1-659. In other embodiments, a GeneChip or microarray can be used to measure the expression of one or more of the target sequences.

Molecular assays measure the relative expression levels of the target sequences, which can be normalized to the expression levels of one or more control sequences, for example array control sequences and/or one or more housekeeping genes, for example GAPDH. Increased (or decreased) relative expression of the target sequences as described herein, including any of SEQ ID NOs:1-659, may thus be used alone or in any combination with each other in the methods described herein. In addition, negative control probes may be included.

Diagnostic Samples

Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising thyroid cancer. The diagnostic sample can be a biological sample used directly in a method of the invention. Alternatively, the diagnostic sample can be a sample prepared from a biological sample.

In one embodiments, the sample or portion of the sample comprising or suspected of comprising thyroid cancer can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs.

The samples may be archival samples, having a known and documented medical outcome, or may be samples from current patients whose ultimate medical outcome is not yet known. Samples to be analyzed for thyroid cancer are typically obtained as fine needle aspirates, a cytology smear, a liquid-based preparation (e.g., ThinPrep®), a cytology pellet, or as bulk samples obtained, for example, from a thyroidectomy. Where samples of a bodily fluid are obtained, cells or cell types may be isolated and/or purified therefrom. For example, circulating epithelial cells can be obtained from peripheral blood and analyzed as described herein. In some embodiments, magnetic separation can be used to obtain circulating epithelial cells (U.S. Pat. No. 6,136,182).

In some embodiments, the sample may be dissected prior to molecular analysis. The sample may be prepared via microdissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek®, V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFM™, Cryo-Gel™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure™ nucleic acid extraction kit, Agencourt Biosciences, Beverly Mass., High Pure FFPE RNA Micro Kit™, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a PSR, and may optionally be labeled. A variety of amplification methods are suitable for use, including polymerase-based methods and ligation-based methods. Exemplary amplification techniques include the polymerase chain reaction method (PCR), the ligase chain reaction (LCR), ribozyme-based methods, self sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the PSR that is used for detection as the target polynucleotide. In some cases, the presence and/or amount of the amplification product itself may be used to determine the expression level of a given PSR. In other instances, the amplification product may be used to hybridize to an array or other substrate comprising sensor polynucleotides which are used to detect and/or quantitate PSR expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Kienow fragment of Pol I, T4, T7, Sequenase® T7, Sequenase® Version 2.0 T7, Tub, Tag, Tth, Pft, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse $H^-$ MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Tag, Tth, Pfx, pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert(R) Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Thyroid Classification Arrays

The present invention contemplates that a thyroid classification set or probes derived therefrom may be provided in an array format. In the context of the present invention, an "array" is a spatially or logically organized collection of polynucleotide probes. Any array comprising sensor probes specific for two or more of the target sequences depicted in SEQ ID NOs: 1-659 or a product derived from the target sequences depicted therein can be used. Desirably, an array will be specific for 5, 10, 15, 20, 25, 30, 50, 75, 100, 150, 200, 250, 300, 350, 400, 450, 500, 600, or more of SEQ ID NOs: 1-659. Expression of these sequences may be detected alone or in combination with other transcripts. In some embodiments, an array is used which comprises a wide range of sensor probes for thyroid-specific expression products, along with appropriate control sequences. An array of interest is the Human Exon 1.0 ST Array (HuEx 1.0 ST, Affymetrix, Inc., Santa Clara, Calif.).

In one embodiment, the array comprising sensor probes specific for the target sequences as set forth in SEQ ID NOs: 1-7; the target sequences as set forth in SEQ ID NOs: 1-12 and 283-306; or the target sequences as set forth in SEQ ID NOs: 261, 657, 658, and 659.

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that will be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the thyroid classification array is a chip.

Data Analysis

Array data can be managed and analyzed using techniques known in the art. The Genetrix suite of tools can be used for microarray analysis (Epicenter Software, Pasadena, Calif.). Probe set modeling and data pre-processing can be derived using the Robust Multi-Array (RMA) algorithm or variant GC-RMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (i.e., an 'expression signature') and converted into a likelihood score. This likelihood score indicates the probability that a biological sample is from malignant thyroid nodule disease or benign disease. The likelihood score can be used to distinguish malignant from benign thyroid nodule disease. The models and/or algorithms can be provided in machine readable format, and may be used to correlate expression levels or an expression profile with a disease state, and/or to designate a treatment modality for a patient or class of patients.

Thus, results of the expression level analysis can be used to correlate increased expression of one or more target sequences in group I (or a subset thereof) and/or decreased expression of one or more target sequences in group II (or a subset thereof) with thyroid cancer, and to designate a treatment modality selected from total thyroidectomy, radioactive iodine treatment, and a combination thereof. Patients with benign disease would be candidates for watchful waiting (careful monitoring at regular intervals), thyroid hormone suppression therapy (treating with levothyroxine or other synthetic forms of thyroxine) to shrink the nodule, radioactive iodine to treat hyperfunctioning adenomas or multinodular goiters and surgery. For benign patients surgical management is much more limited to either cosmetic debulking procedures or only partial thyroidectomy leaving thyroid function largely intact. In contrast, the usual treatment for malignant nodules is surgical removal using more aggressive approaches such as near-total or total thyroidectomy followed by radioactive iodine ablation therapy and permanent thyroid hormone replacement therapy. Results of the expression level analysis can be used to correlate increased expression of one or more target sequences in group II (or a subset thereof) and/or decreased expression of one or more target sequences in group I (or a subset thereof) with benign disease, and to designate a treatment modality selected from near-total thyroidectomy, partial thyroidectomy, or watchful-waiting. The preferred treatment regimen for benign or non-neoplastic disease is observation.

Factors known in the art for diagnosing and/or suggesting, selecting, designating, recommending or otherwise determining a course of treatment for a patient or class of patients suspected of having thyroid disease can be employed in combination with measurements of the target sequence expression. These techniques include FNAB cytology and classification, ultrasound analysis, MRI results, CT scan results, thyroid scans, and measurements of thyroid hormone levels.

For example, factors which may be used to indicate a benign condition include a family history of Hashimoto's thyroiditis, of benign thyroid nodule, or of goiter, symptoms of hyper- or hypothyroidism, pain or tenderness associated with a nodule, a nodule that is soft, smooth and mobile, a multinodular goiter without a predominant nodule, a nodule that is "warm" on a thyroid scan, or an ultrasound indication of a simple cyst structure.

Factors which may be used to indicate a malignant thyroid condition include patient age less than 20 or greater than seventy, male gender, new onset of swallowing difficulties or hoarseness, a history of external neck irradiation, a nodule that is firm, irregular and fixed, cervical lymphadenopathy, a history of thyroid cancer, a nodule that is "cold" on a thyroid scan, and a solid or complex morphology seen on ultrasound.

Certified tests for classifying thyroid disease status and/or designating treatment modalities are also provided. A certified test comprises a means for characterizing the expression levels of one or more of the target sequences of interest, and a certification from a government regulatory agency endorsing use of the test for classifying the thyroid disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing benign from malignant thyroid tissues. Results of detection of expression levels of the target sequences used in the test and correlation with disease status and/or outcome are submitted to the agency. A certification authorizing the diagnostic and/or prognostic use of the test is obtained.

Also provided are portfolios of expression levels comprising a plurality of normalized expression levels of the target sequences described herein, including SEQ ID NOs:1-659. Such portfolios may be provided by performing the methods described herein to obtain expression levels from an individual patient or from a group of patients. The expression levels can be normalized by any method known in the art; exemplary normalization methods that can be used in various embodiments include Robust Multichip Average (RMA), probe logarithmic intensity error estimation (PLIER), nonlinear fit (NLFIT) quantile-based and nonlinear normalization, and combinations thereof. Background correction can also be performed on the expression data; exemplary techniques useful for background correction include mode of intensities, normalized using median polish probe modeling and sketch-normalization.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity. The invention also encompasses the above methods where the specificity is at least about 50% and at least about 60%. The invention also encompasses the above methods where the sensitivity is at least about 90%.

The gene expression profiles of each of the target sequences comprising the portfolio can fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal, benign or diseased. In a more sophisticated embodiment, patterns of the expression signals (e.g., fluorescent intensity) are recorded digitally or graphically.

Comparisons can also be used to determine whether the patient is not likely to experience the disease. The expression profiles of the samples are then compared to a control portfolio. If the sample expression patterns are consistent with the expression pattern for cancer then (in the absence of countervailing medical considerations) the patient is treated as one would treat a thyroid cancer patient. If the sample expression patterns are consistent with the expression pattern from the normal/control cell then the patient is diagnosed negative for cancer.

Genes can be grouped so that information obtained about the set of genes in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, fifty or more of the target sequences depicted in SEQ ID NOs: 1-659, or of the subsets described herein, or of a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known thyroid status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

The reagents may independently be in liquid or solid form. The reagents may be provided in mixtures. Control samples and/or nucleic acids may optionally be provided in the kit. Control samples may include tissue and/or nucleic acids obtained from or representative of benign thyroid tissue, as well as tissue and/or nucleic acids obtained from or representative of malignant thyroid tissue.

The nucleic acids may be provided in an array format, and thus an array or microarray may be included in the kit. The kit optionally may be certified by a government agency for use in classifying the disease status of thyroid tissue and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Devices

Devices useful for performing methods of the invention are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target sequences being studied with a classification of thyroid disease. Such means may comprise one or more of a variety of correlative techniques, including lookup tables, algorithms, multivariate models, and linear or nonlinear combinations of expression models or algorithms. The expression levels may be converted to one or more likelihood scores, reflecting the likelihood that the sample comprises malignant tissue and/or the likelihood that the sample comprises benign tissue. The models and/or algorithms can be provided in machine readable format, and can optionally further designate a treatment modality for a patient or class of patients The device also comprises output means for outputting the thyroid disease status and/or a treatment modality. Such output means can take any form which transmits the results to a patient and/or a healthcare provider, and may include a monitor, a printed format, or both. The device may use a computer system for performing one or more of the steps provided.

CITATIONS

1: Griffith O L, et al., "Meta-analysis and meta-review of thyroid cancer gene expression profiling studies identifies important diagnostic biomarkers," J Clin Oncol. 2006 Nov. 1, 24(31):5043-51.

2: Puskas L G, et al., "Gene profiling identifies genes specific for well-differentiated epithelial thyroid tumors," Cell Mol Biol (Noisy-1e-grand), 2005 Sep. 5, 51(2):177-86.

3: Fujarewicz K, et al., "A multi-gene approach to differentiate papillary thyroid carcinoma from benign lesions: gene selection using support vector machines with bootstrapping," Endocr Relat Cancer. 2007 Sep., 14(3):809-26.

4: Kebebew E, et al., "Diagnostic and extent of disease multigene assay for malignant thyroid neoplasms," Cancer. 2006 Jun. 15, 106(12):2592-7.

5: Finley D J, et al., "Discrimination of benign and malignant thyroid nodules by molecular profiling," Ann Surg. 2004 Sep., 240(3):425-36; discussion 436-7.

6: Mazzanti C, et al., "Using gene expression profiling to differentiate benign versus malignant thyroid tumors," Cancer Res. 2004 Apr. 15; 64(8):2898-903. Erratum in: Cancer Res. 2004 Jul. 15, 64(14):5028.

7: Finley D J, et al., "Advancing the molecular diagnosis of thyroid nodules: defining benign lesions by molecular profiling," Thyroid. 2005 June; 15(6):562-8.

8: Cerutti J M, et al., "Diagnosis of suspicious thyroid nodules using four protein biomarkers," Clin Cancer Res. 2006 Jun. 1; 12(11 Pt 1):3311-8.

9: Fryknas M, et al., "Molecular markers for discrimination of benign and malignant follicular thyroid tumors," Tumour Biol. 2006; 27(4):211-20.

10: Hamada A, et al., "Diagnostic usefulness of PCR profiling of the differentially expressed marker genes in thyroid papillary carcinomas," Cancer Lett. 2005 Jun. 28, 224(2): 289-301.

11: Yukinawa N, et al., "A multi-class predictor based on a probabilistic model: application to gene expression profiling-based diagnosis of thyroid tumors," BMC Genomics. 2006 Jul. 27, 7:190.

12: Griffiths O L, et al., "Biomarker panel diagnosis of thyroid cancer: a critical review," Expert Rev. Anticancer Therapy. 2008 Sep., 8(9): 1399-1413.

13. Prasad N B, et al., "Identification of Genes Differentially Expressed in Benign versus Malignant Thyroid Tumors," Clinical Cancer Res. 2008 Jun. 1, 14(11):3327-37.

14. Shibru D, et al., "Does the 3-gene diagnostic assay accurately distinguish benign from malignant thyroid neoplasms?" Cancer. 2008 Sep. 1; 113(5):930-5.

15. Fontaine J F, et al., "Increasing the number of thyroid lesions classes in microarray analysis improves the relevance of diagnostic markers," PLoS One. 2009 Oct. 29; 4(10): e7632.

Patent Documents

1. US 2005/0042222
2. US 2007/0037186
3. U.S. Pat. No. 7,319,011
4. WO 2005/085471
5. WO 2005/085471
6. WO 2005/100608
7. WO 2005/100608
8. WO 2006/047484
9. WO 2006/127537

EXAMPLES

To gain a better understanding of the invention described herein, the following examples are set forth. It will be understood that these examples are intended to describe illustrative embodiments of the invention and are not intended to limit the scope of the invention in any way. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Identification of Target Sequences Differentially Expressed in Benign and Malignant Thyroid One hundred and ten genes were identified as having increased expression in malignant thyroid nodule disease tissue relative to benign thyroid nodule disease tissue, and fifty eight genes were identified as having increased relative expression in benign thyroid disease relative to malignant thyroid nodule disease from a detailed literature review (see citations #1-15) (Table 1). The 110 and 58 gene lists were used to identify 5491 and 3651 respective target sequences (i.e., probesets) from these genomic regions on the Affymetrix Human Exon 1.0 ST GeneChip microarray, totaling 9,142 candidate target sequences.

These candidate 9,149 target sequences were further analyzed through several rounds of technical and biological data filtering to select those most likely to provide a selective, reproducible assay. The candidate target sequences were evaluated for potential cross-hybridization with transcribed sequences that would interfere with unique detection. Only those target sequences that were predicted to uniquely hybridize to a single target were considered further, reducing the candidate target sequences to 7,826 (i.e., removing 1,252 probeset)). Probesets with known cross-hybridization properties (i.e., probesets that map to multiple locations in the human genome) were obtained from the supporting annotation files downloaded from the Affymetrix website (www.affymetrix.com). Further biological filtering of probesets was performed using a microarray dataset of whole-transcriptome expression profiles from 48 thyroid nodule disease specimens (formalin-fixed paraffin embedded thyroidectomy samples with pathological characteristics as indicated in Table 2). Affymetrix HuEx 1.0 ST microarray expression data was modeled and normalized using the iterPLIER algorithm and log transformation. A background expression filter removed probesets whose maximal expression was lower than the background expression level (100 units of a normalized data range) in all 48 samples leaving 4,917 probesets for differential expression analysis. Differentially expressed probesets between malignant (n=23) and benign (n=25) (based on the 'gold-standard' pathology review diagnosis) thyroid nodule disease were determined based on three probeset selection criteria; a) at least 2-fold mean difference in expression, b) a student's t-test $p<0.001$ (with a Benjamini-Hochberg false discovery correction) and c) mean expression of >100 units (i.e., above background) in either the malignant or benign groups of thyroid nodule disease. With these probeset selection criteria, 279 (from 58 genes) and 377 (from 43 genes) probesets were found at increased expression in malignant and benign thyroid nodule disease samples, respectively (Table 3). Intriguingly, the majority of the probesets (59%) identified in this analysis do not overlap with the protein coding sequence (CDS) as indicated by the start point of initiation codon to the end point termination codon location of the translated protein from the mRNA (FIG. 1). Therefore, this data suggests that in the formalin-fixed paraffin embedded thyroidectomy specimens non-coding target sequences from thyroid nodule disease diagnostic genes identified in the literature are more more likely to be detectable as differentially expressed between malignant and benign clinical samples than are the target sequences from protein coding sequence.

By applying the selection criteria from genes identified in literature as described above, we defined target sequences that are detectable and differentially expressed in routine thyroid nodule disease clinical samples (e.g., FFPE thyroidectomies) and therefore may be of diagnostic value for thyroid nodule disease. Increased relative expression of one or more encoded sequences from the 279 target sequences representing 58 genes in Table 3 having increased expression in thyroid cancer can be used to designate a sample as malignant thyroid cancer. Additionally, a decreased relative level of expression of one or more encoded sequences from the 377 target sequences representing the 43 genes in Table 3 can also be used to designate the sample as malignant thyroid cancer, alone or in combination with one or more increased expression levels from the 58 gene set.

Conversely, increased relative expression of one or more encoded sequences from the 377 target sequences representing the 43 genes in Table 3 having increased expression in benign disease can be used to designate a sample as benign. Similarly, a decreased relative level of expression of one or more encoded sequences from the 279 target sequences representing the 58 genes in Table 3 can also be used to designate the sample as benign, alone or in combination with one or more increased expression levels from the 43 gene set.

The data can be used to designate disease state, and/or to recommend or designate one or more treatment modalities for patients, to produce patient reports, and to prepare expression profiles. By measuring the expression level of each transcript in a patient sample and multiplying it by a weighting factor a linear combination of the expression signature (reduced to one variable) can be determined for each patient. Thresholds will be applied to determine whether or not the weighted expression signature score is indicative of malignant or benign thyroid nodule disease. Similarly, such expression data from the filtered subsets described below may also be employed in these techniques.

Example 2

Identification of Minimal Thyroid Nodule Disease Expression Signatures and Evaluation in Pre-Operative Patient Specimens In order to determine the appropriate number of target sequences necessary to obtain a minimal expression signature we used the Nearest Shrunken Centroids (NSC) method. In this method (see US 20070031873), a standardized centroid is computed for each class. This is the average gene expression for each gene in each class divided by the within-class standard deviation for that gene. Nearest centroid classification was done under cross-validation, so that on each iteration, 5 out of 48 samples was removed for class centroid computation (~10% cross-validation). In this manner, we identified a 36 target sequence signature (Table 4) with an estimated cross-validated error rate of 6.3%. We also identified a subset of 7 target sequences (Table 5), a minimal expression signature that maintained the overall cross-validated error rate of 6.3%. With both signatures, three samples were misclassified by the centroid classification approach of which all were follicular lesions; two follicular carcinomas had a predicted class of benign and one follicular adenoma had a predicted class of malignant.

Figure 2:
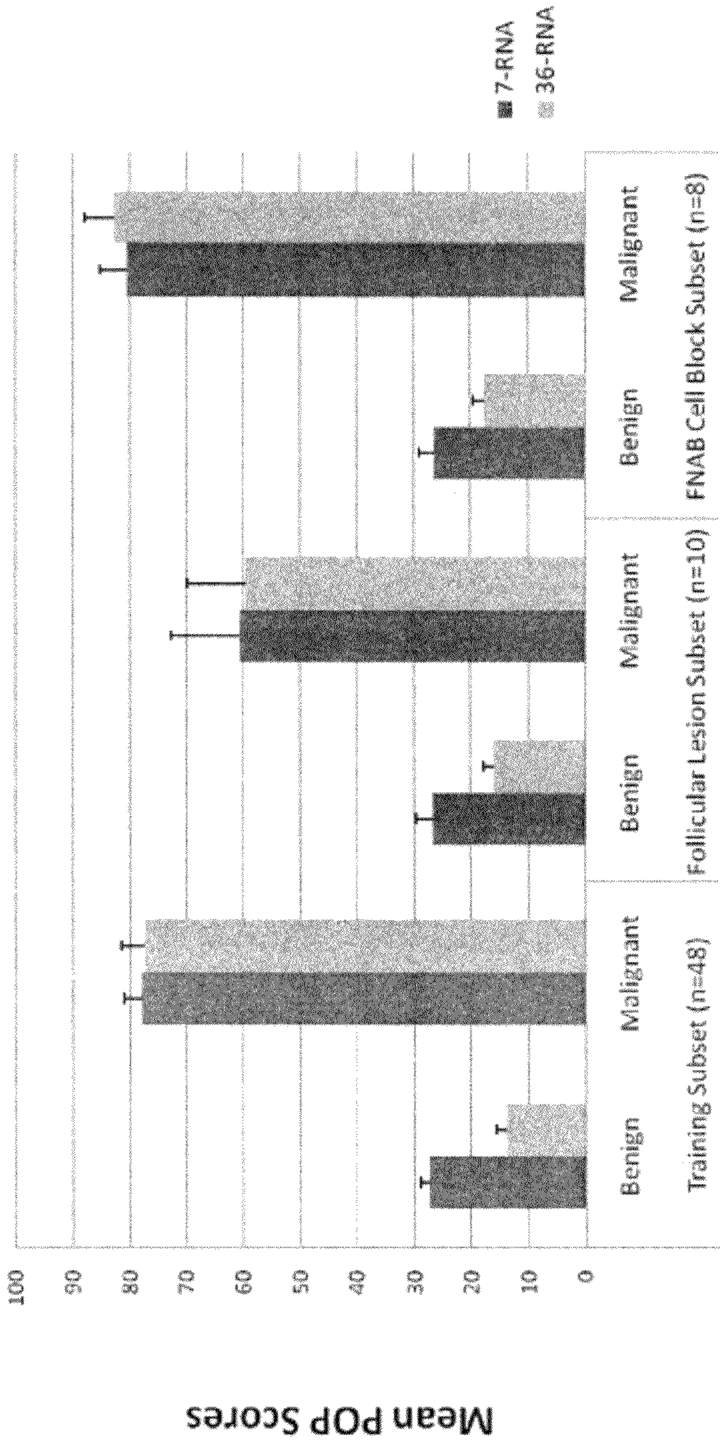
FIG. 2 depicts mean POP scores for pathological diagnostic categories of malignant and benign patient specimens in the three subsets of patient specimens evaluated. 'POP' (patient outcome predictor) scores for thyroid nodule disease benign and malignant sample groups were derived using 7- and 36-RNA target sequence metagenes to generate patient outcome predictor scores normalized on a data range of 0-100 points. Differences in POP scores between benign and malignant thyroid nodule disease groups were highly significant as evaluated by t-tests for significance ($p<1E-6$). Error bars indicate the standard error of the mean.
Figure 3:
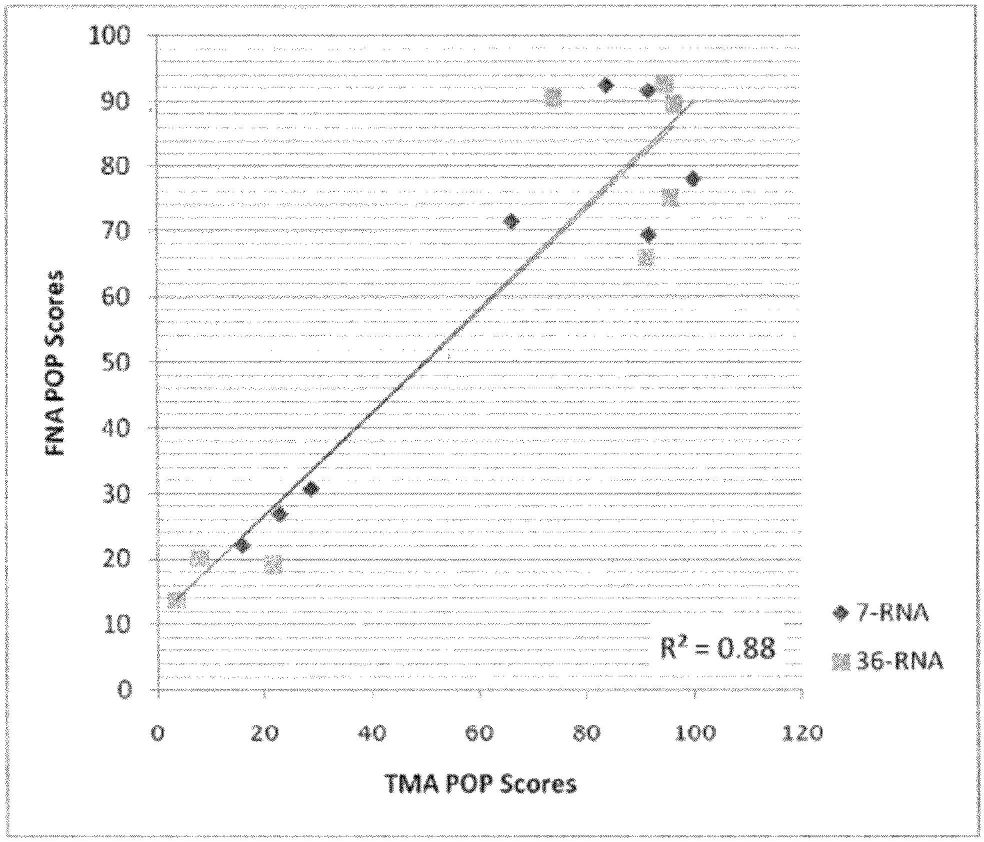
FIG. 3 shows the correlation between POP scores generated using the 7- and 36-RNA metagenes in analysis of pre-operative and post-operative specimens for a subset of eight patients. The correlation coefficient $R^2$ value is 0.88 for both of target sequence metagenes.
Figure 4:
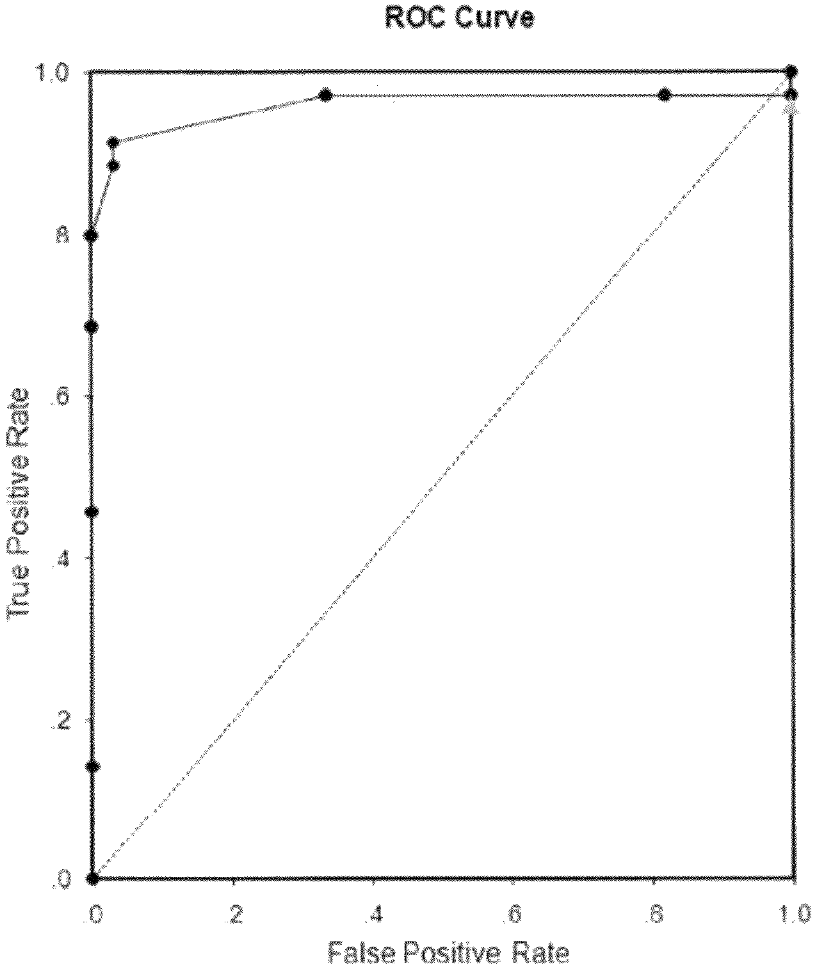
FIG. 4 depicts receiver-operator curves (ROC) of the POP scores derived from the 7-RNA metagene. The area-under-the curve is indicated below the ROC curve and show that the POP scores as a continuous variable (i.e., without setting an arbitrary cut-points) are excellent discriminators of malignant and benign disease.
Figure 5:
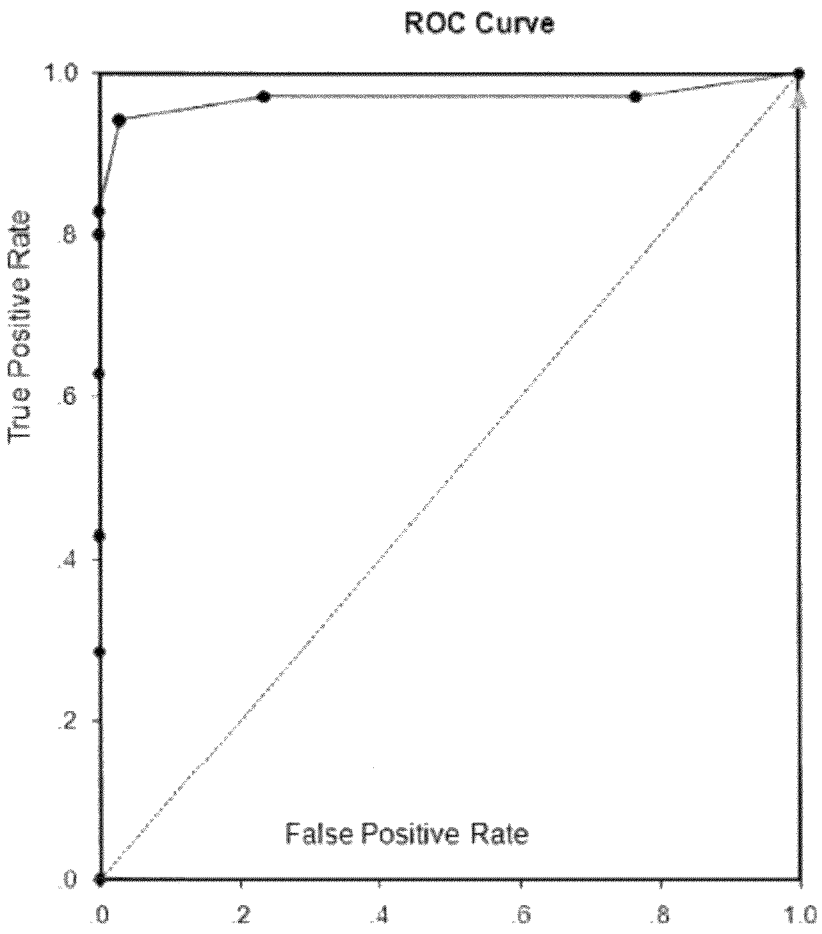
FIG. 5 depicts receiver-operator curves (ROC) of the POP scores derived from the 36-RNA metagene. The area-under-the curve is indicated below the ROC curve and show that the POP scores as a continuous variable (i.e., without setting an arbitrary cut-points) are excellent discriminators of malignant and benign disease.

Next, 36- and 7-target sequence 'metagenes' were created with the target sequences in Table 4 and 5 using a simple linear combination by measuring the expression levels of the corresponding RNAs for each patient and multiplying each measurement by a corresponding weighting factor and combining these values into a single variable. Weighting factors were derived from the test statistic coefficients from a t-test for significance when comparing malignant and benign pathology review diagnoses (Table 4). Patient outcome predictor (TOP') scores were generated from the metagene values for each patient by scaling and normalizing the metagene scores within a range of 0 to 100. We used arbitrary cut-points to establish a diagnostic criteria—a value of between 0-40 points was used to indicate a patient with benign thyroid nodule disease and 40-100 points a patient with malignant thyroid nodule disease (FIG. 2). Using these cut-point criteria, the evaluation of the 7-RNA target sequence metagene in the training subset revealed that 22/23 patients with malignant thyroid nodule disease had POP scores above 40 points and 24/25 patients with benign thyroid nodule disease had scores below 40 points (Table 6). Using the same cut-point criteria, the 36-RNA target sequence metagene in the training subset revealed that 20/23 patients with malignant thyroid nodule disease had POP scores above 40 points and 24/25 patients with benign thyroid nodule disease had scores below 40 points (Table 6). The 7- and 36-RNA target sequence metagenes were further validated on two independent subsets of ten and eight patient specimens (see Table 2) that were not used to identify or select the target sequences described in Table 3. The ten specimen 'follicular lesion only' subset were from patients diagnosed with follicular pattern lesions, that were all indeterminate or 'suspicious for cancer' based on cytology fine-needle aspirate diagnosis. All ten of these patients were treated with total-thyroidectomy however, pathology review diagnosis revealed that only five of these patients actually had a malignant thyroid nodule disease lesion warranting total thyroidectomy. For the 7-RNA target sequence metagene, all five of the follicular adenoma (i.e., patients diagnosed with benign disease) specimens had POP scores of less than 40 points and 4/5 patients with follicular carcinoma or follicular variant of papillary carcinoma had scores of greater than 40 points (Table 6). For the 7-RNA target sequence metagene, all five of the follicular adenoma (i.e., patients diagnosed with benign disease) specimens had POP scores of less than 40 points and 4/5 patients with follicular carcinoma or follicular variant of papillary carcinoma had scores of greater than 40 points (Table 6). For the 36-RNA target sequence metagene, all five of the follicular adenoma (i.e., patients diagnosed with benign disease) specimens had POP scores of less than 40 points and 3/5 patients with follicular carcinoma or follicular variant of papillary carcinoma had scores of greater than 40 points (Table 6). In the second validation subset of specimens, eight samples were from cell blocks prepared from pre-operative fine-needle aspirates. These samples were from a subset of eight patients whose post-operative FFPE thyroidectomy specimens were profiled in the training subset. POP scores for these specimens showed that 3/3 patients with pathology review benign diagnoses had scores of less than 40 points and 5/5 patients with pathology review malignant diagnoses had scores of greater than 40 points. POP scores derived from pre- (i.e., FNA cell blocks) and post-operative (i.e., TMA FFPE thyroidectomy) specimens from the 7- and 36-RNA target sequence metagenes were highly correlated, both with an $R^2$ value of 0.88 (FIG. 3). This data suggests that the 7- and 36-RNA target sequence metagene expression signatures and derived POP scores can be applied to exact an identical diagnosis from patients either before the surgery via a fine-needle aspiration of thyroid cells or after the thyroid is removed from the patient. In order to evaluate the diagnostic accuracy of the 7- and 36-RNA metagene POP scores in comparison to the 'gold-standard' review pathology diagnosis in a manner where no a priori cut-points are pre-determined, receiver-operator characteristic (ROC) curves were generated. ROC curves for the 7- and 36-RNA metagene POP scores are depicted in FIGS. 4 and 5 and show that the area-under-the curve was above 96% and 97%, respectively demonstrating that both expression signatures and the POP specimen scoring method are performing extremely well as a diagnostic test.

Example 3

Differential Expression of SPOCK1 Target Sequences

Intriguingly, several of target sequences showed the reverse correlation in terms of differential expression than a gene-level analysis would suggest. For example, the gene SPOCK1 has been previously reported as found at increased expression in malignant than benign thyroid nodule disease (see Prasad N B et al., citation #13).

Figure 6:
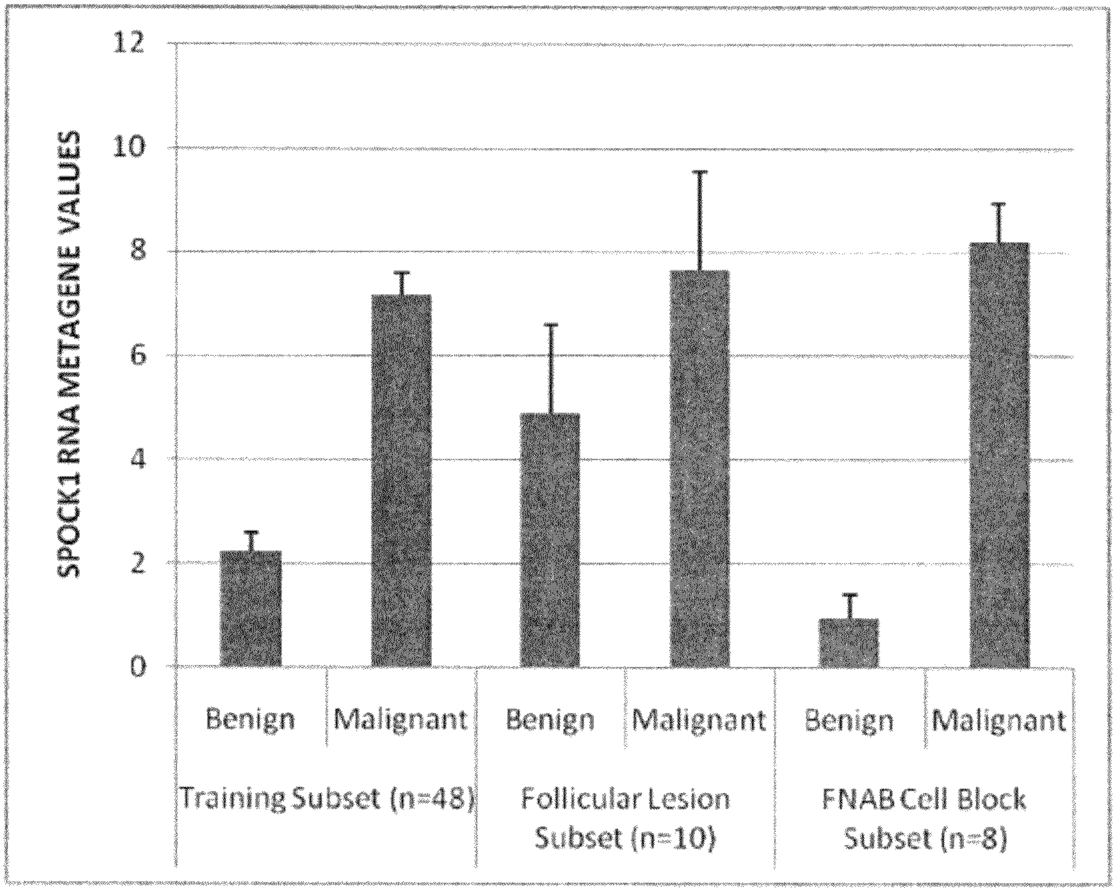
FIG. 6 depicts mean SPOCK1 RNA metagene values for pathological diagnostic categories of malignant and benign patient specimens in the three subsets of patient specimens evaluated. SPOCK1 RNA metagene was generated by a weighted linear combination of expression values for exon 11, intron 2, 3 and 6 RNA target sequences. Error bars indicate the standard error of the mean.

However, on the individual RNA transcript level over 2- and 1.8-fold mean increased expression of exon 11 and intron 2 RNAs, respectively was observed in malignant (rel. to benign) thyroid nodule disease samples, whereas nearly 8.6- and 1.2-fold mean increased expression of intron 6 and intron 3 RNAs, respectively was observed in benign (rel. to malignant) thyroid nodule disease samples (Table 7). Furthermore, the protein-coding strand of the SPOCK1 by convention occurs of the negative (or alternatively, 'bottom') strand and while the RNAs representing the target sequence for the protein-encoding exon 11 RNA is transcribed in this sense direction, the target sequences for introns 2, 3 and 6 are transcribed in an antisense direction to transcription, that is off the positive (or alternatively, 'top') strand of the gene. Using these four SPOCK1 RNAs, a SPOCK1-target sequence metagene was generated as described in Example #1. FIG. 6 shows the mean metagene values for of these SPOCK1 RNAs in the three subsets of patient specimens analyzed. The differences in mean overall expression for SPOCK1 RNAs clearly distinguish malignant from benign thyroid nodule disease in the training subset and the FNAB subset. In the follicular lesion subset, the mean metagene values did show some overlap. In summary, this data suggests that gene-level analysis (e.g., using 3' biased microarrays such as U133 Plus 2.0) can miss important differences in transcription such as intron retention, antisense transcription, alternative splicing or exon usage and non-coding (i.e., translated into protein) RNA expression observed in this whole-transcriptome analysis. In particular, non-coding RNA the predominant RNA species (over 90% of the transcription in the genome) represent functional RNA molecules that are thought to convey key differences between pathological conditions through regulatory roles of protein-encoding gene expression. This is a potentially rich source of diagnostic information that cannot be captured by solely observing differences in protein-encoding gene expression or protein biomarker expression and may improve the diagnosis of specific pathological conditions of clinical importance such as malignant vs. benign in thyroid nodule disease.

These scoring systems can be used to select or guide the selection of treatment modalities such as observation and/or thyroid lobectomy for benign thyroid nodule disease patients, and total thyroid resection for malignant thyroid nodule disease. Other metagenes can similarly be created using other combinations of target sequence expression, for example using one or more of the target sequences depicted in any of the Tables.

Materials and Methods:

Tissue Samples. Sixty (60) formalin-fixed paraffin embedded (FFPE) surgical specimens of human thyroid nodule disease were collected from patients at the Department of Surgery, St. Paul's Hospital (Vancouver, BC, Canada) according to an institutional review board-approved protocol. For a subset of 8 surgical specimens, fine-needle aspirate cell blocks were also available. For surgical specimens, a tissue microarrayer (Beecher Instruments, Silver Spring, Md.) was used to core each FFPE surgical resected specimen once with either a 0.6 mm or 1.0 diameter cylinder ('FFPE TMA'). Surgical resected samples from 60 patients were evaluated. These samples were divided into three subsets consisting of a training (n=48) and a validation (n=10) subset of patients. Table 1 shows the composition of the subsets including the original cytology diagnosis as well as the 'gold-standard' pathology review diagnosis (obtained from careful dissection and histopathological analysis of specimens after thyroidetomy procedures). From cell blocks, 3 ten micron sections were obtained using a microtome. Cell block specimens were matched to 8 of the FFPE TMA surgical specimen samples evaluated.

Extraction of RNA. RNA was extracted and purified from the FFPE TMA cores using a modified protocol for the commercially available Formapure nucleic acid extraction kit (Agencourt Biosciences, Beverly Mass.). Principal modifications to the kit protocol included preheating the lysis buffer to 70° C. before immersing the FFPE sections in lysis buffer and then subjecting FFPE lysates to incubation at 99° C. for 1 min. In addition, FFPE samples were incubated with Proteinase K (20 ul of 40 mg/mL) for 16 hrs in a water bath at 55° C. RNA was further purified using DNAse I treatment (Ambion, Austin, Tex.) to eliminate any contaminating DNA. RNA was eluted with 300 ul of RNAse-free water and subsequently concentrated and purified using sodium acetate precipitation and a series of ethanol washes and resuspended in 15 ul of water. RNA concentrations were calculated using a Nanodrop ND-1000 spectrophotometer (Nanodrop Technologies, Rockland, Del.). These additional purification steps significantly improved the yield of amplified material in subsequent steps described below (data not shown). RNA integrity was evaluated by running electropherograms and RNA integrity number, RIN (a correlative measure that indicates intactness of mRNA) was determined using the RNA 6000 PicoAssay for the Bioanalyzer 2100 (Agilent Technologies, Santa Clara, Calif.). Sufficient RNA (75 ng) was obtained using these procedures from all 60 FFPE TMA cores and 8 cell block microtome sections.

Nucleic Acid Amplification and GeneChip Hybridization. Purified RNA was subjected to whole-transcriptome amplification using the WT-Ovation FFPE system including the WT-Ovation Exon and FL-Ovation Biotin V2 labeling modules, with the following modifications. Seventy-five (75) nanograms of RNA extracted from FFPE TMA cores or FNAB cell blocks was used to generate amplified Ribo-SPIA product. For the WT-Ovation Exon sense-target strand conversion kit 4 ug of Ribo-SPIA product were used. Between 2.5 and 5 micrograms of WT-Ovation Exon product were used to fragment and label using the FL-Ovation Biotin V2 labeling module and labeled product was hybridized to Affymetrix Human Exon 1.0 ST GeneChips following manufacturer's recommendations (Affymetrix, Santa Clara, Calif.).

Microarray Analysis. All data management and analysis was conducted using the Genetrix suite of tools for microarray analysis (Epicenter Software, Pasadena, Calif.). Probe set modeling and data pre-processing were derived using the iterPlier algorithm (Affymetrix, Santa Clarita, Calif.). The mode of intensity values was used for background correction and sketch was used for normalization and probe modeling used a median polish routine. Outlier samples were identified by evaluating the median absolute deviation of the normalized expression values in each sample and $25^{th}$ percentile outlier samples. Two samples from the testing cohort were removed from further analysis because they were clearly outliers using both quality control metrics described above. A variance filter was applied to data pre-processed using the iterPlier algorithm, by removing probe set regions (PSRs) with a mean intensity of <10 intensity units of a normalized data range. PSRs are comprised of an average of four individual probes that interrogate the expression of RNA transcripts or portions thereof. PSR annotations and the sequences (RNAs) that they interrogate were downloaded from the Affymetrix website (www.netaffx.com). An additional filter employed was to remove PSRs with known cross-hybridization properties (i.e., significant homology to more than one transcript from different genes or loci), leaving 1,134,588 PSRs for further analysis. Cross-hybridization properties of PSRs were downloaded from the Affymetrix website. Supervised analysis of differentially expressed RNA transcripts was determined based on the fold difference in the average expression (at least 2 fold difference) and the associated t-test, with a p-value cut-off of $p<0.001$ between malignant and benign thyroid nodule disease samples using the final pathology review diagnosis obtained from analysis of surgical specimens as the benchmark diagnosis.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the claims.

TABLE 1

Examples of Suitable Genes for Inclusion in a Thyroid Classification Library

| Gene Symbol | Gene |
|---|---|
| | Thyroid Malignant- Increased Expression |
| ADORA1 | Adenosine A1 receptor |
| ALOX5 | Arachidonate 5-lipoxygenase |
| AMIGO2 | Adhesion molecule with Ig-like domain 2 |
| APOE | Apolipoprotein E |
| ARHGAP11A | Rho GTPase activating protein 11A |
| ARMCX3 | Armadillo repeat containing, X-linked 3 |
| C7orf24 | Chromosome 7 open reading frame 24 |
| CA4 | Carbonic anhydrase IV |
| CAMK2N1 | Calcium/calmodulin-dependent protein kinase II inhibitor 1 |
| CCND1 | Cyclin D1 |
| CD44 | CD44 molecule (Indian blood group) |
| CD55 | CD55 molecule, decay accelerating factor for complement (Cromer blood group) |
| CDH16 | Cadherin 16, KSP-cadherin |
| CDH3 | Cadherin 3, type 1, P-cadherin (placental) |
| CDKN2A | Cyclin-dependent kinase inhibitor 2A (melanoma, p16, inhibits CDK4) |
| CHI3L1 | Chitinase 3-like 1 (cartilage glycoprotein-39) |
| CHRDL1 | Chordin-like 1 |
| CHST2 | Carbohydrate (N-acetylglucosamine-6-O) sulfotransferase 2 |
| CITED1 | Cbp/p300-interacting transactivator, with Glu/Asp-rich carboxy-terminal domain, 1 |
| CKS2 | CDC28 protein kinase regulatory subunit 2 |
| CSNK1G2 | Casein kinase 1, gamma 2 |
| CST6 | Cystatin E/M |
| CTSC | Cathepsin C |
| CTSH | Cathepsin H |
| CTSS | Cathepsin S |
| DLG7 | Discs, large homolog 7 (*Drosophila*) |
| DPP4 | Dipeptidyl-peptidase 4 (CD26, adenosine deaminase complexing protein 2) |
| DUSP5 | Dual specificity phosphatase 5 |
| DUSP6 | Dual specificity phosphatase 6 |
| ENDOD1 | Endonuclease domain containing 1 |
| EPS8 | Epidermal growth factor receptor pathway substrate 8 |
| ETHE1 | Ethylmalonic encephalopathy 1 |
| ETV5 | Ets variant gene 5 (ets-related molecule) |
| FAM129A | Family with sequence similarity 129, member A |
| FAM129B | Family with sequence similarity 129, member B |
| FAM129C | Family with sequence similarity 129, member C |
| FBLN1 | Fibulin 1 |
| FN1 | Fibronectin 1 |
| GABBR2 | Gamma-aminobutyric acid (GABA) B receptor, 2 |
| GALE | UDP-galactose-4-epimerase |
| GALNT7 | UDP-N-acetyl-alpha-D-galactosamine: polypeptide N-acetylgalactosaminyltransferase 7 (GalNAc-T7) |
| GDF15 | Growth differentiation factor 15 |
| GJB3 | Gap junction protein, beta 3, 31 kDa |
| GPM6A | Glycoprotein M6A |
| HBD | Hemoglobin, delta |
| HLA-DMB | Major histocompatibility complex, class II, DM beta |
| HLA-DQA1 | Major histocompatibility complex, class II, DQ alpha 1 |
| HLA-DRA | Major histocompatibility complex, class II, DR alpha |
| HMGA2 | High mobility group AT-hook 2 |
| ICAM1 | Intercellular adhesion molecule 1 (CD54), human rhinovirus receptor |
| ICAM4 | Intercellular adhesion molecule 4 (Landsteiner-Wiener blood group) |
| IGFBP6 | Insulin-like growth factor binding protein 6 |
| IGSF1 | Immunoglobulin superfamily, member 1 |
| KCNJ2 | Potassium inwardly-rectifying channel, subfamily J, member 2 |
| KIAA0746 | KIAA0746 protein |
| KLK10 | Kallikrein-related Peptidase 10 |
| KRT15 | Keratin 15 |
| KRT19 | Keratin 19 |
| LAMB3 | Laminin, beta 3 |
| LCN2 | Lipocalin 2 |
| LGALS3 | Lectin, galactoside-binding, soluble, 3 |
| LPL | Lipoprotein lipase |

TABLE 1-continued

| Examples of Suitable Genes for Inclusion in a Thyroid Classification Library | |
|---|---|
| Gene Symbol | Gene |
| LRP4 | Low density lipoprotein receptor-related protein 4 |
| MET | Met proto-oncogene (hepatocyte growth factor receptor) |
| MPZL2 | Myelin protein zero-like 2 |
| MPZL3 | Myelin protein zero-like 3 |
| MRC2 | Mannose receptor, C type 2 |
| MUC1 | Mucin 1, cell surface associated |
| MYBPH | Myosin binding protein H |
| NELL2 | NEL-like 2 (chicken) |
| NMU | Neuromedin U |
| NRCAM | Neuronal cell adhesion molecule |
| NRIP1 | Nuclear receptor interacting protein 1 |
| P4HA2 | Procollagen-proline, 2-oxoglutarate 4-dioxygenase (proline 4-hydroxylase), alpha polypeptide II |
| PDLIM4 | PDZ and LIM domain 4 |
| PDZK1IP1 | PDZK1 interacting protein 1 |
| PLAU | Plasminogen activator, urokinase |
| PLXNC1 | Plexin C1 |
| PRMT8 | Protein arginine methyltransferase 8 |
| PROS1 | Protein S (alpha) |
| PRSS23 | Protease, serine, 23 |
| PSD3 | Pleckstrin and Sec7 domain containing 3 |
| PTPRE | Protein tyrosine phosphatase, receptor type, E |
| QPCT | Glutaminyl-peptide cyclotransferase (glutaminyl cyclase) |
| RCN3 | Reticulocalbin 3, EF-hand calcium binding domain |
| RET | Ret proto-oncogene |
| RXRG | Retinoid X receptor, gamma |
| S100A10 | S100 calcium binding protein A10 |
| SCG5 | Secretogranin V (7B2 protein) |
| SDC4 | Syndecan 4 |
| SERPINA1 | Serpin peptidase inhibitor, clade A (alpha-1 antiproteinase, antitrypsin), member 1 |
| SFTPB | Surfactant, pulmonary-associated protein B |
| SLC27A6 | Solute carrier family 27 (fatty acid transporter), member 6 |
| SLC34A2 | Solute carrier family 34 (sodium phosphate), member 2 |
| SLC5A5 | Solute carrier family 5 (sodium iodide symporter), member 5 |
| SLPI | Secretory leukocyte peptidase inhibitor |
| SOX4 | SRY (sex determining region Y)-box 4 |
| SPOCK1 | Sparc/osteonectin, cwcv and kazal-like domains proteoglycan (testican) 1 |
| SPP1 | Secreted phosphoprotein 1 (osteopontin, bone sialoprotein I, early T-lymphocyte activation 1) |
| ST14 | Suppression of tumorigenicity 14 (colon carcinoma) |
| SYN1 | Synapsin I |
| TACSTD2 | Tumor-associated calcium signal transducer 2 |
| TGFA | Transforming growth factor, alpha |
| TIAM1 | T-cell lymphoma invasion and metastasis 1 |
| TIMP1 | TIMP metallopeptidase inhibitor 1 |
| TM7SF4 | Transmembrane 7 superfamily member 4 |
| TNC | Tenascin C (hexabrachion) |
| TPD52L1 | Tumor protein D52-like 1 |
| TRIM14 | Tripartite motif-containing 14 |
| TUSC3 | Tumor suppressor candidate 3 |
| | Thyroid Benign- Increased Expression |
| ABCA8 | ATP-binding cassette, sub-family A (ABC1), member 8 |
| ANK2 | Ankyrin 2, neuronal |
| ARG2 | Arginase, type II |
| BCL2 | B-cell CLL/lymphoma 2 |
| BEX1 | Brain expressed, X-linked 1 |
| BMP8A | Bone morphogenetic protein 8a |
| C1orf212 | Chromosome 1 open reading frame 212 |
| CCL14 | Chemokine (C-C motif) ligand 14 |
| CCL21 | Chemokine (C-C motif) ligand 21 |
| CFD | Complement factor D (adipsin) |
| ChGn | Chondroitin beta1,4 N-acetylgalactosaminyltransferase |
| COL9A3 | Collagen, type IX, alpha 3 |
| CRABP1 | Cellular retinoic acid binding protein 1 |
| DDIT3 | DNA-damage-inducible transcript 3 |
| DIO1 | Deiodinase, iodothyronine, type I |
| DIO2 | Deiodinase, iodothyronine, type II |
| EFEMP1 | EGF-containing fibulin-like extracellular matrix protein 1 |
| ELMO1 | Engulfment and cell motility 1 |
| ENPP1 | Ectonucleotide pyrophosphatase/phosphodiesterase 1 |

TABLE 1-continued

| Examples of Suitable Genes for Inclusion in a Thyroid Classification Library | |
|---|---|
| Gene Symbol | Gene |
| FABP4 | Fatty acid binding protein 4, adipocyte |
| FCGBP | Fc fragment of IgG binding protein |
| FHL1 | Four and a half LIM domains 1 |
| FZD4 | Frizzled homolog 4 (*Drosophila*) |
| HBA2 | Hemoglobin, alpha 2 |
| HLF | Hepatic leukemia factor |
| ID4 | Inhibitor of DNA binding 4, dominant negative helix-loop-helix protein |
| ITM2A | Integral membrane protein 2A |
| ITPR1 | Inositol 1,4,5-triphosphate receptor, type 1 |
| KCNAB1 | Potassium voltage-gated channel, shaker-related subfamily, beta member 1 |
| KIT | V-kit Hardy-Zuckerman 4 feline sarcoma viral oncogene homolog |
| LIPG | Lipase, endothelial |
| LRP2 | Low density lipoprotein-related protein 2 |
| MATN2 | Matrilin 2 |
| MPPED2 | Metallophosphoesterase domain containing 2 |
| MT1F | Metallothionein 1F |
| MT1G | Metallothionein 1G |
| MT1H | Metallothionein 1H |
| MT1M | Metallothionein 1M |
| MT1X | Metallothionein 1X |
| MT2A | Metallothionein 2A |
| MTF1 | Metal-regulatory transcription factor 1 |
| OPRM1 | Opioid receptor, mu 1 |
| PIP3-E | Phosphoinositide-binding protein PIP3-E |
| PPARGC1A | Peroxisome proliferator-activated receptor gamma, coactivator 1 alpha |
| PRIM2 | Primase, DNA, polypeptide 2 (58 kDa) |
| RAB23 | RAB23, member RAS oncogene family |
| RGS16 | Regulator of G-protein signaling 16 |
| RHOBTB3 | Rho-related BTB domain containing 3 |
| SLC1A1 | Solute carrier family 1 (neuronal/epithelial high affinity glutamate transporter, system Xag), member 1 |
| SLC26A4 | Solute carrier family 26, member 4 |
| SOD3 | Superoxide dismutase 3, extracellular |
| STT3A | STT3, subunit of the oligosaccharyltransferase complex, homolog A (*S. cerevisiae*) |
| STT3B | STT3, subunit of the oligosaccharyltransferase complex, homolog B (*S. cerevisiae*) |
| TCEAL2 | Transcription elongation factor A (SII)-like 2 |
| TFF3 | Trefoil factor 3 (intestinal) |
| TPO | Thyroid peroxidase |
| VEGFA | Vascular endothelial growth factor A |
| ZMAT4 | Zinc finger, matrin type 4 |

TABLE 2

Pathological Characteristics of Thyroid Nodule Disease Specimens Used for Data Filtering and Validation of Candidate Target Sequences

| Training Subset | | N |
|---|---|---|
| Fine-Needle Aspirate Cytology Diagnosis | Goiter | 14 |
| | Suspicious for Cancer | 20 |
| | Cancer | 14 |
| Pathology Diagnosis | Benign | 25 |
| | Malignant | 23 |
| Review Histology Diagnosis | Goiter | 15 |
| | Thyroiditis | 1 |
| | Hashimoto's Disease | 1 |
| | Hurthle Cell Adenoma | 4 |
| | Follicular Adenoma | 4 |
| | Follicular Carcinoma | 3 |
| | Papillary Carcinoma | 20 |

TABLE 2-continued

Pathological Characteristics of Thyroid Nodule Disease Specimens Used for Data Filtering and Validation of Candidate Target Sequences

| Follicular Lesion Subset | | n |
|---|---|---|
| Fine-Needle Aspirate Cytology Diagnosis | Suspicious for Cancer | 10 |
| Pathology Diagnosis | Benign | 5 |
| | Malignant | 5 |
| Review Histology Diagnosis | Follicular Adenoma | 5 |
| | Follicular Carcinoma | 3 |
| | Papillary Carcinoma | 2 |

TABLE 2-continued

Pathological Characteristics of Thyroid Nodule Disease Specimens Used for Data Filtering and Validation of Candidate Target Sequences

| Pre-operative Cell Block Subset | | n |
|---|---|---|
| Fine-Needle Aspirate Cytology Diagnosis | Goiter | 2 |
| | Suspicious for Cancer | 1 |
| | Cancer | 5 |
| Pathology Diagnosis | Benign | 3 |
| | Malignant | 5 |
| Review Histology Diagnosis | Goiter | 2 |
| | Hurthle Cell Adenoma | 1 |
| | Papillary Carcinoma | 5 |

TABLE 3

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 1 | 3420365 | 14 | 8.75 | High mobility group AT-hook 2 | NO | intronic |
| 2 | 3696401 | 11 | 8.59 | Cadherin 3, type 1, P-cadherin (placental) | NO | exonic |
| 3 | 3577628 | 3 | 8.12 | Serpin peptidase inhibitor, clade A (alpha-1 antiproteinase, antitrypsin), member 1 | YES | exonic |
| 4 | 3415760 | 4 | 5.94 | Insulin-like growth factor binding protein 6 | NO | exonic |
| 5 | 2537615 | −14 | −11.03 | Thyroid peroxidase | NO | antisense |
| 6 | 2727648 | −5 | −9.09 | V-kit Hardy-Zuckerman 4 feline sarcoma viral oncogene homolog | NO | exonic |
| 7 | 3367706 | −31 | −8.23 | Metallophosphoesterase domain containing 2 | NO | intronic |
| 8 | 2828473 | 8 | 10.26 | PDZ and LIM domain 4 | NO | exonic |
| 9 | 2414960 | 24 | 8.9 | Tumor-associated calcium signal transducer 2 | NO | exonic |
| 10 | 2526829 | 6 | 8.69 | Fibronectin 1 | NO | antisense |
| 11 | 2526817 | 13 | 8.66 | Fibronectin 1 | NO | antisense |
| 12 | 2598305 | 17 | 8.61 | Fibronectin 1 | NO | intronic |
| 13 | 2338243 | 28 | 8.2 | Tumor-associated calcium signal transducer 2 | NO | exonic |
| 14 | 2598348 | 35 | 8.16 | Fibronectin 1 | NO | intronic |
| 15 | 2598349 | 21 | 8.15 | Fibronectin 1 | NO | intronic |
| 16 | 2598307 | 10 | 8.11 | Fibronectin 1 | YES | exonic |
| 17 | 2562439 | 24 | 7.98 | Surfactant, pulmonary-associated protein B | NO | exonic |
| 18 | 3577632 | 17 | 7.92 | Serpin peptidase inhibitor, clade A (alpha-1 antiproteinase, antitrypsin), member 1 | YES | exonic |
| 19 | 2401582 | 4 | 7.82 | UDP-galactose-4-epimerase | NO | exonic |
| 20 | 2598368 | 32 | 7.78 | Fibronectin 1 | NO | intronic |
| 21 | 2598282 | 8 | 7.77 | Fibronectin 1 | NO | intronic |
| 22 | 3549675 | 12 | 7.77 | Serpin peptidase inhibitor, clade A (alpha-1 antiproteinase, antitrypsin), member 1 | NO | antisense |
| 23 | 2526824 | 16 | 7.7 | Fibronectin 1 | NO | antisense |
| 24 | 2598340 | 15 | 7.67 | Fibronectin 1 | YES | exonic |
| 25 | 2598328 | 13 | 7.65 | Fibronectin 1 | YES | exonic |
| 26 | 3460512 | 4 | 7.64 | High mobility group AT-hook 2 | NO | antisense |
| 27 | 2598278 | 10 | 7.63 | Fibronectin 1 | NO | intronic |
| 28 | 3976357 | 2 | 7.58 | Synapsin I | YES | antisense |
| 29 | 3335899 | 8 | 7.56 | Cystatin E/M | NO | exonic |
| 30 | 2598367 | 10 | 7.55 | Fibronectin 1 | YES | exonic |
| 31 | 2598338 | 8 | 7.54 | Fibronectin 1 | YES | exonic |
| 32 | 2598326 | 10 | 7.51 | Fibronectin 1 | NO | intronic |
| 33 | 2598299 | 8 | 7.49 | Fibronectin 1 | YES | exonic |
| 34 | 3549673 | 9 | 7.45 | Serpin peptidase inhibitor, clade A (alpha-1 antiproteinase, antitrypsin), member 1 | NO | antisense |
| 35 | 2598346 | 7 | 7.35 | Fibronectin 1 | YES | exonic |
| 36 | 2598372 | 9 | 7.31 | Fibronectin 1 | YES | exonic |
| 37 | 2598281 | 10 | 7.3 | Fibronectin 1 | YES | exonic |
| 38 | 2598374 | 11 | 7.27 | Fibronectin 1 | YES | exonic |
| 39 | 2598329 | 9 | 7.25 | Fibronectin 1 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 40 | 2598352 | 10 | 7.2 | Fibronectin 1 | YES | exonic |
| 41 | 2400179 | 5 | 7.19 | Calcium/calmodulin-dependent protein kinase II inhibitor 1 | YES | exonic |
| 42 | 2324040 | 5 | 7.19 | Calcium/calmodulin-dependent protein kinase II inhibitor 1 | NO | exonic |
| 43 | 2375629 | 51 | 7.19 | Chitinase 3-like 1 (cartilage glycoprotein-39) | NO | exonic |
| 44 | 2598342 | 10 | 7.16 | Fibronectin 1 | YES | exonic |
| 45 | 3577630 | 12 | 7.15 | Serpin peptidase inhibitor, clade A (alpha-1 antiproteinase, antitrypsin), member 1 | YES | exonic |
| 46 | 2526820 | 9 | 7.13 | Fibronectin 1 | NO | antisense |
| 47 | 2598358 | 17 | 7.12 | Fibronectin 1 | YES | exonic |
| 48 | 2598321 | 16 | 7.1 | Fibronectin 1 | YES | intronic |
| 49 | 2598302 | 10 | 7.09 | Fibronectin 1 | YES | exonic |
| 50 | 3536718 | 13 | 7.09 | Lectin, galactoside-binding, soluble, 3 | NO | intronic |
| 51 | 2598289 | 19 | 7.09 | Fibronectin 1 | YES | exonic |
| 52 | 3976358 | 7 | 7.07 | Synapsin I | YES | antisense |
| 53 | 3335898 | 7 | 7.07 | Cystatin E/M | YES | exonic |
| 54 | 2598296 | 14 | 7.06 | Fibronectin 1 | YES | exonic |
| 55 | 2598271 | 8 | 7.05 | Fibronectin 1 | YES | exonic |
| 56 | 2526809 | 10 | 7.05 | Fibronectin 1 | NO | exonic |
| 57 | 2598277 | 10 | 7.04 | Fibronectin 1 | YES | exonic |
| 58 | 2598280 | 8 | 7.01 | Fibronectin 1 | YES | exonic |
| 59 | 2562441 | 32 | 7.01 | Surfactant, pulmonary-associated protein B | NO | intronic |
| 60 | 2598320 | 10 | 7 | Fibronectin 1 | NO | intronic |
| 61 | 3460465 | 18 | 7 | High mobility group AT-hook 2 | NO | antisense |
| 62 | 2598313 | 8 | 6.98 | Fibronectin 1 | YES | exonic |
| 63 | 2598354 | 10 | 6.97 | Fibronectin 1 | YES | exonic |
| 64 | 2598286 | 10 | 6.96 | Fibronectin 1 | YES | exonic |
| 65 | 2526813 | 6 | 6.94 | Fibronectin 1 | NO | antisense |
| 66 | 2598332 | 8 | 6.93 | Fibronectin 1 | NO | intronic |
| 67 | 2598356 | 11 | 6.93 | Fibronectin 1 | YES | exonic |
| 68 | 2598267 | 18 | 6.9 | Fibronectin 1 | NO | exonic |
| 69 | 2598365 | 15 | 6.88 | Fibronectin 1 | NO | intronic |
| 70 | 3270357 | 6 | 6.86 | Protein tyrosine phosphatase, receptor type, E | NO | exonic |
| 71 | 2598301 | 9 | 6.85 | Fibronectin 1 | YES | exonic |
| 72 | 2598371 | 8 | 6.84 | Fibronectin 1 | YES | exonic |
| 73 | 2685324 | 5 | 6.83 | Protein S (alpha) | YES | exonic |
| 74 | 3536724 | 8 | 6.83 | Lectin, galactoside-binding, soluble, 3 | NO | extra-genic |
| 75 | 3451841 | 9 | 6.82 | NEL-like 2 (chicken) | YES | exonic |
| 76 | 2598270 | 11 | 6.82 | Fibronectin 1 | YES | exonic |
| 77 | 2598288 | 8 | 6.81 | Fibronectin 1 | YES | exonic |
| 78 | 2827683 | 41 | 6.8 | Solute carrier family 27 (fatty acid transporter), member 6 | YES | exonic |
| 79 | 2598324 | 7 | 6.79 | Fibronectin 1 | YES | exonic |
| 80 | 2598303 | 9 | 6.79 | Fibronectin 1 | NO | intronic |
| 81 | 2562442 | 21 | 6.73 | Surfactant, pulmonary-associated protein B | NO | intronic |
| 82 | 2598363 | 10 | 6.71 | Fibronectin 1 | YES | exonic |
| 83 | 2598273 | 9 | 6.7 | Fibronectin 1 | YES | exonic |
| 84 | 2598304 | 2 | 6.66 | Fibronectin 1 | YES | exonic |
| 85 | 3020344 | 2 | 6.64 | Met proto-oncogene (hepatocyte growth factor receptor) | NO | exonic |
| 86 | 2325319 | 3 | 6.64 | UDP-galactose-4-epimerase | NO | exonic |
| 87 | 3460510 | 2 | 6.63 | High mobility group AT-hook 2 | NO | antisense |
| 88 | 2598339 | 8 | 6.61 | Fibronectin 1 | YES | exonic |
| 89 | 3371816 | 3 | 6.59 | Low density lipoprotein receptor-related protein 4 | NO | extra-genic |
| 90 | 2400181 | 4 | 6.59 | Calcium/calmodulin-dependent protein kinase II inhibitor 1 | YES | exonic |
| 91 | 3536743 | 4 | 6.58 | Lectin, galactoside-binding, soluble, 3 | YES | exonic |
| 92 | 3536736 | 9 | 6.54 | Lectin, galactoside-binding, soluble, 3 | NO | intronic |
| 93 | 3634838 | 2 | 6.51 | Cathepsin H | YES | exonic |
| 94 | 3976359 | 3 | 6.46 | Synapsin I | NO | antisense |
| 95 | 2598268 | 10 | 6.46 | Fibronectin 1 | NO | exonic |
| 96 | 3451865 | 3 | 6.42 | NEL-like 2 (chicken) | NO | intronic |
| 97 | 2526825 | 8 | 6.41 | Fibronectin 1 | NO | antisense |
| 98 | 2721993 | 10 | 6.4 | Solute carrier family 34 (sodium phosphate), member 2 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 99 | 2827693 | 32 | 6.39 | Solute carrier family 27 (fatty acid transporter), member 6 | NO | exonic |
| 100 | 2598309 | 12 | 6.38 | Fibronectin 1 | NO | intronic |
| 101 | 2722006 | 11 | 6.37 | Solute carrier family 34 (sodium phosphate), member 2 | NO | exonic |
| 102 | 2598330 | 19 | 6.37 | Fibronectin 1 | YES | exonic |
| 103 | 2598283 | 4 | 6.35 | Fibronectin 1 | NO | intronic |
| 104 | 2685316 | 3 | 6.34 | Protein S (alpha) | YES | exonic |
| 105 | 3666402 | 8 | 6.34 | Cadherin 3, type 1, P-cadherin (placental) | NO | exonic |
| 106 | 2685306 | 5 | 6.33 | Protein S (alpha) | NO | exonic |
| 107 | 2526814 | 8 | 6.31 | Fibronectin 1 | NO | antisense |
| 108 | 2598344 | 7 | 6.3 | Fibronectin 1 | YES | exonic |
| 109 | 2491742 | 4 | 6.28 | Surfactant, pulmonary-associated protein B | NO | exonic |
| 110 | 2598318 | 11 | 6.28 | Fibronectin 1 | YES | exonic |
| 111 | 3839605 | 3 | 6.27 | Kallikrein-related peptidase 10 | NO | exonic |
| 112 | 2598325 | 11 | 6.27 | Fibronectin 1 | YES | exonic |
| 113 | 2451595 | 13 | 6.27 | Chitinase 3-like 1 (cartilage glycoprotein-39) | NO | exonic |
| 114 | 2721980 | 3 | 6.24 | Solute carrier family 34 (sodium phosphate), member 2 | YES | exonic |
| 115 | 2721989 | 5 | 6.24 | Solute carrier family 34 (sodium phosphate), member 2 | YES | exonic |
| 116 | 2722000 | 9 | 6.24 | Solute carrier family 34 (sodium phosphate), member 2 | NO | exonic |
| 117 | 3087187 | 4 | 6.23 | Tumor suppressor candidate 3 | YES | exonic |
| 118 | 2526818 | 5 | 6.22 | Fibronectin 1 | NO | antisense |
| 119 | 2598331 | 3 | 6.21 | Fibronectin 1 | YES | exonic |
| 120 | 2721991 | 18 | 6.21 | Solute carrier family 34 (sodium phosphate), member 2 | YES | exonic |
| 121 | 2400180 | 6 | 6.2 | Calcium/calmodulin-dependent protein kinase II inhibitor 1 | NO | exonic |
| 122 | 2598287 | 5 | 6.19 | Fibronectin 1 | YES | intronic |
| 123 | 2584026 | 4 | 6.18 | Dipeptidyl-peptidase 4 (CD26, adenosine deaminase complexing protein 2) | YES | exonic |
| 124 | 3536744 | 6 | 6.17 | Lectin, galactoside-binding, soluble, 3 | YES | exonic |
| 125 | 2598284 | 8 | 6.17 | Fibronectin 1 | YES | exonic |
| 126 | 2598294 | 4 | 6.15 | Fibronectin 1 | YES | exonic |
| 127 | 3451875 | 3 | 6.14 | NEL-like 2 (chicken) | YES | exonic |
| 128 | 2598308 | 11 | 6.14 | Fibronectin 1 | YES | exonic |
| 129 | 3825011 | 5 | 6.08 | Growth differentiation factor 15 | NO | exonic |
| 130 | 3464873 | 4 | 6.07 | Dual specificity phosphatase 6 | NO | exonic |
| 131 | 3263765 | 5 | 6.07 | Dual specificity phosphatase 5 | NO | intronic |
| 132 | 2562440 | 30 | 6.07 | Surfactant, pulmonary-associated protein B | NO | intronic |
| 133 | 3536745 | 7 | 5.99 | Lectin, galactoside-binding, soluble, 3 | YES | exonic |
| 134 | 2598290 | 10 | 5.98 | Fibronectin 1 | YES | exonic |
| 135 | 2526822 | 14 | 5.98 | Fibronectin 1 | NO | antisense |
| 136 | 2526816 | 7 | 5.94 | Fibronectin 1 | NO | antisense |
| 137 | 2584027 | 4 | 5.92 | Dipeptidyl-peptidase 4 (CD26, adenosine deaminase complexing protein 2) | YES | exonic |
| 138 | 3329530 | 4 | 5.91 | Low density lipoprotein receptor-related protein 4 | NO | exonic |
| 139 | 3020368 | 2 | 5.88 | Met proto-oncogene (hepatocyte growth factor receptor) | NO | intronic |
| 140 | 3451912 | 5 | 5.86 | NEL-like 2 (chicken) | YES | exonic |
| 141 | 3917691 | 4 | 5.83 | T-cell lymphoma invasion and metastasis 1 | NO | intronic |
| 142 | 3420343 | 10 | 5.82 | High mobility group AT-hook 2 | NO | intronic |
| 143 | 3343460 | 3 | 5.81 | Protease, serine, 23 | NO | exonic |
| 144 | 2721982 | 8 | 5.8 | Solute carrier family 34 (sodium phosphate), member 2 | YES | exonic |
| 145 | 2598310 | 9 | 5.79 | Fibronectin 1 | YES | exonic |
| 146 | 3270278 | 7 | 5.76 | Protein tyrosine phosphatase, receptor type, E | NO | intronic |
| 147 | 3577627 | 2 | 5.75 | Serpin peptidase inhibitor, clade A (alpha-1 antiproteinase, antitrypsin), member 1 | YES | exonic |
| 148 | 2598276 | 10 | 5.74 | Fibronectin 1 | YES | exonic |
| 149 | 3907236 | 4 | 5.71 | Syndecan 4 | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 150 | 3464882 | 3 | 5.69 | Dual specificity phosphatase 6 | NO | extra-genic |
| 151 | 2598295 | 4 | 5.68 | Fibronectin 1 | NO | intronic |
| 152 | 2477461 | 4 | 5.67 | Glutaminyl-peptide cyclotransferase (glutaminyl cyclase) | NO | exonic |
| 153 | 2562463 | 10 | 5.67 | Surfactant, pulmonary-associated protein B | YES | exonic |
| 154 | 3907239 | 4 | 5.66 | Syndecan 4 | YES | exonic |
| 155 | 2944958 | 3 | 5.65 | SRY (sex determining region Y)-box 4 | NO | antisense |
| 156 | 2512878 | 8 | 5.65 | Dipeptidyl-peptidase 4 (CD26, adenosine deaminase complexing protein 2) | NO | exonic |
| 157 | 3020350 | 3 | 5.64 | Met proto-oncogene (hepatocyte growth factor receptor) | YES | exonic |
| 158 | 3928670 | 6 | 5.64 | T-cell lymphoma invasion and metastasis 1 | NO | intronic |
| 159 | 3460452 | 4 | 5.61 | High mobility group AT-hook 2 | NO | antisense |
| 160 | 2721987 | 5 | 5.61 | Solute carrier family 34 (sodium phosphate), member 2 | NO | intronic |
| 161 | 2598357 | 9 | 5.61 | Fibronectin 1 | YES | exonic |
| 162 | 2722004 | 12 | 5.59 | Solute carrier family 34 (sodium phosphate), member 2 | NO | exonic |
| 163 | 3420360 | 6 | 5.58 | High mobility group AT-hook 2 | NO | intronic |
| 164 | 2721988 | 6 | 5.54 | Solute carrier family 34 (sodium phosphate), member 2 | YES | exonic |
| 165 | 2721976 | 8 | 5.54 | Solute carrier family 34 (sodium phosphate), member 2 | YES | exonic |
| 166 | 3634817 | 4 | 5.5 | Cathepsin H | NO | exonic |
| 167 | 2584025 | 4 | 5.5 | Dipeptidyl-peptidase 4 (CD26, adenosine deaminase complexing protein 2) | NO | exonic |
| 168 | 2722002 | 3 | 5.47 | Solute carrier family 34 (sodium phosphate), member 2 | NO | exonic |
| 169 | 3312464 | 7 | 5.47 | Protein tyrosine phosphatase, receptor type, E | NO | intronic |
| 170 | 3263773 | 5 | 5.44 | Dual specificity phosphatase 5 | NO | exonic |
| 171 | 3460456 | 5 | 5.43 | High mobility group AT-hook 2 | NO | antisense |
| 172 | 2598373 | 15 | 5.41 | Fibronectin 1 | YES | exonic |
| 173 | 3730395 | 3 | 5.39 | Mannose receptor, C type 2 | NO | exonic |
| 174 | 2377256 | 3 | 5.38 | CD55 molecule, decay accelerating factor for complement (Cromer blood group) | NO | exonic |
| 175 | 3312484 | 5 | 5.38 | Protein tyrosine phosphatase, receptor type, E | NO | exonic |
| 176 | 3451913 | 7 | 5.38 | NEL-like 2 (chicken) | NO | extra-genic |
| 177 | 2400178 | 7 | 5.38 | Calcium/calmodulin-dependent protein kinase II inhibitor 1 | NO | exonic |
| 178 | 2451596 | 20 | 5.38 | Chitinase 3-like 1 (cartilage glycoprotein-39) | NO | exonic |
| 179 | 2827686 | 7 | 5.37 | Solute carrier family 27 (fatty acid transporter), member 6 | YES | exonic |
| 180 | 2685329 | 6 | 5.34 | Protein S (alpha) | NO | intronic |
| 181 | 2584058 | 9 | 5.33 | Dipeptidyl-peptidase 4 (CD26, adenosine deaminase complexing protein 2) | YES | exonic |
| 182 | 2598306 | 8 | 5.32 | Fibronectin 1 | YES | exonic |
| 183 | 3928671 | 2 | 5.3 | T-cell lymphoma invasion and metastasis 1 | NO | intronic |
| 184 | 3069235 | 2 | 5.3 | Met proto-oncogene (hepatocyte growth factor receptor) | NO | exonic |
| 185 | 2562462 | 3 | 5.29 | Surfactant, pulmonary-associated protein B | NO | intronic |
| 186 | 2632440 | 4 | 5.29 | Protein S (alpha) | NO | exonic |
| 187 | 3420356 | 4 | 5.29 | High mobility group AT-hook 2 | NO | intronic |
| 188 | 3263784 | 4 | 5.24 | Dual specificity phosphatase 5 | NO | intronic |
| 189 | 3769232 | 3 | 5.23 | Potassium inwardly-rectifying channel, subfamily J, member 2 | NO | exonic |
| 190 | 2377249 | 4 | 5.23 | CD55 molecule, decay accelerating factor for complement (Cromer blood group) | NO | intronic |
| 191 | 2377248 | 3 | 5.18 | CD55 molecule, decay accelerating factor for complement (Cromer blood group) | NO | exonic |

TABLE 3-continued

| Thyroid Nodule Disease Candidate Gene RNA Sequences | | | | | | |
|---|---|---|---|---|---|---|
| SEQ ID | ID | MFD | Weights | Gene | Probeset Overlaps CDS | Target Sequence Subtype |
| 192 | 3067479 | 3 | 5.17 | Neuronal cell adhesion molecule | NO | exonic |
| 193 | 3020359 | 6 | 5.16 | Met proto-oncogene (hepatocyte growth factor receptor) | NO | intronic |
| 194 | 3451874 | 7 | 5.16 | NEL-like 2 (chicken) | YES | exonic |
| 195 | 2491744 | 9 | 5.16 | Surfactant, pulmonary-associated protein B | NO | intronic |
| 196 | 3464875 | 3 | 5.08 | Dual specificity phosphatase 6 | NO | intronic |
| 197 | 2584067 | 3 | 5.06 | Dipeptidyl-peptidase 4 (CD26, adenosine deaminase complexing protein 2) | YES | exonic |
| 198 | 2722005 | 10 | 5.06 | Solute carrier family 34 (sodium phosphate), member 2 | NO | exonic |
| 199 | 3721357 | 7 | 5.05 | Keratin 19 | NO | antisense |
| 200 | 3020391 | 3 | 5.04 | Met proto-oncogene (hepatocyte growth factor receptor) | YES | exonic |
| 201 | 3868840 | 5 | 5.04 | Kallikrein-related peptidase 10 | NO | extra-genic |
| 202 | 3306643 | 3 | 5.02 | Dual specificity phosphatase 5 | NO | extra-genic |
| 203 | 2721994 | 3 | 5.02 | Solute carrier family 34 (sodium phosphate), member 2 | YES | exonic |
| 204 | 3329532 | 3 | 5.01 | Low density lipoprotein receptor-related protein 4 | NO | antisense |
| 205 | 2377247 | 3 | 5 | CD55 molecule, decay accelerating factor for complement (Cromer blood group) | YES | exonic |
| 206 | 2558642 | 3 | 5 | Transforming growth factor, alpha | NO | exonic |
| 207 | 2830378 | 2 | 4.99 | Sparc/osteonectin, cwcv and kazal-like domains proteoglycan (testican) 1 | NO | antisense |
| 208 | 2477456 | 4 | 4.98 | Glutaminyl-peptide cyclotransferase (glutaminyl cyclase) | YES | exonic |
| 209 | 3451868 | 6 | 4.98 | NEL-like 2 (chicken) | YES | exonic |
| 210 | 3087225 | 6 | 4.98 | Tumor suppressor candidate 3 | NO | extra-genic |
| 211 | 3020384 | 3 | 4.89 | Met proto-oncogene (hepatocyte growth factor receptor) | YES | exonic |
| 212 | 2735072 | 5 | 4.87 | Secreted phosphoprotein 1 (osteopontin, bone sialoprotein I, early T-lymphocyte activation 1) | NO | exonic |
| 213 | 2598353 | 8 | 4.87 | Fibronectin 1 | YES | exonic |
| 214 | 3385809 | 3 | 4.85 | Cathepsin C | NO | intronic |
| 215 | 2721985 | 9 | 4.85 | Solute carrier family 34 (sodium phosphate), member 2 | YES | exonic |
| 216 | 3020363 | 4 | 4.77 | Met proto-oncogene (hepatocyte growth factor receptor) | YES | exonic |
| 217 | 2437139 | 3 | 4.76 | Mucin 1, cell surface associated | YES | intronic |
| 218 | 3460453 | 3 | 4.72 | High mobility group AT-hook 2 | NO | antisense |
| 219 | 3020356 | 3 | 4.72 | Met proto-oncogene (hepatocyte growth factor receptor) | NO | intronic |
| 220 | 2830183 | 9 | 4.72 | Sparc/osteonectin, cwcv and kazal-like domains proteoglycan (testican) 1 | NO | exonic |
| 221 | 2562444 | 2 | 4.7 | Surfactant, pulmonary-associated protein B | NO | intronic |
| 222 | 2830181 | 4 | 4.68 | Sparc/osteonectin, cwcv and kazal-like domains proteoglycan (testican) 1 | NO | exonic |
| 223 | 2764175 | 13 | 4.68 | Solute carrier family 34 (sodium phosphate), member 2 | NO | exonic |
| 224 | 3907240 | 3 | 4.66 | Syndecan 4 | YES | exonic |
| 225 | 3917721 | 5 | 4.66 | T-cell lymphoma invasion and metastasis 1 | NO | intronic |
| 226 | 2442021 | 9 | 4.65 | Retinoid X receptor, gamma | YES | exonic |
| 227 | 3907235 | 3 | 4.64 | Syndecan 4 | NO | exonic |
| 228 | 3451838 | 3 | 4.64 | NEL-like 2 (chicken) | YES | exonic |
| 229 | 3769234 | 5 | 4.64 | Potassium inwardly-rectifying channel, subfamily J, member 2 | NO | exonic |
| 230 | 3577636 | 4 | 4.63 | Serpin peptidase inhibitor, clade A (alpha-1 antiproteinase, antitrypsin), member 1 | YES | exonic |
| 231 | 2377236 | 3 | 4.61 | CD55 molecule, decay accelerating factor for complement (Cromer blood group) | YES | exonic |
| 232 | 2435391 | 4 | 4.61 | S100 calcium binding protein A10 | NO | exonic |
| 233 | 2400186 | 3 | 4.6 | Calcium/calmodulin-dependent protein kinase II inhibitor 1 | NO | extra-genic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 234 | 2751991 | 3 | 4.59 | UDP-N-acetyl-alpha-D-galactosamine:polypeptide N-acetylgalactosaminyltransferase 7 (GalNAc-T7) | NO | intronic |
| 235 | 2377265 | 3 | 4.53 | CD55 molecule, decay accelerating factor for complement (Cromer blood group) | NO | intronic |
| 236 | 3464878 | 4 | 4.53 | Dual specificity phosphatase 6 | NO | intronic |
| 237 | 3835890 | 6 | 4.53 | Apolipoprotein E | NO | exonic |
| 238 | 2721999 | 15 | 4.53 | Solute carrier family 34 (sodium phosphate), member 2 | NO | exonic |
| 239 | 3125505 | 3 | 4.5 | Tumor suppressor candidate 3 | NO | antisense |
| 240 | 2562443 | 5 | 4.5 | Surfactant, pulmonary-associated protein B | NO | intronic |
| 241 | 2453163 | 3 | 4.45 | CD55 molecule, decay accelerating factor for complement (Cromer blood group) | NO | antisense |
| 242 | 3263752 | 6 | 4.43 | Dual specificity phosphatase 5 | NO | extra-genic |
| 243 | 3825012 | 3 | 4.4 | Growth differentiation factor 15 | NO | exonic |
| 244 | 2377237 | 3 | 4.39 | CD55 molecule, decay accelerating factor for complement (Cromer blood group) | NO | intronic |
| 245 | 3907194 | 6 | 4.39 | Secretory leukocyte peptidase inhibitor | NO | exonic |
| 246 | 2377268 | 3 | 4.36 | CD55 molecule, decay accelerating factor for complement (Cromer blood group) | YES | exonic |
| 247 | 3343458 | 3 | 4.36 | Protease, serine, 23 | NO | exonic |
| 248 | 2377271 | 4 | 4.36 | CD55 molecule, decay accelerating factor for complement (Cromer blood group) | NO | exonic |
| 249 | 2359172 | 5 | 4.36 | S100 calcium binding protein A10 | NO | exonic |
| 250 | 3733280 | 3 | 4.35 | Potassium inwardly-rectifying channel, subfamily J, member 2 | NO | exonic |
| 251 | 3020355 | 3 | 4.34 | Met proto-oncogene (hepatocyte growth factor receptor) | NO | intronic |
| 252 | 2453796 | 3 | 4.32 | Laminin, beta 3 | YES | exonic |
| 253 | 3460455 | 3 | 4.31 | High mobility group AT-hook 2 | NO | antisense |
| 254 | 3928709 | 2 | 4.3 | T-cell lymphoma invasion and metastasis 1 | YES | exonic |
| 255 | 3351275 | 3 | 4.3 | Myelin protein zero-like 2 | NO | exonic |
| 256 | 3217301 | 2 | 4.21 | Gamma-aminobutyric acid (GABA) B receptor, 2 | NO | intronic |
| 257 | 2377263 | 2 | 4.18 | CD55 molecule, decay accelerating factor for complement (Cromer blood group) | NO | intronic |
| 258 | 3976345 | 3 | 4.18 | Synapsin I | YES | antisense |
| 259 | 2377245 | 5 | 4.16 | CD55 molecule, decay accelerating factor for complement (Cromer blood group) | YES | exonic |
| 260 | 2414961 | 4 | 4.14 | Tumor-associated calcium signal transducer 2 | NO | exonic |
| 261 | 2876911 | 2 | 4.12 | Sparc/osteonectin, cwcv and kazal-like domains proteoglycan (testican) 1 | YES | exonic |
| 262 | 2764272 | 4 | 4.12 | KIAA0746 protein | YES | exonic |
| 263 | 3406425 | 3 | 4.08 | Epidermal growth factor receptor pathway substrate 8 | NO | intronic |
| 264 | 3222204 | 7 | 4.06 | Tenascin C (hexabrachion) | NO | intronic |
| 265 | 3928687 | 3 | 4.05 | T-cell lymphoma invasion and metastasis 1 | YES | exonic |
| 266 | 3067480 | 4 | 4.04 | Neuronal cell adhesion molecule | NO | exonic |
| 267 | 3451908 | 7 | 3.99 | NEL-like 2 (chicken) | YES | exonic |
| 268 | 3928672 | 5 | 3.98 | T-cell lymphoma invasion and metastasis 1 | NO | intronic |
| 269 | 2437119 | 4 | 3.97 | Mucin 1, cell surface associated | NO | exonic |
| 270 | 3252064 | 3 | 3.93 | Plasminogen activator, urokinase | NO | exonic |
| 271 | 2751985 | 2 | 3.92 | UDP-N-acetyl-alpha-D-galactosamine:polypeptide N-acetylgalactosaminyltransferase 7 (GalNAc-T7) | NO | exonic |
| 272 | 2830201 | 2 | 3.9 | Sparc/osteonectin, cwcv and kazal-like domains proteoglycan (testican) 1 | NO | antisense |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 273 | 3126229 | 3 | 3.9 | Pleckstrin and Sec7 domain containing 3 | NO | intronic |
| 274 | 3252057 | 2 | 3.83 | Plasminogen activator, urokinase | NO | intronic |
| 275 | 3222218 | 3 | 3.82 | Tenascin C (hexabrachion) | NO | intronic |
| 276 | 3217284 | 3 | 3.8 | Gamma-aminobutyric acid (GABA) B receptor, 2 | YES | exonic |
| 277 | 3401511 | 3 | 3.76 | Protein arginine methyltransferase 8 | NO | exonic |
| 278 | 3020380 | 3 | 3.74 | Met proto-oncogene (hepatocyte growth factor receptor) | YES | exonic |
| 279 | 3371817 | 2 | 3.71 | Low density lipoprotein receptor-related protein 4 | NO | exonic |
| 280 | 2377242 | 2 | 3.7 | CD55 molecule, decay accelerating factor for complement (Cromer blood group) | YES | exonic |
| 281 | 2558708 | 2 | 3.7 | Transforming growth factor, alpha | NO | intronic |
| 282 | 3351271 | 2 | 3.63 | Myelin protein zero-like 3 | NO | antisense |
| 283 | 2466609 | −8 | −10.87 | Thyroid peroxidase | YES | exonic |
| 284 | 2537610 | −6 | −9.87 | Thyroid peroxidase | NO | antisense |
| 285 | 3727592 | −3 | −9.81 | Hepatic leukemia factor | YES | exonic |
| 286 | 3367674 | −11 | −9.45 | Metallophosphoesterase domain containing 2 | NO | extra-genic |
| 287 | 2537568 | −19 | −9.37 | Thyroid peroxidase | NO | antisense |
| 288 | 2466585 | −26 | −9.14 | Thyroid peroxidase | YES | exonic |
| 289 | 3095405 | −9 | −9.07 | Zinc finger, matrin type 4 | NO | exonic |
| 290 | 3933538 | −16 | −8.91 | Trefoil factor 3 (intestinal) | NO | exonic |
| 291 | 2763591 | −3 | −8.86 | Peroxisome proliferator-activated receptor gamma, coactivator 1 alpha | YES | exonic |
| 292 | 2466562 | −30 | −8.84 | Thyroid peroxidase | NO | extra-genic |
| 293 | 3662208 | −6 | −8.84 | Metallothionein 1F | YES | exonic |
| 294 | 2466570 | −55 | −8.64 | Thyroid peroxidase | YES | exonic |
| 295 | 2466631 | −19 | −8.52 | Thyroid peroxidase | NO | extra-genic |
| 296 | 3367675 | −14 | −8.49 | Metallophosphoesterase domain containing 2 | NO | exonic |
| 297 | 3367709 | −24 | −8.39 | Metallophosphoesterase domain containing 2 | NO | intronic |
| 298 | 2466600 | −5 | −8.37 | Thyroid peroxidase | NO | intronic |
| 299 | 3367737 | −9 | −8.35 | Metallophosphoesterase domain containing 2 | NO | intronic |
| 300 | 3018629 | −8 | −8.35 | Solute carrier family 26, member 4 | YES | exonic |
| 301 | 3132624 | −6 | −8.35 | Zinc finger, matrin type 4 | YES | exonic |
| 302 | 3018633 | −7 | −8.33 | Solute carrier family 26, member 4 | YES | exonic |
| 303 | 3367689 | −13 | −8.27 | Metallophosphoesterase domain containing 2 | NO | intronic |
| 304 | 3693001 | −14 | −8.22 | Metallothionein 1G | NO | exonic |
| 305 | 3018617 | −6 | −8.21 | Solute carrier family 26, member 4 | YES | exonic |
| 306 | 3018618 | −8 | −8.16 | Solute carrier family 26, member 4 | YES | exonic |
| 307 | 2763563 | −6 | −8.12 | Peroxisome proliferator-activated receptor gamma, coactivator 1 alpha | NO | exonic |
| 308 | 3862190 | −3 | −8.03 | Fc fragment of IgG binding protein | NO | exonic |
| 309 | 2721305 | −4 | −8 | Peroxisome proliferator-activated receptor gamma, coactivator 1 alpha | NO | exonic |
| 310 | 2466569 | −26 | −7.98 | Thyroid peroxidase | YES | exonic |
| 311 | 3367712 | −15 | −7.98 | Metallophosphoesterase domain containing 2 | YES | exonic |
| 312 | 3833280 | −2 | −7.97 | Fc fragment of IgG binding protein | NO | exonic |
| 313 | 3018642 | −10 | −7.93 | Solute carrier family 26, member 4 | NO | exonic |
| 314 | 3367697 | −16 | −7.85 | Metallophosphoesterase domain containing 2 | NO | intronic |
| 315 | 3018616 | −13 | −7.79 | Solute carrier family 26, member 4 | YES | exonic |
| 316 | 3367743 | −28 | −7.77 | Metallophosphoesterase domain containing 2 | NO | extra-genic |
| 317 | 2537609 | −12 | −7.73 | Thyroid peroxidase | NO | antisense |
| 318 | 3933539 | −19 | −7.71 | Trefoil factor 3 (intestinal) | NO | exonic |
| 319 | 2586066 | −4 | −7.7 | Low density lipoprotein-related protein 2 | YES | exonic |
| 320 | 3132617 | −13 | −7.68 | Zinc finger, matrin type 4 | NO | extra-genic |
| 321 | 2727647 | −11 | −7.6 | V-kit Hardy-Zuckerman 4 feline sarcoma viral oncogene homolog | NO | intronic |
| 322 | 3067233 | −20 | −7.53 | Solute carrier family 26, member 4 | NO | extra-genic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 323 | 2763565 | −5 | −7.53 | Peroxisome proliferator-activated receptor gamma, coactivator 1 alpha | NO | exonic |
| 324 | 3018631 | −13 | −7.51 | Solute carrier family 26, member 4 | YES | exonic |
| 325 | 2586118 | −7 | −7.5 | Low density lipoprotein-related protein 2 | YES | exonic |
| 326 | 2466608 | −9 | −7.49 | Thyroid peroxidase | YES | exonic |
| 327 | 2586111 | −5 | −7.46 | Low density lipoprotein-related protein 2 | YES | exonic |
| 328 | 3367703 | −9 | −7.44 | Metallophosphoesterase domain containing 2 | NO | intronic |
| 329 | 2586171 | −4 | −7.36 | Low density lipoprotein-related protein 2 | YES | exonic |
| 330 | 2331562 | −3 | −7.34 | Bone morphogenetic protein 8a | NO | exonic |
| 331 | 3108614 | −4 | −7.32 | Matrilin 2 | YES | exonic |
| 332 | 2537604 | −6 | −7.31 | Thyroid peroxidase | NO | antisense |
| 333 | 2466626 | −3 | −7.31 | Thyroid peroxidase | YES | exonic |
| 334 | 3018640 | −7 | −7.28 | Solute carrier family 26, member 4 | NO | exonic |
| 335 | 2466621 | −14 | −7.27 | Thyroid peroxidase | NO | intronic |
| 336 | 2586151 | −3 | −7.27 | Low density lipoprotein-related protein 2 | YES | exonic |
| 337 | 2466629 | −16 | −7.25 | Thyroid peroxidase | NO | exonic |
| 338 | 3367739 | −8 | −7.24 | Metallophosphoesterase domain containing 2 | NO | intronic |
| 339 | 3811356 | −3 | −7.22 | B-cell CLL/lymphoma 2 | NO | exonic |
| 340 | 3108604 | −3 | −7.19 | Matrilin 2 | YES | exonic |
| 341 | 2466601 | −35 | −7.17 | Thyroid peroxidase | NO | intronic |
| 342 | 2466566 | −9 | −7.16 | Thyroid peroxidase | YES | exonic |
| 343 | 2586065 | −5 | −7.14 | Low density lipoprotein-related protein 2 | YES | exonic |
| 344 | 3095521 | −5 | −7.14 | Zinc finger, matrin type 4 | NO | intronic |
| 345 | 2586168 | −4 | −7.14 | Low density lipoprotein-related protein 2 | YES | exonic |
| 346 | 2466628 | −21 | −7.13 | Thyroid peroxidase | YES | exonic |
| 347 | 2466564 | −13 | −7.1 | Thyroid peroxidase | YES | exonic |
| 348 | 3160700 | −5 | −7.04 | Chromosome 9 open reading frame 68 | NO | intronic |
| 349 | 3325106 | −9 | −7 | Metallophosphoesterase domain containing 2 | NO | antisense |
| 350 | 2721311 | −7 | −6.99 | Peroxisome proliferator-activated receptor gamma, coactivator 1 alpha | NO | antisense |
| 351 | 3018619 | −6 | −6.98 | Solute carrier family 26, member 4 | YES | exonic |
| 352 | 2586130 | −6 | −6.9 | Low density lipoprotein-related protein 2 | YES | exonic |
| 353 | 3018636 | −12 | −6.87 | Solute carrier family 26, member 4 | YES | exonic |
| 354 | 3108616 | −8 | −6.86 | Matrilin 2 | YES | exonic |
| 355 | 3862193 | −4 | −6.86 | Fc fragment of IgG binding protein | YES | exonic |
| 356 | 2586039 | −4 | −6.84 | Low density lipoprotein-related protein 2 | NO | extragenic |
| 357 | 3833286 | −4 | −6.83 | Fc fragment of IgG binding protein | NO | antisense |
| 358 | 2586132 | −2 | −6.83 | Low density lipoprotein-related protein 2 | YES | exonic |
| 359 | 2763561 | −6 | −6.82 | Peroxisome proliferator-activated receptor gamma, coactivator 1 alpha | NO | exonic |
| 360 | 2466620 | −15 | −6.8 | Thyroid peroxidase | YES | exonic |
| 361 | 2586145 | −5 | −6.79 | Low density lipoprotein-related protein 2 | YES | exonic |
| 362 | 3018615 | −7 | −6.78 | Solute carrier family 26, member 4 | YES | exonic |
| 363 | 4023363 | −6 | −6.77 | Four and a half LIM domains 1 | NO | exonic |
| 364 | 2537578 | −6 | −6.76 | Thyroid peroxidase | NO | antisense |
| 365 | 2763557 | −6 | −6.74 | Peroxisome proliferator-activated receptor gamma, coactivator 1 alpha | NO | exonic |
| 366 | 2586159 | −4 | −6.74 | Low density lipoprotein-related protein 2 | YES | exonic |
| 367 | 3862199 | −4 | −6.74 | Fc fragment of IgG binding protein | YES | exonic |
| 368 | 3811391 | −2 | −6.74 | B-cell CLL/lymphoma 2 | NO | intronic |
| 369 | 3046252 | −4 | −6.73 | Engulfment and cell motility 1 | NO | intronic |
| 370 | 2466563 | −7 | −6.72 | Thyroid peroxidase | NO | extragenic |
| 371 | 2721641 | −5 | −6.72 | Superoxide dismutase 3, extracellular | NO | exonic |
| 372 | 3108607 | −3 | −6.71 | Matrilin 2 | NO | intronic |
| 373 | 2721309 | −5 | −6.7 | Peroxisome proliferator-activated receptor gamma, coactivator 1 alpha | NO | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 374 | 2586135 | −4 | −6.7 | Low density lipoprotein-related protein 2 | YES | exonic |
| 375 | 2537607 | −9 | −6.69 | Thyroid peroxidase | NO | antisense |
| 376 | 3018628 | −8 | −6.67 | Solute carrier family 26, member 4 | YES | exonic |
| 377 | 2466583 | −8 | −6.66 | Thyroid peroxidase | NO | intronic |
| 378 | 2586149 | −5 | −6.65 | Low density lipoprotein-related protein 2 | YES | exonic |
| 379 | 3662230 | −16 | −6.63 | Metallothionein 1G | NO | exonic |
| 380 | 2586140 | −3 | −6.61 | Low density lipoprotein-related protein 2 | YES | exonic |
| 381 | 3367740 | −6 | −6.53 | Metallophosphoesterase domain containing 2 | NO | intronic |
| 382 | 2466598 | −5 | −6.53 | Thyroid peroxidase | NO | intronic |
| 383 | 3367691 | −6 | −6.52 | Metallophosphoesterase domain containing 2 | NO | intronic |
| 384 | 3367679 | −4 | −6.49 | Metallophosphoesterase domain containing 2 | YES | exonic |
| 385 | 2763590 | −3 | −6.47 | Peroxisome proliferator-activated receptor gamma, coactivator 1 alpha | NO | intronic |
| 386 | 2586102 | −3 | −6.46 | Low density lipoprotein-related protein 2 | YES | exonic |
| 387 | 3367693 | −12 | −6.44 | Metallophosphoesterase domain containing 2 | NO | intronic |
| 388 | 2586067 | −4 | −6.44 | Low density lipoprotein-related protein 2 | YES | exonic |
| 389 | 3095516 | −3 | −6.42 | Zinc finger, matrin type 4 | NO | intronic |
| 390 | 2466573 | −10 | −6.41 | Thyroid peroxidase | YES | intronic |
| 391 | 3145950 | −5 | −6.41 | Matrilin 2 | NO | antisense |
| 392 | 2586043 | −3 | −6.41 | Low density lipoprotein-related protein 2 | YES | exonic |
| 393 | 3104982 | −23 | −6.37 | Fatty acid binding protein 4, adipocyte | NO | exonic |
| 394 | 2336909 | −7 | −6.37 | Deiodinase, iodothyronine, type I | NO | exonic |
| 395 | 3108620 | −6 | −6.37 | Matrilin 2 | NO | exonic |
| 396 | 3095473 | −4 | −6.31 | Zinc finger, matrin type 4 | NO | antisense |
| 397 | 2763580 | −4 | −6.31 | Peroxisome proliferator-activated receptor gamma, coactivator 1 alpha | YES | exonic |
| 398 | 3367742 | −3 | −6.31 | Metallophosphoesterase domain containing 2 | NO | extra-genic |
| 399 | 3662219 | −17 | −6.29 | Metallothionein 1H | NO | exonic |
| 400 | 2331563 | −11 | −6.29 | Bone morphogenetic protein 8a | NO | exonic |
| 401 | 3727624 | −9 | −6.29 | Hepatic leukemia factor | NO | exonic |
| 402 | 2586061 | −4 | −6.29 | Low density lipoprotein-related protein 2 | NO | intronic |
| 403 | 2997517 | −4 | −6.28 | Engulfment and cell motility 1 | NO | exonic |
| 404 | 2586088 | −3 | −6.28 | Low density lipoprotein-related protein 2 | YES | exonic |
| 405 | 3992449 | −5 | −6.27 | Four and a half LIM domains 1 | NO | exonic |
| 406 | 2586155 | −9 | −6.25 | Low density lipoprotein-related protein 2 | YES | exonic |
| 407 | 2586139 | −4 | −6.25 | Low density lipoprotein-related protein 2 | YES | exonic |
| 408 | 3126609 | −3 | −6.25 | Chondroitin beta1,4 N-acetylgalactosaminyltransferase | NO | intronic |
| 409 | 2586113 | −4 | −6.2 | Low density lipoprotein-related protein 2 | YES | exonic |
| 410 | 2586160 | −4 | −6.2 | Low density lipoprotein-related protein 2 | YES | exonic |
| 411 | 2608611 | −3 | −6.2 | Inositol 1,4,5-triphosphate receptor, type 1 | YES | exonic |
| 412 | 2586152 | −3 | −6.19 | Low density lipoprotein-related protein 2 | YES | exonic |
| 413 | 2466574 | −10 | −6.17 | Thyroid peroxidase | NO | intronic |
| 414 | 2763558 | −4 | −6.14 | Peroxisome proliferator-activated receptor gamma, coactivator 1 alpha | NO | exonic |
| 415 | 3662224 | −4 | −6.13 | Metallothionein 1F | NO | extra-genic |
| 416 | 3367741 | −3 | −6.13 | Metallophosphoesterase domain containing 2 | YES | exonic |
| 417 | 2466582 | −3 | −6.12 | Thyroid peroxidase | YES | exonic |
| 418 | 3108615 | −5 | −6.08 | Matrilin 2 | YES | exonic |
| 419 | 2721643 | −2 | −6.08 | Superoxide dismutase 3, extracellular | NO | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 420 | 2586153 | −4 | −6.07 | Low density lipoprotein-related protein 2 | YES | exonic |
| 421 | 2537572 | −8 | −6.05 | Thyroid peroxidase | NO | antisense |
| 422 | 2586068 | −3 | −6.04 | Low density lipoprotein-related protein 2 | YES | exonic |
| 423 | 2586143 | −5 | −6.03 | Low density lipoprotein-related protein 2 | YES | exonic |
| 424 | 3893028 | −15 | −6.01 | Collagen, type IX, alpha 3 | YES | exonic |
| 425 | 3367676 | −7 | −6.01 | Metallophosphoesterase domain containing 2 | YES | exonic |
| 426 | 2586172 | −5 | −6.01 | Low density lipoprotein-related protein 2 | YES | exonic |
| 427 | 3142383 | −25 | −6 | Fatty acid binding protein 4, adipocyte | NO | exonic |
| 428 | 3367677 | −3 | −5.97 | Metallophosphoesterase domain containing 2 | NO | intronic |
| 429 | 2763566 | −7 | −5.96 | Peroxisome proliferator-activated receptor gamma, coactivator 1 alpha | NO | exonic |
| 430 | 3763228 | −5 | −5.94 | Hepatic leukemia factor | NO | extra-genic |
| 431 | 3108580 | −4 | −5.92 | Matrilin 2 | YES | exonic |
| 432 | 2608485 | −3 | −5.92 | Inositol 1,4,5-triphosphate receptor, type 1 | YES | exonic |
| 433 | 2331560 | −3 | −5.91 | Bone morphogenetic protein 8a | YES | exonic |
| 434 | 2763602 | −3 | −5.89 | Peroxisome proliferator-activated receptor gamma, coactivator 1 alpha | NO | intronic |
| 435 | 3811360 | −2 | −5.89 | B-cell CLL/lymphoma 2 | NO | exonic |
| 436 | 2586150 | −4 | −5.86 | Low density lipoprotein-related protein 2 | YES | exonic |
| 437 | 2586050 | −7 | −5.84 | Low density lipoprotein-related protein 2 | YES | exonic |
| 438 | 2586041 | −3 | −5.84 | Low density lipoprotein-related protein 2 | YES | exonic |
| 439 | 3811354 | −3 | −5.84 | B-cell CLL/lymphoma 2 | NO | exonic |
| 440 | 3088273 | −5 | −5.82 | Chondroitin beta1,4 N-acetylgalactosaminyltransferase | NO | exonic |
| 441 | 3046251 | −3 | −5.81 | Engulfment and cell motility 1 | NO | intronic |
| 442 | 2336897 | −5 | −5.8 | Deiodinase, iodothyronine, type I | YES | exonic |
| 443 | 3108574 | −5 | −5.8 | Matrilin 2 | YES | exonic |
| 444 | 3354771 | −2 | −5.8 | STT3, subunit of the oligosaccharyltransferase complex, homolog A (*S. cerevisiae*) | YES | exonic |
| 445 | 3367705 | −7 | −5.77 | Metallophosphoesterase domain containing 2 | NO | intronic |
| 446 | 3791751 | −5 | −5.77 | B-cell CLL/lymphoma 2 | NO | antisense |
| 447 | 2514350 | −4 | −5.77 | Low density lipoprotein-related protein 2 | NO | extra-genic |
| 448 | 2586107 | −5 | −5.75 | Low density lipoprotein-related protein 2 | YES | exonic |
| 449 | 3108602 | −9 | −5.74 | Matrilin 2 | YES | exonic |
| 450 | 2980482 | −4 | −5.73 | Opioid receptor, mu 1 | NO | antisense |
| 451 | 3126512 | −3 | −5.72 | Chondroitin beta1,4 N-acetylgalactosaminyltransferase | NO | intronic |
| 452 | 3913484 | −22 | −5.71 | Collagen, type IX, alpha 3 | NO | exonic |
| 453 | 2763571 | −4 | −5.71 | Peroxisome proliferator-activated receptor gamma, coactivator 1 alpha | YES | exonic |
| 454 | 2980481 | −10 | −5.7 | Opioid receptor, mu 1 | NO | antisense |
| 455 | 2608604 | −6 | −5.68 | Inositol 1,4,5-triphosphate receptor, type 1 | NO | intronic |
| 456 | 2586064 | −6 | −5.66 | Low density lipoprotein-related protein 2 | YES | exonic |
| 457 | 3018621 | −4 | −5.66 | Solute carrier family 26, member 4 | YES | exonic |
| 458 | 3126626 | −4 | −5.66 | Chondroitin beta1,4 N-acetylgalactosaminyltransferase | NO | intronic |
| 459 | 2649002 | −6 | −5.65 | Potassium voltage-gated channel, shaker-related subfamily, beta member 1 | NO | intronic |
| 460 | 2763573 | −4 | −5.65 | Peroxisome proliferator-activated receptor gamma, coactivator 1 alpha | YES | exonic |
| 461 | 3396651 | −2 | −5.65 | STT3, subunit of the oligosaccharyltransferase complex, homolog A (*S. cerevisiae*) | NO | antisense |
| 462 | 3893026 | −12 | −5.64 | Collagen, type IX, alpha 3 | YES | exonic |
| 463 | 3046250 | −4 | −5.64 | Engulfment and cell motility 1 | NO | intronic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 464 | 2586114 | −3 | −5.62 | Low density lipoprotein-related protein 2 | YES | exonic |
| 465 | 3573880 | −6 | −5.61 | Deiodinase, iodothyronine, type II | YES | exonic |
| 466 | 2586101 | −4 | −5.61 | Low density lipoprotein-related protein 2 | YES | exonic |
| 467 | 3126515 | −3 | −5.57 | Chondroitin beta1,4 N-acetylgalactosaminyltransferase | NO | intronic |
| 468 | 2608689 | −3 | −5.57 | Inositol 1,4,5-triphosphate receptor, type 1 | NO | intronic |
| 469 | 4023359 | −4 | −5.55 | Four and a half LIM domains 1 | NO | exonic |
| 470 | 3046202 | −2 | −5.55 | Engulfment and cell motility 1 | YES | exonic |
| 471 | 2586075 | −5 | −5.53 | Low density lipoprotein-related protein 2 | YES | exonic |
| 472 | 3046247 | −6 | −5.52 | Engulfment and cell motility 1 | NO | intronic |
| 473 | 2608629 | −2 | −5.51 | Inositol 1,4,5-triphosphate receptor, type 1 | YES | exonic |
| 474 | 3126548 | −3 | −5.49 | Chondroitin beta1,4 N-acetylgalactosaminyltransferase | YES | exonic |
| 475 | 3046198 | −3 | −5.46 | Engulfment and cell motility 1 | NO | exonic |
| 476 | 3573882 | −3 | −5.45 | Deiodinase, iodothyronine, type II | YES | exonic |
| 477 | 3088320 | −3 | −5.43 | Chondroitin beta1,4 N-acetylgalactosaminyltransferase | NO | antisense |
| 478 | 3095470 | −2 | −5.43 | Zinc finger, matrin type 4 | NO | antisense |
| 479 | 3142384 | −13 | −5.42 | Fatty acid binding protein 4, adipocyte | YES | exonic |
| 480 | 2721315 | −5 | −5.42 | Peroxisome proliferator-activated receptor gamma, coactivator 1 alpha | NO | antisense |
| 481 | 3933546 | −3 | −5.42 | Trefoil factor 3 (intestinal) | YES | exonic |
| 482 | 2608677 | −3 | −5.42 | Inositol 1,4,5-triphosphate receptor, type 1 | NO | exonic |
| 483 | 3893027 | −8 | −5.41 | Collagen, type IX, alpha 3 | YES | exonic |
| 484 | 3811420 | −4 | −5.41 | B-cell CLL/lymphoma 2 | NO | intronic |
| 485 | 2608644 | −3 | −5.41 | Inositol 1,4,5-triphosphate receptor, type 1 | YES | exonic |
| 486 | 3811357 | −2 | −5.41 | B-cell CLL/lymphoma 2 | NO | exonic |
| 487 | 2932274 | −6 | −5.38 | Opioid receptor, mu 1 | YES | exonic |
| 488 | 3811424 | −3 | −5.37 | B-cell CLL/lymphoma 2 | NO | intronic |
| 489 | 3354786 | −2 | −5.37 | STT3, subunit of the oligosaccharyltransferase complex, homolog A (*S. cerevisiae*) | YES | exonic |
| 490 | 2740186 | −5 | −5.35 | Ankyrin 2, neuronal | NO | intronic |
| 491 | 2586104 | −3 | −5.33 | Low density lipoprotein-related protein 2 | NO | intronic |
| 492 | 3046236 | −5 | −5.32 | Engulfment and cell motility 1 | NO | intronic |
| 493 | 3126509 | −4 | −5.31 | Chondroitin beta1,4 N-acetylgalactosaminyltransferase | YES | exonic |
| 494 | 2608546 | −4 | −5.3 | Inositol 1,4,5-triphosphate receptor, type 1 | YES | exonic |
| 495 | 3108613 | −5 | −5.29 | Matrilin 2 | YES | exonic |
| 496 | 2997541 | −3 | −5.29 | Engulfment and cell motility 1 | NO | antisense |
| 497 | 3088362 | −2 | −5.29 | Chondroitin beta1,4 N-acetylgalactosaminyltransferase | NO | intronic |
| 498 | 3662157 | −5 | −5.28 | Metallothionein 1M | NO | exonic |
| 499 | 2586125 | −3 | −5.28 | Low density lipoprotein-related protein 2 | NO | intronic |
| 500 | 2608612 | −7 | −5.27 | Inositol 1,4,5-triphosphate receptor, type 1 | YES | exonic |
| 501 | 2608627 | −7 | −5.25 | Inositol 1,4,5-triphosphate receptor, type 1 | NO | intronic |
| 502 | 2586096 | −5 | −5.25 | Low density lipoprotein-related protein 2 | YES | exonic |
| 503 | 3811405 | −3 | −5.25 | B-cell CLL/lymphoma 2 | NO | intronic |
| 504 | 3862194 | −3 | −5.25 | Fc fragment of IgG binding protein | NO | intronic |
| 505 | 3126514 | −4 | −5.24 | Chondroitin beta1,4 N-acetylgalactosaminyltransferase | YES | exonic |
| 506 | 3992437 | −4 | −5.23 | Four and a half LIM domains 1 | NO | intronic |
| 507 | 2702151 | −3 | −5.22 | Potassium voltage-gated channel, shaker-related subfamily, beta member 1 | NO | exonic |
| 508 | 2649018 | −7 | −5.21 | Potassium voltage-gated channel, shaker-related subfamily, beta member 1 | NO | intronic |
| 509 | 2908192 | −2 | −5.19 | Vascular endothelial growth factor A | YES | exonic |
| 510 | 3573883 | −4 | −5.18 | Deiodinase, iodothyronine, type II | YES | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 511 | 2608610 | −4 | −5.17 | Inositol 1,4,5-triphosphate receptor, type 1 | YES | exonic |
| 512 | 3126563 | −3 | −5.17 | Chondroitin beta1,4 N-acetylgalactosaminyltransferase | NO | intronic |
| 513 | 2897465 | −2 | −5.17 | Inhibitor of DNA binding 4, dominant negative helix-loop-helix protein | NO | exonic |
| 514 | 2649054 | −6 | −5.16 | Potassium voltage-gated channel, shaker-related subfamily, beta member 1 | NO | intronic |
| 515 | 2608569 | −3 | −5.16 | Inositol 1,4,5-triphosphate receptor, type 1 | YES | exonic |
| 516 | 2897464 | −2 | −5.16 | Inhibitor of DNA binding 4, dominant negative helix-loop-helix protein | NO | exonic |
| 517 | 2980483 | −3 | −5.14 | Opioid receptor, mu 1 | NO | antisense |
| 518 | 3791695 | −3 | −5.14 | B-cell CLL/lymphoma 2 | NO | antisense |
| 519 | 3603305 | −10 | −5.13 | Cellular retinoic acid binding protein 1 | NO | exonic |
| 520 | 2608568 | −4 | −5.11 | Inositol 1,4,5-triphosphate receptor, type 1 | YES | exonic |
| 521 | 2586115 | −3 | −5.11 | Low density lipoprotein-related protein 2 | YES | exonic |
| 522 | 3811408 | −2 | −5.11 | B-cell CLL/lymphoma 2 | NO | intronic |
| 523 | 2466604 | −2 | −5.11 | Thyroid peroxidase | YES | exonic |
| 524 | 2586166 | −3 | −5.09 | Low density lipoprotein-related protein 2 | YES | exonic |
| 525 | 3018611 | −4 | −5.08 | Solute carrier family 26, member 4 | NO | extra-genic |
| 526 | 3693008 | −4 | −5.07 | Metallothionein 1G | YES | exonic |
| 527 | 3862192 | −4 | −5.07 | Fc fragment of IgG binding protein | YES | exonic |
| 528 | 2649046 | −3 | −5.07 | Potassium voltage-gated channel, shaker-related subfamily, beta member 1 | YES | exonic |
| 529 | 2763600 | −4 | −5.05 | Peroxisome proliferator-activated receptor gamma, coactivator 1 alpha | NO | intronic |
| 530 | 3546098 | −3 | −5.05 | Deiodinase, iodothyronine, type II | NO | exonic |
| 531 | 3385513 | −2 | −5.05 | Frizzled homolog 4 (*Drosophila*) | NO | exonic |
| 532 | 2586141 | −3 | −5.02 | Low density lipoprotein-related protein 2 | YES | exonic |
| 533 | 3046243 | −5 | −5 | Engulfment and cell motility 1 | NO | intronic |
| 534 | 3046224 | −2 | −5 | Engulfment and cell motility 1 | YES | exonic |
| 535 | 4023361 | −2 | −5 | Four and a half LIM domains 1 | NO | exonic |
| 536 | 3546096 | −5 | −4.99 | Deiodinase, iodothyronine, type II | NO | antisense |
| 537 | 3046199 | −5 | −4.98 | Engulfment and cell motility 1 | YES | exonic |
| 538 | 2740233 | −4 | −4.97 | Ankyrin 2, neuronal | NO | intronic |
| 539 | 2980484 | −9 | −4.96 | Opioid receptor, mu 1 | NO | antisense |
| 540 | 2980450 | −7 | −4.96 | Opioid receptor, mu 1 | YES | antisense |
| 541 | 2763628 | −3 | −4.96 | Peroxisome proliferator-activated receptor gamma, coactivator 1 alpha | NO | intronic |
| 542 | 2649009 | −4 | −4.95 | Potassium voltage-gated channel, shaker-related subfamily, beta member 1 | NO | intronic |
| 543 | 3791690 | −4 | −4.94 | B-cell CLL/lymphoma 2 | NO | antisense |
| 544 | 2980485 | −7 | −4.93 | Opioid receptor, mu 1 | YES | antisense |
| 545 | 3811446 | −3 | −4.9 | B-cell CLL/lymphoma 2 | NO | extra-genic |
| 546 | 3811358 | −3 | −4.89 | B-cell CLL/lymphoma 2 | NO | exonic |
| 547 | 3573884 | −8 | −4.88 | Deiodinase, iodothyronine, type II | YES | exonic |
| 548 | 2925965 | −5 | −4.88 | Ectonucleotide pyrophosphatase/phosphodiesterase 1 | YES | exonic |
| 549 | 2608614 | −5 | −4.87 | Inositol 1,4,5-triphosphate receptor, type 1 | NO | intronic |
| 550 | 3787876 | −3 | −4.86 | Lipase, endothelial | YES | exonic |
| 551 | 2331561 | −4 | −4.85 | Bone morphogenetic protein 8a | NO | exonic |
| 552 | 2661102 | −2 | −4.85 | Inositol 1,4,5-triphosphate receptor, type 1 | NO | antisense |
| 553 | 2586047 | −3 | −4.84 | Low density lipoprotein-related protein 2 | YES | exonic |
| 554 | 3787860 | −2 | −4.84 | Lipase, endothelial | YES | exonic |
| 555 | 3791668 | −2 | −4.84 | B-cell CLL/lymphoma 2 | NO | antisense |
| 556 | 3126507 | −3 | −4.83 | Chondroitin beta1,4 N-acetylgalactosaminyltransferase | NO | exonic |
| 557 | 2608643 | −3 | −4.82 | Inositol 1,4,5-triphosphate receptor, type 1 | YES | exonic |
| 558 | 3807530 | −2 | −4.82 | Lipase, endothelial | NO | antisense |

TABLE 3-continued

| Thyroid Nodule Disease Candidate Gene RNA Sequences | | | | | | |
|---|---|---|---|---|---|---|
| SEQ ID | ID | MFD | Weights | Gene | Probeset Overlaps CDS | Target Sequence Subtype |
| 559 | 2763570 | −4 | −4.81 | Peroxisome proliferator-activated receptor gamma, coactivator 1 alpha | NO | intronic |
| 560 | 2925993 | −4 | −4.81 | Ectonucleotide pyrophosphatase/phosphodiesterase 1 | YES | exonic |
| 561 | 2908205 | −2 | −4.81 | Vascular endothelial growth factor A | YES | exonic |
| 562 | 2586123 | −4 | −4.8 | Low density lipoprotein-related protein 2 | YES | exonic |
| 563 | 3791749 | −4 | −4.79 | B-cell CLL/lymphoma 2 | NO | antisense |
| 564 | 2586195 | −6 | −4.78 | Low density lipoprotein-related protein 2 | NO | intronic |
| 565 | 2763627 | −3 | −4.78 | Peroxisome proliferator-activated receptor gamma, coactivator 1 alpha | NO | intronic |
| 566 | 2608559 | −4 | −4.74 | Inositol 1,4,5-triphosphate receptor, type 1 | YES | exonic |
| 567 | 3126535 | −4 | −4.74 | Chondroitin beta1,4 N-acetylgalactosaminyltransferase | YES | exonic |
| 568 | 3791743 | −4 | −4.74 | B-cell CLL/lymphoma 2 | NO | antisense |
| 569 | 3727623 | −5 | −4.73 | Hepatic leukemia factor | NO | exonic |
| 570 | 2586057 | −5 | −4.73 | Low density lipoprotein-related protein 2 | YES | exonic |
| 571 | 2763598 | −3 | −4.73 | Peroxisome proliferator-activated receptor gamma, coactivator 1 alpha | NO | intronic |
| 572 | 2925966 | −3 | −4.72 | Ectonucleotide pyrophosphatase/phosphodiesterase 1 | YES | exonic |
| 573 | 4016044 | −3 | −4.7 | Transcription elongation factor A (SII)-like 2 | NO | antisense |
| 574 | 2980475 | −8 | −4.69 | Opioid receptor, mu 1 | YES | antisense |
| 575 | 2944441 | −2 | −4.68 | Inhibitor of DNA binding 4, dominant negative helix-loop-helix protein | NO | exonic |
| 576 | 2608634 | −3 | −4.66 | Inositol 1,4,5-triphosphate receptor, type 1 | NO | intronic |
| 577 | 2727646 | −6 | −4.64 | V-kit Hardy-Zuckerman 4 feline sarcoma viral oncogene homolog | NO | exonic |
| 578 | 2925978 | −3 | −4.63 | Ectonucleotide pyrophosphatase/phosphodiesterase 1 | YES | exonic |
| 579 | 2608490 | −3 | −4.58 | Inositol 1,4,5-triphosphate receptor, type 1 | NO | intronic |
| 580 | 3992448 | −3 | −4.58 | Four and a half LIM domains 1 | YES | exonic |
| 581 | 3985030 | −4 | −4.57 | Transcription elongation factor A (SII)-like 2 | YES | exonic |
| 582 | 3753968 | −2 | −4.57 | Chemokine (C-C motif) ligand 14 | NO | exonic |
| 583 | 3573878 | −4 | −4.56 | Deiodinase, iodothyronine, type II | YES | exonic |
| 584 | 2586112 | −2 | −4.56 | Low density lipoprotein-related protein 2 | YES | exonic |
| 585 | 3354794 | −2 | −4.56 | STT3, subunit of the oligosaccharyltransferase complex, homolog A (*S. cerevisiae*) | NO | extra-genic |
| 586 | 2925981 | −5 | −4.55 | Ectonucleotide pyrophosphatase/phosphodiesterase 1 | YES | exonic |
| 587 | 3787884 | −3 | −4.55 | Lipase, endothelial | NO | exonic |
| 588 | 3791660 | −2 | −4.55 | B-cell CLL/lymphoma 2 | NO | antisense |
| 589 | 3569378 | −2 | −4.54 | Arginase, type II | YES | exonic |
| 590 | 2932285 | −7 | −4.53 | Opioid receptor, mu 1 | NO | intronic |
| 591 | 2586165 | −2 | −4.53 | Low density lipoprotein-related protein 2 | NO | intronic |
| 592 | 3787881 | −3 | −4.52 | Lipase, endothelial | NO | intronic |
| 593 | 2925998 | −5 | −4.5 | Ectonucleotide pyrophosphatase/phosphodiesterase 1 | NO | exonic |
| 594 | 2925975 | −4 | −4.5 | Ectonucleotide pyrophosphatase/phosphodiesterase 1 | YES | exonic |
| 595 | 3126541 | −3 | −4.5 | Chondroitin beta1,4 N-acetylgalactosaminyltransferase | NO | intronic |
| 596 | 2782529 | −2 | −4.5 | Ankyrin 2, neuronal | NO | exonic |
| 597 | 2763596 | −3 | −4.47 | Peroxisome proliferator-activated receptor gamma, coactivator 1 alpha | NO | intronic |
| 598 | 2649079 | −5 | −4.45 | Potassium voltage-gated channel, shaker-related subfamily, beta member 1 | NO | exonic |
| 599 | 2925973 | −2 | −4.44 | Ectonucleotide pyrophosphatase/phosphodiesterase 1 | YES | exonic |
| 600 | 2925999 | −4 | −4.43 | Ectonucleotide pyrophosphatase/phosphodiesterase 1 | NO | exonic |
| 601 | 3126508 | −3 | −4.43 | Chondroitin beta1,4 N-acetylgalactosaminyltransferase | NO | exonic |

TABLE 3-continued

Thyroid Nodule Disease Candidate Gene RNA Sequences

| SEQ ID | ID | MFD | Weights | Gene | Probeset Overlaps CDS | Target Sequence Subtype |
|---|---|---|---|---|---|---|
| 602 | 2586072 | −4 | −4.42 | Low density lipoprotein-related protein 2 | YES | exonic |
| 603 | 2661165 | −3 | −4.41 | Inositol 1,4,5-triphosphate receptor, type 1 | NO | exonic |
| 604 | 3018623 | −3 | −4.4 | Solute carrier family 26, member 4 | YES | exonic |
| 605 | 2944443 | −2 | −4.4 | Inhibitor of DNA binding 4, dominant negative helix-loop-helix protein | NO | extra-genic |
| 606 | 3573881 | −6 | −4.38 | Deiodinase, iodothyronine, type II | YES | exonic |
| 607 | 3573895 | −4 | −4.38 | Deiodinase, iodothyronine, type II | YES | exonic |
| 608 | 3811395 | −3 | −4.38 | B-cell CLL/lymphoma 2 | NO | intronic |
| 609 | 3787879 | −4 | −4.36 | Lipase, endothelial | NO | intronic |
| 610 | 2608590 | −4 | −4.35 | Inositol 1,4,5-triphosphate receptor, type 1 | NO | intronic |
| 611 | 2763629 | −5 | −4.34 | Peroxisome proliferator-activated receptor gamma, coactivator 1 alpha | NO | intronic |
| 612 | 3992441 | −4 | −4.34 | Four and a half LIM domains 1 | NO | intronic |
| 613 | 3727625 | −4 | −4.33 | Hepatic leukemia factor | NO | exonic |
| 614 | 2615655 | −2 | −4.33 | STT3, subunit of the oligosaccharyltransferase complex, homolog B (*S. cerevisiae*) | NO | extra-genic |
| 615 | 3603302 | −3 | −4.27 | Cellular retinoic acid binding protein 1 | YES | exonic |
| 616 | 2586098 | −3 | −4.24 | Low density lipoprotein-related protein 2 | NO | intronic |
| 617 | 2925996 | −5 | −4.22 | Ectonucleotide pyrophosphatase/phosphodiesterase 1 | YES | exonic |
| 618 | 3791650 | −3 | −4.21 | B-cell CLL/lymphoma 2 | NO | exonic |
| 619 | 2925967 | −4 | −4.19 | Ectonucleotide pyrophosphatase/phosphodiesterase 1 | YES | exonic |
| 620 | 2586147 | −3 | −4.17 | Low density lipoprotein-related protein 2 | YES | exonic |
| 621 | 3992436 | −4 | −4.14 | Four and a half LIM domains 1 | NO | intronic |
| 622 | 2740285 | −3 | −4.13 | Ankyrin 2, neuronal | NO | exonic |
| 623 | 2740135 | −2 | −4.13 | Ankyrin 2, neuronal | NO | intronic |
| 624 | 2586097 | −3 | −4.08 | Low density lipoprotein-related protein 2 | YES | exonic |
| 625 | 3985031 | −3 | −4.07 | Transcription elongation factor A (SII)-like 2 | NO | exonic |
| 626 | 2954890 | −2 | −4.07 | Vascular endothelial growth factor A | NO | antisense |
| 627 | 2586154 | −4 | −4.06 | Low density lipoprotein-related protein 2 | YES | exonic |
| 628 | 4013550 | −2 | −4.06 | Integral membrane protein 2A | NO | exonic |
| 629 | 3811377 | −3 | −4.03 | B-cell CLL/lymphoma 2 | NO | intronic |
| 630 | 3763258 | −4 | −3.99 | Hepatic leukemia factor | NO | exonic |
| 631 | 3753974 | −2 | −3.98 | Chemokine (C-C motif) ligand 14 | YES | exonic |
| 632 | 3088318 | −2 | −3.97 | Chondroitin beta1,4 N-acetylgalactosaminyltransferase | NO | antisense |
| 633 | 2925979 | −4 | −3.94 | Ectonucleotide pyrophosphatase/phosphodiesterase 1 | YES | exonic |
| 634 | 3811413 | −3 | −3.94 | B-cell CLL/lymphoma 2 | NO | intronic |
| 635 | 2980497 | −3 | −3.91 | Phosphoinositide-binding protein PIP3-E | NO | intronic |
| 636 | 3811431 | −4 | −3.9 | B-cell CLL/lymphoma 2 | NO | intronic |
| 637 | 2608556 | −3 | −3.9 | Inositol 1,4,5-triphosphate receptor, type 1 | NO | intronic |
| 638 | 3108611 | −3 | −3.9 | Matrilin 2 | YES | exonic |
| 639 | 3160684 | −3 | −3.9 | Chromosome 9 open reading frame 68 | YES | exonic |
| 640 | 4023355 | −2 | −3.87 | Four and a half LIM domains 1 | NO | antisense |
| 641 | 3862191 | −3 | −3.83 | Fc fragment of IgG binding protein | NO | exonic |
| 642 | 2997556 | −3 | −3.83 | Engulfment and cell motility 1 | NO | antisense |
| 643 | 3787882 | −3 | −3.79 | Lipase, endothelial | NO | exonic |
| 644 | 2483130 | −2 | −3.79 | EGF-containing fibulin-like extracellular matrix protein 1 | NO | antisense |
| 645 | 3811426 | −3 | −3.78 | B-cell CLL/lymphoma 2 | NO | intronic |
| 646 | 3787871 | −2 | −3.78 | Lipase, endothelial | YES | exonic |
| 647 | 2660997 | −3 | −3.74 | Inositol 1,4,5-triphosphate receptor, type 1 | NO | antisense |
| 648 | 3787872 | −3 | −3.72 | Lipase, endothelial | YES | exonic |
| 649 | 2763609 | −3 | −3.7 | Peroxisome proliferator-activated receptor gamma, coactivator 1 alpha | YES | exonic |
| 650 | 2980500 | −3 | −3.68 | Phosphoinositide-binding protein PIP3-E | NO | intronic |
| 651 | 2586129 | −4 | −3.66 | Low density lipoprotein-related protein 2 | YES | exonic |

TABLE 3-continued

| Thyroid Nodule Disease Candidate Gene RNA Sequences | | | | | | |
|---|---|---|---|---|---|---|
| SEQ ID | ID | MFD | Weights | Gene | Probeset Overlaps CDS | Target Sequence Subtype |
| 652 | 4023341 | −3 | −3.65 | Four and a half LIM domains 1 | NO | antisense |
| 653 | 2897466 | −2 | −3.64 | Inhibitor of DNA binding 4, dominant negative helix-loop-helix protein | NO | extra-genic |
| 654 | 3791755 | −3 | −3.63 | B-cell CLL/lymphoma 2 | NO | antisense |
| 655 | 3811429 | −3 | −3.62 | B-cell CLL/lymphoma 2 | NO | intronic |
| 656 | 2649081 | −2 | −3.59 | Potassium voltage-gated channel, shaker-related subfamily, beta member 1 | NO | extra-genic |
| 657 | 2830194 | −8.6 | −7.06 | Sparc/osteonectin, cwcv and kazal-like domains proteoglycan (testican) 1 | NO | antisense |
| 658 | 2830301 | −1.2 | −3.02 | Sparc/osteonectin, cwcv and kazal-like domains proteoglycan (testican) 1 | NO | antisense |
| 659 | 2830378 | 1.8 | 4.94 | Sparc/osteonectin, cwcv and kazal-like domains proteoglycan (testican) 1 | NO | antisense |

TABLE 4

| Thyroid Nodule Disease 7-RNA Expression Signature | | | | | | |
|---|---|---|---|---|---|---|
| SEQ ID | MFD | Weights | Gene | Probeset Overlaps CDS | Target Sequence Subtype | Probeset Sequence |
| 1 | 14 | 8.75 | High mobility group AT-hook 2 | NO | intronic | attctttggagttgcgtcattaggagctttacagt aagatatcttactagccaatattagcctgccac agg |
| 2 | 11 | 8.59 | Cadherin 3, type 1, P-cadherin (placental) | NO | exonic | gggcaacctaggcacactcagtataaaaac gcagagatccatccgaatgggaggcattggg gtctggaaaccagaaatgcaggacggccag t |
| 3 | 3 | 8.12 | Serpin peptidase inhibitor, clade A (alpha-1 antiproteinase, antitrypsin), member 1 | YES | exonic | ctgcctctcgctcctcaacccctccc |
| 4 | 4 | 5.94 | Insulin-like growth factor binding protein 6 | NO | exonic | tggagctgtcatcactcaacaaaaaaaccgag gccctcaatccaccttcaggccccgccccatg ggcccctcaccgctggttggaaagagtgttgg tgttggctggggtgtcaataaagctgt |
| 5 | -14 | -11.03 | Thyroid peroxidase | NO | antisense | agcctgtgagtatcccggccttccatcccagc actctcctgcaaaaatgcagaacaaacatta ataacgtctgaattctgactgctccagtaacag cacacacttgatacaagacagaagggcctg gacaggagctcttttcacaaaggaccgctggc gagatgagccatccttcttgcttgtcatgctgga gggaagtttctggcttccggacaaatgcttgttt gcaggaggccacagaggatccacgtggca aaggttcctactcacagagtgggatctgcaat ccgcaggcagggtccttcaggaagaagccgt gctgagcacacaggtccctgcgaccacagat gaacagaacgcctggccttgcccctggtgtca gtcagactaattaggggcccaggggacttgct ggcactgcccttgctgtggctggaaaagctatt taaattcacaaagagcctcacttccaggccag gtccttttggttccatgcgtgggagccaggtgc aaagacgaatgtgctctcagcagaacgaccc tgggctctgcttatctccgaggacaggatctaa tctcacactgaatttcagaagggagaccgatc atgttggcaatgccccccctcctgtatgcaagta agtgact |

TABLE 4-continued

Thyroid Nodule Disease 7-RNA Expression Signature

| SEQ ID | MFD | Weights | Gene | Probeset Overlaps CDS | Target Sequence Subtype | Probeset Sequence |
|---|---|---|---|---|---|---|
| 6 | −5 | −9.09 | V-kit Hardy-Zuckerman 4 feline sarcoma viral oncogene homolog | NO | exonic | aagcccatgagtccttgaaaatatttttatatat acagtaactttatgtgtaaatacataagcggcg taagtttaaaggatgttggtgttccacgtgttttat tcctgtatgttgtccaattgttgaca |
| 7 | −31 | −8.23 | Metallophos-phoesterase domain containing 2 | NO | intronic | ttttgcctgcacattctgagagagccatttggca aacaacaataataaatttacatttggatggtgt atttccactcagagaactttcatatgtattatctcat ttggggctcacaacaattctttaaccagggtat gtattactaataataattaacaatagccagcatt tacagtgtttatatgtcaactgctgttcattattgc ctccttttgacagagaccaaca |

TABLE 5

Thyroid Nodule Disease 36-RNA Expression Signature

| SEQ ID | MFD | Weights | Gene | Probeset Overlaps CDS | Target Sequence Subytpe | Probeset Sequence |
|---|---|---|---|---|---|---|
| 1 | 14 | 8.75 | High mobility group AT-hook 2 | NO | intronic | attctttggagttgcgtcattaggagcttta cagtaagatatcttactagccaatattag cctgccacagg |
| 2 | 11 | 8.59 | Cadherin 3, type 1, P-cadherin (placental) | NO | exonic | gggcaacctaggcacactcagtataaa aacgcagagatccatccgaatgggag gcattggggtctggaaaccagaaatgc aggacggccagt |
| 3 | 3 | 8.12 | Serpin peptidase inhibitor, clade A (alpha-1 antiproteinase, antitrypsin), member 1 | YES | exonic | ctgcctctcgctcctcaacccctccc |
| 4 | 4 | 5.94 | Insulin-like growth factor binding protein 6 | NO | exonic | tggagctgtcatcactcaacaaaaaacc gaggccctcaatccaccttcaggccccg ccccatgggcccctcaccgctggttgga aagagtgttggtgttggctggggtgtcaa taaagctgt |
| 5 | −14 | −11.03 | Thyroid peroxidase | NO | antisense | agcctgtgagtatcccggccttccatccc agcactctcctgcaaaaatgcagaaca aacattaataacgtctgaattctgactgct ccagtaacagcacacacttgatacaag acagaagggcctggacaggagctctttt cacaaaggaccgctggcgagatgagc catccttcttgcttgtcatgctggagggaa gtttctggcttccggacaaatgcttgtttgc aggaggccacagaggatccacgtggc aaaggttcctactcacagagtgggatct gcaatccgcaggcagggtccttcagga agaagccgtgctgagcacacaggtccc tgcgaccacagatgaacagaacgcctg gccttgcccctggtgtcagtcagactaatt aggggcccaggggacttgctggcactg cccttgctgtggctggaaaagctatttaa attcacaaagagcctcacttccaggcca ggtccttttggttccatgcgtgggagcca ggtgcaaagacgaatgtgctctcagca |

TABLE 5-continued

Thyroid Nodule Disease 36-RNA Expression Signature

| SEQ ID | MFD | Weights | Gene | Probeset Overlaps CDS | Target Sequence Subytpe | Probeset Sequence |
|---|---|---|---|---|---|---|
| | | | | | | gaacgaccctgggctctgcttatctccga ggacaggatctaatctcacactgaatttc agaagggagaccgatcatgttggcaat gcccccctcctgtatgcaagtaagtgact |
| 6 | -5 | -9.09 | V-kit Hardy-Zuckerman 4 feline sarcoma viral oncogene homolog | NO | exonic | aagcccatgagtccttgaaaatattttttat atatacagtaactttatgtgtaaatacata agcggcgtaagtttaaaggatgttggtgt tccacgtgttttattcctgtatgttgtccaatt gttgaca |
| 7 | -31 | -8.23 | Metallophos-phoesterase domain containing 2 | NO | intronic | ttttgcctgcacattctgagagagccattt ggcaaacaacaataataaatttacatttg gatggtgtatttcactcagagaactttcat atgtattatctcatttggggctcacaacaa ttctttaaccagggtatgtattactaataat aattaacaatagccagcatttacagtgttt atatgtcaactgctgttcattattgcctccttt tgacagagaccaaca |
| 8 | 8 | 10.26 | PDZ and LIM domain 4 | NO | exonic | tgctcccacgcctgcttcttaaggtccctg ctcggccggtgtaaatatgtttcaccctgt ccctctaataaagctcctctgc |
| 9 | 24 | 8.9 | Tumor-associated calcium signal transducer 2 | NO | exonic | gacaacccgggatcgtttgcaagtaact gaatccattgcgacattgtgaaggcttaa atgagtttagatgggaaatagcgttgttat cgccttgggtttaaattatttgatgagttcc acttgtatcatggcctacccgaggagaa gaggagtttgttaactgggcctatgtagta gcctcatttaccatcgtttgtattactgacc acatatgcttgtcactgggaaagaagcc tgtttcagctgcctgaacgcagtttggatg tctttgaggacagacattgcccggaaac tcagtctattta |
| 10 | 6 | 8.69 | Fibronectin 1 | NO | antisense | acgcccaggactatttgaactgatgaaa tatccaaatgtccagtcctatagcctactt acacctaagtgaacactacagcgaagt gttcagtgaacagaccttgagaaggtct gtaattagatgataaggaagggtcacctt gccccatggcctctcgaagccctccattc cacctgtgagtgtgactcagctggatttc gagtgggatgaagttgctgcaacagctg gatatttctcgcatccacctgagagtatgt ctctggagggcacatgataatccttgctg tggtgctgtggattgccatttatgcctcac aacaaccctggaaggtagtttgctcctttt aaaagcaatttcttgtcatacaacgtact gcatatctttaaagtgatgggtttttacatat gtgtgacttgggagaccatcaccgcattc |
| 11 | 13 | 8.66 | Fibronectin 1 | NO | antisense | cttcaaggacaaatcgtaaaggtagtgtt ttagacttctgcacacaaatggaaattca ggtagaatatctttcttttctagaatcatcta tcttactcaaaaagg |
| 12 | 17 | 8.61 | Fibronectin 1 | NO | intronic | gtctgaatgcccacgacatgtcttttgcaa ttacacatagggaaagtgaacttgttggtt agtttatgtcttgagctgagccctttacga acatcttttttccttctcagtgccaagcgag gaatttacagagaaagaagttgtgaaa ccaccatagttagttgctgtgctttgaattt cttttgctcaaatggcctcagcgaaatctt atttgc |
| 283 | -8 | -10.87 | Thyroid peroxidase | YES | exonic | cgacaagtgtggcttcccagagagcgt ggagaatggggactttgtgcactgtgag gagtctgggaggcgcgtgctggtgtattc ctgc |
| 284 | -6 | -9.87 | Thyroid peroxidase | NO | antisense | ggaggttgcacagattgcgggggatttg gggaga |

TABLE 5-continued

Thyroid Nodule Disease 36-RNA Expression Signature

| SEQ ID | MFD | Weights | Gene | Probeset Overlaps CDS | Target Sequence Subytpe | Probeset Sequence |
|---|---|---|---|---|---|---|
| 285 | -3 | -9.81 | Hepatic leukemia factor | YES | exonic | atggagaaaatgtcccgaccgctcccc ctgaatcccacctttatcccgcctccctac ggcgtgctcaggtccctg |
| 286 | -11 | -9.45 | Metallophos-phoesterase domain containing 2 | NO | extra-genic | atggtggaggatggtagtttcgtcctggg gaaggagggatttattcatatgcaacatc agtaatgcctttcaga |
| 287 | -19 | -9.37 | Thyroid peroxidase | NO | antisense | tccaactttcacgagaagattaagaaaa tccacaaacaatacctgttgttgcaagct cctgtgatgggcctgtatttgttcgccagg ca |
| 288 | -26 | -9.14 | Thyroid peroxidase | YES | exonic | cgctattctgacctcctgatggcatgggg acaatacatcgaccacgacatcgcgttc acaccacagagcaccagcaaagctgc cttcgggggaggggctgactgccagat gacttgtgagaacca |
| 289 | -9 | -9.07 | Zinc finger, matrin type 4 | NO | exonic | cttattttacacatccgaagaaacaccat caca |
| 290 | -16 | -8.91 | Trefoil factor 3 (intestinal) | NO | exonic | agttcatatctggagcctgatgtcttaacg aataaaggtcccatgctc |
| 291 | -3 | -8.86 | Peroxisome proliferator-activated receptor gamma, coactivator 1 alpha | YES | exonic | aagacgtccctgctcggagcttctcaaat atctgaccacaaacgatgaccctcctca caccaaacccacagagaacagaaac agcagcagagacaaatgcacctccaa aaagaagtcccacacacagtcgcagtc acaacacttacaag |
| 292 | -30 | -8.84 | Thyroid peroxidase | NO | extra-genic | gtccctggaaggcaattaaggcgcccat ttcagaagagttacagccgtgaaaatta ctcagc |
| 293 | -6 | -8.84 | Metallothionein 1F | YES | exonic | gctgtgtttgcaaaggggcgtcagagaa g |
| 294 | -55 | -8.64 | Thyroid peroxidase | YES | exonic | tgctgagcatcattgcaaacatgtctgga tgtctcccttacatgctgcccccaaaatg cccaaacacttgcctggcgaacaaata caggcccatcacaggagcttgcaacaa ca |
| 295 | -19 | -8.52 | Thyroid peroxidase | NO | extra-genic | ctcctgggaagagcactcctggcttcctg cagggccggtgggaggaggaaagtga ttctgagggagaggctggagccttaagg accaacaaggcaaagtgacttgtctcat cctccagagattcaccaacacatgagc ctcagaccccaggcttctgcctccagca gccgccctgccgcacactgctcttactcc tccttataccctcactcacggggaacac agcccagtgatcccggaggaaactcac tccctccctgactcaacaaggcagtctc gggggcaccgttagccacgcgaccctg taaagctgccgtcctcatttcacatgtgaa gcagctgaattccagagtgctgggtccc agcccaggcagccctcagcctcacgca aggcaatagttaggagtccttcggcattg aaagcaaactcagacacatctgacctg gagttctacctgcactaagagaagaga gtggtaactaattcatggataaaacaga ccatcgaggcagcactgaatgatctcac ccacgaatgacaacagtggcacagga gggctatgaacattttgcttcaggatgtttt atttcgctctactgttatgtagagaaagca tggtttgctttttataacttttgtgacccaaa aataccagactgtt |

TABLE 5-continued

Thyroid Nodule Disease 36-RNA Expression Signature

| SEQ ID | MFD | Weights | Gene | Probeset Overlaps CDS | Target Sequence Subytpe | Probeset Sequence |
|---|---|---|---|---|---|---|
| 296 | -14 | -8.49 | Metallophos-phoesterase domain containing 2 | NO | exonic | gttagtgttcgccaaaggacagccaag ctttcttttaaaaagtgataaaagtcttatttt aatatgctttaagctgaaagaaaaaaa aataagaaacaggcagtgttttaaaaac caacacagatttgcacaactgtttaaga gtattgtttgaaatattttaattttcaatgtttt gttgttgttgtttttcttggtaatgcttctttttgc agatgtggtcccaatttatagcaatcttct caacagaagtaggcatggaaaagactt cttttcatactctcactataaagaaagctg cattgagaagaaaatggctgtcatttaaa ggatggtttaactagtgagattcctattgtg gttatacaaggtctcattgtttgtttgtttctttt aaattatttcagctttaaaaatacagaaat ggaatctgtcaagagcaggtatttcatac ggttaaaaaaatgaacatgcagactcct tttcaatatgggtttatatatataagtatttttt gtgtattatgactacgttaggagtttattatt gtcaaggacagtacaactgcaaaggg atgctgtatagcaacacatcagaagtcg gaaggaactgacacattctctcagagct caaggtcttaaagagcttgagttaaatct aggtacagttacaggcatgtatagactta aatggatgcaatggaagctaactaaaat aaggcttagttgtcctttctatttaaatacc ccaagttgtcttcttacttcctctcccctctc ccattttgcactgtgtgtcgatgcaatcttc g |
| 297 | -24 | -8.29 | Metallophos-phoesterase domain containing 2 | NO | intronic | gttctgcattgctgataccgctagtggtttt aaaaatagaaatcaaaataagaaccct gatattaaggattcacag |
| 298 | -5 | -8.37 | Thyroid peroxidase | NO | intronic | cccaggccacacaagactcacggctct ccctggtctc |
| 299 | -9 | -8.35 | Metallophos-phoesterase domain containing 2 | NO | intronic | gagctacccagtctacgctattttgttaat agcatctcaaacagcccaaggcaggta ggcagggaatataatgggaagatgaat tttatagagggaacaagaggagaaatg ggcgtatttgtgaaggagagagggaaa aagtaggagggaatatatagcagatgt gtttgtgagatcataactcttccttgtcagtt acgatgtcctgaccttgggcttgactttag caccgggagcaggtcagcatccctaga cttcagtcaacagggagatg |
| 300 | -8 | -8.35 | Solute carrier family 26, member 4 | YES | exonic | tctgggtgtttacgtgtatagtgtccatcatt ctggggctggatctcggtttactagctgg ccttatatttggactgttga |
| 301 | -6 | -8.35 | Zinc finger, matrin type 4 | YES | exonic | catctgcagtgtctccctaaactcaatag aacagtatcatgcccatctgaaa |
| 302 | -7 | -8.33 | Solute carrier family 26, member 4 | YES | exonic | ctggaggacttgatatcccaaccaag gaaatagagattcaagtggattggaact ctgagcttccagtcaaagtgaacgttccc aaagtgccaatccatagccttgtgcttga ctgtggagctatatctttcctggacgttgtt ggagtgagatcac |
| 303 | -13 | -8.27 | Metallophos-phoesterase domain containing 2 | NO | intronic | ctgcatctcttgagaccttgttagaagtgc aagttctttggctccatcctatagccacag aaccttggagtggcttcaagtgactgatg tctaaagtttgagaaacattgcattacag gatgctacttttccagacttggttcttacatt ccataaatatttatcaagtactcaataagt ggcagggactattggagatacagc |

TABLE 5-continued

Thyroid Nodule Disease 36-RNA Expression Signature

| SEQ ID | MFD Weights | Gene | Probeset Overlaps CDS | Target Sequence Subytpe | Probeset Sequence |
|---|---|---|---|---|---|
| 304 | -14 -8.22 | Metallothionein 1G | NO | exonic | ccctgctcccaagtacaaatagagtgac ccgtaaaatccaggat |
| 305 | -6 -8.21 | Solute carrier family 26, member 4 | YES | exonic | accttttccagtggtgagtttaatggtggg atctgttgttctgagcatggcccccgacg aacactttctcgtatccagcagcaatgga actgtattaaatactactatgatagacact gcagctagagatacagctagagtcctg attgccagtgccctgactctgctggttg |
| 306 | -8 -8.16 | Solute carrier family 26, member 4 | YES | exonic | tggtggcttgcagattggattcatagtgag gtacttggcagatcctttggttggtggcttc acaacagctgctgccttccaagtgctggt ctcacagctaaagattgtc |

TABLE 6

7-RNA and 36-RNA POP scores for each of the samples evaluated in the three subsets of patient specimens

| Specimen Number | Study | Cytology Diagnosis | Pathology Diagnosis | Final Review Histology | 7-RNA POP Score | 36-RNA POP Score |
|---|---|---|---|---|---|---|
| 1 | Training Subset | Benign | Benign | Goiter | 21.9 | 0.0 |
| 2 | Training Subset | Benign | Benign | Goiter | 15.9 | 4.1 |
| 3 | Training Subset | Benign | Benign | Goiter | 28.4 | 5.8 |
| 4 | Training Subset | Benign | Benign | Goiter | 22.4 | 7.6 |
| 5 | Training Subset | Benign | Benign | Goiter | 15.9 | 7.8 |
| 6 | Training Subset | Benign | Benign | Goiter | 25.7 | 7.8 |
| 7 | Training Subset | Benign | Benign | Goiter | 12.4 | 8.1 |
| 8 | Training Subset | Benign | Benign | Goiter | 19.9 | 10.8 |
| 9 | Training Subset | Benign | Benign | Goiter | 34.2 | 11.6 |
| 10 | Training Subset | Benign | Benign | Goiter | 27.5 | 11.9 |
| 11 | Training Subset | Benign | Benign | Goiter | 27.3 | 13.1 |
| 12 | Training Subset | Benign | Benign | Goiter | 31.7 | 15.1 |
| 13 | Training Subset | Benign | Benign | Goiter | 30.4 | 18.9 |
| 14 | Training Subset | Benign | Benign | Goiter | 28.6 | 21.5 |
| 15 | Training Subset | Benign | Benign | Hashimoto's | 28.3 | 26.7 |
| 16 | Training Subset | Suspicious for Cancer | Benign | Follicular Adenoma | 34.3 | 16.9 |
| 17 | Training Subset | Suspicious for Cancer | Benign | Follicular Adenoma | 37.6 | 21.8 |
| 18 | Training Subset | Suspicious for Cancer | Benign | Follicular Adenoma | 31.5 | 21.8 |
| 19 | Training Subset | Suspicious for Cancer | Benign | Follicular Adenoma | 52.9 | 40.4 |
| 20 | Training Subset | Suspicious for Cancer | Benign | Goiter | 17.0 | 13.1 |
| 21 | Training Subset | Suspicious for Cancer | Benign | Hurthle Cell Adenoma | 22.8 | 3.5 |
| 22 | Training Subset | Suspicious for Cancer | Benign | Hurthle Cell Adenoma | 28.2 | 11.3 |
| 23 | Training Subset | Suspicious for Cancer | Benign | Hurthle Cell Adenoma | 30.8 | 16.6 |
| 24 | Training Subset | Suspicious for Cancer | Benign | Hurthle Cell Adenoma | 31.6 | 19.8 |
| 25 | Training Subset | Suspicious for Cancer | Benign | Thyroiditis | 25.0 | 11.3 |
| 26 | Training Subset | Cancer | Malignant | Papillary Carcinoma | 73.9 | 63.1 |
| 27 | Training Subset | Cancer | Malignant | Papillary Carcinoma | 64.5 | 63.1 |
| 28 | Training Subset | Cancer | Malignant | Papillary Carcinoma | 72.0 | 71.8 |
| 29 | Training Subset | Cancer | Malignant | Papillary Carcinoma | 82.5 | 77.6 |
| 30 | Training Subset | Cancer | Malignant | Papillary Carcinoma | 78.7 | 79.4 |
| 31 | Training Subset | Cancer | Malignant | Papillary Carcinoma | 84.7 | 84.6 |
| 32 | Training Subset | Cancer | Malignant | Papillary Carcinoma | 86.6 | 90.1 |
| 33 | Training Subset | Cancer | Malignant | Papillary Carcinoma | 100.0 | 91.3 |
| 34 | Training Subset | Cancer | Malignant | Papillary Carcinoma | 83.7 | 94.8 |
| 35 | Training Subset | Cancer | Malignant | Papillary Carcinoma | 85.6 | 94.8 |
| 36 | Training Subset | Cancer | Malignant | Papillary Carcinoma | 91.7 | 95.9 |
| 37 | Training Subset | Cancer | Malignant | Papillary Carcinoma | 91.7 | 96.5 |
| 38 | Training Subset | Cancer | Malignant | Papillary Carcinoma | 86.0 | 100.0 |
| 39 | Training Subset | Suspicious for Cancer | Malignant | Follicular Carcinoma | 52.7 | 34.9 |
| 40 | Training Subset | Suspicious for Cancer | Malignant | Follicular Carcinoma | 58.0 | 38.1 |
| 41 | Training Subset | Suspicious for Cancer | Malignant | Follicular Carcinoma | 68.4 | 69.2 |
| 42 | Training Subset | Suspicious for Cancer | Malignant | Papillary Carcinoma | 32.2 | 20.9 |
| 43 | Training Subset | Suspicious for Cancer | Malignant | Papillary Carcinoma | 77.7 | 69.5 |
| 44 | Training Subset | Suspicious for Cancer | Malignant | Papillary Carcinoma | 88.3 | 77.0 |
| 45 | Training Subset | Suspicious for Cancer | Malignant | Papillary Carcinoma | 73.4 | 79.1 |
| 46 | Training Subset | Suspicious for Cancer | Malignant | Papillary Carcinoma | 87.2 | 89.2 |

TABLE 6-continued

7-RNA and 36-RNA POP scores for each of the samples evaluated in the three subsets of patient specimens

| Specimen Number | Study | Cytology Diagnosis | Pathology Diagnosis | Final Review Histology | 7-RNA POP Score | 36-RNA POP Score |
|---|---|---|---|---|---|---|
| 47 | Training Subset | Suspicious for Cancer | Malignant | Papillary Carcinoma | 87.5 | 93.0 |
| 48 | Training Subset | Suspicious for Cancer | Malignant | Papillary Carcinoma | 85.9 | 96.5 |
| 49 | Follicular Subset | Suspicious for Cancer | Benign | Follicular Adenoma | 26.5 | 12.5 |
| 50 | Follicular Subset | Suspicious for Cancer | Benign | Follicular Adenoma | 21.7 | 13.1 |
| 51 | Follicular Subset | Suspicious for Cancer | Benign | Follicular Adenoma | 19.0 | 14.8 |
| 52 | Follicular Subset | Suspicious for Cancer | Benign | Follicular Adenoma | 32.0 | 17.7 |
| 53 | Follicular Subset | Suspicious for Cancer | Benign | Follicular Adenoma | 34.3 | 22.1 |
| 54 | Follicular Subset | Suspicious for Cancer | Malignant | Follicular Carcinoma | 0.0 | 1.5 |
| 55 | Follicular Subset | Suspicious for Cancer | Malignant | Follicular Carcinoma | 53.1 | 41.0 |
| 56 | Follicular Subset | Suspicious for Cancer | Malignant | Follicular Carcinoma | 75.5 | 65.1 |
| 57 | Follicular Subset | Suspicious for Cancer | Malignant | Papillary Carcinoma | 43.3 | 32.8 |
| 58 | Follicular Subset | Suspicious for Cancer | Malignant | Papillary Carcinoma | 39.9 | 39.5 |
| 59 | Pre-operative Cell Block Subset | Benign | Benign | Goiter | 30.7 | 19.2 |
| 60 | Pre-operative Cell Block Subset | Benign | Benign | Goiter | 22.0 | 20.1 |
| 61 | Pre-operative Cell Block Subset | Suspicious for Cancer | Benign | Hurthle Cell Adenoma | 26.8 | 13.7 |
| 62 | Pre-operative Cell Block Subset | Cancer | Malignant | Papillary Carcinoma | 77.9 | 66.0 |
| 63 | Pre-operative Cell Block Subset | Cancer | Malignant | Papillary Carcinoma | 69.4 | 75.0 |
| 64 | Pre-operative Cell Block Subset | Cancer | Malignant | Papillary Carcinoma | 91.5 | 89.5 |
| 65 | Pre-operative Cell Block Subset | Cancer | Malignant | Papillary Carcinoma | 71.5 | 90.4 |
| 66 | Pre-operative Cell Block Subset | Cancer | Malignant | Papillary Carcinoma | 92.3 | 92.4 |

TABLE 7

Thyroid Nodule Disease SPOCK1-RNA Expression Signature

| SEQ ID | ID | MFD | Weights | Probe Location rel. to Gene | Gene | Probeset Overlaps CDS | Target Sequence Subtype | Probeset Sequence |
|---|---|---|---|---|---|---|---|---|
| 261 | 2876911 | 2.0 | 4.24 | In EXON #11 | Sparc/osteonectin, cwcv and kazal-like domains proteoglycan (testican) 1 | YES | exonic | ctgagggtgcacacccgagccgtgacagagg |
| 657 | 2830194 | -8.6 | -7.06 | In INTRON #6 | Sparc/osteonectin, cwcv and kazal-like domains proteoglycan (testican) 1 | NO | antisense | atgaactccctcgtggcggccgaaggcctgg |
| 658 | 2830301 | -1.2 | -3.02 | In INTRON #3 | Sparc/osteonectin, cwcv and kazal-like domains proteoglycan (testican) 1 | NO | antisense | ttatttcgtgtgtgtctcttggctctgtag |
| 659 | 2830378 | 1.8 | 4.94 | In INTRON #2 | Sparc/osteonectin, cwcv and kazal-like domains proteoglycan (testican) 1 | NO | antisense | tgcttgcacccacagtccatagacatccaaccgcccaatgcatatccaacctcagcaactttacaatccccaacgccagcccacaacttgactttta |

The embodiments of the invention in which an exclusive property or privilege is claimed are defined as follows:

1. A method, comprising:

(a) assaying by sequencing, array hybridization or nucleic acid amplification the expression level of each of a first group of transcripts and a second group of transcripts in a fine needle aspirate test sample from a thyroid nodule of a subject, wherein said first group of transcripts includes least two transcripts corresponding to at least two sequences selected from SEQ ID No. 1-4 and 8-282, and said second group of transcripts includes at least two transcripts corresponding to at least two sequences selected from SEQ ID No. 5-7 and 283-659; and (b) in a programmed computer, comparing said expression level of each of said first group of transcripts and second group of transcripts with reference expression levels of transcripts corresponding to sequences as set forth in SEQ ID No. 1 to 659 to (1) classify said thyroid nodule as malignant if there is an increase in an expression level corresponding to said first group or a decrease in an expression level corresponding to said second group, or (2) classify said thyroid nodule as benign if there is an increase in said expression level corresponding to said second group or a decrease in said expression level corresponding to said first group.

2. The method of claim 1, wherein an increased relative level of expression of one or more transcripts, a decreased relative level of expression of one or more transcripts, or a combination thereof is used to classify the thyroid nodule as malignant.

3. The method of claim 1, wherein an increased relative level of expression of one or more transcripts, a decreased relative level of expression of one or more transcripts, or a combination thereof is used to classify the thyroid nodule as benign.

4. The method of claim 1, wherein said assaying comprises determining the expression level by a method selected from the group consisting of RT-PCR, Northern blotting, ligase chain reaction, and a combination thereof.

5. The method of claim 1, further comprising measuring the expression level of at least one control nucleic acid in the test sample.

6. The method of claim 1, wherein the test sample is fresh-frozen or fixed.

7. The method of claim 1, wherein the expression level is measured by pattern recognition.

8. The method of claim 7, wherein said pattern recognition comprises a linear combination of expression levels of the target sequences.

9. The method of claim 1, wherein (b) comprises using said programmed computer to (1) classify said thyroid nodule as malignant if there is an increase in an expression level corresponding to said first group and a decrease in an expression level corresponding to said second group, or (2) classify said thyroid nodule as benign if there is an increase in said expression level corresponding to said second group and a decrease in said expression level corresponding to said first group.

10. The method of claim 1, wherein said assaying is by nucleic acid amplification using at least two primers that each amplify a transcript corresponding to a sequence as set forth in any one of SEQ ID No. 1 to 659.

11. The method of claim 1, further comprising (c) based upon a classification of said thyroid nodule as malignant or benign, (i) designating a treatment modality for said subject or (ii) generating a report that designates said thyroid nodule as malignant or benign.

12. The method of claim 11, wherein said treatment modality is selected from the group consisting of total thyroidectomy, near-total thyroidectomy, partial thyroidectomy, cosmetic debulking, radioactive iodine treatment, watchful waiting, thyroid hormone suppression therapy, total or near-total thyroidectomy followed by radioactive iodine ablation therapy and permanent thyroid hormone replacement therapy, or a combination thereof.

13. The method of claim 1, wherein said first group of transcripts includes a sequence as set forth in any one of SEQ ID No. 1-4, 8-12 and 261.

14. The method of claim 1, wherein said second group of transcripts includes a sequence as set forth in any one of SEQ ID No. 5-7, 283-306, 657, 658 and 659.

* * * * *

SEQUENCE LISTING

<160> NUMBER OF SEQ ID NOS: 659

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3420365

<400> SEQUENCE: 1
attctttgga gttgcgtcat taggagcttt acagtaagat atcttactag ccaatattag 60
cctgccacag g 71

<210> SEQ ID NO 2
<211> LENGTH: 92
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3696401

<400> SEQUENCE: 2
gggcaaccta ggcacactca gtataaaaac gcagagatcc atccgaatgg gaggcattgg 60
ggtctggaaa ccagaaatgc aggacggcca gt 92

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3577628

<400> SEQUENCE: 3
ctgcctctcg ctcctcaacc cctccc 26

<210> SEQ ID NO 4
<211> LENGTH: 122
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3415760

<400> SEQUENCE: 4
tggagctgtc atcactcaac aaaaaaccga ggccctcaat ccaccttcag gccccgcccc 60
atgggcccct caccgctggt tggaaagagt gttggtgttg gctggggtgt caataaagct 120
gt 122

<210> SEQ ID NO 5
<211> LENGTH: 647
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2537615

<400> SEQUENCE: 5
agcctgtgag tatcccggcc ttccatccca gcactctcct gcaaaaatgc agaacaaaca 60
ttaataacgt ctgaattctg actgctccag taacagcaca cacttgatac aagacagaag 120
ggcctggaca ggagctcttt tcacaaagga ccgctggcga gatgagccat ccttcttgct 180
tgtcatgctg gagggaagtt tctggcttcc ggacaaatgc ttgtttgcag gaggccacag 240
aggatccacg tggcaaaggt tcctactcac agagtgggat ctgcaatccg caggcagggt 300
ccttcaggaa gaagccgtgc tgagcacaca ggtccctgcg accacagatg aacagaacgc 360
ctggccttgc ccctggtgtc agtcagacta attaggggcc caggggactt gctggcactg 420
cccttgctgt ggctggaaaa gctatttaaa ttcacaaaga gcctcacttc caggccaggt 480
ccttttggtt ccatgcgtgg gagccaggtg caaagacgaa tgtgctctca gcagaacgac 540
cctgggctct gcttatctcc gaggacagga tctaatctca cactgaattt cagaagggag 600
accgatcatg ttggcaatgc ccccctcctg tatgcaagta agtgact 647

<210> SEQ ID NO 6
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2727648

<400> SEQUENCE: 6
aagcccatga gtccttgaaa atatttttta tatatacagt aactttatgt gtaaatacat 60
aagcggcgta agtttaaagg atgttggtgt tccacgtgtt ttattcctgt atgttgtcca 120
attgttgaca 130

<210> SEQ ID NO 7
<211> LENGTH: 228
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367706

<400> SEQUENCE: 7
ttttgcctgc acattctgag agagccattt ggcaaacaac aataataaat ttacatttgg 60
atggtgtatt tcactcagag aactttcata tgtattatct catttggggc tcacaacaat 120
tctttaacca gggtatgtat tactaataat aattaacaat agccagcatt tacagtgttt 180
atatgtcaac tgctgttcat tattgcctcc ttttgacaga gaccaaca 228

<210> SEQ ID NO 8
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2828473

<400> SEQUENCE: 8
tgctcccacg cctgcttctt aaggtccctg ctcggccggt gtaaatatgt ttcaccctgt 60
ccctctaata aagctcctct gc 82

<210> SEQ ID NO 9
<211> LENGTH: 305
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2414960

<400> SEQUENCE: 9
gacaacccgg gatcgtttgc aagtaactga atccattgcg acattgtgaa ggcttaaatg 60
agtttagatg ggaaatagcg ttgttatcgc cttgggttta aattatttga tgagttccac 120
ttgtatcatg gcctacccga ggagaagagg agtttgttaa ctgggcctat gtagtagcct 180
catttaccat cgtttgtatt actgaccaca tatgcttgtc actgggaaag aagcctgttt 240
cagctgcctg aacgcagttt ggatgtcttt gaggacagac attgcccgga aactcagtct 300
attta 305

<210> SEQ ID NO 10
<211> LENGTH: 437
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526829

<400> SEQUENCE: 10
acgcccagga ctatttgaac tgatgaaata tccaaatgtc cagtcctata gcctacttac 60
acctaagtga acactacagc gaagtgttca gtgaacagac cttgagaagg tctgtaatta 120
gatgataagg aagggtcacc ttgccccatg gcctctcgaa gccctccatt ccacctgtga 180
gtgtgactca gctggatttc gagtgggatg aagttgctgc aacagctgga tatttctcgc 240
atccacctga gagtatgtct ctggagggca catgataatc cttgctgtgg tgctgtggat 300
tgccatttat gcctcacaac aaccctggaa ggtagtttgc tccttttaaa agcaatttct 360
tgtcatacaa cgtactgcat atctttaaag tgatgggttt ttacatatgt gtgacttggg 420
agaccatcac cgcattc 437

<210> SEQ ID NO 11
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526817

<400> SEQUENCE: 11
cttcaaggac aaatcgtaaa ggtagtgttt tagacttctg cacacaaatg gaaattcagg 60
tagaatatct ttcttttcta gaatcatcta tcttactcaa aaagg 105

<210> SEQ ID NO 12
<211> LENGTH: 215
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598305

<400> SEQUENCE: 12
gtctgaatgc ccacgacatg tcttttgcaa ttacacatag ggaaagtgaa cttgttggtt 60
agtttatgtc ttgagctgag ccctttacga acatcttttt tccttctcag tgccaagcga 120
ggaatttaca gagaaagaag ttgtgaaacc accatagtta gttgctgtgc tttgaatttc 180
ttttgctcaa atggcctcag cgaaatctta tttgc 215

<210> SEQ ID NO 13
<211> LENGTH: 739
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2338243

<400> SEQUENCE: 13
tctcctcggg taggccatga tacaagtgga actcatcaaa taatttaaac ccaaggcgat 60
aacaacgcta tttcccatct aaactcattt aagccttcac aatgtcgcaa tggattcagt 120
tacttgcaaa cgatcccggg ttgtcataca gatacttgtt ttttacacat aacgctatgc 180
catcccttcc ttcactgccc cagtcaggtt tcctgttgtt ggaccgaaag gggatacatt 240
ttagaaatgc ttccttcaag acagaagtga gaaagaaagg agaccctgag gccaggatct 300
attaaacctg gtgtgtgcgc aaaagggagg gggaaggcag gaatttgaaa ggataaacgt 360
ctcctttgcg ccgaggaatc aggaagcgtg actcacttgg gtctgggacg ataccgaaat 420
ccggtacccc accccatccc ctgccccgcc gggtacctac aagctcggtt cctttctcaa 480
ctcccccagt tccttgatct ccaccttctt gtacttcccc gactttctcc ggttggtgat 540
caccaggacg gccatgccgg cgacgagggc caccacgacc accacgatga cggcgatgag 600
gccggcggtg aggcgcttca tggagaactt cgggggaatc tcgtccaggt aatagatgag 660
cgtgcgctcc acctgcaggg gttctccgcg cacgcgcaag tccaggccgc cgcggccctg 720
gaatagagac tcgcccttg 739

<210> SEQ ID NO 14
<211> LENGTH: 169
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598348

<400> SEQUENCE: 14
gaatcgtgtc tttctcattg gctcaatgta gtctccgtag agtctagaat gcttcagcac 60
ctggcacact gcttaacaaa tggtgaatga aaaaaaaaaa aagaaaagtc attctttttc 120
ttctttcacc ctatgtccat aatctggcca tttgcagaac ttgatgtcc 169

<210> SEQ ID NO 15
<211> LENGTH: 865
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598349

<400> SEQUENCE: 15
gtcttctata ctcagccagg ttatcaatca aatatgaggg caaaataata ttttcagaca 60
gattttaggc agtttatctt ccatatatcc ttttctttaa gggtatttgt agatacactc 120
cagaaaaaca agagtgaaat atgaaggaag ttgtggggtc cagcaaacag tgcttccaaa 180
tcagacccct gatagaggtg gaaaactttg caatgcaaca actgcgtagc tggcttagag 240
gacagccaat acagatggaa cagaaagatg aggatgggat tgagggatca gggattgagg 300
tctccaagaa taaaaaggga cttcatggaa aaagtaggct tgtggataat taatcacagg 360
ggcaaataat gcagttaaaa taacaacatg acaatcaggt ggaggaatgt ataataaacc 420
caaatgtggc tgggtagagt ggctcacacc tgtaatccca gcactttggg aggccaagcc 480
gggcagatta cctgaggtca ggagttcgag accagcttgg ccaacatggc gaaaccccgt 540
ctctactaaa aatacaaaaa ttagccaggc ttgggggcgc acgcctgtag tcccagctcc 600
tcaggagctg aggtaggaga atcacttgaa cccaggaggc aaaggttgca gggagttgag 660
ccaagatcgc gccattgcac cctagcctgg gcaacagagc gagattctgt ttcaaaaaac 720
ccccaagtgt attataaggc aataattcct atacgaagca aactaaaatg cagcaatatt 780
aaggtataaa aacaaagagg aataattcca ttgaaccttg attctggaaa ctttgatcca 840
cccagcagtc atgatgttag actca 865

<210> SEQ ID NO 16
<211> LENGTH: 131
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598307

<400> SEQUENCE: 16
ttgacaaacc atcccagatg caagtgaccg atgttcagga caacagcatt agtgtcaagt 60
ggctgccttc aagttcccct gttactggtt acagagtaac caccactccc aaaaatggac 120
caggaccaac a 131

<210> SEQ ID NO 17
<211> LENGTH: 541
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2562439

<400> SEQUENCE: 17
ccgtccttta aagtgctgca gtatggccag acgtggtggc tcacacctgc aatcccagca 60
ccttaggagg ccgaggcagg aggatccttg aggtcaggag ttcgagacca gcctcgccaa 120
catggtgaaa ccccatttct actaaaaata caaaaaatta gccaagtgtg gtggcatatg 180
cctgtaatcc caactactca gaaggccgag gcaggagaat tacttgaacg caggagaatc 240
actgcagccc aggaggcaga ggttgcagtg agccgagatt gcaccactgc actccagcct 300
gggtgacaga gcaagactcc atctcagtaa ataaataaat aaataaaaag cgctgcagta 360
gctgtggcct caccctgaag tcagcgggcc caggcctacc tcactctctc ccttggcaga 420
gaagcagacg tccatagctc ctctccctca caagcgctcc cagcctgccc tccagctgct 480
gctctcccct cccagtctct actcactggg atgaggttag gtcatgagga caccaaaaac 540
c 541

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3577632

<400> SEQUENCE: 18
gggtcaactg ggcatcacta aggtcttcag caatggggct gacctctccg gggtcacaga 60

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2401582

<400> SEQUENCE: 19
ggggcaaggc tctggcacaa aacctcctcc tcccaggcac tcatttatat tgctct 56

<210> SEQ ID NO 20
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598368

<400> SEQUENCE: 20
gccaccgcgc ttagcctgtt tttagttttc taaagcaagg tccctattga aaggcaggcc 60
ataaacagtg atgactaaga aaaatcctgg aagagcctga gaaggaaaaa gatgaaatat 120
aatgccagag aatgaagtta gtcaaaggaa cagtgtgaaa acaataaata aatagataaa 180
tgaaaatgtt atttgacaga gagatgaaac tagactaaac cattcagctg cctttccact 240
gtaacaaatg taatttcatc tttcagaagt gtaatacctt gcagcaccag agctgaatat 300
gaacatatta ccaaaaatag attaccaggc atagatagca ttcctttttt aagtttgaat 360
tgaccacttg cgactctcga cctgatgtat gta 393

<210> SEQ ID NO 21
<211> LENGTH: 86
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598282

<400> SEQUENCE: 21
tttaaactcc ttattcccag cagcagtatt ctacattcta accaggttct cccagctttg 60
agacgtctca gacttaccag ttctcc 86

<210> SEQ ID NO 22
<211> LENGTH: 221
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3549675

<400> SEQUENCE: 22
ccaggaactt ggtgatgata tcgtgggtga gttcattttc caggtgctgt agtttcccct 60
catcaggcag gaagaagatg gcggtggcat tgcccaggta tttcatcagc agcacccagc 120
tggacagctt cttacagtgc tggatgttaa acatgcctaa acgcttcatc ataggcacct 180
tcacggtggt cacctggtcc acgtggaagt cctcttcctc g 221

<210> SEQ ID NO 23
<211> LENGTH: 260
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526824

<400> SEQUENCE: 23
tgtctccacg gccagtgaca gcatacacag tgatggtata atcaactcca ggtttaaggc 60
cgctgatggt agctgtagac ttgctcccag gcacagtgaa ctcctggaca gggctatttc 120
ctcctgtatg aaaaagggtt agttcagagt gtgaggggtt tagagctact tgggtattac 180
tgattaattg aattaccaca tttatagcag catgtaaatc acatcttctt gcttattccc 240
ttttaaagag cgctatcttg 260

<210> SEQ ID NO 24
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598340

<400> SEQUENCE: 24
tgatgcccct cctgacacga ctgtggacca agttgatgac acctcaattg ttgttcgctg 60
gagca 65

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598328

<400> SEQUENCE: 25
gcaaaccctg acactggagt gctcac 26

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3460512

<400> SEQUENCE: 26
gtaccaccag ccctaatcag catcaaacaa aaatatcccc aagagtattc tatgagttga 60

<210> SEQ ID NO 27
<211> LENGTH: 389
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598278

<400> SEQUENCE: 27
ggagcgggga tgtcaagttc atttatgtga ctctttggct caacttacat aatctttgtt 60
ttgatatcac agttgtctaa ttattttact ttgtagctta aggcaggctg aattgttgat 120
aaaatggaaa aagtagtata ttgttatata agcttctgag gtgtgttttg ttgtataagc 180
cctggaggtt aaaaagtcat cccttatgta tagtagttaa aggcataaaa ctgtgacttt 240
tagatattcc acagaaccag acttatttga tgtggataat aaccaatgat ttagcatttt 300
gtttgctttt gttttatttt atccgggttc attttttact cttcccatgt acatgaaaca 360
ggtggtggcg tgtagagatc agctgatcc 389

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3976357

<400> SEQUENCE: 28
cttccagtcc cgtcaccttg cctgcct 27

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Affymetrix ID 3335899

<400> SEQUENCE: 29
ggcacttcag gtccgtgggc cgtatctgtc acaataaat 39

<210> SEQ ID NO 30
<211> LENGTH: 143
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598367

<400> SEQUENCE: 30
atgcaacgat caggacacaa ggacatccta tagaattgga gacacctgga gcaagaagga 60
taatcgagga aacctgctcc agtgcatctg cacaggcaac ggccgaggag agtggaagtg 120
tgagaggcac acctctgtgc aga 143

<210> SEQ ID NO 31
<211> LENGTH: 150
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598338

<400> SEQUENCE: 31
gacagacgtg aaggtcacca tcatgtggac accgcctgag agtgcagtga ccggctaccg 60
tgtggatgtg atccccgtca acctgcctgg cgagcacggg cagaggctgc ccatcagcag 120
gaacaccttt gcagaagtca ccgggctgtc 150

<210> SEQ ID NO 32
<211> LENGTH: 112
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598326

<400> SEQUENCE: 32
gcccacacat atggatgacc actagcaagt gtaatgatct caatatttat ttctcattca 60
gttgggtttc cttgtatttg ccacattagt gtttaccctg ttcctaatgg ca 112

<210> SEQ ID NO 33
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598299

<400> SEQUENCE: 33
caagaagggc tcgtgtgaca gatgctactg agaccaccat caccattagc tggagaacca 60
agactgagac gatcactggc ttccaagttg atgccgttcc agcca 105

<210> SEQ ID NO 34
<211> LENGTH: 179
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3549673

<400> SEQUENCE: 34
ggtgggattc accacttttc ccatgaagag gggagacttg gtattttgtt caatcattaa 60
gaagacaaag ggtttgttga acttgacctc ggggggggata gacatgggta tggcctctaa 120
aaacatggcc ccagcagctt cagtcccttt ctcgtcgatg gtcagcacag ccttatgca 179

<210> SEQ ID NO 35
<211> LENGTH: 139
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598346

<400> SEQUENCE: 35
tggaaggaag ctaccatacc aggccactta aactcctaca ccatcaaagg cctgaagcct 60
ggtgtggtat acgagggcca gctcatcagc atccagcagt acggccacca agaagtgact 120
cgctttgact tcaccacca 139

<210> SEQ ID NO 36
<211> LENGTH: 125
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598372

<400> SEQUENCE: 36
ccatgaaggg ggtcagtcct acaagattgg tgacacctgg aggagaccac atgagactgg 60
tggttacatg ttagagtgtg tgtgtcttgg taatggaaaa ggagaatgga cctgcaagcc 120
catag 125

<210> SEQ ID NO 37
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598281

<400> SEQUENCE: 37
tcaacgaagg cttgaaccaa cctacggatg actcgtgctt tgacccctac acagtttccc 60
attatgccgt tggagatgag tg 82

<210> SEQ ID NO 38
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598374

<400> SEQUENCE: 38
atcaacagtg ggagcggacc tacctaggca atgcgttggt ttgtacttgt tatggaggaa 60
gccgaggttt taactgcgag agta 84

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598329

<400> SEQUENCE: 39
cattgtctcc accaacaaac ttgcatctgg ag 32

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598352

<400> SEQUENCE: 40
gctcaagtgg tcctgtcgaa gtatttatca ctgagactcc gagtcagccc aact 54

<210> SEQ ID NO 41
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2400179

<400> SEQUENCE: 41
gaaatttatt actagcttgc tacccacgat gaaatcaaca acctgtatct ggtatcaggc 60
cgggagaca 69

<210> SEQ ID NO 42
<211> LENGTH: 1102
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2324040

<400> SEQUENCE: 42
cagctggtgt gccttaagag aatccctata aataacagaa aagacactcc aagcattcct 60
gtacgtggac tcagagcaca gagaaaagaa actaaaatgc cttttggcat ttcaagatat 120
ttggcactct tgtgattaca ttttttttaca gtccattaaa gagaataaac tgacataata 180
ttagagaaat aaacaggctg ctcacacaac agactgcaag gggaagttag aaaaagctca 240
agcatttttt tctttgtttt tcgtgtgtgt gtgtgtgtgt gtgtgtgtgt gtgtgtgttt 300
ttctgacata aaaaatgtgt ccatttgcat taacttgggc agatagcttg cagcaacaaa 360
gaaacacaag ctttacaact cattttaaaa taaaatcttt tctatgtatc attccttaga 420
aaagttctct tcttgtttta aacacattcc tgataacttc taaagatgac caaaataaaa 480
cagaatatct acagagatca ttttctgaat tttttgtaca tccaaggata acaacataaa 540
aaaaataaaa ctggacagca tttcacatcc aagtgcacag aaccattttt gcaagattaa 600
ataatgtaaa cattgggaac agccaaatca gcgaagaatg ccaacacctc aaaacacctg 660
gtgttgccgc ttcattaagt ggttcaaaat ccagatctat aattgcgcaa tattcaccgt 720
atataaaaag aaatggatat taattttgac aaatagctgc aactgagact tctttttatt 780
tctttatatg tgtatatagt gaatttttat tatttttaaa attttattta tttttttatt 840 tttattttg cagaggagcc cagagccttc tcctcctcct cctcctcctc tcgcctcatc 900
tgtctcccgg cctgatacca gatacaggtt gttgatttca tcgtgggtag caagctagta 960
ataaatttca aagtgctttc tcttttcatg ctttttgcca ataactgtta ccgccgttct 1020
tattctctcc cttaactcat tgtctttggg ggagttagac accaggaggt gccttgtcgg 1080
tcatattttt cagcacgtca tc 1102

<210> SEQ ID NO 43
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2375629

<400> SEQUENCE: 43
taggataggg gacacgatta cgttcctaag tgaaggtttc aagctgggct ttgcaggggg 60
tataattagt atggtcactg tgtcttgtag gatgtttggc tccttggtga tagagcttgc 120
caaaatggtg tcctttgata aggagggctg gggggcaggg agttgaagaa attcccttgc 180
caggcttggg gatctgtaaa catttccatt aatcaacaag tgtgtactaa tcccgagtct 240
tacattgcga tgcctcacta tccccacagc cccatcccta cctctctgcc caccagggct 300
gagctcaaat ctgtgtgttg tggacctctg cataggccc 339

<210> SEQ ID NO 44
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598342

<400> SEQUENCE: 44
tccaagcaca gccacttctg tgaacatccc tgacctgctt cctggccgaa aatacattgt 60
aaatgtctat cagatatctg aggatgggga 90

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3577630

<400> SEQUENCE: 45
ccgtgcataa ggctgtgctg accatcgacg agaaagggac tgaagct 47

<210> SEQ ID NO 46
<211> LENGTH: 603
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526820

<400> SEQUENCE: 46
gcctctgctc aaattagacc taatggaact gaaatgtgca gtctttctct ttctctcttt 60 ctttttaaa tttgagaagc aagttgtagg aagtagaatc cagactaatc atatcagtgt 120
cataagtatg agaattacag aggtttggct caacagtttt tcatggtttg aaatggtaaa 180
aatagataaa acacacatgt tcatttttga aattttccta tatcaggaat acacattttc 240
ttgaaattaa ctgaaactgg atgcaaaagt aagacattat ttagctctaa gttgtagaaa 300
ccaaataaag ataaatgtga gaggtttctc tccctccttt aaaaaaggaa acattttaaa 360
attcaacaga aggtataaaa gaagagcaat gatagctctt cttttacatt ttaacatctt 420
gtttgaattt ttaaaaggtg aataacaagg ctttatattg agtggctgta gtaaagaaaa 480
aaaataaaac caaactctgc agtgcatgtt aaattatttc tcctattaaa gaatacaata 540
tatacactat gctgttagat aaaaaaaatc acaagaaatg catcaaaaca tggagaacct 600
ttt 603

<210> SEQ ID NO 47
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598358

<400> SEQUENCE: 47
catctttggt gcagcacaac ttcgaattat gagcaggacc agaaatactc tttctgcaca 60
gacca 65

<210> SEQ ID NO 48
<211> LENGTH: 148
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598321

<400> SEQUENCE: 48
ttgggtaccg catcacagta gttgcggcag gagaaggtat ccctattttt gaagattttg 60
tggactcctc agtaggatac tacacagtca cagggctgga gccgggcatt gactatgata 120
tcagcgttat cactctcatt aatggcgg 148

<210> SEQ ID NO 49
<211> LENGTH: 181
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598302

<400> SEQUENCE: 49
ctattcctgc accaactgac ctgaagttca ctcaggtcac acccacaagc ctgagcgccc 60
agtggacacc acccaatgtt cagctcactg gatatcgagt gcgggtgacc cccaaggaga 120
agaccggacc aatgaaagaa atcaaccttg ctcctgacag ctcatccgtg gttgtatcag 180
g 181

<210> SEQ ID NO 50
<211> LENGTH: 192
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3536718

<400> SEQUENCE: 50
tcagcactta gtccagattc tggggagaag tttgatgatg gtccttgaat atttagcact 60
tagaagtgct aggaggatgc ctcactaagt tacgtaagaa gcagaagagg acgagtaccg 120
cctgatggat tgaccccgaa aactagctgt gtccaagtag aataggtgtc tcgctctgtt 180
aagcggtctt ta 192

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598289

<400> SEQUENCE: 51
cttcatggac cagagatctt ggatgttcct tcca 34

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3976358

<400> SEQUENCE: 52
agtccctgcg gtcccagata gcctga 26

<210> SEQ ID NO 53
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3335898

<400> SEQUENCE: 53
aagctgcgct gtgactttga ggtccttgtg gttccctggc agaactcctc tcagctccta 60
aagcacaact gtgtgcagat gt 82

<210> SEQ ID NO 54
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598296

<400> SEQUENCE: 54
ttacaaccag gcactgacta caagatctac ctgtacacct tgaatgacaa tgctcggagc 60
tcccctgtgg tcatcgacgc ctccactg 88

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598271

<400> SEQUENCE: 55
tgttaattgc ccaattgagt gcttcatgcc tt 32

<210> SEQ ID NO 56
<211> LENGTH: 353
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526809

<400> SEQUENCE: 56
ttcctacagt attgcgggcc agacacttaa gtgaaagcag aagtgtttgg gtgactttcc 60
tacttaaaat tttggtcata tcatttcaaa acatttgcat cttggttggc tgcatatgct 120
ttcctattga tcccaaacca aatcttagaa tcacttcatt taaaatactg agcggtattg 180
aatacttcga agcagaacag gcaatgtgca gccctcattt atgagaaaac cctcaggaaa 240
ctcccagggt gatgcttgga gaagctgtga gttgagctga agctggagaa cttcctccag 300
agcaaagggc ttaagaaaga aagaagaact ctaagctggg tctgctaaca tca 353

<210> SEQ ID NO 57
<211> LENGTH: 28
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598277

<400> SEQUENCE: 57
gatggtgcca tgacaatggt gtgaacta 28

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598280

<400> SEQUENCE: 58
aaactgttgt gccagtgctt aggctttgga agtggtca 38

<210> SEQ ID NO 59
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2562441

<400> SEQUENCE: 59
ttgattgaaa gtcctagggt gattctattt ctgctgtgat ttatctgctg aaagctcagc 60
tggggttgtg caagctaggg acccattcct gtgtaataca a 101

<210> SEQ ID NO 60
<211> LENGTH: 559
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598320

<400> SEQUENCE: 60
acatagatgg tgttgcatgc tgccaccagt tactccggtt aaatatggat gtttcatggg 60
ggaagtcagc aattggccaa agattcagat agggtggatt ggggggataa ggaatcaaat 120
gcatctgcta aactgattgg agaaaaacac atgcaagtat tcttcagtac actctcattt 180
aaaccacaag tagatataaa gctagagaaa tacagatgtc tgctctgtta aatataaaat 240
agcaaatgtt cattcaattt gaagacctag aatttttcgt cttaaatacc aaacacgaat 300
accaaattgc gtaagtacca attaattata agaaatatat caccaaaatg taccatcatg 360
atcttccttc taccctttga taaactctac catgctcctt ctttgtagct aaaaacccat 420
caaaatttag ggtagagtgg atgggcattg ttttgaggta ggagaaaagt aaacttggga 480
gcattctagg ttttgttgct gtcactaggt aaagaaacac ctctttaacc acagtctggg 540
gacaagcatg caacatttt 559

<210> SEQ ID NO 61
<211> LENGTH: 39

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3460465

<400> SEQUENCE: 61
cagtatgttc attctgctct tgtgactaca gtctttttg 39

<210> SEQ ID NO 62
<211> LENGTH: 222
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598313

<400> SEQUENCE: 62
ccaactggca ttgacttttc tgatattact gccaactctt ttactgtgca ctggattgct 60
cctcgagcca ccatcactgg ctacaggatc cgccatcatc ccgagcactt cagtgggaga 120
cctcgagaag atcgggtgcc ccactctcgg aattccatca ccctcaccaa cctcactcca 180
ggcacagagt atgtggtcag catcgttgct cttaatggca ga 222

<210> SEQ ID NO 63
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598354

<400> SEQUENCE: 63
tgacatcact tacaatgtga acgacacatt ccacaagcgt catgaagagg ggcacatgct 60
gaactgtaca tgcttcggtc aggg 84

<210> SEQ ID NO 64
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598286

<400> SEQUENCE: 64
caagaagctc tctctcagac aaccatctca tgggccccat tccaggacac ttctgagtac 60
atcattt 67

<210> SEQ ID NO 65
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2526813

-continued

<400> SEQUENCE: 65
tttccgttcc caagacatgt gcagctcatc atctggccat tttctccctg acggtcccac 60
ttctctccaa tcttgta 77

<210> SEQ ID NO 66
<211> LENGTH: 480
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598332

<400> SEQUENCE: 66
ctacattcta ttactttggg cattgaatag taactataaa tgcagaataa aaatatctat 60
ggattgaatg ggaaccaact aattgaacat gaagccaagg aaatgatttc tttatgagtg 120
ttggctgcag aagattaaag tacttttgca gacggaatcg ctcttttctt aaattactct 180
tgaaattcct cagaggagaa aaatactaac aataattttt ggtcatgtct atccttttgc 240
tcaacatttt aaaggaagtg gtcttaaatc tcccacatat ctacatcaca ataacaacct 300
ctattcacaa accgattcct attaaataca tttccattta cattacagag aattatgaga 360
ctccttattt ctagctgaac atcatttgtt attttcaact cgacattttg aattatagaa 420
gcacctaaca taagtacttt ttcagcatat attctaacca tggactagtt tgcaattttc 480

<210> SEQ ID NO 67
<211> LENGTH: 145
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598356

<400> SEQUENCE: 67
ggaaatctgc acaaccaatg aaggggtcat gtaccgcatt ggagatcagt gggataagca 60
gcatgacatg ggtcacatga tgaggtgcac gtgtgttggg aatggtcgtg gggaatggac 120
atgcattgcc tactcgcagc ttcga 145

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598267

<400> SEQUENCE: 68
gttctgcttc gaagtattca ataccgctca gtatt 35

<210> SEQ ID NO 69
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598365

<400> SEQUENCE: 69
tttccgcaaa tccatctttc ctttgacatg ccatttgagg ataatttgca gtgtttcagc 60
taataaccta agata 75

<210> SEQ ID NO 70
<211> LENGTH: 821
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3270357

<400> SEQUENCE: 70
ggccacctgc tatacagttg ttaaatctta aatatgcttt ttaaaaattg gaataatgta 60
ttaaggtcaa ataatatccc ataaaatata tatttctgct aatattagta aatatcttaa 120
tttttcatta gattcatatc atttaatttc acatattcaa cacctttaaa tgttgtaatc 180
ttaatatgcg aagtgtgcct ctgcaagata ctaacacaaa gctcatgtta agaaaacagt 240
tgaggactca gaagtcagtt cgaaaatgca ctttcctaac agtgaattca caaccctgaa 300
cagcagcatt tttggaaggc aaactgttcg tgatggtaca atgtaaatgg ggacttctgt 360
aaagttctca gtttcggtcc atgtggttta tctttacatt ttaaagatca aagaagtctt 420
tacaacctga atccaggtct aaaacacact agagtagctg gtgactataa ataatatttt 480
aaaatgctgt gtctacacca tcaagactgt gtctacacta tcttggctga acgagaagag 540
atgtaaatgc tgggtggtcc cgttgaccca cggcgttggg tacaacaaaa ccagccatcg 600
gagttacacc ccaaagcacc atttgctgtc cagctgcctg tcgtttggcc cagaccaccc 660
tcagaaaaaa accagctgcc tctcccattc tcccctcccg ttctgccaca gcggcctggg 720
ctggtccagt gctatgcctg gaggctcaac acaaaacttc ccatccaaac attcagatga 780
actgagcgtc ttacacacgc agtacagagg agcacacatt a 821

<210> SEQ ID NO 71
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2598301

<400> SEQUENCE: 71
gtgagtgtct atgctcttaa ggacactttg acaagcagac cagctcaggg agttgtcacc 60
actct 65

<210> SEQ ID NO 72
<211> LENGTH: 110
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598371

<400> SEQUENCE: 72
gacttcctat gtggtcggag aaacgtggga gaagccctac caaggctgga tgatggtaga 60
ttgtacttgc ctgggagaag gcagcggacg catcacttgc acttctagaa 110

<210> SEQ ID NO 73
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2685324

<400> SEQUENCE: 73
tttcaaactg ggttattcac tgctgcacgt cag 33

<210> SEQ ID NO 74
<211> LENGTH: 230
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3536724

<400> SEQUENCE: 74
ggtcattgtc tttcctgtct cagtagtaat caatcactgc ttatcttcaa aaacccagag 60
taggggatgg ggcagttagt ggggacagag ggcagatggg taagattcag agcacaggct 120
agtgtgacgg aagtttaaac ttgtgagtta aatagggttt ggcaatctag ctggatagca 180
tccctgcccc ttgaagagat gtttttgtgg cgccacacta ctgacttagg 230

<210> SEQ ID NO 75
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3451841

<400> SEQUENCE: 75
gcacagctgt gccaatgata ccatttgctt caatttggat ggcggatatg attgtcgatg 60
tcctcatgga aagaattgca caggggact 89

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2598270

<400> SEQUENCE: 76
ctgacagaga agattcccga gagtaa 26

<210> SEQ ID NO 77
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598288

<400> SEQUENCE: 77
cacccaccct gggtatgaca ctggaaatgg tattcagctt cctggcactt ctggtcagca     60
acccagtgtt gggcaacaaa tgatctttga ggaacatggt tttaggcgga ccacaccgcc    120
cacaacggcc acccccataa ggcataggcc aagaccatac ccgc                     164

<210> SEQ ID NO 78
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2827683

<400> SEQUENCE: 78
tttcagcaag ccagttttgg agtgactgca agaagtatga tgtgactgtg tttcagtata     60
ttggagaact ttgtcgctac ctttgcaaac aatc                                 94

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598324

<400> SEQUENCE: 79
gtgtccctat ctctgatacc atcatcccag                                      30

<210> SEQ ID NO 80
<211> LENGTH: 1027
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2598303

<400> SEQUENCE: 80
caaactcggg catttcatag cagcatgatt ctgagcacac gtgggtaaga cctttcttct     60
ctggttagat atcatatgct ggtgtataat tagcttaaat gattgtgatt tagacaccta    120
ggaaataatc aatagggcaa ttgctttcca taatacttta tcttcttgtg ctttatttct    180
gaagcagagt agaatgctaa agatgtatcc tagtgacagc ataaacccta gaggtgacag    240
tctgtattat tgcttttcgc ttctcttttc tgcttctgtt gggagccagt tttcttctta    300
cgccgcatta cagagagaac gtcaaattta gcagccatat ctgccatagg gtccaaataa    360
agagacaata aaaacattat tctctctttt ttggatggaa tactgcgtga aatggttatc    420
catacaaaga tactttatgt agaatagaaa aaggaggccg ggtgcagtgg ctcacacatg    480
taatcctagt gctttgggag gctaagccgg gagcactgat tgaggccagg agttcatgat    540
cagcctgggc aatgaagtga gaccccgtct ctacaaaaaa atatgaaaaa attagcgagg    600

-continued

```
tgtggtgaca catgcctgta gtcccagcta ctcaagaggc tgaggtagag gatcacttga    660

gcctacgagt tcaaggctgc agtgagctat gataactcca ctgcactgcc gcctggatga    720

cacagagaga ccgtttctaa attaattaat taacaatttt aagaaagaaa aagggccatt    780

gcttattttt ccatacaaaa gtaaaataaa tcataatggc caataagcca atgtaacttt    840

ttttttaag ggaaagcaaa acttgtaaaa cctaaaatct cttagagttt tggcatttac    900

ccaaatgttt tcagtgattc tgagaattgg tggatataaa acacatttct cagcaaacac    960

tttcttcatt ttgcatccct tactgtacgt actttcttgt actgaatctt tgcttgacca   1020

gggaacc                                                             1027
```

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2562442

<400> SEQUENCE: 81

```
ctctgctgct tgagagctat tgctttgtta agat                                 34
```

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2598363

<400> SEQUENCE: 82

```
tctggcccct tcaccgatgt tcgtgcagct gtttaccaac cgcagcct                   48
```

<210> SEQ ID NO 83
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2598273

<400> SEQUENCE: 83

```
gctgtgacaa ctgccgcaga cctgggggtg aacccagtcc cgaaggcact actggccagt     60

cctacaacca gtattc                                                     76
```

<210> SEQ ID NO 84
<211> LENGTH: 243
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598304

<400> SEQUENCE: 84

```
tgatcgccct aaaggactgg cattcactga tgtggatgtc gattccatca aaattgcttg     60

ggaaagccca caggggcaag tttccaggta cagggtgacc tactcgagcc ctgaggatgg    120
```

aatccatgag ctattccctg cacctgatgg tgaagaagac actgcagagc tgcaaggcct 180
cagaccgggt tctgagtaca cagtcagtgt ggttgccttg cacgatgata tggagagcca 240
gcc 243

<210> SEQ ID NO 85
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3020344

<400> SEQUENCE: 85
gagccgagtg gagggcgcga gccagatgcg gggcgacagc tgacttgctg agaggaggcg 60
gggaggcgcg gagcgcgcgt gtggtccttg cgccgctgac 100

<210> SEQ ID NO 86
<211> LENGTH: 382
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2325319

<400> SEQUENCE: 86
aggaggtttt gtgccagagc cttgccccct cactcactct tgggggtcct gatgaactct 60
tggaccctgt ggaagataag agttagagac ctcggcctcc tggtcagtgg agcccttggc 120
ctcatgcctg gtgggctaag cgggcccagc tggggtttga ggtaggggag gccttggctt 180
ggccccagca gctccagggc cctgagttcc tgccagaggc tggagagcag gcagctgctg 240
cttttcctgg tccttggtag gggagggtcc tcaggcttgc gtgccaaagc ctgaaggatt 300
ctgcttctgc cagcgccaga gatcctcacc tgcaacacgg cgaggtgtgt gctcagggcc 360
cacggtggaa tgcagagcct cc 382

<210> SEQ ID NO 87
<211> LENGTH: 158
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3460510

<400> SEQUENCE: 87
tgtatgccca taagatgcta tcatcggagg cactgacccc ccaagtgacc cctgacagtc 60
ccctcacctc tcccacaaga cttccaaagg atcgcccctc caagccattg ttatgtgtga 120
cctcatggca acttcccgac atgagtttag ctgcaggc 158

<210> SEQ ID NO 88
<211> LENGTH: 106
<212> TYPE: DNA
<213> ORGANISM: Artificial Sequence
<220> FEATURE:
<223> OTHER INFORMATION: Description of Artificial Sequence: Synthetic
polynucleotide -continued <220> FEATURE:
<223> OTHER INFORMATION: Affymetrix ID 2598339

<400> SEQUENCE: 88
tattcgccat cagtagaagg tagcagcaca gaactcaacc ttcctgaaac tgcaaactcc 60
gtcaccctca gtgacttgca acctggtgtt cagtataaca tcacta 106

<210> SEQ ID NO 89
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3371816

<400> SEQUENCE: 89
acctgcttac agacatcact tttaagtcct ttgtggatgt gggcacagtg aagagcaata 60
aagagtgtga ggttcc 76

<210> SEQ ID NO 90
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2400181

<400> SEQUENCE: 90
ttgttattga agatgatagg attgatgacg tgctgaaaaa tatgaccgac aaggcacctc 60
ctg 63

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3536743

<400> SEQUENCE: 91
atacaagtac tggttgaacc tgaccacttc aag 33

<210> SEQ ID NO 92
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3536736

<400> SEQUENCE: 92
cactttgaga aactcaggga tggggttagt caaagaggac ttgtgtttgc attaacctcc 60
agggag 66

<210> SEQ ID NO 93
<211> LENGTH: 84
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3634838

<400> SEQUENCE: 93
caccgtaaga cctacagtac ggaggagtac caccacaggc tgcagacgtt tgccagcaac 60
tggaggaaga taaacgccca caac 84

<210> SEQ ID NO 94
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3976359

<400> SEQUENCE: 94
gcctgcacag tgtccaccct gttcccactc ccatctttct tccggacaat gaaa 54

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598268

<400> SEQUENCE: 95
tgttagcaga cccagcttag agttctt 27

<210> SEQ ID NO 96
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3451865

<400> SEQUENCE: 96
atgatttatg agtgcgctgc gggtggagtg aagtgtcatg gtcgtcgtta tgataacgct 60
ggaaaga 67

<210> SEQ ID NO 97
<211> LENGTH: 523
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526825

<400> SEQUENCE: 97
aggtaagccc tcaacccagg attgcatgca ttgtgtcctt tttaaaactt ttaacagaat 60
acattccttt taaataaaat ttggaaaata cagaaaagta aagagaagaa aaaataaaaa 120
tcacttattt ccaccactga taatatgttt gtgaatttac aatcctttta tttcctcagc 180
tctgccgttc cccctctagt tgtagtatat aaacaacttt ttatttgggt tttagaacaa 240
attatatcat ctatatctta cgtattttct tggaaaaaac aagggctccg ttgaatggac 300
ttgccaaagt ttctttaatt ctttgttcac tgttgggctt tcaggttatc cacaacagaa 360
tctgatttaa tcagagtgta aaatagcatt ttactgctgt acctgtctct ccgtaagtga 420
tcctgtaata tctcactgtg acagcaggag catcccagct gatcagtagg ctggtggggg 480
tcgcagcaac aacttccagg tccctcggaa catcagaaac tag 523

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2721993

<400> SEQUENCE: 98
ttcttcaaca tctccggcat cttgctgtgg tacccgatcc cgttcactcg cctgcccatc 60

<210> SEQ ID NO 99
<211> LENGTH: 269
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2827693

<400> SEQUENCE: 99
tcatatgctt tcttaggaag agtgagaggg gggtatatga ttctttatga aatggggaaa 60
gggagctaac attaattatg catgtactat atttccttaa tatgagagat aattttttaa 120
ttgcataaga attttaattt cttttaattg atataaacag tagttgatta ttctttttat 180
ctatttggag attcagtgca taactaagta ttttccttaa tactaaagat tttaaataat 240
aaatagtggc tagcggtttg gacaatcac 269

<210> SEQ ID NO 100
<211> LENGTH: 479
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598309

<400> SEQUENCE: 100
tctgttgtgg ataacctgaa agcccaacag tgaacaaaga attaaagaaa ctttggcaag 60
tccattcaac ggagcccttg ttttttccaa gaaaatacgt aagatataga tgatataatt 120
tgttctaaaa cccaaataaa aagttgttta tatactacaa ctagaggggg aacggcagag 180
ctgaggaaat aaaaggattg taaattcaca aacatattat cagtggtgga aataagtgat 240
ttttattttt tcttctcttt acttttctgt attttccaaa ttttatttaa aaggaatgta 300
ttctgttaaa agttttaaaa aggacacaat gcatgcaatc ctgggttgag ggcttacctt 360
ctcccacttc taatgctact ctactactca gtgacatttt aaagctgaaa tgttaaaaca 420
gcgctaactg taattttctc tcaatgttta tacacttacc aaggtttgct acatgcata 479

<210> SEQ ID NO 101
<211> LENGTH: 334
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2722006

<400> SEQUENCE: 101
tccaccatcc cagcaagtca ggatatcaga cagtcctccc ctgaccctcc cccttgtaga 60
tatcaattcc caaacagagc caaatactct atatctatag tcacagccct gtacagcatt 120
tttcataagt tatatagtaa atggtctgca tgatttgtgc ttctagtgct ctcatttgga 180
aatgaggcag gcttcttcta tgaaatgtaa agaaagaaac cactttgtat attttgtaat 240
accacctctg tggccatgcc tgccccgccc actctgtata tatgtaagtt aaacccgggc 300
aggggctgtg gccgtctttg tactctggtg attt 334

<210> SEQ ID NO 102
<211> LENGTH: 134
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598330

<400> SEQUENCE: 102
gaggcaccac gagaagtgac ttcagactca ggaagcatcg ttgtgtccgg cttgactcca 60
ggagtagaat acgtctacac catccaagtc ctgagagatg gacaggaaag agatgcgcca 120
attgtaaaca aagt 134

<210> SEQ ID NO 103
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598283

<400> SEQUENCE: 103
tgagttgata tagggcacag gtttcctgat gtcttttccc agaccctctc catctcacca 60
tgctgctgtc ctcttgagtg attaaatact gaaacgatta cctataaaga aaatacccct 120
tctgcagaca tggggacagt tggcttttgc tcctgatata aaatgctacc aacattgtgc 180
atttctgtct gcagagaatg ttattccaat gttatttcca ttttttttcca atgttatttc 240 catttttttt tctgactata caggttaaaa gcttctatag aggttaaaag atcattaact 300
cttctttgta gcacctggga aatcctttta aatcaatagc gtgccacctg g 351

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2685316

<400> SEQUENCE: 104
tactttactt ggcggagcag tttgcaggg 29

<210> SEQ ID NO 105
<211> LENGTH: 385
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3666402

<400> SEQUENCE: 105
tctgacgtta gagtggtggc ttccttagcc tttcaggatg gaggaatgtg ggcagtttga 60
cttcagcact gaaaacctct ccacctgggc cagggttgcc tcagaggcca agtttccaga 120
agcctcttac ctgccgtaaa atgctcaacc ctgtgtcctg ggcctgggcc tgctgtgact 180
gacctacagt ggactttctc tctggaatgg aaccttctta ggcctcctgg tgcaacttaa 240 ttttttttt taatgctatc ttcaaaacgt tagagaaagt tcttcaaaag tgcagcccag 300
agctgctggg cccactggcc gtcctgcatt tctggtttcc agaccccaat gcctcccatt 360
cggatggatc tctgcgtttt tatac 385

<210> SEQ ID NO 106
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2685306

<400> SEQUENCE: 106
aaattttgct gtgtgggtca cacaaggtct acattacaaa agacagaatt cagggatgga 60
aaggagaatg aacaaatgtg ggagttcata gttttccttg aatccaactt ttaattacca 120
gagtaagttg ccaaaatgtg attgttgaag tacaaaagga actatgaaaa ccagaacaaa 180
ttttaacaaa aggacaacca cagagggata tagtgaatat cgtatcattg taatcaaaga 240
agtaaggagg taagattgcc acgtgcctgc tggtactgtg atgcatttca agtggcagtt 300
ttatcacgtt tgaatctacc attcatagcc agatgtgtat cagatgtttc actgacagtt 360
tttaac 366

<210> SEQ ID NO 107
<211> LENGTH: 437
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2526814

<400> SEQUENCE: 107
gtaggggtca aagcacgagt catccgtagg ttggttcaag ccttcgttga ctatgaagaa 60
aaggaagaaa aagcaaaaag agacatctta ttaatcgatt tggaccataa gaagaaaatc 120
gaatgactgt atacaatgac ttaatctaaa acaagaattc caggaggatt aagaggcatt 180
catctgttct atcaaggcat taactgctct aaaaaaccat ggttagatgt gacacctgtc 240
acaggcaccc gacaggaagc ccatctttta tttttccctt gcttctaaga taattgccat 300
ttctgttgaa actacttcat agaacatgga acagatcttg aggcaattga agctagtgga 360
gaactttagt gggatgcaaa gactaatgat gcctctccat tggtacctga gtgaccttgg 420
gccagctatt taatacc 437

<210> SEQ ID NO 108
<211> LENGTH: 138
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598344

<400> SEQUENCE: 108
acaggagaga cgactccctt ttctcctctt gtggccactt ctgaatctgt gaccgaaatc 60
acagccagta gctttgtggt ctcctgggtc tcagcttccg acaccgtgtc gggattccgg 120
gtggaatatg agctgagt 138

<210> SEQ ID NO 109
<211> LENGTH: 152
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2491742

<400> SEQUENCE: 109
tcatgaccta acctcatccc agtgagtaga gactgggagg ggagagcagc agctggaggg 60
caggctggga gcgcttgtga gggagaggag ctatggacgt ctgcttctct gccaagggag 120
agagtgaggt aggcctgggc ccgctgactt ca 152

<210> SEQ ID NO 110
<211> LENGTH: 168
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598318

<400> SEQUENCE: 110
ctgacctgcg attcaccaac attggtccag acaccatgcg tgtcacctgg gctccacccc 60
catccattga tttaaccaac ttcctggtgc gttactcacc tgtgaaaaat gaggaagatg 120
ttgcagagtt gtcaatttct ccttcagaca atgcagtggt cttaacaa 168

<210> SEQ ID NO 111
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3839605

<400> SEQUENCE: 111
agaggggaga tgtttagagg tgtggagggc ggcagaggtt tgaacagtgc agacaagg 58

<210> SEQ ID NO 112
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598325

<400> SEQUENCE: 112
cctacaaacg gccagcaggg aaattctttg gaagaagtgg tccatgctga tcagagctcc 60
tgcacttttg ataacctgag tcccggcctg gagtacaatg tcagtgttta cactgtcaag 120
gatgac 126

<210> SEQ ID NO 113
<211> LENGTH: 127
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2451595

<400> SEQUENCE: 113
caaaggacac cattttggca agctctatca ccaaggagcc aaacatccta caagacacag 60
tgaccatact aattataccc cctgcaaagc ccagcttgaa accttcactt aggaacgtaa 120
tcgtgtc 127

<210> SEQ ID NO 114
<211> LENGTH: 103
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2721980

<400> SEQUENCE: 114
actgttcggg ctgccatccc cattatcatg ggggccaaca ttggaacgtc aatcaccaac 60
actattgttg cgctcatgca ggtgggagat cggagtgagt tca 103

<210> SEQ ID NO 115
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2721989

<400> SEQUENCE: 115
tgcatggttg actggctacc tggccatcct cgtcggggca ggcatgacct tcatcgtaca 60
gagcagctct 70

<210> SEQ ID NO 116
<211> LENGTH: 155

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2722000

<400> SEQUENCE: 116
gatgtctaat cctgcgccta gctgggttgg tcagtagaac ctattttcag actcaaaaac 60
catcttcaga aagaaaaggc ccagggaagg aatgtatgag aggctctccc agatgaggaa 120
gtgtactctc tatgactatc aagctcaggc ctctc 155

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3087187

<400> SEQUENCE: 117
ctatgatgag gggacagacg tttttcagca g 31

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2526818

<400> SEQUENCE: 118
atgtactcag aagtgtcctg gaatggggcc c 31

<210> SEQ ID NO 119
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2598331

<400> SEQUENCE: 119
tctattccac cttacaacac cgaggtgact gagaccacca ttgtgatcac atggacgcct 60
gctccaagaa ttggtttta 79

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2721991

<400> SEQUENCE: 120
gaatcggcgt gataaccatt gagagggctt atccactcac 40

<210> SEQ ID NO 121
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2400180

<400> SEQUENCE: 121
ggagagaata agaacggcgg taacagttat tggcaaaaag c 41

<210> SEQ ID NO 122
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2598287

<400> SEQUENCE: 122
aggaaatcca aattggtcac atccccaggg aagatgtaga ctatcacctg tacccacacg 60
gtccgggact caatccaaa 79

<210> SEQ ID NO 123
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2584026

<400> SEQUENCE: 123
tggtatactg atgaagacca tggaatagct agcagcacag cacaccaaca tatatatacc 60
cacatgagcc acttcataaa acaatgtttc 90

<210> SEQ ID NO 124
<211> LENGTH: 110
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3536744

<400> SEQUENCE: 124
tgcagtgaat gatgctcact tgttgcagta caatcatcgg gttaaaaaac tcaatgaaat 60
cagcaaactg ggaatttctg gtgacataga cctcaccagt gcttcatata 110

<210> SEQ ID NO 125
<211> LENGTH: 110
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2598284

<400> SEQUENCE: 125
cactctgaca ggcctcacca gaggtgccac ctacaacgtc atagtggagg cactgaaaga 60
ccagcagagg cataaggttc gggaagaggt tgttaccgtg ggcaactctg 110

<210> SEQ ID NO 126
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598294

<400> SEQUENCE: 126
tgatgcacca tccaacctgc gtttcctggc caccacaccc aattccttgc tggtatcatg 60
gcagccgcca cgtgccagga ttaccggcta catcatcaag 100

<210> SEQ ID NO 127
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3451875

<400> SEQUENCE: 127
ctgaaaggca taactgcatg gagaattcca tctgcagaaa tctgaatgac agggctgttt 60
gtagctgtcg a 71

<210> SEQ ID NO 128
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598308

<400> SEQUENCE: 128
tgggagcaag tctacagcta ccatcagcgg ccttaaacct ggagttgatt ataccatcac 60
tgtgtatgct 70

<210> SEQ ID NO 129
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3825011

<400> SEQUENCE: 129
cggaggacgc gacctcagtt gtcctgccct gtggaatggg ctcaaggttc ctgagacacc 60
cgattcctgc ccaaacagct g 81

<210> SEQ ID NO 130
<211> LENGTH: 337
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3464873

<400> SEQUENCE: 130
tcagcagttt ctcttggcag catcagctgg gctgctttct ttgtgtgtgg ccccaggtgt 60
caaaatgaca ccagctgtct gtactagaca aggttaccaa gtgcggaatt ggttaatact 120
aacagagaga tttgctccat tctctttgga ataacaggac atgctgtata gatacaggca 180
gtaggtttgc tctgtaccca tgtgtacagc ctacccatgc agggactggg attcgaggac 240
ttccaggcgc atagggtaga accaaatgat agggtaggag catgtgttct ttagggcctt 300
gtaaggctgt ttccttttgc atctggaact gactata 337

<210> SEQ ID NO 131
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3263765

<400> SEQUENCE: 131
tgcagagtcc tacagctggt tcaaggcagc atcaggctca gaaccccttt ctctcagctc 60
tctgttgtga ttatttcagg accttgttct gttttccaca tggcctctaa tctagacacc 120
tgacctggtg ggagtaacct ttca 144

<210> SEQ ID NO 132
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2562440

<400> SEQUENCE: 132
ctgcaccaat gctaataaag tcctattctc tt 32

<210> SEQ ID NO 133
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3536745

<400> SEQUENCE: 133
accttacatg tgtaaaggtt tcatgttcac tgtgagtgaa aatttttaca ttcatcaata 60
tccctct 67

<210> SEQ ID NO 134
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Affymetrix ID 2598290

<400> SEQUENCE: 134
ccgggaaccg aatatacaat ttatgtcatt gccctgaaga ataatcagaa gagcgagccc 60
ctgattggaa ggaaaa 76

<210> SEQ ID NO 135
<211> LENGTH: 317
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526822

<400> SEQUENCE: 135
ggcctcaatc agtgctcccg gcttagcctc ccaaagcact aggattacat gtgtgagcca 60
ctgcacccgg cctccttttt ctattctaca taaagtatct ttgtatggat aaccatttca 120
cgcagtattc catccaaaaa agagagaata atgtttttat tgtctcttta tttggaccct 180
atggcagata tggctgctaa atttgacgtt ctctctgtaa tgcggcgtaa gaagaaaact 240
ggctcccaac agaagcagaa aagagaagcg aaaagcaata atacagactg tcacctctag 300
ggtttatgct gtcacta 317

<210> SEQ ID NO 136
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2526816

<400> SEQUENCE: 136
ttcccgaacc ttatgcctct gctggtcttt cagtgcctcc actatgacgt tgtaggtggc 60
acctctggtg aggcctgtca gagtggcact ggtagaagtt cc 102

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2584027

<400> SEQUENCE: 137
tccaaagccc tggtcgatgt tggagtggat ttc 33

<210> SEQ ID NO 138
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3329530

<400> SEQUENCE: 138
gaaagtccaa tctctccagt gagtaacgtt aaaaccatta cacatgagca tgggagaatc 60
gcttccatta gtttaggaca gagagatttt gctttttaca gagtaaatca gtgctcaaat 120
agatacttcc tcaaatatgt cctttctaca ttctgaacag cccaagtgca ataagatcct 180
tccccctttc caatcaagaa aatgccactt ttctacttgc tcttcctccc cagacgtgag 240
tctaaggacc caaagtgctc actcctttac tgcttgttaa gtgtaatgtg gggaggctca 300
gaactggggc tgacgctact gagagcaagg ctaagggcct ggtatctctc tcta 354

<210> SEQ ID NO 139
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3020368

<400> SEQUENCE: 139
ggcaagtgga gggtcaacac ccatgggtgg ct 32

<210> SEQ ID NO 140
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3451912

<400> SEQUENCE: 140
atggagtctc gggtcttact gagaacattc tgtttgatct tcggtctcgg agca 54

<210> SEQ ID NO 141
<211> LENGTH: 141
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3917691

<400> SEQUENCE: 141
agcttccgaa catggacaca gagtaagacc agccatagac caaaacagga aggaaaaaaa 60
aaaagaggct cattgaaaca tgaatcgcca ccctctcctc acacattctt aaaatacacg 120
gagattctca gacatggaag a 141

<210> SEQ ID NO 142
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3420343

<400> SEQUENCE: 142
gaggagtttt acattgcagc ttagaagcct ttcttccaat agcagagatt tggtgtcatg 60
tggtgttcat cagtttgaaa agaagtattt ctgctgtttg cctcaagatg tacatacaga 120

-continued gatgtgctga ttctcagaac ttctatagaa ttccattagc cagtcctgcc aattgaaatt 180
tggcatttaa ttatttgcat ttttctattc ttgcctagga aaggagctcg tcacatacct 240
agtttagtga tggaaagtat ttggagaaag ttttagagag tggggctcag gctcaagaat 300
acaatg 306

<210> SEQ ID NO 143
<211> LENGTH: 197
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3343460

<400> SEQUENCE: 143
gcatatttgc ctagtaaggc tagtagaacc acatttccca aagtgtgctc cttaaacact 60
catgccttat gatttctac caaaagtaaa aagggttgta ttaagtcaga ggaagatgcc 120
tctccatttt ccctctcttt atcagaggtt cacatgcctg tctgcacatt aaaagctctg 180
ggaagacctg ttgtaaa 197

<210> SEQ ID NO 144
<211> LENGTH: 165
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2721982

<400> SEQUENCE: 144
ttcttcaact ggctgtccgt gttggtgctc ttgcccgtgg aggtggccac ccattacctc 60
gagatcataa cccagcttat agtggagagc ttccacttca agaatggaga agatgcccca 120
gatcttctga aagtcatcac taagcccttc acaaagctca ttgtc 165

<210> SEQ ID NO 145
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2598310

<400> SEQUENCE: 145
ggacctggaa gttgttgctg cgaccccccac cagcctactg atcagctggg atgctcctgc 60
tgtcacagtg agatattaca ggatcactta cggaga 96

<210> SEQ ID NO 146
<211> LENGTH: 177
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3270278

<400> SEQUENCE: 146
ttcctctaca ggaatggggt ttggcagtga tccaaagact cactgttatg acatgttctc 60
agggaagtag gtcatatgtc cccagggtat tcagagaggc ctgtgagtgt gagatgtttg 120
ggctgagcag ggctttcttc ctctcaaggc tccaaagggc gggccaacag gtcattt 177

<210> SEQ ID NO 147
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3577627

<400> SEQUENCE: 147
ctggccccct ccctggatga cattaa 26

<210> SEQ ID NO 148
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598276

<400> SEQUENCE: 148
tgatgggaag acataccacg taggagaaca gtggcagaag gaatatctcg gtgccatttg 60
ctcctgcaca tgctttgga 79

<210> SEQ ID NO 149
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3907236

<400> SEQUENCE: 149
atcgtgggca tcctctttgc cgtcttcctg atcctactgc tcatgtaccg tatgaagaag 60
aaggatgaag gcagctatga cctgggcaag aaacccatct acaagaaagc ccccaccaat 120
gagttctacg cgtga 135

<210> SEQ ID NO 150
<211> LENGTH: 242
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3464882

<400> SEQUENCE: 150
tcgagtctta aataatccgg ggagaaagac gcccgggtag atttgaggtg cagccttgga 60
gggagggatt agaagccgct agactttttt tcctcccctc tcagtagcac ggagtccgaa 120
ttaattggat ttcattcact ggggaggaac aaaaactatc tgggcagctt cattgagaga 180
gattcattga cactaagagc cagcggctgc agctgggtgc agagagaacc tccggcttta 240
ct 242

<210> SEQ ID NO 151
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598295

<400> SEQUENCE: 151
tgacttgtat gcaatcagtt tcatgaactc aaaaaacaaa tgtgaggcgt atatttttgt 60
attatagatt ccagagaatc ttgtttccgg tttacagtat tctcagattc ttttaagtgt 120
gtttagaacg gctcgggaga aaagtgtggg agtaattttc ttggttattt gccttcttag 180
agactt 186

<210> SEQ ID NO 152
<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2477461

<400> SEQUENCE: 152
tttctcaaca gtacttaaat agcggttgga aaacgtagcc ttcattttat gattttttca 60
tatgtggaaa tctattacat gtaatacaaa acaaacatgt agtttgaagg cggtcagatt 120
tctttga 127

<210> SEQ ID NO 153
<211> LENGTH: 107
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2562463

<400> SEQUENCE: 153
cctggagcag gagtgcaacg tcctcccctt gaagctgctc atgccccagt gcaaccaagt 60
gcttgacgac tacttccccc tggtcatcga ctacttccag aaccaga 107

<210> SEQ ID NO 154
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3907239

<400> SEQUENCE: 154
aactagagga gaatgaggtt atccccaaga gaatctcacc cgttgaagag agtgaggatg 60
tgtccaacaa ggtgtcaatg tccagcactg tgc 93

-continued

<210> SEQ ID NO 155
<211> LENGTH: 884
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2944958

<400> SEQUENCE: 155
tcgggtcatt tcctagcgcc ggtcacactg gctggcctcc tcccctcaac atctcctcct 60
ccggctgcag agggggcaag gggaaaagag ggaggaaaaa aaagccccaa acgggaattc 120
gcctgcgtgg agtctctcag tcccggcgtt cccccaaaac atctgccatc ggccaaattc 180
gtcaccccgg agccttctgt cttcatcacg cgtttaaaaa aaggggggga ggggtgcgct 240
gggttctccc ctcctttctt gaccaagaag caaaataaaa caaaaccaag gtggtgatgc 300
aggaaggggg agactccttc aagtctctag aaaactaact cgccttcttg ctgggggtgc 360
agacaagtcc ggaagctcgt tggaaggggg agggggtctc ttcaagcaaa ggggagcaaa 420
ctcgaagtcg cttttttttt tttgccatca acaacaacat caataacaac aatcacaggt 480
cgcccctgtc taccctcttc ctcctccgcg tccctccggc tgggcagagt gggtccccgg 540
cccgggaagg tgggggatgg gagcgcgggt ccaaaacgcc gccgcgctcc ttgatccgac 600
gacgagaacg cgggcgaagc cagccctgct tactttttct ttcttttttc cctttctct 660 ttaaactctt cgtctgtcct tttcgtttct ttttttcact ttttttttct cctctcctac 720
cccccccggc ccttctccct gcctgcgcgc ccttcagtag gtgaaaacca ggttggagat 780
gctggactcg agccagtctc ccgagatcat ctcgctcacc tcgggcgtgc agtagtccgg 840
gaactcgaag tgcgagccgg agccgggctc gaagttaaaa tcca 884

<210> SEQ ID NO 156
<211> LENGTH: 236
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2512878

<400> SEQUENCE: 156
catcatcttg acagtgcagt tttgagataa tgaaaacaaa aatgagtttt aataagcttt 60
aaatggcatg gtattttgag gtgctaaggt aaagagaaac attgttttat gaagtggctc 120
atgtgggtat atatatgttg gtgtgctgtg ctgctagcta ttccatggtc ttcatcagta 180
taccactaga gagagaaaga aaagaagtta gaattaggaa gtcagtactc ttctta 236

<210> SEQ ID NO 157
<211> LENGTH: 662
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3020350

<400> SEQUENCE: 157
cgccctggga gccaaagtcc tttcatctgt aaaggaccgg ttcatcaact tctttgtagg 60
caataccata aattcttctt atttcccaga tcatccattg cattcgatat cagtgagaag 120

```
gctaaaggaa acgaaagatg gttttatgtt tttgacggac cagtcctaca ttgatgtttt    180

acctgagttc agagattctt accccattaa gtatgtccat gcctttgaaa gcaacaattt    240

tatttacttc ttgacggtcc aaagggaaac tctagatgct cagacttttc acacaagaat    300

aatcaggttc tgttccataa actctggatt gcattcctac atggaaatgc ctctggagtg    360

tattctcaca gaaaagagaa aaaagagatc cacaaagaag gaagtgttta atatacttca    420

ggctgcgtat gtcagcaagc ctggggccca gcttgctaga caaataggag ccagcctgaa    480

tgatgacatt cttttcgggg tgttcgcaca aagcaagcca gattctgccg aaccaatgga    540

tcgatctgcc atgtgtgcat tccctatcaa atatgtcaac gacttcttca acaagatcgt    600

caacaaaaac aatgtgagat gtctccagca tttttacgga cccaatcatg agcactgctt    660

ta                                                                   662


<210> SEQ ID NO 158
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3928670

<400> SEQUENCE: 158

cataaggtca tgacgtgtct atgtcaaaag ttcttatata tttcttttat aagctgaaag     60

aaggtctatt tttatgtttt taggtctatg aatggaacgt tgtaaatgct tgtc          114


<210> SEQ ID NO 159
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3460452

<400> SEQUENCE: 159

tgcagaaagg aaggtgcagt caatttcggg aaccaggact tgcacttgtg ccct           54


<210> SEQ ID NO 160
<211> LENGTH: 257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721987

<400> SEQUENCE: 160

taatgttttt tccaacccag ccatccttcg ttattctaat tactccttac atatactttt     60

gtatatctct gcttctctct tctcaccctc ccaccacatt aattctgagc actatatctt    120

aatactctag gtatgattac cccaaagaat caagttaact taccacctcc cacattctag    180

gcactataca ttcattcata taaccatgtt ttgctgggat tatctggggg atgcagaagg    240

ggctttataa ttagcaa                                                   257


<210> SEQ ID NO 161
<211> LENGTH: 110
```

<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598357

<400> SEQUENCE: 161
ccttcctata caacaaccac aattacactg attgcacttc tgagggcaga agagacaaca 60
tgaagtggtg tgggaccaca cagaactatg atgccgacca gaagtttggg 110

<210> SEQ ID NO 162
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2722004

<400> SEQUENCE: 162
gtggctaaag tctaacgctc ctctcttggt cagataacaa aagccctccc tgttggatct 60
tttgaaataa aacgtgcaag ttatccaggc tcgtagcctg catgctgcca ccttgaatcc 120
cagggagta 129

<210> SEQ ID NO 163
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3420360

<400> SEQUENCE: 163
gatttatggg ccatacatca ccttcctggt tggctttgtt gacaccttgt cacattcttg 60
cttgggcttg aggaattcat tgttc 85

<210> SEQ ID NO 164
<211> LENGTH: 104
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2721988

<400> SEQUENCE: 164
gtgaatttcc acctcccgga tcttgctgtg ggcaccatct tgctcatact ctccctgctg 60
gtcctctgtg gttgcctgat catgattgtc aagatcctgg gctc 104

<210> SEQ ID NO 165
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2721976

<400> SEQUENCE: 165
cctactccac ggctacactg atagatgagc ccactgaggt ggatgacccc tggaacctac 60
ccactcttca ggactcgggg atcaagtg 88

<210> SEQ ID NO 166
<211> LENGTH: 107
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3634817

<400> SEQUENCE: 166
gagttccacc atgagctcac ccgtgtctat gacgcaaaga tcaccagcca tgtgccttag 60
tgtccttctt aacagactca aaccacatgg accacgaata ttctttc 107

<210> SEQ ID NO 167
<211> LENGTH: 521
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2584025

<400> SEQUENCE: 167
ctttgcatag attccctgag caggatttta atctttttct aactggactg gttcaaatgt 60
tgttctcttc tttaaaggga tggcaagatg tgggcagtga tgtcactagg gcagggacag 120
gataagaggg attagggaga gaagatagca gggcatggct gggaacccaa gtccaagcat 180
accaacacga gcaggctact gtcagctccc ctcggagaag agctgttcac agccagactg 240
gcacagtttt ctgagaaaga ctattcaaac agtctcagga aatcaaatat gcaaagcact 300
gacttctaag taaaaccaca gcagttgaaa agactccaaa gaaatgtaag ggaaactgcc 360
agcaacgcag gcccccaggt gccagttatg gctataggtg ctacaaaaac acagcaaggg 420
tgatgggaaa gcattgtaaa tgtgctttta aaaaaaaata ctgatgttcc tagtgaaaga 480
ggcagcttga aactgagatg tgaacacatc agcttgccct g 521

<210> SEQ ID NO 168
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2722002

<400> SEQUENCE: 168
cttcctcacg tggacaggtg tgctagtcca ggcagttcac ttgcagtttc cttgtcctca 60
tgcttcgggg atgggagcca cgcctgaact agagttcagg ctggatacat gtgctca 117

<210> SEQ ID NO 169
<211> LENGTH: 144
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3312464

<400> SEQUENCE: 169
tatgcgacac cactgacact gcttttactg agcatgcaat ccggagaagc tccttttcag 60
cagttttctc tagagcagat caatttaaga agcagttacc atcaatgcaa ttatgtgccc 120
ctgcgctcct gaacgctggt caga 144

<210> SEQ ID NO 170
<211> LENGTH: 764
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3263773

<400> SEQUENCE: 170
agccattacg ggagcacagc atgtgctgac tactgtactt ccagacccct gccctcttgg 60
gactgcccag tccttgcacc tcagagttcg ccttttcatt tcaagcataa ggcaataaat 120
acctgcagca acgtgggaga aagaagttgc tggaccagga gaaaaggcag ttatgaagcc 180
aattcatttt gaaggaagca caatttccac cttatttttt gaactttggc agtttcaatg 240
tctgtctctg ttgcttcggg gcataagctg atcaccgtct agttgggaaa gtaaccctac 300
agggtttgta gggacatgat cagcatcctg atttgaaccc tgaaatgttg tgtagacacc 360
ctcttgggtc caatgaggta gttggttgaa gtagcaagat gttggctttt ctggattttt 420
tttgccatgg gttcttcact gaccttggac tttggcatga ttcttagtca tacttgaact 480
tgtctcattc cacctcttct cagagcaact cttcctttgg gaaaagagtt cttcagatca 540
tagaccaaaa aagtcatacc ttcgaggtgg tagcagtaga ttccaggagg agaagggtac 600
ttgctaggta tcctgggtca gtggcggtgc aaactggttt cctcagctgc ctgtccttct 660
gtgtgcttat gtctcttgtg acaattgttt tcctccctgc ccctggaggt tgtcttcaag 720
ctgtggactt ctgggatttg cagattttgc aacgtggtac tact 764

<210> SEQ ID NO 171
<211> LENGTH: 222
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3460456

<400> SEQUENCE: 171
ttctgagatg gagcaccaaa ctggaaaagg gagagatgag cccattgggg caaatcttta 60
aactcttcta ctatttttaa gcgtacttgt gaaaatgttt acctgtatgt atacatacag 120
aaaaacaaat gagtttgaac tatgattatc cattacttta tttttttaaa aaagatatct 180
tgccaagtct taaggtggtt ctgcgggtaa atcagggtag ca 222

<210> SEQ ID NO 172
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide <220> FEATURE:
<223> OTHER INFORMATION: Affymetrix ID 2598373

<400> SEQUENCE: 172
acacttaccg agtgggtgac acttatgagc gtcctaaaga ctccatgatc tgggactgta 60
cctgcatcgg ggctgggcga gggagaataa gctgtaccat c 101

<210> SEQ ID NO 173
<211> LENGTH: 694
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3730395

<400> SEQUENCE: 173
cccttctttg cagagcccga ggagcctccc ctgtcccctc gggcagatct gttgtgtctc 60
tcttcccacc tggcagcctc agctctgtgc cctcaccct gctccctctc gcccccttctc 120 tcccacccct tccttctgag ccgggccctg gggattgggg agccctcttg ttcctgatga 180
gggtcagctg agggggctga gcatccatca ctcctgtgcc tgctggggtg gctgtggggc 240
gtggcaggag gggcctaggt gggttgggcc tgagaaccag ggcacgggtg tggtgtctgc 300
tgggctggag ataagactgg ggagagacac cccaacctcc cagggtggga gctgggccgg 360
gctgggatgt catctcctgc cgggcggggg agggctctgc ccctggaaga gtcccctgtg 420
gggaccaaaa taagttccct aacatctcca gctcctggct ctggtttgga gcaaggggaa 480
gggttgccag agtcctgggg gccccagagg agcaggagtc tgggagggcc cagagttcac 540
cctctagtgg atccaggagg agcagcaccc gagccctgga gtggcccagt acccttccaa 600
gaggccacag tcccagccag gacaaagtat gcggcccatc ctggtgcgac agcgtgggac 660
aatgtgaaca tggactcgaa gacatggccc tttc 694

<210> SEQ ID NO 174
<211> LENGTH: 162
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2377256

<400> SEQUENCE: 174
agttgacact gttcaggttt actgagtatg gatctaatgt gctatggtgg aaatatgaac 60
ttgaccaaga ttgcaggatt aaatggtctc taatttattg tagccagggt ttttcatact 120
aatacttttt actttatttg gaagcggact tggattgtac ta 162

<210> SEQ ID NO 175
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3312484

<400> SEQUENCE: 175
cctggggttg catttgcaca cactgttaat gaatagggga cgaacactgc aacatgaggg 60
tgcgatcagt tatc 74

<210> SEQ ID NO 176
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3451913

<400> SEQUENCE: 176
agggagacga tggactgagc tgatccgcac c 31

<210> SEQ ID NO 177
<211> LENGTH: 700
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2400178

<400> SEQUENCE: 177
tgttggcatt cttcgctgat ttggctgttc ccaatgttta cattatttaa tcttgcaaaa 60
atggttctgt gcacttggat gtgaaatgct gtccagtttt attttttta tgttgttatc 120 cttggatgta caaaaaattc agaaaatgat ctctgtagat attctgtttt attttggtca 180
tctttagaag ttatcaggaa tgtgtttaaa acaagaagag aacttttcta aggaatgata 240
catagaaaag attttatttt aaaatgagtt gtaaagcttg tgtttctttg ttgctgcaag 300
ctatctgccc aagttaatgc aaatggacac attttttatg tcagaaaaac acacacacac 360
acacacacac acacacacac acacgaaaaa caaagaaaaa aatgcttgag ctttttctaa 420
cttccccttg cagtctgttg tgtgagcagc ctgtttattt ctctaatatt atgtcagttt 480
attctcttta atggactgta aaaaaatgta atcacaagag tgccaaatat cttgaaatgc 540
caaaaggcat tttagtttct tttctctgtg ctctgagtcc acgtacagga atgcttggag 600
tgtcttttct gttatttata gggattctct taaggcacac cagctgcctg ttttgcatgg 660
tatttgcaaa aatgcctctt gcgtgaggaa atcttttacc 700

<210> SEQ ID NO 178
<211> LENGTH: 62
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2451596

<400> SEQUENCE: 178
gggatagtga ggcatcgcaa tgtaagactc gggattagta cacacttgtt gattaatgga 60
aa 62

<210> SEQ ID NO 179
<211> LENGTH: 86
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2827686

<400> SEQUENCE: 179
aaaaggatca taaggtgcgt ttggcaattg gaaatggcat acggagtgat gtatggagag 60
aatttttaga cagatttgga aatata 86

<210> SEQ ID NO 180
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2685329

<400> SEQUENCE: 180
gaaatgattt tatatacaac cgtgcatgca tttctgtatt ggtcggctta tctggatgca 60
atttt 65

<210> SEQ ID NO 181
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2584058

<400> SEQUENCE: 181
ggatcactac ttgtgtgatg tgacatgggc aacacaagaa agaatttctt tgcagtggct 60
caggaggatt cagaactatt cggtc 85

<210> SEQ ID NO 182
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2598306

<400> SEQUENCE: 182
gcccacagtg gagtatgtgg ttagtgtcta tgctcagaat ccaagcggag agagtcagcc 60
tct 63

<210> SEQ ID NO 183
<211> LENGTH: 98
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3928671

<400> SEQUENCE: 183
cagaggcttc taatcgtcgc atttactggc tccagtgcaa cacatccatc tgaaaacact 60
cggaagtctg gtgcttggag agggtgccat tgtctctt 98

<210> SEQ ID NO 184
<211> LENGTH: 269
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3069235

<400> SEQUENCE: 184
tcccagtctg acataccttt tctaaaatgt tcacagtgca gtgtttttgt ggcctaacaa 60
aatttttctc atatcattaa aaataaacat ttttataaaa aatataacac tttaaatgtt 120
tacgtcgaca aaaccagtta gagtaaccta caccacatgc actatacagt agcaagcaca 180
aaattccaca gaatgaagca tcacaaagtt ctgctcaggg tggctattcc atctaggtga 240
aatagctggg attttcaatt gcctttttc 269

<210> SEQ ID NO 185
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2562462

<400> SEQUENCE: 185
acacagcacc ctatccagac acatac 26

<210> SEQ ID NO 186
<211> LENGTH: 264
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2632440

<400> SEQUENCE: 186
ctgccacttg aaatgcatca cagtaccagc aggcacgtgg caatcttacc tccttacttc 60
tttgattaca atgatacgat attcactata tccctctgtg gttgtccttt tgttaaaatt 120
tgttctggtt ttcatagttc cttttgtact tcaacaatca cattttggca acttactctg 180
gtaattaaaa gttggattca aggaaaacta tgaactccca catttgttca ttctcctttc 240
catccctgaa ttctgtcttt tgta 264

<210> SEQ ID NO 187
<211> LENGTH: 140
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3420356

<400> SEQUENCE: 187
atccaaggga tatgttgcag gtgtcttaag agtcaggtaa aaggcaagat gattcattat 60
atctgttctt tttgtgatac ccatgtaact acctataagc ttcaaagtga aataaacatt 120
acctcttgta ccttagcccg 140

<210> SEQ ID NO 188
<211> LENGTH: 567
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3263784

<400> SEQUENCE: 188
actgccagag tctaaccagc ggttcatttt agttttgcct caaggtggat ggtctctggt 60 tccccttga ctagaaatct ggggtgtggg tagcctccca aaaggatggc tctgtaagcg 120
ggtctcacca gcaccttcaa caaaccccg tgtgaagaag gtcagaggcg gggaagcccc 180
tctgcttgtg gcctgacaac attttttatc taaagattct gagtaggtag tggttatttt 240
catttctaaa aagcatactt ttttgtggag gtggaggtgc attttaacat ctctaaaacc 300
tgggtgcatc ttaggatcaa cagtgtctta ggtttgatga aatacaccat ataggctagg 360
cttggtagct catgcctata atcccagcac ttcaggaggc tgaggtagga agatcgcttg 420
aggccaggag ttgaagacca ttctgggcaa catagcaaga actcatctct accaaaaaaa 480
ttataaaatt agccaggcat ggtggtacat gcctgtaggc ccagctactc gggagactga 540
gacggtagga tctcttcagc gtaggaa 567

<210> SEQ ID NO 189
<211> LENGTH: 404
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3769232

<400> SEQUENCE: 189
caacagtgcc atagtgacat ccttaaaatg tctgattcaa gtatactctt agagggatag 60
aaaactactc ctttctcaat aatcaaaata gagttcactt tgtctacatt ttgtttaaaa 120
ataggataac caggaatcta tggctcctcc caaaaatata gtgcccttcc agatatgggc 180
aaaaattctt taaaagggaa taaatccgaa gtaaatccaa cagggaatct gcttgcaata 240
gagaagcaac acacatctgg gaatcaaccc cagatattca tggtgagtcc cctccgtctg 300
cattctaatg acatgtgtac attaattaag gagacccagt caataaggac aaatattttg 360
aaggtaaaat gcagcaatca atgtcgtgca ttacctgtgt cttg 404

<210> SEQ ID NO 190
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2377249

<400> SEQUENCE: 190
aatgtcccag ctacaatagt cacaccaaca cc 32

<210> SEQ ID NO 191
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2377248

<400> SEQUENCE: 191
agagactcca tcagttcttc aaaaacacac cacagaaaat gtttcagcta caagaac 57

<210> SEQ ID NO 192
<211> LENGTH: 95
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3067479

<400> SEQUENCE: 192
tgagtgtgaa tgtccaagta atggtgtatg taatggtaca ggcaaatgtg actggatttc 60
cctcaaaaaa gtaactatta aacagtcttg atctc 95

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3020359

<400> SEQUENCE: 193
gtagaagcat ttgccaggat tgacaaacga tag 33

<210> SEQ ID NO 194
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3451874

<400> SEQUENCE: 194
atggttttag ggctcttcga gaggataatg cctactgtga ag 42

<210> SEQ ID NO 195
<211> LENGTH: 572
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2491744

<400> SEQUENCE: 195
ggaatgggtc cctagcttgc acaaccccag ctgagctttc agcagataaa tcacagcaga 60

-continued

```
aatagaatca ccctaggact ttcaatcaaa agctggaagt ccaccttaca gaaagacaaa    120

aagaaacccc tttttatatc ttaacaaagc aatagctctc aagcagcaga gcatctcgag    180

gaagaaagct tgcccggtcg ccatcccatc atgccagagc gtgcagtgtc cacccttgac    240

tacgctgggg aattgctgat tttttgaaaa agcttaactt aacaatttct gatgtctatc    300

ttttagagtt ctgtatgttc ccattttttta ttcttctgaa ttttgaattg caagtagctg    360

taaaatccaa tctttgagtg catgggggtg ggtgtgaggc ggggctcagc ttcaaccccc    420

tgtcctgtaa agcagtggct ggtttttcct gagcccagcc ctgggaggtc gtggtaggtg    480

tggaggctgc agagctcctc cagatgctgc cctcgctgtg cctcacacca gagaggatgg    540

aagtgggctc tggtgtcaga ctgtggttga gc                                   572
```

<210> SEQ ID NO 196
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3464875

<400> SEQUENCE: 196

```
aactcatttt caggccgtgt cgacatcctg ttcctcctaa tgggccgtcc cctgtgactt     60

ccctctctct tttaaaatgc ctgaatacct ccattgttag ctgcacaaca tttggagcat    120

aatttaatag acccttgcag tctggttgtc tgtgtaaaag gcattcacga acatattgca    180

gggtttctgg tattcacatg ccgaggcaaa                                      210
```

<210> SEQ ID NO 197
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2584067

<400> SEQUENCE: 197

```
cagtgcctac tctgctctgt ggtggt                                           26
```

<210> SEQ ID NO 198
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2722005

<400> SEQUENCE: 198

```
atgggctttg attagctgtc ctctctccat gcctgcaaag ctccagattt ttggggaaag     60

ctgtacccaa ctggactgcc cagtgaactg ggatcattaa gtacagtcga gcacacgtgt    120

gtgcatgggt caaaggggtg tgttccttct catcctagat gccttctctg tgccttccac    180

agcctcctgc ctgattacac cactgccccc gccccaccct cagccatccc aattcttcct    240

ggccagtgcg ctccagcctt atctaggaaa ggaggagtgg gtgtagccgt gcagcaagat    300

tggggcctc                                                             309
```

<210> SEQ ID NO 199
<211> LENGTH: 101
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3721357

<400> SEQUENCE: 199
ctccagccgc gacttgatgt ccatgagccg ctggtactcc tgattctgcc gctcactatc 60
agctcgcaca tcgcccagct gggcttcaat accgctgatc a 101

<210> SEQ ID NO 200
<211> LENGTH: 137
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3020391

<400> SEQUENCE: 200
tgggcagtga attagttcgc tacgatgcaa gagtacacac tcctcatttg gataggcttg 60
taagtgcccg aagtgtaagc ccaactacag aaatggtttc aaatgaatct gtagactacc 120
gagctacttt tccagaa 137

<210> SEQ ID NO 201
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3868840

<400> SEQUENCE: 201
gcctctgtcc ctcctactca acctgcttta tctctaggcc ttcct 45

<210> SEQ ID NO 202
<211> LENGTH: 238
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3306643

<400> SEQUENCE: 202
gcttcacgga cgtgggctga gaacccgccc gcgccgcgct gagcagggcc gagggagccg 60
gccagggccc cagaggagtc cggaacggat tcccgtcgct accgaggtct gcgcgtgtaa 120
ggagaggacg tcggagattt gcctcgaggg gtggggtata gatgactgga gaggtcaggc 180
gcgggttggt catcgctgag gctgggtgat gggtggccgg attcgttata ctgttttc 238

<210> SEQ ID NO 203
<211> LENGTH: 137
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Affymetrix ID 2721994

<400> SEQUENCE: 203
atctctgcca agtatcgctg gttcgccgtc ttctacctga tcatcttctt cttcctgatc     60
ccgctgacgg tgtttggcct ctcgctggcc ggctggcggg tgctggttgg tgtcggggtt    120
cccgtcgtct tcatcat                                                   137

<210> SEQ ID NO 204
<211> LENGTH: 272
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3329532

<400> SEQUENCE: 204
tatagtcctt ccttactgac tcctaggccc atccccagct gatggagaag ctaagcagaa     60
actgcagcta agacagagat tcaaaaggta attgtggtga ggggttcaca gggtagggga    120
agaacaaccc aaagaactca caggagctaa gaaaacataa gaaaaacatg agcaagagaa    180
agaagcgcct ttttcccctc ctttcctctt gttaaatgat gattgacaca cccgggctca    240
atttccagtt cattacgtaa cactctgagc aa                                  272

<210> SEQ ID NO 205
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377247

<400> SEQUENCE: 205
ttccaaggtc ccaccaacag ttcagaaacc taccacagta aatgttccaa ctacagaagt     60
ctcaccaact tctcaga                                                    77

<210> SEQ ID NO 206
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2558642

<400> SEQUENCE: 206
tctgtaatgt gttaatgtga ttagcagtta ttttccttaa tatctgaatt atacttaaag     60
agtagtgagc aatataagac gcaattgtgt ttttcagtaa tgtgcattgt tattgagttg    120
tactgtacct tatttggaag                                                140

<210> SEQ ID NO 207
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2830378

<400> SEQUENCE: 207
tgcttgcacc cacagtccat agacatccaa ccgcccaatg catatccaac ctcagcaact 60
ttacaatccc caacgccagc ccacaacttg actttta 97

<210> SEQ ID NO 208
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2477456

<400> SEQUENCE: 208
ttccagttct gcatctgata ccgtctcctt tccct 35

<210> SEQ ID NO 209
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3451868

<400> SEQUENCE: 209
tgagtgtgct gaagggcgcc attactgtcg tgaaaataca atgtgtgtca acaccccggg 60
ttcttttatg tgcatctgc 79

<210> SEQ ID NO 210
<211> LENGTH: 112
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3087225

<400> SEQUENCE: 210
gttttagagc tgtttactca ttagtaaagg accgcaatgt tagtaaagaa aacctatgaa 60
atgtatgtta aagattctta gtattgtaca gggataaagc aaatgcatga aa 112

<210> SEQ ID NO 211
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3020384

<400> SEQUENCE: 211
gcatgtcaac atcgctctaa ttcagagata atctgttgta ccactccttc cctgcaacag 60

<210> SEQ ID NO 212
<211> LENGTH: 56

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2735072

<400> SEQUENCE: 212
tttggtggtg tcaattgctt atttgttttc ccacggttgt ccagcaatta ataaaa 56

<210> SEQ ID NO 213
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2598353

<400> SEQUENCE: 213
gacgttttat caaattggag attcatggga gaagtatgtg catggtgtca gataccagtg 60
ctactgctat ggccgtggca ttggggagtg gcattgccaa c 101

<210> SEQ ID NO 214
<211> LENGTH: 597
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3385809

<400> SEQUENCE: 214
acgttgatga gcctaggcct ttgcagacct cttacagtta ctctgtcaca gcccttcaaa 60
ggttctttga cttcagatta agaatcaatt gcatgtggaa tgcatgtgca aaggaagaga 120
tattcaaggc aattgttacc atgtaccata aaccttgtac ataatttttt gtcattttct 180
tttcctctgt ctctatccct tcttctttga cacacaatag acacctagtc aatttattac 240
aaaaaaaatg aatgaatgaa gtggaattca gttgggaaat aggttaaata aattatttag 300
gagatgagga ataggtaaaa agagacaagt acatagttta ttcttttgac ttagaaaact 360
tttgattctt aaattctgca gaattggaga aactggtggg gaaacttcta aaatcattat 420
ttaattacca gagatgtaat agatatagac aaaagcagtt ttcttctttt attatttttt 480
catcagttag ttcttagctt aaatagtagt ccaaagctgg tagggacaga gggaattagc 540
tggtggctga atgaggaatt gtatcacttt ttgtgaatca cggtgtaagc acatttg 597

<210> SEQ ID NO 215
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2721985

<400> SEQUENCE: 215
gttccctcga ctgctaactg cacctcccct tccctctgtt ggacggatgg catccaaaac 60
tggaccatga 70

<210> SEQ ID NO 216
<211> LENGTH: 137
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3020363

<400> SEQUENCE: 216
agcgcgccgt gatgaatatc gaacagagtt taccacagct ttgcagcgcg ttgacttatt 60
catgggtcaa ttcagcgaag tcctcttaac atctatatcc accttcatta aaggagacct 120
caccatagct aatcttg 137

<210> SEQ ID NO 217
<211> LENGTH: 153
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2437139

<400> SEQUENCE: 217
actctggtgc acaacggcac ctctgccagg gctaccacaa ccccagccag caagagcact 60
ccattctcaa ttcccagcca ccactctgat actcctacca cccttgccag ccatagcacc 120
aagactgatg ccagtagcac tcaccatagc acg 153

<210> SEQ ID NO 218
<211> LENGTH: 105
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3460453

<400> SEQUENCE: 218
tttacctgac tcttaagaca cctgcaacat atcccttgga tgttccgcct tgtcacactc 60
ataaccgagg ggaaaaagaa gacaaaggtg aatgctcagt tagcc 105

<210> SEQ ID NO 219
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3020356

<400> SEQUENCE: 219
cattgatgcc aataagataa aactagacct cagtggctcc tcctcaactc cacccaatct 60
atttgtctcc aaagtgct 78

<210> SEQ ID NO 220
<211> LENGTH: 336
<212> TYPE: DNA
<213> ORGANISM: Artificial Sequence -continued
<220> FEATURE:
<223> OTHER INFORMATION: Description of Artificial Sequence: Synthetic
      polynucleotide
<220> FEATURE:
<223> OTHER INFORMATION: Affymetrix ID 2830183

<400> SEQUENCE: 220
ggaagtatcc agacaccaat ttttaataaa atgaattccc caaagggagt cttgactgaa 60
ttaaggctgt tgtttatagg aagccagata taatgatgtg aaaaaaacta atttttaata 120
ataatcaccg gcagtaacgg gggcaggggg aaaaagtaca gtgtggtgta ttttttgttt 180
ttttcttttt cacaacatct acaggacaca agagaagcac ttagacactg taaggctggg 240
aaccatgctg taataaccac cagtgtgggt aatcaaaaag ggtctttgac atttaagagg 300
gttggggctc cctgcactgt cagaattcca cgtaaa 336

<210> SEQ ID NO 221
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2562444

<400> SEQUENCE: 221
acctaccacg acctcccagg gctgggctca ggaaaaacca gccactgctt tacaggacag 60
ggggttgaag ctgagccccg cctcacaccc acccccatgc actcaaagat tggattttac 120
agctacttg 129

<210> SEQ ID NO 222
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2830181

<400> SEQUENCE: 222
gataagtcta cgtggaaaag cattcagaat ttactaggtt tttgctacat cactatttca 60
tctacaatag ggacaacaaa ctgacactca ggatttgatg ggctctcatt 110

<210> SEQ ID NO 223
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2764175

<400> SEQUENCE: 223
acacacgtgt gctcgactgt acttaatgat cccagttcac tgggcagtcc agttgggtac 60
agctttcccc aaaaatctgg agctttgcag gcatggagag aggacagcta atcaaagccc 120
atctgtggga aaatggaaaa atgtttggaa agagattcca gtgggtgggt ggatggaaag 180
aaggaagtta acccaggaag tcatcttgca cagaaagtaa ggaggcagag aggggtggag 240
agctattcca ggtgcagata ctccctggga ttcaaggtgg cagcatgcag gctacgagcc 300

-continued

```
tggataactt gcacgtttta tttcaaaaga tccaacaggg agggcttttg ttatctgacc    360

aagagaggag cgttagactt tagccacaat gcttttgaat tgggcttctt agtttgctaa    420

attaagaatc tggggccctt ttggcagaat gctatgctac tcattcctca ctttcttctc    480

ctccatctgc cccactctct gtctcttagg aagacaagag cagcaggtga gcacatgtat    540

ccagcctgaa ctctagttca ggcgtggctc cca                                 573


<210> SEQ ID NO 224
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3907240

<400> SEQUENCE: 224

tgacttggaa gactccatga tcggccctga agttgtccat cccttg                    46


<210> SEQ ID NO 225
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3917721

<400> SEQUENCE: 225

gctggggcta tggatgctac acaaaggaac t                                    31


<210> SEQ ID NO 226
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2442021

<400> SEQUENCE: 226

aggcagaatg tgctaccagt ggtcatgaag acatgcctgt ggagaggatt ctagaagctg     60

aacttgctgt tga                                                        73


<210> SEQ ID NO 227
<211> LENGTH: 640
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3907235

<400> SEQUENCE: 227

tccagctctg attacctttg aagtgttcag aagagacatt gtcttctact gttctgccag     60

gttcttcttg agctttgggc ctcagttgcc ctggcagaaa aatggattca acttggcctt    120

tctgaaggca agactgggat tggatcactt cttaaacttc cagttaagaa tctaggtccg    180

ccctcaagcc catactgacc atgcctcatc cagagctcct ctgaagccag ggggctaacg    240

gatgttgtgt ggagtcctgg ctggaggtcc tcccccagtg gccttcctcc cttcctttca    300
```

```
cagccggtct ctctgccagg aaatggggga aggaactaga accacctgca ccttgagatg      360

tttctgtaaa tgggtacttg tgatcacact acgggaatct ctgtggtata tacctggggc      420

cattctaggc tctttcaagt gacttttgga aatcaacctt ttttatttgg gggggaggat      480

ggggaaaaga gctgagagtt tatgctgaaa tggatttata gaatatttgt aaatctattt      540

ttagtgtttg ttcgtttttt taactgttca ttcctttgtg cagagtgtat atctctgcct      600

gggcaagagt gtggaggtgc cgaggtgtct tcattctctc                             640

<210> SEQ ID NO 228
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3451838

<400> SEQUENCE: 228

aatggattcg ttatgtgtcg acggatggtc tgtgactgtg agaatcccac agttgatctt      60

tt                                                                      62

<210> SEQ ID NO 229
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3769234

<400> SEQUENCE: 229

tcacgattgt caatggctag gattgttcaa cttgccagag cccagagcgg aaacccaaaa      60

ttaccagaaa agagattcta ctttgctgag ggttggggat gggcaggtag ctatgccaca     120

cttttt                                                                 126

<210> SEQ ID NO 230
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3577636

<400> SEQUENCE: 230

gaccctttga agtcaaggac accgaggaag aggacttcca cgtggaccag gtgaccaccg      60

tgaaggtgcc tatgatgaag cgtttaggca tgtttaacat ccagcactgt aagaagctgt     120

ccagctgggt gctgctgatg aaatacctgg gcaatgccac cgccatcttc ttcctgcctg     180

atgag                                                                  185

<210> SEQ ID NO 231
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Affymetrix ID 2377236

<400> SEQUENCE: 231
cgtacaagtt ttcccgagga tactgtaata acgtacaaat gtgaagaaag ctttgtgaaa 60
attcctggcg agaaggactc agtgatctgc cttaagggca gtcaatggtc aga 113

<210> SEQ ID NO 232
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2435391

<400> SEQUENCE: 232
gcagaaatga gcagttcgct cctccctgat aagagttgtc ccaaagggtc gcttaaggaa 60
tctgccccac agcttccccc atagaaggat ttcatgagca gatcaggaca cttagcaaat 120
gta 123

<210> SEQ ID NO 233
<211> LENGTH: 553
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2400186

<400> SEQUENCE: 233
ccctgtctct ccgttctagc tcgtccccca ccccaccttt tcttctttct cctcctctcc 60
ttcctctccc cctctcctct gtctccttcc accgtctccc ctgcctccct gtctttcagt 120
ccctgttttt cagccccgtc tccctctcgg tttctctccc ccaccctccc tccgggtttc 180
ctccccggtg ccctccctcc tctctccctc ccctccccct ccgcccctcg cagccccgcc 240
gctcgcagct cccagtctgc ctccccgaac cggcgccgcc gcccgcactc gccgcaggac 300
cggcccgccc ggctcccggg gtgcgccctc ctcggtcccg cgccctccgg gctcgcaggg 360
acgtctcctc cctcccggct cgcggccccg cccggcccgg cccccgccca gagccccagc 420
gcgccgagga tgtgagtcct gctcgcctct ggcggagcag cagccactcg cgcgcggagc 480
cggagcgcag cgcagcgcag ccgcgggcgc tctccgggcc gctcgcgcga gtgccgcgct 540
cttgccctag cgg 553

<210> SEQ ID NO 234
<211> LENGTH: 238
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2751991

<400> SEQUENCE: 234
ccctagggct agtatgcacc atattgcatt taaaaaaatg tttggaaagc tgttggaaac 60
tttttgtcaa cacgtccaca tttgcagtaa tattctgtgg ctttgaatgt aaatttagga 120
atttatcatg ttcacaaata aaggagagat gaagtttact aataataaaa tgaaactgat 180

-continued aatcagtttt gaatctaagc agttgtttca gaggcggttt catgtgagtc tttgatta 238

<210> SEQ ID NO 235
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2377265

<400> SEQUENCE: 235
tttaaaagat agaaagatgc tcatcctagt gacagaccaa gagacaatac aacccaaatt 60
ggac 64

<210> SEQ ID NO 236
<211> LENGTH: 94
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3464878

<400> SEQUENCE: 236
cttgtggtgt ttcttgcgcc gggctgcggt tcttacaagc tgtgaaaact actacggctt 60
ctcaggttag atgattgctt ttctcgttct ggca 94

<210> SEQ ID NO 237
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3835890

<400> SEQUENCE: 237
cgcgcagcct gcagcgggag accctgtccc cgccccagcc gtcctcctgg ggtggaccct 60
agtttaataa agattcacca agt 83

<210> SEQ ID NO 238
<211> LENGTH: 124
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2721999

<400> SEQUENCE: 238
cccattagcg aatgaaattg atgcagtcct acctaactcg attccctttg gcttggtggt 60
aggcctgcag ggcactttta ttccaacccc tggtcactca gtaatctttt actccaggaa 120
ggca 124

<210> SEQ ID NO 239
<211> LENGTH: 126
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Affymetrix ID 3125505

<400> SEQUENCE: 239
ttgcctgtgt caatgaatcc tgttctcact acctgggatt ttccattcac cctcctcctt     60
caccaccccc acccatacac acatattcca gatccaacgg gcagcctcca tcatgtcaca    120
ctcttc                                                               126

<210> SEQ ID NO 240
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2562443

<400> SEQUENCE: 240
tcagcaattc cccagcgtag tcaagggtgg acactgcacg ctctggcatg atgggatggc     60
gaccgggcaa gctttcttcc t                                               81

<210> SEQ ID NO 241
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2453163

<400> SEQUENCE: 241
acttgtaggg aatcacggca ccttaattgt ccaatttggg ttgtattgtc tcttggtctg     60
tcactaggat gagcatctt                                                  79

<210> SEQ ID NO 242
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3263752

<400> SEQUENCE: 242
gttctggcaa gtccatatca gctcatgtct agattaccca tgaaatcctc ccatc          55

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3825012

<400> SEQUENCE: 243
ggctggtctg atggaactgt gtatttattt                                      30

<210> SEQ ID NO 244

```
<211> LENGTH: 224
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2377237

<400> SEQUENCE: 244

ccgtgtttga tactgatacc tagtagaatt aaaagaaatg aagatttctt gttttaggtg     60

aatatacata cagtcatcca caccttatgt gccctttgat ttcataaaat atatattggc    120

attatcttgg aggaaaaaaa tctgttactt acatagccct gtattagctt tgagatatat    180

gagtagagat aaagataaag agacccgata acctgacttt gaac                     224


<210> SEQ ID NO 245
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3907194

<400> SEQUENCE: 245

accctgagac ttggctccac cactgatatc ctcctttggg gaaaggct                  48


<210> SEQ ID NO 246
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2377268

<400> SEQUENCE: 246

ggcacacgtg tttcacgttg acaggtttgc ttgggacgct agtaaccatg ggcttgctga     60


<210> SEQ ID NO 247
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3343458

<400> SEQUENCE: 247

ttaagttaat cttcacgttt ttgcaaactt tgatttttat ttcatctgaa cttgtttcaa     60

agattta                                                               67


<210> SEQ ID NO 248
<211> LENGTH: 572
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2377271

<400> SEQUENCE: 248
```

-continued

```
ggcagtcctg gaatcacatt cttagcacac ctacacctct tgaaaataga acaacttgca     60

gaattgagag tgattccttt cctaaaagtg taagaaagca tagagatttg ttcgtattta    120

gaatgggatc acgaggaaaa gagaaggaaa gtgatttttt tccacaagat ctgtaatgtt    180

atttccactt ataaaggaaa taaaaaatga aaaacattat ttggatatca aaagcaaata    240

aaaacccaat tcagtctctt ctaagcaaaa ttgctaaaga gagatgaacc acattataaa    300

gtaatctttg gctgtaaggc attttcatct ttccttcggg ttggcaaaat attttaaagg    360

taaaacatgc tggtgaacca ggggtgttga tggtgataag ggaggaatat agaatgaaag    420

actgaatctt cctttgttgc acaaatagag tttggaaaaa gcctgtgaaa ggtgtcttct    480

ttgacttaat gtctttaaaa gtatccagag atactacaat attaacataa gaaaagatta    540

tatattattt ctgaatcgag atgtccatag tc                                  572
```

<210> SEQ ID NO 249
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2359172

<400> SEQUENCE: 249

```
gctaagtgtc ctgatctgct catgaaatcc ttctatgggg gaagctgtgg ggcagattcc     60

ttaagcgacc ctttgggaca actcttatca gggaggagcg aactgctc                 108
```

<210> SEQ ID NO 250
<211> LENGTH: 2882
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3733280

<400> SEQUENCE: 250

```
acacggtctg ttggtcagag gcccaaaaca gttatacaga tgacggtact ggtcaagatg     60

ggtcaagcaa gcggccacaa gggactgagg caagcacaat ggtttcaaag aaagactgta    120

agctccatga ttagcataaa gcactaacca tgtctccatg tgacccgatg gcacatagat    180

gttgtagaat aagttatggg tttttatgtt ttgttttgtg tttttccaaa acttgaactt    240

gcaggcaagc cttggttggg tatttgattt atccagaatg cttctcttta gggaacaagg    300

atgtttttaa tggcataaca aaggcaagac tctgccttaa tttttgaaaa gctgctaact    360

acatgaacac aaatgtgtat ttttgttgca gtgtagtttt ccttttgtgt aattttaaag    420

tcagtgttga attttattga aagctcatga tgcgcttcaa agtggcaagt atttggctat    480

taactgccaa aacaagagcc tgattttttg aggccagtaa ttcgtttgct agaattgatt    540

tttttctct ctctctttgt tacataaggg cattatgtaa cactagccga atggtagcct     600

ctgggttgtt gttttttttct tttcctccat gatgttaatg ggttatctca aattttaagt   660

taaactacct aaaataaata ccaaagataa tgcatatttt tgcacagtgg agcttacact    720

taaaagaaaa caaagcccca tgggctgcct tgaaatcaag agacaataac tttgaacctc    780

agcaagacct tgaaccgccg gttcattttg caccttattc agaaaataga gcatcatact    840

caccgagtct agtcagtgta gtgcttttaa aaattttgtc ctttcatgta actttttttat   900
```

-continued

```
tttaagagga agaagaagaa aggggcacac acacacaata ccgacgtcta tcctttcctg    960
ctaggcagtg ctggccaggc tcatgtgtag tgtgcgagat ggtgatgtac tcttatattt   1020
ttctgggctt ttccttttgc acattccaaa attcatttca taagacaaga tcttcatagg   1080
acctccttgg catcctggca ttctcaaaac tgagccatcc agcatgaaag ataaatgggt   1140
ttaaaccctt gctgctgaat ttattgcctg gactgtcagg acatcaccag cccaccttca   1200
ccttagggaa gatgccacac ctggcctcca cacttgctct tctgatcagt ctgtctggat   1260
tgagtcctac agtgtcagat agggcggcaa atgccaaagc agggaaacag ggaggtgtgg   1320
acaagccagt ttgatgcagc acttcagatc aagtgcttag gaaggagagg aaacttgcct   1380
tttttatggc agaggatagt aatgaaaatg tctcagtatt ttagggtcaa tgagagccat   1440
aaaaatataa cataatcaca agtaaaggag ataatggtct aaaacagcta tttccctttt   1500
ctgtgtgcat acttatgact gaatgtgagc taagcatttt ctcctgtgga gccctagagc   1560
aggttactaa ggaaggacac attgttttcc agaagcctcc cctgcctggc tgactgcctt   1620
gctagaaaca taattttttt tttctcactg aagctcaata atggaactct tttttttttt   1680
tttttaatt taaagttccc tatttgtgaa ttctgggatt actgactttt ctttttaatt   1740
ggagtctcaa aatcaactct cttatggtat tatatctctg tatgccatta aaaaacagct   1800
tgttctagaa tcatgtattt tgtaaactga tgtttgtgat ggtctctggt tcttgaacag   1860
ccatatctga atgccgtgcc tgcaaaacta tgacaatttt tgctgttttc agccttcaga   1920
tttgatggct tgggaaactg aggtgttatt ttcaatgaaa caaagaaaga gatgttaagc   1980
aagtggttgt tttagatcca aatgtaaagg caggtttggg aaggtgttta aagagttgga   2040
ggaattgggg attgagttgt aaagaaaact tacagaagag gcaacaattt ggttcttgac   2100
agtgagagga tattgagggc ttcagctgct gctattatga tgttttgcaa aggaaaataa   2160
tcaaaccaaa gagtattcag tgatatgtaa attaaatgaa gatacagtgg agaatggggg   2220
tgaccacaaa agaggctccc cctaaacaca cagtgctgcc acttaaaaag acttgagaaa   2280
tttgaaaggg ggtgggtatg gggggggcaa gaaagaggga gggaaatctt tcaacttatt   2340
tctgaaaaag agaaaaaaat ataaaatttc tggtgcacag gtttgttttt tcaagaaaat   2400
tttgcagaag ctatgttttt aaagtgtaca ttttataaag tttatcagat attttcatat   2460
ttaaagccaa atgtaaatag aggtctgtaa agaaaaataa ttgccataga aagtataatt   2520
tcagtgcagt aatttctgag agctagtacc tatatgctac cggttagcat ggttttagca   2580
aatatatacc agccttataa ggttcgtatt gctatgttct tctgttattt atttcagcat   2640
ggactgttca tttgaaacct ttttctagtt attagcgttt taacagttac aagctttaaa   2700
tggcaatttt tttttttttt tttttttttt tttttttttt gtcaagagcc aagacacagg   2760
taatgcacga cattgattgc tgcattttac cttcaaaata tttgtcctta ttgactgggt   2820
ctccttaatt aatgtacaca tgtcattaga atgcagacgg aggggactca ccatgaatat   2880
ct                                                                  2882
```

<210> SEQ ID NO 251
<211> LENGTH: 460
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3020355

<400> SEQUENCE: 251
cagacttctg ccttatcagt ggccatccca ccctatgttc ttatctcctc agtctaaaaa 60
gaaaaatggg gacccatcag aatttggata gaagaccctc caggaatttc tgccactgct 120
tattcatggg ttggcacaga cactgattca gtgggcacac agagttcaga atgattcaga 180
gcccagatat gtgccctaag tcacatctcc agcgtccagg gaggactgta aagtgctcgt 240
tatcaggaaa atgaaaccaa gggctcagct actcctgaag tcattaaaac tccttccctt 300
gatttttttt tttttttttt taaatagtat atgtggtaac cgaatctagg atcctggata 360
cattccagtc tgctaattac atattttttt ctaactaaaa tgttccaggc aggttcattt 420
gcatgtgaat tacttgctga gccatgttga cttcctattc 460

<210> SEQ ID NO 252
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2453796

<400> SEQUENCE: 252
ggaccggttg ggtcagagtt ccatgctgg 29

<210> SEQ ID NO 253
<211> LENGTH: 149
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3460455

<400> SEQUENCE: 253
agcgaccata tgttaaacct ccatgtgtgc ctgctctttt cagtcatcta ataaatgatt 60
ctgccattat tgttactctt gtgcaagcac gggcaaatac cacaagcaag acttgaaaac 120
aaatcctcag ttccctgtct ttaacaatg 149

<210> SEQ ID NO 254
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3928709

<400> SEQUENCE: 254
cctgccctga cggtcgtccg gccaggcgac actgcacggg acaccctgga gct 53

<210> SEQ ID NO 255
<211> LENGTH: 439
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3351275

<400> SEQUENCE: 255
cccttgacta tttagccaag acataagcta caaattttgc cggaaaaact gtccatacat 60
ttttaactac ttcttcatta ttcttatgga ccatcatcca ggacatctgt ttgaagaaat 120
atccagttat aatattttca aaggttagaa ttgtgaagaa aaaatataaa atgtgattaa 180
aggatatata gccttcagat gtaatttaca gttttaaaat tgcactttaa aactttgctt 240
ttttagacag tataaaaggc agaatgagac agatatgtaa tgaatttcag aactgaggtt 300
catatgtaaa tcatacaatt ttttaaaaaa tagtattgga aaaatatcaa ggtctataca 360
tttaaataca gataatctgt ttgaaaattc cagtttgtta aaagaaaaaa catctgcagt 420
ccagtcgatt aaaaactga 439

<210> SEQ ID NO 256
<211> LENGTH: 153
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3217301

<400> SEQUENCE: 256
gaggagtcaa gagccttgct tgcctgcgtc agcgctgtgc cagcagccac ctctttccag 60
agggctcctc ttctctctct ccatcttatc acagcctctt cttctgacct catccaacgc 120
ttctgcttca acatcaaagg aggacacttt taa 153

<210> SEQ ID NO 257
<211> LENGTH: 220
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2377263

<400> SEQUENCE: 257
tgagcatgtg gtcaatctta gagtatgtgc tatgtgcaga tgagaagaat gtatatcctg 60
ttgttcttgg gtgtaatgtt atgtagatgt ctgttaagtc catttggtca agtgtcaagt 120
ttaggtcatg aatatctttg ttagttttct gccttgatta tgtgtctaac attgtcaatg 180
gggtgttgaa gtctcccact atattgtgtg gttatttcca 220

<210> SEQ ID NO 258
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3976345

<400> SEQUENCE: 258
tggcttctgg catcctgttg ttgctgtggc tgatagcccc cagcagggcc tgcacctgtg 60
tcccacccca cccacagacg gccttctgca attccgacct cg 102

<210> SEQ ID NO 259
<211> LENGTH: 88
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2377245

<400> SEQUENCE: 259
tcaaggggaa cgtgaccatt atggatatag acagtctgta acgtatgcat gtaataaagg 60
attcaccatg attggagagc actctatt 88

<210> SEQ ID NO 260
<211> LENGTH: 109
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2414961

<400> SEQUENCE: 260
gtgagtcacg cttcctgatt cctcggcgca aaggagacgt ttatcctttc aaattcctgc 60
cttccccctc ccttttgcgc acacaccagg tttaatagat cctggcctc 109

<210> SEQ ID NO 261
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2876911

<400> SEQUENCE: 261
ctgagggtgc acacccgagc cgtgacagag g 31

<210> SEQ ID NO 262
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2764272

<400> SEQUENCE: 262
agtagtaacc actagcattg gacaggattt 30

<210> SEQ ID NO 263
<211> LENGTH: 109
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3406425

<400> SEQUENCE: 263
ctcaggaata cagagaatac taaccaaaag aagctactcc gaggtgacgg caaagttaag 60
gataaaaagc atgctcaaag aaaaaatcgg agcagactag aaatcttgt 109

<210> SEQ ID NO 264

```
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3222204

<400> SEQUENCE: 264

ctaccggatc gccatgactt taacatcttt gttcacattc cctacttaat ccataaatgt     60

agtctactgt ttcaccttct ccccacactc cctcttgtca tatgtactta atgaacactc    120

cccactccca ccccagaaat gagaaggtcg aaatatttct gctttgtatt caaaatcctt    180

tagaccttgt cttgtccata gctcttgtgt gcttacctca tatcatcgtc ccttgtgatc    240

aacctggctg gtccccagct acatttcagc cttctcaaaa gaaatatacc aatgagtata    300

tttccaaaac gtatttaaaa cttttgccat ctcaaaatct caaccatgat cttaacaaac    360

ttacccagtg ggctcgtcat tggaaaacca aatgtgaact tattttatcg gtaatcacta    420

atatcagaga gactctgcaa cacggactaa atccataatt ttctcaagac taatgattcc    480

tacagaaatt aacaacggaa tagtcaaaca tctgtgtttc ccaaagtctt tctagagatt    540

actagctcca cagaatgttc aaaggtccta ctcggtgagg aaattccacg ttcaaataag    600

tttggaaaga ctgagttaaa caaagttaaa gaggatcttt aactgcacgg cttttcagaa    660

caccctaacg tgcatcatct ccaagaagta cttatccagg cagtattttc caaacttatt    720

tgacaaagga tactttttaa ggaagaggat caaacaggaa tagttcactg tgagcacact    780

ttgggaaact cagctctaaa tctacattga cattgagttt tgtctagtta aggcaatgca    840

agatgaaacc ctgggtcc                                                  858


<210> SEQ ID NO 265
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3928687

<400> SEQUENCE: 265

ctctctgggg ggatcattcc tgtattatgc tgaccgcttc aagctctaca gtgccttctg     60

cgccagccac acaaaagttc ccaagg                                          86


<210> SEQ ID NO 266
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3067480

<400> SEQUENCE: 266

catactggta gatgcgaaat ttatctgtgc atgaaagggt cacttctgta atagtgcaac     60

agatttggta                                                            70


<210> SEQ ID NO 267
<211> LENGTH: 96
<212> TYPE: DNA
```

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3451908

<400> SEQUENCE: 267
ccctacagat tgacgtctta acagagttag aacttgggga gtccacgacc ggagtgcgtc 60
aggtcccggg gctgcataat gggacgaaag cctttc 96

<210> SEQ ID NO 268
<211> LENGTH: 1255
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3928672

<400> SEQUENCE: 268
ttgccgtgtt ctgactgtac ccttccctct tccatgtctg agaatctccg tgtattttaa 60
gaatgtgtga ggagagggtg gcgattcatg tttcaatgag cctctttttt tttttccttc 120
ctgttttggt ctatggctgg tcttactctg tgtccatgtt cggaagctct agttttgcat 180
agaattatag agatgccaaa ctctttgaaa agagatccaa atttatcgct tgagagaaag 240
aaaagaaaca ctatttttg tattttacct gagatacagg ggcacaaata gatgagaatt 300
ttacagtgtt agtgtatgta tccctgagcc taaaaaatga ggatataacc ttttacagag 360
agagtgaggc gtggtggttt tatatttata tatgaaaggc cagcaagctc atgcgaagga 420
tatacttttc ttccaaaaag cggatttttt ttttttaatg tttgaatcta tatttgagat 480
gggagtttgg ttggattaaa catgacaccc cggtgggcgg tgtgtgtgtc tgttgcacat 540
ggcagggagg ggagcctcct tctcatgggg ttgccatggt gatcattggt ttttccatca 600
aaattgcatc ttcatccata gattaccttc cccttccctg acagtccata accaaacctt 660
taaacagaac aacctcttta aaaacttctc ttgtgtttaa cactttcttc atgccaacga 720
aacagggtaa acatgctcaa aacattaaca gtctaaacag atatccaaat actaagaaga 780
aaaacaagtt atagcacttt caattttttt ttttttttta aaaaaaggtt tatagctttt 840
tcttttccca tgtcacaatg tccacttcct aagaagggtt taaaatacta tgaaaacttt 900
ctttttgggg aaaatatcta tttggtgttt gacacatcag taggtacttt aaagacctga 960
attttatagt agctttagga gttatatttt ataaaaatca gttatgactt tatatttcca 1020
gacaatagag agttcagtac atcatgctct tgtgcctctg cctgcttttc ctgcgttccc 1080
accctgtatt ccccccgcct ttcgggtttc cagggcttcg agcttgatct tttgaaagtt 1140
ttattctatt aaatttttgc tatatcttct ggttttctga aaaagcttta gaatggtttc 1200 tataccctttt gtatcactgc atttttccat atcatctccg gttcgatcgc gtcca 1255

<210> SEQ ID NO 269
<211> LENGTH: 199
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2437119

<400> SEQUENCE: 269
ctgcaccctg tttgggctgg tgagctggga gttcaggtgg gctgctcaca gcctccttca 60
gaggccccac caatttctcg gacacttctc agtgtgtgga agctcatgtg ggcccctgag 120
ggctcatgcc tgggaagtgt tgtggtgggg gctcccagga ggactggccc agagagccct 180
gagatagcgg ggatcctga 199

<210> SEQ ID NO 270
<211> LENGTH: 370
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3252064

<400> SEQUENCE: 270
cactaacgac ttcagggcag ggctctgata ttccatgaat gtatcaggaa atatatatgt 60
gtgtgtatgt ttgcacactt gtgtgtgggc tgtgagtgta agtgtgagta agagctggtg 120
tctgattgtt aagtctaaat atttccttaa actgtgtgga ctgtgatgcc acacagagtg 180
gtctttctgg agaggttata ggtcactcct ggggcctctt gggtccccca cgtgacagtg 240
cctgggaatg tattattctg cagcatgacc tgtgaccagc actgtctcag tttcactttc 300
acatagatgt ccctttcttg gccagttatc ccttcctttt agcctagttc atccaatcct 360
cactgggtgg 370

<210> SEQ ID NO 271
<211> LENGTH: 1017
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2751985

<400> SEQUENCE: 271
actgaaaacc gcctgaaacc tgctgcaact attgttatta actctgtata gctccaaacc 60
tggaacctcc tgatcagttt gaaggacatt gataaactgt gattttacaa taacattatc 120
atctgcagtt actgtttaca agactgcttt taccttaaac tttgtagatg tttacatctt 180
tttgttgtgt tttaagatga tgttggtaat ttgtgccttt agctctgttt tattagacag 240
agttaaagca tgttgtcttc tttgggatta cactcagggg tctgaaaggc agtttgattt 300
ttatttttaa cacacttgaa aaaaggttgg agtagccaga ctttcatata taacttggtg 360
attatcaacc tgttgtgtct ttatttaatt ttacatcttt ttgaagcact gccacaggtt 420
attagccaag gtggccttcc ttcacagtca tgctgctttt ttgaaaggtg aatttcaaca 480
catttagtgc ctctttcatt tctcagtata tatttcaaga gcttgtgatg aaatctatag 540
gatggtaatg atggacttgt cacctgtatg gggaatactt ttactactca gaaatgaatt 600
tatgtgctgc catttgctat aaagttgaac tttgtatggc ttgaaaaaga aatgacaata 660
tggaacatcc caaggctgtc ccatagggtt ggaagttgtg tagcattcac tcccttacct 720
actggcattc ccagtgccct ctgtccatac ctacttctag gattgcaaag gagtcttcca 780
actagagaaa aattgtccac tgacatttgg gatttacttt tctccaatac ctgccaatac 840
agaaaactat tatcagttgt tattgttatc ccttgaaagc gagggtgaca aaaacaacaa 900
aacaccgtta taaacacatc aaaggttcat tctgactgag gtaagacttt ccaagccctt 960
gttagattag gccttataaa acttgtgtgc attataacct aagctgtgca acctgtg 1017

<210> SEQ ID NO 272
<211> LENGTH: 164
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2830201

<400> SEQUENCE: 272
aagactcaag ttggaagatg caaattcaga ttacaagcta cctcacctgc tacctgccac 60
ctctctggct ctcctacaaa ccagatcatc catgcaacag gtcccacgcc cccatgggca 120
gggcccacac catcagtagg aaaggctttg ctaatgatgg ccta 164

<210> SEQ ID NO 273
<211> LENGTH: 191
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3126229

<400> SEQUENCE: 273
ggggaaacat agctctactt ggagagttta gtttgaggtg ttgaattcag agtgtgtgga 60
ataataaatg gatgtgtcca gtaagcaatt atgcatactt tgatctggag ccaatgaagg 120
ggccagaaat gcagatctga acagtcatta acaaaaaatt ggtaatttaa gccatgcaag 180
tagatgatgt c 191

<210> SEQ ID NO 274
<211> LENGTH: 154
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3252057

<400> SEQUENCE: 274
tgtttaggga gcgatgggct gcaaaggtaa atagatggta ggggctatag gtggagtaaa 60
ggctcagatt tgcatggaag agaataaggg ccttccctgg tagagatact ttatggttcc 120
cctctctggc agactcccag tggacagata aatc 154

<210> SEQ ID NO 275
<211> LENGTH: 301
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3222218

<400> SEQUENCE: 275
gaaacacttg gcttctaggg cagtaagtcc acagtatgtc atttgcagtt gaaatgtgga 60
gccagcattt atgtgaagcc tcttggtcct catctcaact attgtccact gtatttttta 120
ttcataatat tccccttct ttcataattc tgaccccctc tctctttaat ttagctactg 180
attttatttg tggaagttgt accttttact cacttggcta gcatttattt aataaaggga 240
tctggatggg gcacacgtag catccactac tgacatggcc acagtactgc ctctctgagt 300
t 301

<210> SEQ ID NO 276
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3217284

<400> SEQUENCE: 276
agtacaacgc tgtggccgac acactggaga tc 32

<210> SEQ ID NO 277
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3401511

<400> SEQUENCE: 277
tgggcgctca ataaacacac atgagaac 28

<210> SEQ ID NO 278
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3020380

<400> SEQUENCE: 278
aacagtattc ttgaatgtta taccccagcc caaaccattt caactgagtt tgctgttaaa 60
ttgaaaattg acttagccaa ccgagagaca agcatcttca gttaccgtga agatcccatt 120
gtc 123

<210> SEQ ID NO 279
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3371817

<400> SEQUENCE: 279
tcaccttgcc tggcttggag tcatgactaa tcctgcacct g 41

<210> SEQ ID NO 280
<211> LENGTH: 82
<212> TYPE: DNA
<213> ORGANISM: Artificial Sequence -continued
<220> FEATURE:
<223> OTHER INFORMATION: Description of Artificial Sequence: Synthetic
oligonucleotide
<220> FEATURE:
<223> OTHER INFORMATION: Affymetrix ID 2377242

<400> SEQUENCE: 280
caaattattt ggctcgactt ctagtttttg tcttatttca ggcagctctg tccagtggag 60
tgacccgttg ccagagtgca ga 82

<210> SEQ ID NO 281
<211> LENGTH: 326
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2558708

<400> SEQUENCE: 281
gagaggccat tgtaggttta ttgattggcc tagttttaat attattgtgt ctcagggaat 60
agggaggcct gaggagaagg agagagatgg agaaatgact gataaatgtg tgttctgact 120
gctccattga tcagctaagt ttgctgtctt ctacgggtgt ggttcatggc accccgaaac 180
aattacaata gtaacatcaa agatcactga gcacctgtca ccataacaga tattataata 240
ataatgaatt gtgattatta ccaaaatgtg acacagagac acgaagtgag cgcttgctgt 300
tggatagatg ccacaaactt taaatt 326

<210> SEQ ID NO 282
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3351271

<400> SEQUENCE: 282
ctgcatcccg gcagctcttc agatgcttgc acaccttgtt tacagctccc ggtaacgaca 60

<210> SEQ ID NO 283
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2466609

<400> SEQUENCE: 283
cgacaagtgt ggcttcccag agagcgtgga gaatggggac tttgtgcact gtgaggagtc 60
tgggaggcgc gtgctggtgt attcctgc 88

<210> SEQ ID NO 284
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2537610

<400> SEQUENCE: 284
ggaggttgca cagattgcgg gggatttggg gaga 34

<210> SEQ ID NO 285
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3727592

<400> SEQUENCE: 285
atggagaaaa tgtcccgacc gctccccctg aatcccacct ttatcccgcc tccctacggc 60
gtgctcaggt ccctg 75

<210> SEQ ID NO 286
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3367674

<400> SEQUENCE: 286
atggtggagg atggtagttt cgtcctgggg aaggagggat ttattcatat gcaacatcag 60
taatgccttt caga 74

<210> SEQ ID NO 287
<211> LENGTH: 89
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2537568

<400> SEQUENCE: 287
tccaactttc acgagaagat taagaaaatc cacaaacaat acctgttgtt gcaagctcct 60
gtgatgggcc tgtatttgtt cgccaggca 89

<210> SEQ ID NO 288
<211> LENGTH: 125
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2466585

<400> SEQUENCE: 288
cgctattctg acctcctgat ggcatgggga caatacatcg accacgacat cgcgttcaca 60
ccacagagca ccagcaaagc tgccttcggg ggaggggctg actgccagat gacttgtgag 120
aacca 125

<210> SEQ ID NO 289
<211> LENGTH: 33
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095405

<400> SEQUENCE: 289
cttattttac acatccgaag aaacaccatc aca 33

<210> SEQ ID NO 290
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3933538

<400> SEQUENCE: 290
agttcatatc tggagcctga tgtcttaacg aataaaggtc ccatgctc 48

<210> SEQ ID NO 291
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763591

<400> SEQUENCE: 291
aagacgtccc tgctcggagc ttctcaaata tctgaccaca aacgatgacc ctcctcacac 60
caaacccaca gagaacagaa acagcagcag agacaaatgc acctccaaaa agaagtccca 120
cacacagtcg cagtcacaac acttacaag 149

<210> SEQ ID NO 292
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466562

<400> SEQUENCE: 292
gtccctggaa ggcaattaag gcgcccattt cagaagagtt acagccgtga aaattactca 60
gc 62

<210> SEQ ID NO 293
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3662208

<400> SEQUENCE: 293
gctgtgtttg caaaggggcg tcagagaag 29

<210> SEQ ID NO 294

<211> LENGTH: 114
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466570

<400> SEQUENCE: 294
tgctgagcat cattgcaaac atgtctggat gtctccctta catgctgccc ccaaaatgcc 60
caaacacttg cctggcgaac aaatacaggc ccatcacagg agcttgcaac aaca 114

<210> SEQ ID NO 295
<211> LENGTH: 662
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466631

<400> SEQUENCE: 295
ctcctgggaa gagcactcct ggcttcctgc agggccggtg ggaggaggaa agtgattctg 60
agggagaggc tggagcctta aggaccaaca aggcaaagtg acttgtctca tcctccagag 120
attcaccaac acatgagcct cagaccccag gcttctgcct ccagcagccg ccctgccgca 180
cactgctctt actcctcctt ataccctcac tcacggggaa cacagcccag tgatcccgga 240
ggaaactcac tccctccctg actcaacaag gcagtctcgg gggcaccgtt agccacgcga 300
ccctgtaaag ctgccgtcct catttcacat gtgaagcagc tgaattccag agtgctgggt 360
cccagcccag gcagccctca gcctcacgca aggcaatagt taggagtcct tcggcattga 420
aagcaaactc agacacatct gacctggagt tctacctgca ctaagagaag agagtggtaa 480
ctaattcatg gataaaacag accatcgagg cagcactgaa tgatctcacc cacgaatgac 540
aacagtggca caggagggct atgaacattt tgcttcagga tgttttattt cgctctactg 600
ttatgtagag aaagcatggt ttgcttttta taacttttgt gacccaaaaa taccagactg 660
tt 662

<210> SEQ ID NO 296
<211> LENGTH: 811
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367675

<400> SEQUENCE: 296
gttagtgttc gccaaaggac agccaagctt tcttttaaaa agtgataaaa gtcttatttt 60
aatatgcttt aagctgaaag aaaaaaaaat aagaaacagg cagtgtttta aaaaccaaca 120
cagatttgca caactgttta agagtattgt ttgaaatatt ttaattttca atgttttgtt 180
gttgttgttt tcttggtaat gcttcttttt tgcagatgtg gtcccaattt atagcaatct 240
tctcaacaga agtaggcatg gaaaagactt cttttcatac tctcactata aagaaagctg 300
cattgagaag aaaatggctg tcatttaaag gatggtttaa ctagtgagat tcctattgtg 360
gttatacaag gtctcattgt ttgtttgttt cttttaaatt atttcagctt taaaaataca 420
gaaatggaat ctgtcaagag caggtatttc atacggttaa aaaaatgaac atgcagactc 480
cttttcaata tgggtttata tatataagta ttttttgtgt attatgacta cgttaggagt 540
ttattattgt caaggacagt acaactgcaa agggatgctg tatagcaaca catcagaagt 600
cggaaggaac tgacacattc tctcagagct caaggtctta aagagcttga gttaaatcta 660
ggtacagtta caggcatgta tagacttaaa tggatgcaat ggaagctaac taaaataagg 720
cttagttgtc ctttctattt aaatacccca agttgtcttc ttacttcctc tcccctctcc 780
cattttgcac tgtgtgtcga tgcaatcttc g 811

<210> SEQ ID NO 297
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3367709

<400> SEQUENCE: 297
gttctgcatt gctgataccg ctagtggttt taaaaataga aatcaaaata agaaccctga 60
tattaaggat tcacag 76

<210> SEQ ID NO 298
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2466600

<400> SEQUENCE: 298
cccaggccac acaagactca cggctctccc tggtctc 37

<210> SEQ ID NO 299
<211> LENGTH: 274
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367737

<400> SEQUENCE: 299
gagctaccca gtctacgcta ttttgttaat agcatctcaa acagcccaag gcaggtaggc 60
agggaatata atgggaagat gaattttata gagggaacaa gaggagaaat gggcgtattt 120
gtgaaggaga gagggaaaaa gtaggaggga atatatagca gatgtgtttg tgagatcata 180
actcttcctt gtcagttacg atgtcctgac cttgggcttg actttagcac cgggagcagg 240
tcagcatccc tagacttcag tcaacaggga gatg 274

<210> SEQ ID NO 300
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3018629

<400> SEQUENCE: 300
tctgggtgtt tacgtgtata gtgtccatca ttctggggct ggatctcggt ttactagctg 60
gccttatatt tggactgttg a 81

<210> SEQ ID NO 301
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3132624

<400> SEQUENCE: 301
catctgcagt gtctccctaa actcaataga acagtatcat gcccatctga aa 52

<210> SEQ ID NO 302
<211> LENGTH: 157
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018633

<400> SEQUENCE: 302
ctggaggaac ttgatatccc aaccaaggaa atagagattc aagtggattg gaactctgag 60
cttccagtca aagtgaacgt tcccaaagtg ccaatccata gccttgtgct tgactgtgga 120
gctatatctt tcctggacgt tgttggagtg agatcac 157

<210> SEQ ID NO 303
<211> LENGTH: 204
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367689

<400> SEQUENCE: 303
ctgcatctct tgagaccttg ttagaagtgc aagttctttg gctccatcct atagccacag 60
aaccttggag tggcttcaag tgactgatgt ctaaagtttg agaaacattg cattacagga 120
tgctactttt ccagacttgg ttcttacatt ccataaatat ttatcaagta ctcaataagt 180
ggcagggact attggagata cagc 204

<210> SEQ ID NO 304
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3693001

<400> SEQUENCE: 304
ccctgctccc aagtacaaat agagtgaccc gtaaaatcca ggat 44

<210> SEQ ID NO 305

<211> LENGTH: 173
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018617

<400> SEQUENCE: 305 acctttcca gtggtgagtt taatggtggg atctgttgtt ctgagcatgg cccccgacga 60
acactttctc gtatccagca gcaatggaac tgtattaaat actactatga tagacactgc 120
agctagagat acagctagag tcctgattgc cagtgccctg actctgctgg ttg 173

<210> SEQ ID NO 306
<211> LENGTH: 109
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018618

<400> SEQUENCE: 306
tggtggcttg cagattggat tcatagtgag gtacttggca gatcctttgg ttggtggctt 60
cacaacagct gctgccttcc aagtgctggt ctcacagcta aagattgtc 109

<210> SEQ ID NO 307
<211> LENGTH: 121
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763563

<400> SEQUENCE: 307
ccacaggttc catagaacta atatcctgtc tctctctctc tctctctctc tctcttttt 60 ttttcttttt ccttttgcca tggaatctgg gtgggagagg atactgcggg caccagaatg 120
c 121

<210> SEQ ID NO 308
<211> LENGTH: 112
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3862190

<400> SEQUENCE: 308
catccaccag gaacgaagat ttcctgaaga agacctggtc cctctggagg ttgcagtggc 60
tgaaggatgc atcatgtgct cctaccctgc tctaccgctt ttctgggtca ca 112

<210> SEQ ID NO 309
<211> LENGTH: 239
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:

<223> OTHER INFORMATION: Affymetrix ID 2721305

<400> SEQUENCE: 309
ctggaagctc acatctaaag gcatgaaaag gtttcctttt atcaactgac ccaaacatca 60
taccccaata gtgcaaagtt ccctctctgc tgctttgaat gttgacagcc caactgttgt 120
tctcggagtc gtttagcaaa aaattgattt tgttgcactg gaagaattat tctgctacat 180
ctcttttaaa aaagaaaaaa atccacatta ctaaagcacc agttcggtta ccaaaattg 239

<210> SEQ ID NO 310
<211> LENGTH: 106
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466569

<400> SEQUENCE: 310
cctgagccaa caagcggagt gattgcccga gcagcagaga taatggaaac atcaatacaa 60
gcgatgaaaa gaaaagtcaa cctgaaaact caacaatcac agcatc 106

<210> SEQ ID NO 311
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3367712

<400> SEQUENCE: 311
gtgaagggat tcaggatata cggtgcacct tg 32

<210> SEQ ID NO 312
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3833280

<400> SEQUENCE: 312
tgtgacccag aaaagcggta gagcagggta ggagcacatg atgca 45

<210> SEQ ID NO 313
<211> LENGTH: 1859
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018642

<400> SEQUENCE: 313
taataatgtt cacgtgggcc ctggcatatc tctgttcagt tagagtgagt gctgacccaa 60
cagcctctgt ggtcaagcga gtcacgaatg attaatcata aagaaaaatc agtttttgac 120
tgacctggat atccatgagc tgcactgatc accatgtaag gtcacattta gtaaatgctg 180
aaataaaatg attaatgcat ttatcaataa aagcctttga aaatactttg gataataaat 240
tggagtttta aaaatgcaaa tttgcttagt atctaataat gaagtgttat tacatatagc 300
cggaattgag gatctctttg atcctggaaa tggtttacct aaaagctaca gaaccaggcc 360
aatatatttt gaaatattga tgcagacaaa tgaaataata aagagatttt catggtttat 420
aaaaatcttt tttgatatga taataatcat gatcacaact gagatcaaaa aaatatatga 480
cagattattt tgtttaaaaa tgcagtttta attatcttag tctatagaaa tgatcattgc 540
atggaggcat gtataggtat gatctgtgta aaatctgaca taaaaacagt gctattctga 600
gtgaaaattt ttttgatgtg cttacataac catggtgatt aaaatgagtt tatatttttt 660
ctcaaaaatt ttagcagtgt gtaaagtaag taatctttaa ctgaactctg accacttaaa 720
aaaaaatcta aaaattgaac tacctatagt agtctgtgtt taaagtgaat ttttaaagac 780
aaagcattct aaatgaactc aatataaaaa cattcatttg gaatgtacat actgaaaaat 840
acaggttttt ttgaccaaaa gtttttatat cttttctttt tatttatttt tttcctaagt 900
gccaacaatt ttctagatat tatatacaac acaggctttg atcttgggga cttttcccat 960
atatttcaca ctggagtgaa tgaagttgta cttcatttct agagaaaagt tatacccagg 1020
tccccaattg agaatgtctt gcttgattga aaacgacatc atcccttggt atactccagg 1080
gattggtttc aggacccctg catttaccaa aatttgtgca cactcaagtc ctgcagtcac 1140
ccctgcctaa agatagaatg gcttctctgt ttttcttctg aaatacaacc agaaacaatg 1200
tgtctatttc tgaaagaata ggattaatga tcatacaaat gggttaatcc tgaattctgg 1260
ttgtaaatct ggttacagca taactaggat tataatgctg cctcattttc acagcactac 1320
ttgcttatat tgacaacaaa tcatctcgct aaagagtgaa tgtaggccag gcgcggtggc 1380
tcatgcctgt aatcccagca ctttgggagg ccgaggcggg tggatcacga ggtcaggaga 1440
tcgagaccat cctggctaac atggtaaaac cccgtctcta ctaaaaatag aaaaaaagaa 1500
attagcctag cgtggtggct ggcgggcgcc tgtagtccca gctatttggg aggctaaggc 1560
aggagaatgg cgtgaacccg ggaggcggag cttgcagtga gccgaggtcg tgccactgca 1620
ctccagcctg ggcgacagag caagactccg tctcaaaaaa aaaaaaaaaa aaaaaaaaag 1680
agtgaatgta atagtcttgc agaaaatgaa tgaatacctt tgttcaataa aggaaatatg 1740
cactgctcac ttttttgaag gaaatgccaa agttacgttt tacaacaagg ctagagtttg 1800
taaattctgg gttcatttgt gatgacataa gtcagcaaac tgcgggaata ctgtctctt 1859

<210> SEQ ID NO 314
<211> LENGTH: 513
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367697

<400> SEQUENCE: 314
agtgcttgtt aacccagtgc ctcagccctt cttagacatg aatcagaacc tttggtggta 60
gagcaggaaa ttggcacttt agcacccagg gtgattttta tgcctactaa agtgtgagaa 120
caactgactt tgaagctgta ggtgtttggg ttggtggcgt atttatccct agaattgctc 180
cgtgtaattt gatgatgagg acatctttct gtttctttcc tccaaaatgg aaggcaaact 240
aaattaaaat ccagttaatt caggttctga gttgattggg acatggataa ttgtgatctt 300
tttgctgatt tctaaaatat tttcccttca ttatctgttg gatttcaagt gcattctgct 360
ctgtgttata gaatgagggt tgatgtgaaa cttagggaga ctccaattat atacatggtt 420
caattactgg ttccataatt tagggtgtcc tcttttccca ttgactttca ctttcttcgt 480
acttaaatgg caaggttgta ctctctgatc tca 513

<210> SEQ ID NO 315
<211> LENGTH: 103
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018616

<400> SEQUENCE: 315
tatgccctac tagctgcagt tcctgtcgga tatggtctct actctgcttt tttccctatc 60
ctgacatact ttatctttgg aacatcaaga catatctcag ttg 103

<210> SEQ ID NO 316
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3367743

<400> SEQUENCE: 316
aaatgcacag cggtattgat gagtagatcc ttg 33

<210> SEQ ID NO 317
<211> LENGTH: 131
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2537609

<400> SEQUENCE: 317
gttggattta tggaggttgc acagaaagga gatctgggga ggttgcacac agagtggggg 60
ggatttgggg aggtttcaca aagctagggg catttgagga gaatgcacac agtggggcga 120
tttggggacg t 131

<210> SEQ ID NO 318
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3933539

<400> SEQUENCE: 318
atgcgaggct cggagcaccc ttgcccggct gtgattgctg ccaggcactg ttcatctcag 60
cttttctgtc cctttgctcc cggcaagcgc ttctgc 96

<210> SEQ ID NO 319
<211> LENGTH: 81
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586066

<400> SEQUENCE: 319
taccaaagga agttatgagt gtgtctgtgc tgatggcttc acgtctatga gtgaccgccc     60
tggaaaacga tgtgcagctg a                                               81

<210> SEQ ID NO 320
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3132617

<400> SEQUENCE: 320
tgaccagaat aaggagggtc caatcaacat attattgtgg agatagcctt tttttttttt     60
ttctggcttc tacctaattt atttataata aagacaagct aggctacctc ataggattct    120
ggtgtggatt cgctaattaa ta                                             142

<210> SEQ ID NO 321
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2727647

<400> SEQUENCE: 321
ttctttgcag tggcttaatg tttgaa                                          26

<210> SEQ ID NO 322
<211> LENGTH: 2123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3067233

<400> SEQUENCE: 322
ggagctggag ctatcctacc tcatcagtgt tttgtcttct gttgggatga actttgttaa     60
aactaatgca tggttaagat gaaaggcaga aggaagggtt tgataaacca gaacattctc    120
gcctgattgt tagtgttctg aagtaaatac agaagaggct ccaaaataca gacctctgta    180
catcaacctt ccgtaatcca cctgccttgc atatgcagac catgacaatt ctacgagctc    240
ctggaaacag aactcagaac tcctccccag agaaccctga tgcaaattct ctgaaatggt    300
agtcagcatg tgcgttttcc tgagaagtga atgagtcaac agctttcaac agatcttcaa    360
aggcttactt cacccaatga agttaagaac cactaaagaa gaaacctaaa aggaaaatcc    420
aggtcatgaa ctttgcaatt tttattcaca tacagagaag aggggaggaa tctcttgtgt    480
atgttttact tatgtatacc actggttctt aataaagggc tttttttgcc tccagaggtc    540
aatgcctgga gacatttttg gttgtcacac ctagggagat gctattggga tctagtgagt    600
agagaccaga gatgctgcta aacatcctac aatgaagttt gctatcactc caaggttttg 660
catgcgactt aaactgtaca tttattaatc aattgctaca tgtactaaaa tatgtatctc 720
tctccatata tgtatatatg cgtgtatttt ttcattattg ttggatgtat agctcaactc 780
cactacaaca gaggaaagta tttgttttaa agtagaatct gaatatactc actctgtata 840
ccctcatcca taccttcaag atctggtgaa aacactatct cttgcaagaa cattctttga 900
tgctgttcag aattaatcca gacccttttc tgtattctct taataccttta tctgatcctc 960 tcttaagtta cttctcacta tctaccttag taacacaatt ttatttacat acaagttctc 1020
tctccctcac tagacaaaaa cttcttgagg gcaagcactg tgtctccttt caaccattat 1080
tatcttctct catgtttttt gaacagattt atctatagcc caaacatacc ttttcaaaaa 1140
actaaaaatt actttacata tttgatctaa ggctttgttt ttctccatta agagcatgct 1200
gtggatatct ttgcaagtga gtgcataagg atttttctta accttggaga tggctgtcta 1260
ggatttcaga atatcaactc atatttgtag ctccatggca actcacctac acaactcaca 1320
actctttatt gaaggcattc tgtaccaata taaatatagt ccatatccca ttctaatatg 1380
gatttctgct ccttgttgct tgctattttg aacactttta gtctggtcca gtcaggccta 1440
taaaccactt tgcatcagaa cttggcaatg gtttgctggt tcagaggatt aaggagtggg 1500
gtaaggctgg cagaaggaca gaagagaaaa gacttgagta acaacaggag gcaaaagagt 1560
aacttagctt ggctaataga attcttattt gaaatgcatc tctctatata agagtttggt 1620
tcaataatca caatataata agtcctgcat gtatctggat gaagataatt gctttttttct 1680 gttcaatgct tttccatagc agaaatagct ggggcagaac aaaatggtat ctctgttaca 1740
ggattctata agggtataga actgcttttc tcataggtaa aaggcagacc gtttgaattt 1800
ggctttttaa aaacagaaga gtaggaggaa ataacagctt gctctctcca ccctatttaa 1860
ttgtgatatt aaacacctta gattactcac ttgggcttta taaggcaacc ttctcctgtt 1920
tcacacagag gtgggtggtt cttatttatc agacttttaa aatattcagg acttctttcc 1980
aaagaaatag atgcatcact taaaaataaa tatcagacaa tattattgat actttacagt 2040
acttatttag cagttaatac ttttttaaaa ggcattttct tatttatcat ttaggcattt 2100
gcagtgtaag acaaactccc ttg 2123

<210> SEQ ID NO 323
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2763565

<400> SEQUENCE: 323
cacatgttta ttcatgggtg tcagctttgc ttttcctgga gtctcttggt gatggagtgt 60
gcgtgtgtgc atgtatgtgt gtgtgtatgt atgtgtgtgg tgtgtgtgct tggtttaggg 120
gaagtatgtg tgggtacatg tgaggactgg gggcacctga ccagaatgcg caagggcaaa 180
ccatttcaaa tggcagcagt tccatgaaga cacgcttaaa acctagaact tcaaaatgtt 240
cgtattctat tcaaaaggaa atatatatat atatatatat atatatatat atatatataa 300
attaaaaagg aaagaaaact aacaaccaac caaccaacca accaaccaca aaccacccta 360
aaatgacagc cgctgatg 378

<210> SEQ ID NO 324
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3018631

<400> SEQUENCE: 324
gaagaacctc aaggagtgaa gattcttaga ttttccagtc ctattttcta tggcaatgtc 60
gatggtttta aaaaa 75

<210> SEQ ID NO 325
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586118

<400> SEQUENCE: 325
atgccgccga atcctcaaat ggctgtagca acaacatgaa tgcctgtcag cagatttgcc 60

<210> SEQ ID NO 326
<211> LENGTH: 150
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2466608

<400> SEQUENCE: 326
agccacgtct tcacggatgc acagaggcgt gagctggaga agcactccct gtctcgggtc 60
atctgtgaca acactggcct caccagggtg cccatggatg ccttccaagt cggcaaattc 120
cccgaagact ttgagtcttg tgacagcatc 150

<210> SEQ ID NO 327
<211> LENGTH: 246
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586111

<400> SEQUENCE: 327
gtcattgtca atgcagccgt tcatgctttt ggcttgactc tctatggcca gtatatttac 60
tggactgact tgtacacaca aagaatttac cgagctaaca aatatgacgg gtcaggtcag 120
attgcaatga ccacaaattt gctctcccag cccaggggaa tcaacactgt tgtgaagaac 180
cagaaacaac agtgtaacaa tccttgtgaa cagtttaatg gggctgcag ccatatctgt 240 gcacca 246

<210> SEQ ID NO 328
<211> LENGTH: 249
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367703

<400> SEQUENCE: 328
aggcccatga gagacgagcg aattttcagg gtattgagtg ccttgctaca ttcacactgt 60
atgtgccgtt caagattact attgaaggga aaatcacaag gtattggttt ttaaggaggg 120
tattcgtatt taaggctatt tgctgtagga attaccttct acagagtttg aactctgttc 180
tgaaaagtct gagagaaata gaaacagttc ataggaaatt ttgaagtttg gctagcctgt 240
aaaccacag 249

<210> SEQ ID NO 329
<211> LENGTH: 118
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586171

<400> SEQUENCE: 329
gtgacctgcc agcagggcta tttcaagtgc cagagtgagg gacaatgcat ccccaactcc 60
tgggtgtgtg accaagatca agactgtgat gatggctcag atgaacgtca agattgct 118

<210> SEQ ID NO 330
<211> LENGTH: 284
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2331562

<400> SEQUENCE: 330
ctgccctttt gaggcctcca tgagggccaa atgtgccatg ggacacttag tgccatgcct 60
gcgcagacct gtggaataaa cagcaattct gagcaggctc attttaaagg gacttgcaaa 120
tttgggcgtt ccttgtgtgc cttcctcata aaacccactc ctcccagaat atgcttagag 180
gtgctgctgt atttacctga gagctatgct tttcatcaaa aacctaaacg tgatcatctc 240
ttggatgagg tgtggccctg cacactcgcc tgctcgtgga agga 284

<210> SEQ ID NO 331
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3108614

<400> SEQUENCE: 331
atctgagcca gtcaccataa atatccaaga cctactttcc 40

<210> SEQ ID NO 332
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2537604

<400> SEQUENCE: 332
gtgaaggact taccacctgc aaatcaccgt cgaggtgaga cctgcgaagc ctccgatcag 60
cagagcagcc agcgacatgg agatccaagt cacccgaggg agcctcccgg agtctg 116

<210> SEQ ID NO 333
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466626

<400> SEQUENCE: 333
atctcggaga caggcggagg aactcccgag ctgagatgcg gaaagcacca ggccgtaggg 60
acctcaccgc agcg 74

<210> SEQ ID NO 334
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3018640

<400> SEQUENCE: 334
ttcgggaggt ctctatgagc aaggaataca agacaaaact tcctcaatgc attgactatt 60
tcttcagact caaaacactc attctttttt ctattaagcc attgaaagag aagcactaag 120
actgcttcta ggctttatt 139

<210> SEQ ID NO 335
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2466621

<400> SEQUENCE: 335
atctcaacct ggcttcgaat gttcaagtct gacacatcgc aaaggctaca cccaaaca 58

<210> SEQ ID NO 336
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586151

<400> SEQUENCE: 336
aagactgtag ttcatggagg ctccctcatt cctcatccct ttggagtaag cttatttgaa 60
ggtcaggtgt tctttacaga ttggacaaag atggccgtgc tgaaggcaaa caagttcaca 120
gagaccaacc cacaagtg 138

<210> SEQ ID NO 337
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2466629

<400> SEQUENCE: 337
atctagtacc atgtcgtagt tactctcagg catggatgaa taaa 44

<210> SEQ ID NO 338
<211> LENGTH: 362
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3367739

<400> SEQUENCE: 338
aggcctggtg ctcattctct atgagaccct tccaatgtct aacatgagtc tttcatagta 60
ggactaaacc tctttgaaaa ctattgtata gtcaagatag aaaggaggtt agagctctgt 120
tgactgtttt taccactcct ggaagaattg aactcggggc atgtccaagt cacaagctct 180
ttttttagga attgttttac atgagcattt aaaaaaaaat agtaggacac cccaaataca 240
cacacccccc caccctggaa tttacaaacg ctaaccaaac aaaagggtct ttccattgac 300
tgcctggata ttagtgtaaa tactaggatg ttgctttgca agtatattct ggagagcgag 360
tc 362

<210> SEQ ID NO 339
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3811356

<400> SEQUENCE: 339
ggaggatgga aaggctcgct caatcaagaa aattc 35

<210> SEQ ID NO 340
<211> LENGTH: 114
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3108604

<400> SEQUENCE: 340
ggaaagatgt ctgccaagct atagaccatg gctgtgaaca catttgtgtg aacagtgatg 60
actcatacac gtgcgagtgc ttggagggat tccggctcgc tgaggatggg aaac 114

<210> SEQ ID NO 341

<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2466601

<400> SEQUENCE: 341
atgcattctg gcacatggaa gaaaca 26

<210> SEQ ID NO 342
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2466566

<400> SEQUENCE: 342
gaaagcctga ggagtctcgt gtctctagcg tcttggagga aagcaagcgc ctggtggaca 60
ccgccatgta cgccacg 77

<210> SEQ ID NO 343
<211> LENGTH: 130
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586065

<400> SEQUENCE: 343
gctctccttt gttgctactg cctgacaatg tccgaattcg aaaatataat ctctcatctg 60
agaggttctc agagtatctt caagatgagg aatatatcca agctgttgat tatgattggg 120
atcccaagga 130

<210> SEQ ID NO 344
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3095521

<400> SEQUENCE: 344
agtcttccag agttttcggg agctaattaa ttatgtgatt tcctctcctc tgagaactgt 60
tttgctggcg tgtcaccaag ttgtcac 87

<210> SEQ ID NO 345
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586168

<400> SEQUENCE: 345
caacatgtga gcagcttact tgtgacaatg gggcctgcta taacaccagt caga 54

<210> SEQ ID NO 346
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2466628

<400> SEQUENCE: 346
ttcatgttcc caaaatcacc gtacgactct tttccaaaca caggcaaatc cgaaatcagc 60
aggacgactg ttttcccaac acgg 84

<210> SEQ ID NO 347
<211> LENGTH: 86
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2466564

<400> SEQUENCE: 347
cgctcgctgt gctgtctgtc acgctggtta tggcctgcac agaagccttc ttccccttca 60
tctcgagagg gaaagaactc ctttgg 86

<210> SEQ ID NO 348
<211> LENGTH: 786
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3160700

<400> SEQUENCE: 348
tttggggctt atcagaactc ctttctaagg agcactagaa tgagaaatca tgttgttcga 60
tcgtttcaca tctgtatatc agctctaaag cagagatgta ttatggtgat actccaaggt 120
ggcatagcca ttcatttaca acttccagat ttgagctgcc tggagggaat ccatatcagc 180
tctgcataag attatataca aagctgtcac tcacaaaagg ctggatgtgc tttcatccaa 240
ctggaaggct ttattcttcc aagttcattc atactcaaag aggccagtac tttgccatcc 300
ttgcacttct gttatcaggg cccaaataac agtggcaagc taccaactaa gttgtatttt 360
aataaagatt ccatgggttg aacaagccac gttgcagaaa aagagcttcc cctaacctgg 420
gttgttgcag agtaaatccc acgacataag ctggtatcag tggttcgggg gaaatagttc 480
cattctatga ctcttgtctc ctcctccagg aggactgttc taactagtaa tcttggccct 540
attcattaca tcctctgctt gtcattctgc taatttatga agatagttta ttatagtctg 600
tacttcagtt ctcatcttgt aaataatgct taacataaac ttgtacttac actgaaatcc 660
aaaatagtca tgtttctgca gtattctgta gccaacttaa acctgtgctt tcatgtttaa 720
gaaatgagaa attgtgccaa agatagcaga agagtagata agtgctcagt attgacgacc 780
tacatc 786

<210> SEQ ID NO 349

<211> LENGTH: 164
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3325106

<400> SEQUENCE: 349
ggcctgacag ggaccagaaa atatggcttt ggtgttgctg tttattagca atgctgagac 60
cagttgtaat aggagccgag cagtgtgtgg gtgataaagt gtggggtgtc aagaagcggc 120
agcaaccaga aattagactg acaagagcca gcactcgctg gata 164

<210> SEQ ID NO 350
<211> LENGTH: 393
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2721311

<400> SEQUENCE: 350
ctgcctggag accttgatct tgacctggaa tatggtgatc gggaacacga cctgtgtcga 60
gaaaaggacc ttgaacgaga gcgcatcctt tggggtcttt gagaaaataa ggatttgggt 120
ggtgacacag aatctctaca tggagagtta aaagaagaac aagaaggaga cacattgaac 180
aatgaatagg attgcgtgcc atcccaaggg tagctcagtt tatcactttc atcttcgctg 240
tcatcaaaca ggccatccat ggctagtcct gaatttataa acataggtag tttggagaat 300
tgttcattac tgaaatcact gtccctcagt tcaccggtct tgtctgcttc gtcgtcaaaa 360
acagcttgac tgggatgacc gaagtgcttg ttc 393

<210> SEQ ID NO 351
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018619

<400> SEQUENCE: 351
tgctggattg ctcaccattg tcgtctgtat ggcagttaag gaattaaatg atcggtttag 60
acacaaaatc ccagtcccta ttcctataga agtaattgtg 100

<210> SEQ ID NO 352
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586130

<400> SEQUENCE: 352
acagactgct ctacttcatg gactcctatc ttgattacat ggacttttgt gattataatg 60
gacaccatcg gagacaggtg atagccagtg att 93

<210> SEQ ID NO 353
<211> LENGTH: 111
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018636

<400> SEQUENCE: 353
tgcgggttct ttgacgacaa cattagaaag gacacattct ttttgacggt ccatgatgct 60
atactctatc tacagaacca agtgaaatct caagagggtc aaggttccat t 111

<210> SEQ ID NO 354
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3108616

<400> SEQUENCE: 354
aaaacacgat caatgcaaat gtgaaaacct tataatgttc cagaaccttg caaacgaaga 60
a 61

<210> SEQ ID NO 355
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3862193

<400> SEQUENCE: 355
atggtctccg agtggatctc ccagctgaga agttagcatc tgtgtccgtg agtcgtacac 60
ctgatggctc cctgctagtc cgccagaag 89

<210> SEQ ID NO 356
<211> LENGTH: 619
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586039

<400> SEQUENCE: 356
tgtgttctct cactagctgc caagacaaca tttttatttg tgatgtctat gaggaaatcc 60
catatcatta agtgccagtg tcctgcattg agtttgtggt taattaaatg agctcttctg 120
ctgatggacc ctggagcaat ttctcccctc acctgacatt caaggtggtc acctgcccta 180
gtagttggag ctcagtagct gaatttctga aaccaaatct gtgtcttcat aaaataaggt 240
gcaaaaaaaa aaaataccag ttaagtaaag cctcaactgg gtttttgttt ctatgaaaat 300
atcattataa tcactattta tttcctaagt tgaacctgaa tagaaaggga aaccattctt 360
attaagcttt ttattaggcc ctgtggctaa atgtgtacat ttatattaga atgtactgta 420
cagtccagat cttttcttta attcttattg gttttttttt ttttttttt tttagagatg 480 gagtcttgct atattgccaa ggctgatctt gaagtcctgg gctcaagtga tcctcccacc 540
tcagcctcct gagtggttgg ggttacgggc gtgagccact gtgcctggct tccagctctc 600
ctcttaaata gtgggtata 619

<210> SEQ ID NO 357
<211> LENGTH: 211
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3833286

<400> SEQUENCE: 357
tcaggggagg gtttaaagct tcagagcccg tggtcatatt tagaaagatc tttaccactg 60
ccacgtggag ggtggaccag agggagcaaa ggtaggagct gggagggacc caggtgggag 120
aggaccagct ggaccaaggg agggccatgg ggacggggaa aggagtgggt acaagagaca 180
ttgaagagac tgagtggact agctgtggtg g 211

<210> SEQ ID NO 358
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586132

<400> SEQUENCE: 358
tgagcatcta ctgttctggt ctgactgggg ccaccaccct cgcatcgagc gagccagc 58

<210> SEQ ID NO 359
<211> LENGTH: 165
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763561

<400> SEQUENCE: 359
tcctattatg tgttcaagga ccacatgtgt tctctatttt gcctttaaat ttttgtgaac 60
caattttaaa tacattctcc tttttgccct ggattgttga catgagtgga atacttggtt 120
tcttttctta cttatcaaaa gacagcacta cagatatcat attga 165

<210> SEQ ID NO 360
<211> LENGTH: 99
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2466620

<400> SEQUENCE: 360
ctccgggagg ctccctcggg tgacttggat ctccatgtcg ctggctgctc tgctgatcgg 60
aggcttcgca ggtctcacct cgacggtgat ttgcaggtg 99

<210> SEQ ID NO 361
<211> LENGTH: 125
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586145

<400> SEQUENCE: 361
ttcacgattg tactgggtag atgcctattt tgataaaatt gagcacagca cctttgatgg 60
tttagacaga agaagactgg gccatataga gcagatgaca catccgtttg gacttgccat 120
ctttg 125

<210> SEQ ID NO 362
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3018615

<400> SEQUENCE: 362
gcctttggtg tgctaaagac tcttgtgccc atcttggagt ggctccccaa ataccgagtc 60
aaggaatggc tgcttagtga cgtcatttcg ggagttagta ctgggcta 108

<210> SEQ ID NO 363
<211> LENGTH: 222
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 4023363

<400> SEQUENCE: 363
tcaggtaagc ggtaggtgga aatccagatt tcctcttgag gaaaagtcct aggaatcaca 60
acagaaggga ctttgcagtc ctcattaaca catggacaaa gagcagacaa ctactacgtt 120
acaagggatt caactagtca ctgttgtgaa atgtcatatc catgttgatg acagccctgg 180
cgcctgctca actccccctc tagagttttg cggttacttc cg 222

<210> SEQ ID NO 364
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2537578

<400> SEQUENCE: 364
tctcgagcag tgaaacaatg gaacaattta atttaaaatt aaggactagc agaaactccc 60
gctatcattg ttggtactta gtactatctc agttagacca aagtc 105

<210> SEQ ID NO 365
<211> LENGTH: 493
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Affymetrix ID 2763557

<400> SEQUENCE: 365
tggtaaccga actggtgctt tagtaatgtg gattttttc tttttaaaa gagatgtagc    60 agaataattc ttccagtgca acaaaatcaa tttttgcta aacgactccg agaacaacag   120
ttgggctgtc aacattcaaa gcagcagaga gggaactttg cactattggg gtatgatgtt   180
tgggtcagtt gataaaagga aaccttttca tgcctttaga tgtgagcttc cagtaggtaa   240
tgattatgtg tcctttcttg atggctgtaa tgagaacttc aatcactgta gtctaagacc   300
tgatctatag atgacctaga atagccatgt actataatgt gatgattcta aatttgtacc   360
tatgtgacag acattttcaa taatgtgaac tgctgatttg atggagctac tttaagattt   420
gtaggtgaaa gtgtaatact gttggttgaa ctatgctgaa gagggaaagt gagcgattag   480
ttgagccctt gcc                                                     493

<210> SEQ ID NO 366
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586159

<400> SEQUENCE: 366
tgggatttta gattgcccag gaagagaaga tgaaaacaac actagtaccg gaaaatactg    60
t                                                                    61

<210> SEQ ID NO 367
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862199

<400> SEQUENCE: 367
atctgcactc gcacctgcca gggatcctgt gcggctctct ccggcctcac gggctgcacc    60
acccgctgtt ttgagggctg tgagtgcgac gaccgcttcc tgctttccca gggtgtctgc   120
atccctgtcc aagattgtgg ctgcacccat aatggccgat acttgc                  166

<210> SEQ ID NO 368
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811391

<400> SEQUENCE: 368
ggtgggcatt tttcctgggc tgttcctacc aatagacttg ctgctggttt catgttagtt    60
aggtggcaca ccaagagggg actcagaaag aacagaagat cagaacttgc tggtgtcaga   120
ca                                                                  122

<210> SEQ ID NO 369
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3046252

<400> SEQUENCE: 369
gagcccggag ccgcttgatt gtgttgct 28

<210> SEQ ID NO 370
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2466563

<400> SEQUENCE: 370
ttggaacttg taaagtggcc caagagtggc tgtaatttgg gccattat 48

<210> SEQ ID NO 371
<211> LENGTH: 157
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2721641

<400> SEQUENCE: 371
gaggtctcac cttcgccttt gctgaagtct ccccgcagcc ctctccaccc agaggtctcc 60
ctataccgag acccaccatc cttccatcct gaggaccgcc ccaaccctcg gagcccccca 120
ctcagtaggt ctgaaggcct ccatttgtac cgaaaca 157

<210> SEQ ID NO 372
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3108607

<400> SEQUENCE: 372
gagggcttaa ctgcagcacc tgtgaaaaca ctttcggttt taattgacag taaattcatt 60
atcagccaag aggctagggt gatcgtaggc tgaacagcaa tgtctgcatg agggaggtgg 120
agagagctgt gctctgctct gtgctggaga attacattca gttctgggca tggtac 176

<210> SEQ ID NO 373
<211> LENGTH: 279
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2721309

<400> SEQUENCE: 373
tttaagcgtg tcttcatgga actgctgcca tttgaaatgg tttgcccttg cgcattctgg 60
tcaggtgccc ccagtcctca catgtaccca cacatacttc ccctaaacca agcacacaca 120
ccacacacat acatacacac acacatacat gcacacacgc acactccatc accaagagac 180
tccaggaaaa gcaaagctga cacccatgaa taaacatgtg cttactggat atcattctgt 240
ctcttgcctc ttcagcagct gtgttcatgt aaaccattg 279

<210> SEQ ID NO 374
<211> LENGTH: 175
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586135

<400> SEQUENCE: 374
cacgagtgtg ttcaagagcc ctttggggct aaatgcctat gtccattggg attcttactt 60
gccaatgatt ctaagacctg tgaagacata gatgaatgtg atattctagg ctcttgtagc 120
cagcactgtt acaatatgag aggttctttc cggtgctcgt gtgatacagg ctaca 175

<210> SEQ ID NO 375
<211> LENGTH: 200
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2537607

<400> SEQUENCE: 375
atttgaggag gttgctcgca gtagggggat ttgaggaggt tgcacacagt ggggggattt 60
ttggggggtg cacacagtgg gggactagag gaggttgcac acagtgggag ggatttgggg 120
aggctggaca cagtgggggg atttgaggag gttgcacata gtgggggaga ttttgcgagg 180
ttgcacatag ggagattttg 200

<210> SEQ ID NO 376
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3018628

<400> SEQUENCE: 376
cctgaaaggg atgtttatgc agctgtgtga cattcctcgt ctgtggagac aga 53

<210> SEQ ID NO 377
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466583

<400> SEQUENCE: 377
gtgctgcgtg caatcccttc agatcctccc agcctccctt tgatgtagca atcactgttt 60
ctgccctatg gcttaggagc caaggctcag ggagattgaa atctcttagt gagtggaacc 120
ctgcagattt aaa 133

<210> SEQ ID NO 378
<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586149

<400> SEQUENCE: 378
ccaagttgct attcgtggga tcccgttcac cttgtctacc caggaagatg tcatggttcc 60
agtttcgggg aatccttctt tctttgtcgg gattgatttt gacgcccagg acagcactat 120
ctttttt 127

<210> SEQ ID NO 379
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3662230

<400> SEQUENCE: 379
gattttacgg gtcactctat ttgtacttgg gagcagggct g 41

<210> SEQ ID NO 380
<211> LENGTH: 98
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586140

<400> SEQUENCE: 380
gagacatgcc aacctagtca gtttaattgc cccaatcatc gatgtattga cctatcgttt 60
gtctgtgatg gtgacaagga ttgtgttgat ggatctga 98

<210> SEQ ID NO 381
<211> LENGTH: 242
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367740

<400> SEQUENCE: 381
agcgaatttg cctgagactc ctgaccccta gttcaatttg ctttacattg tattgcttgc 60
ctccattctg aaatatttct ttaaaatttc tgtagttttt ttttttttc ccacacctca 120 ccccactagc cctttacatt cagctgggaa ataggcctaa ttgggactaa ttgtccagct 180
actgctagat ccattgtctt gcctgttgct agtgaaacgt gtgctgcatg ctacaggact 240
ca 242

<210> SEQ ID NO 382
<211> LENGTH: 180
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466598

<400> SEQUENCE: 382
aagcagtcga gagtcagaaa gttcagagga gcctgtgcca ggggctacgc ggctgtttcc 60
caccgtcggt gacaaggatc gcatctccag gtctcttcgt cctggtctcc ccgtgtgctg 120
gggtcctggc ttcccgtcac cttcacgccc atcattttcc caagtgtgga cctttcagtc 180

<210> SEQ ID NO 383
<211> LENGTH: 388
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367691

<400> SEQUENCE: 383
tttaattaag gtagtgcagg ggctggttcc atattaaaca tggtgatggg gatttaagat 60
aataatgcta ccatcagtac atctaaaatt gtttaatgtt ttactgcaaa tattttttag 120
ctagaagaaa ttaaacaagt ggggaagatt ctcagaaacc aacacagccc aaaatgtgca 180
gataaagaac caaaaaataa cgtagaaagg agcaagatta taataaatat ttttaatgag 240
ttaatttatt tcctcttttt aagtcttaac ttgtaacatt atttgaaatc acagtaaatg 300
tacattttat ttcttgtttc agccctgagg tgagtttatt tggaatgttt gttttaaatg 360
gatttagcca tcatggaatt aggtcatc 388

<210> SEQ ID NO 384
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3367679

<400> SEQUENCE: 384
gagctgttaa acacggttca gaggcgagtc cggcccaagc tccatg 46

<210> SEQ ID NO 385
<211> LENGTH: 240
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763590

<400> SEQUENCE: 385
caaaatgtcg tggtcttaga agcccaaaga ccccttgaaa tgggcagttg atttaaaaca 60
tgccagcttc tactttaacc ttgtggtgga agtaggcata ttataacaca ccaattataa 120
acatatacct cttttttttt ttcactttca ttttcccaac ttttcctttt aactgcagag 180
tgggagccag tgatttctgc tttgaaccat gattaattcg tgtaggtatg ctgttattgc 240

<210> SEQ ID NO 386
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586102

<400> SEQUENCE: 386
tgcatcccaa gcgaatggat ctgtgacggt gataatgact gtggggatat gagtgacgag 60
gataaaaggc accagtgtc 79

<210> SEQ ID NO 387
<211> LENGTH: 182
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3367693

<400> SEQUENCE: 387
ggccgaatta attggtgtga ttccattctc aatttaagaa atcaaggtta aatgacttgc 60
ccacaattgc attgagctgg aactagggca taggtctgct gtctccagat ctccagctga 120
cttcccaccg cagcctgtca gtcagtgaaa ttaatctgca gtcattcgca gacacctgaa 180
aa 182

<210> SEQ ID NO 388
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586067

<400> SEQUENCE: 388
atatatgcga gcaaaattgt acccaattaa atgaaggagg atttatctgc tcctgtacag 60
ctgggttcga aaccaatgtt tttgacagaa cctcctg 97

<210> SEQ ID NO 389
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3095516

<400> SEQUENCE: 389
tgctcagttc accaatttat cttgcttcct acttggctca aaccaacaca aagcaaaacc 60
ctccacagct ggtcacggcc tcattct 87

<210> SEQ ID NO 390
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2466573

<400> SEQUENCE: 390
atgaaatata agcccgacca ttccgaaact gccaactaa 39

<210> SEQ ID NO 391
<211> LENGTH: 395
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3145950

<400> SEQUENCE: 391
ctatggccag tgttctacag aagtaagact gtgcaaactt tatcgtatag tcaaatgaga 60
ttgcacacta aggcaggatg aggcagaagc aagttgtgtc cacagtatat tacaaaatac 120
cttgcatagc ttattcattc tcacctggta aattcatctt agaattctga aggatttttt 180
tcctagataa atttatacaa gttagtgtat acttcttgtc tttgttctgt ggcaaaccag 240
gtttctcagt actgattgtt ttacttcaca acattattga tttaacaata gcctgagctt 300
tggggctctg cactgcgttc attgtaatcc gtgatacaat gactacaaat gtgtcgcgat 360
ttctaatctt catctgtatc tcaggcgatt ttcca 395

<210> SEQ ID NO 392
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586043

<400> SEQUENCE: 392
ggataataag aattatggaa gtcccataaa cccttctgag atagttccag agacaaaccc 60
aactt 65

<210> SEQ ID NO 393
<211> LENGTH: 85
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3104982

<400> SEQUENCE: 393
tcccacagaa tgttgtagag ttcaatgcga acttcagtcc aggtcaacgt cccttggctt 60
atgctctctc ataaactctc gtgga 85

<210> SEQ ID NO 394
<211> LENGTH: 1000

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2336909

<400> SEQUENCE: 394
cctcaattct aggtgaccaa cgggagggct tctcaaggct tagctctccc tgagacccag 60
ctggctttta cccttgacct gtgtccctag ctgaatcact agctcagatt tttctgatct 120
aagcaaacaa ctcccagctg aggaatgcag gccacagcac ccaatcaaga caaattgtta 180
ttatcagaaa atgaagcaac acttgagctg ttcaggccag ttccctgttg aagaaacagt 240
tccctgttga agaaagtaga gcctgacact gctcccactt tggagaccac attccctgca 300
cacggtcttt gagagagcag ttgcactcta caggcacact tctgaggtac ggtatctctc 360
tccagccact ctgataccaa gtaattcaag ctggcattcc ttctattagg gaaattcatt 420
ttacccaatt tgcatttatg gaattgatca tttaagacac taaattagtt tttagaacca 480
attatgggaa gaattccagt tgttaggaag agatgaggag ttggaagagg agggattaga 540
aacaggagga ggcagtcatc ctctccttgc caaaagattt aaacctgtcc acattggtgg 600
tgatgatggg tgagtttcca tggtaacaca tccctaattt taccagggaa gaggagagta 660
ctcactttac catctttgaa tatatttcat agaaatctag ctctctgtac cctgaaatct 720
tccactagcc tcacttttca acagagtcat ctagaaggga gggttggctt cccaaaagca 780
taaccttgac caaaccaaac aataggcacc agcaatgctg tcattcagtt atgcagaagc 840
tcatttgtga aattctgttt ctctgatttc ttcgcaagtc tcttaatggt catttgtgtt 900
agattacatc aaactgatgg atagccattg gtattcatct attttaactc tgtgtcttta 960
catatttgtt tatgatggcc acagcctaaa gtacacacgg 1000

<210> SEQ ID NO 395
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3108620

<400> SEQUENCE: 395
cggattacaa tgaacgcagt gcagagcccc aaagctcagg ctattgttaa atcaataatg 60
ttgtgaagta aaacaatcag tactgagaaa cctggtttgc cacagaacaa agacaagaag 120
tatacactaa cttgtataaa tttatctagg aaaaaaatcc ttcagaattc taagatgaat 180
ttaccaggtg agaatgaata agctatgcaa ggtattttgt aatatactgt ggacacaact 240
tgcttctgcc tcatcctgcc ttagtgtgca atctcatttg actatacgat aaagtttgca 300
cagtcttact tctgtagaac actggccata gga 333

<210> SEQ ID NO 396
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3095473

<400> SEQUENCE: 396
atgttgttac agatcccgtt gcgttccaaa aatgaa 36

<210> SEQ ID NO 397
<211> LENGTH: 492
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2763580

<400> SEQUENCE: 397
gcaggggcag atttgttctt ccacagattc agaccagtgc tacctgagag agactttgga 60
ggcaagcaag caggtctctc cttgcagcac aagaaaacag ctccaagacc aggaaatccg 120
agccgagctg aacaagcact tcggtcatcc cagtcaagct gtttttgacg acgaagcaga 180
caagaccggt gaactgaggg acagtgattt cagtaatgaa caattctcca aactacctat 240
gtttataaat tcaggactag ccatggatgg cctgtttgat gacagcgaag atgaaagtga 300
taaactgagc tacccttggg atggcacgca atcctattca ttgttcaatg tgtctccttc 360
ttgttcttct tttaactctc catgtagaga ttctgtgtca ccacccaaat ccttattttc 420
tcaaagaccc caaaggatgc gctctcgttc aaggtccttt tctcgacaca ggtcgtgttc 480
ccgatcacca ta 492

<210> SEQ ID NO 398
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3367742

<400> SEQUENCE: 398
aacgcaccat gcctgcttcc atcttt 26

<210> SEQ ID NO 399
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3662219

<400> SEQUENCE: 399
ctacaactcc gactcatttg ctacattc 28

<210> SEQ ID NO 400
<211> LENGTH: 279
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2331563

<400> SEQUENCE: 400
ctgaaaagtc ttgagcaaac agttgccgct ctccaccccc tgctttttaa aaaaaatttt 60
ttctcacgta agaaaatgtt atctgtgtgc tggggaaaat tttgaaaata acaaaaacca 120
gaatacaaac acccataatc aatcacagag ataaccactg ttcataattc cttccagtct 180
tcttacttgg cacatataca tttgtctttc tttatatatg acatatggat attttacaaa 240
gttaggatcc tactctatgc actgcttggt gatcggatc 279

<210> SEQ ID NO 401
<211> LENGTH: 265
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3727624

<400> SEQUENCE: 401
gcttgtgatg acgaatcctg ctctaaaata cacaaggagc tttcttgttt cttattaggc 60
ctcagaaaga agtcagttaa cgtcacccaa aagcacaaaa tggattttag tcaaatattt 120
attggatgat acagtgtttt ttaggaaaag catctgccac aaaaatgttc acttcgaaat 180
tctgagttcc tggaatggca cgttgctgcc agtgccccag acagttcttt tctaccctgc 240
gggcccgcac gttttatgag gttga 265

<210> SEQ ID NO 402
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586061

<400> SEQUENCE: 402
cttcaagttt ttgggagtag cgtctatgac tgtttcaaga attataacat gcccttgaga 60
tcatatagaa ccaaccatt 79

<210> SEQ ID NO 403
<211> LENGTH: 222
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2997517

<400> SEQUENCE: 403
aacgcttgga tagcaacagt ccgtcctaga ggcatttagg tttagtctat tagagatgga 60
gcgagactac tgatttcacc atttgtgctt tcagctaaga ggctgggagc gtgggtggaa 120
atgaagaagg cagttctggc ctggggcagg gagaggaaac cccagactag ctggtgagga 180
gggaagattt gtcacgatca cagtgcagac gcaaagtggg ca 222

<210> SEQ ID NO 404
<211> LENGTH: 210
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586088

<400> SEQUENCE: 404
agggccacca tcgacacacg gtgtatgatg gggcactgcc tcaccctttc gctattacca 60
tttttgaaga cactatttat tggacagatt ggaatacaag gacagtggaa aagggaaaca 120
aatatgatgg atcaaataga cagacactgg tgaacacaac acacagacca tttgacatcc 180
atgtgtacca tccatatagg cagcccattg 210

<210> SEQ ID NO 405
<211> LENGTH: 702
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3992449

<400> SEQUENCE: 405
agctgggacc caccgtgtag acacacgaca tgcaagagtt gcagcggctg ctccaactca 60
ctgctcaccc tcttctgtga gcaggaaaag aaccctactg acatgcatgg tttaacttcc 120
tcatcagaac tctgcccttc cttctgttct tttgtgcttt caaataacta acacgaactt 180
ccagaaaatt aacatttgaa cttagctgta attctaaact gacctttccc cgtactaacg 240
tttggtttcc ccgtgtggca tgttttctga gcgttcctac tttaaagcat ggaacatgca 300
ggtgatttgg gaagtgtaga aagacctgag aaaacgagcc tgtttcagag gaacatcgtc 360
acaacgaata cttctggaag cttaacaaaa ctaaccctgc tgtccttttt attgttttta 420
attaatattt ttgttttaat tgatagcaaa atagtttatg ggtttggaaa cttgcatgaa 480
aatattttag ccccctcaga tgttcctgca gtgctgaaat tcatcctacg gaagtaaccg 540
caaaactcta gagggggagt tgagcaggcg ccagggctgt catcaacatg gatatgacat 600
ttcacaacag tgactagttg aatcccttgt aacgtagtag ttgtctgctc tttgtccatg 660
tgttaatgag gactgcaaag tcccttctgt tgtgattcct ag 702

<210> SEQ ID NO 406
<211> LENGTH: 115
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586155

<400> SEQUENCE: 406
gattgccaga tatggggaat ttgtgaccag aagtgtgaaa gccgacctgg ccgtcacctg 60
tgccactgtg aagaagggta tatcttggag cgtggacagt attgcaaagc taatg 115

<210> SEQ ID NO 407
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586139

<400> SEQUENCE: 407
ctcaattcaa gtgtgccagt ggggataaat gtattggcgt cacaaatcgt tgtgatggtg 60
tttttgattg cagtgacaac tcggatgaag caggctg 97

<210> SEQ ID NO 408
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3126609

<400> SEQUENCE: 408
atgacagtgt tgatcggatg ggatgtatgg cagttgga 38

<210> SEQ ID NO 409
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586113

<400> SEQUENCE: 409
ttacagtgac tacctcaacc agatgattaa ttccatggct gaagatgggt ctaaccgcac 60
tgtgatagcc cgcgttccaa aaccaagagc aattgtgtta gatccctg 108

<210> SEQ ID NO 410
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586160

<400> SEQUENCE: 410
aatggtcttg cccagagtcg ggacgatgca tctccattta ta 42

<210> SEQ ID NO 411
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608611

<400> SEQUENCE: 411
atgagtctgg ccgaggttca gtgtcac 27

<210> SEQ ID NO 412
<211> LENGTH: 107
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586152

<400> SEQUENCE: 412
gcattcatgg atggcagcaa ccgtaaagac ttggtgaaaa caaagctggg atggcctgct 60
ggggtaactc tggatatgat atcgaagcgt gtttactggg ttgactc 107

<210> SEQ ID NO 413
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466574

<400> SEQUENCE: 413
tgacgtctac atccacctgc aaagcctgcc cctgggtcct gcagtagagc ctgaaccttt 60
ctttggtttg atgcttcctg attcataaat catgatcact caaaaaaaac tctttaaaaa 120
atgtattgtg cctaagttta cattttaaca acctcaagac cagggcctca gccggcagca 180
gtgagttcct gctcggccct tctgaaaggc cctgctgctg tcttgggcgc ctctgcccca 240
gctgctgggc gggctccact gacgctcctg ggagaatctc tgctgaccac acaatgacat 300
tggcactggg agctgtgatc tggggacact tagatctgag ctggtttc 348

<210> SEQ ID NO 414
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2763558

<400> SEQUENCE: 414
atatttcaaa tgaacacgtg caccccatca tcactggagg caaatttcag catagatctg 60
taggattttt agaagaccgt gggccattgc ctt 93

<210> SEQ ID NO 415
<211> LENGTH: 319
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3662224

<400> SEQUENCE: 415
cactggctac tggttcgaga attgctatct gatgttcaat cacagaggaa gaggagttaa 60
gtggcccagg agtcaggacc atgcttgccc gcaggtgccc tttgtgaaga gggcatttca 120
gaaggcagcg tgggtcatgt gcaagtttgg gtgtcacata accagattca cagcccactt 180
cacaccttcc tggctgtgta gctggcacaa gtcacttaac ctctctgtgc ctccatttcc 240
tcacttgtag aaagcagatt ataaatatat gtagggatta aatgtgatag tgccctggta 300
cctggctcgg gcttaataa 319

<210> SEQ ID NO 416
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3367741

<400> SEQUENCE: 416
ctcaaggcaa agttaccata acggtggatg agtacagctc aaaccccacc caggcattca 60
cgcactacaa catcaac 77

<210> SEQ ID NO 417
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466582

<400> SEQUENCE: 417
ggcgcctcca acacggccct ggcacgatgg ctccctccag tctatgagga cggcttcagt 60
cagccccgag gctggaaccc cggcttcttg tacaacgggt tcccactg 108

<210> SEQ ID NO 418
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3108615

<400> SEQUENCE: 418
agaagacaat cttttacggt ctacacaaaa gctttcccat tca 43

<210> SEQ ID NO 419
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2721643

<400> SEQUENCE: 419
ggaagccagc ccgtgcaacg gaagccaggc caactgcccc gcgtcttcag ctgtttcgca 60
tccaccgcca cc 72

<210> SEQ ID NO 420
<211> LENGTH: 202
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586153

<400> SEQUENCE: 420
ggtttaaata tccaagaggt tctcaatgtt tctgttgaaa ccccagagaa cctggctgtg 60
gactgggtta ataataaaat ctatctagtg gaaaccaagg tcaaccgcat agatatggta 120
aatttggatg gaagctatcg ggttaccctt ataactgaaa acttggggca tcctagagga 180
attgccgtgg acccaactgt tg 202

<210> SEQ ID NO 421
<211> LENGTH: 165
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2537572

<400> SEQUENCE: 421
ctgcagtttt gttctattgg tcaaaatata ttctgacaaa aatgtatttg aagtgcatga 60
taaggtaaag gtgtgttgaa tattttgatt tcacacttag ttccgagtgt actgtgttaa 120
gcaaggtgcc cctaagttga aggggtgtag gcacaattaa cagtc 165

<210> SEQ ID NO 422
<211> LENGTH: 109
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586068

<400> SEQUENCE: 422
ccttgtacag aatatgaata taagtgtggc aatgggcatt gcattccaca tgacaatgtg 60
tgtgatgatg ccgatgactg tggtgactgg tccgatgaac tgggttgca 109

<210> SEQ ID NO 423
<211> LENGTH: 105
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586143

<400> SEQUENCE: 423
tgggtgccat tattcgagtc aggaaagcag atggtggaga aatgacagtt atccgaagtg 60
gcattgctta catactgcat ttgaaatcgt atgatgtcaa catcc 105

<210> SEQ ID NO 424
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3893028

<400> SEQUENCE: 424
ttaatgactg gctacagagt aacaaaa 27

<210> SEQ ID NO 425
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Affymetrix ID 3367676

<400> SEQUENCE: 425
gttatggcat catgaccgac ggttacacaa cgtacatcaa tgcctcgacg tgtacagtca 60
gctttcaacc gaccaa 76

<210> SEQ ID NO 426
<211> LENGTH: 99
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586172

<400> SEQUENCE: 426
agtgcgcatt ttcgctgtgg aagtgggcat tgcatccctg cagactggag gtgtgatggg 60
accaaagact gttcagatga cgcggatgaa attggctgc 99

<210> SEQ ID NO 427
<211> LENGTH: 142
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3142383

<400> SEQUENCE: 427
acctggactg aagttcgcat tgaactctac aacattctgt gggatatatt gttcaaaaag 60
atattgttgt tttccatgat ttagcaagca actaattttc tcccaagctg attttattca 120
atatggttac gttggttaaa ta 142

<210> SEQ ID NO 428
<211> LENGTH: 384
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3367677

<400> SEQUENCE: 428
cctgaggagt aatccttata ttactcattt tattccctag aactcaatag ttaacacaag 60
gctttgaaat gaaaatccta ttttaaaagg aggaaaaaag tttttcttta ttctccctag 120
taaagaaatc acagcccttc ttcaacaagt ttagcattta aataaagaaa aaaaaattgc 180
tcttagttga aggagaagat tctaccattt aaagaaaata gagtaaaatt gggcagtagc 240
ttctgaaagt cattatatct gaggaggctc aactgaattt catctcactg cccactgaca 300
aaaatttttt gttttccttg cctgacagcc ctacattcca tcactctcat ttgtatatat 360
tacagtaaat gtgacacgct ctcc 384

<210> SEQ ID NO 429
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2763566

<400> SEQUENCE: 429
atgacagagg gatggcgaat acctcatggg acagcgcgtc cttccctaaa gactattgca 60
agtcatactt aggaatttct cc 82

<210> SEQ ID NO 430
<211> LENGTH: 295
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3763228

<400> SEQUENCE: 430
cgggacattt tctccatcgc gatgcactca aattttttcc ccttaaaaaa agaaataaga 60
aagaaacaac cgccccctaa aatgttgctg agcttttcct ccgtcctttg ccaaaagtac 120
tcgctctcaa ggcggtggag aaaagggaag aaaaaaatta cttatatctt tataaataca 180
tctgcataaa aatatatatt aaaaaaaaac tttcgggttt ccagtgcaga cggtcccagg 240
agagcgcgcc aagtgcccgc gggctccccg gcgacgtgca ggatgctctc acctg 295

<210> SEQ ID NO 431
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3108580

<400> SEQUENCE: 431
tgtgcctcat ctaatcacgg atgtcagcac gagtgtgtta acacagatga ttcctattcc 60
tgccactgcc tgaaaggctt taccctgaat c 91

<210> SEQ ID NO 432
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608485

<400> SEQUENCE: 432
cctggttgat gatcgttgtg ttgtacagcc agaaaccggg gaccttaaca atccacctaa 60
gaaattcaga g 71

<210> SEQ ID NO 433
<211> LENGTH: 202
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2331560

<400> SEQUENCE: 433
ctcttcagtg cccagtgtgt aacctggcat ggtttgggtg tgctaggagt ttgtgaaatg 60
aatgttttca agacgcaaac gctgctatgc ccatcaggtg tgcacagcag gcctgaggat 120
catgatgaga ctcccttttt atgcagcaaa gcacaaagtg tgacagtcgt ggccttcctg 180
gtggccagac ttctagcaac tt 202

<210> SEQ ID NO 434
<211> LENGTH: 250
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763602

<400> SEQUENCE: 434
gtctggacca ctttgcaaca tttgttcaaa ctgaaaattt tgacaaagac attctgttca 60
caaagagcca acaaatgttc tgtgtttcga tacatttgga ggttacaaaa tgttgcctgg 120
tcttggcaga taactaagtc tggggaccca catagtgcaa gccatgccct gtttaatttg 180
tctttcaatg gcaaatgtgt ttcttctgtg attcagcata agggatgata ccctccaata 240
ggactgtgtg 250

<210> SEQ ID NO 435
<211> LENGTH: 410
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3811360

<400> SEQUENCE: 435
taggcccgtt ttcacgtgga gcatgggagc cacgaccctt cttaagacat gtatcactgt 60
agagggaagg aacagaggcc ctgggccctt cctatcagaa ggacatggtg aaggctggga 120
acgtgaggag aggcaatggc cacggcccat tttggctgta gcacatggca cgttggctgt 180
gtggccttgg cccacctgtg agtttaaagc aaggctttaa atgactttgg agagggtcac 240
aaatcctaaa agaagcattg aagtgaggtg tcatggatta attgacccct gtctatggaa 300
ttacatgtaa aacattatct tgtcactgta gtttggtttt atttgaaaac ctgacaaaaa 360
aaaagttcca ggtgtggaat atgggggtta tctgtacatc ctggggcatt 410

<210> SEQ ID NO 436
<211> LENGTH: 136
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586150

<400> SEQUENCE: 436
accaatccgt gtaaagataa caatgggggc tgtgagcagg tctgtgtcct cagccacaga 60
acagataatg atggtttggg tttccgttgc aagtgcacat tcggcttcca actggataca 120
gatgagcgcc actgca 136

<210> SEQ ID NO 437
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586050

<400> SEQUENCE: 437
tgtgctgttg acaatcctct tgatcgtcgt aattggagct ctggcaattg caggattctt 60
ccact 65

<210> SEQ ID NO 438
<211> LENGTH: 125
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586041

<400> SEQUENCE: 438
ggaaagtgtt gctgcgacac cacctccatc accttcgctc cctgctaagc ctaagcctcc 60
ttcgagaaga gacccaactc caacctattc tgcaacagaa gacactttta aagacaccgc 120
aaatc 125

<210> SEQ ID NO 439
<211> LENGTH: 239
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3811354

<400> SEQUENCE: 439
tgtattgaaa gcttttgtta tcaagatttt catactttta ccttccatgg ctctttttaa 60
gattgatact tttaagaggt ggctgatatt ctgcaacact gtacacataa aaaatacggt 120
aaggatactt tacatggtta aggtaaagta agtctccagt tggccaccat tagctataat 180
ggcactttgt ttgtgttgtt ggaaaaagtc acattgccat taaactttcc ttgtctgtc 239

<210> SEQ ID NO 440
<211> LENGTH: 851
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3088273

<400> SEQUENCE: 440
agcggtccct acttctgagg agaaaatgtg gtttctgact tttaggtaca tcacgatatc 60
accagtctga atgagtttcc ttttctgtaa agcagaaagt gtcattttct tttcctccag 120
tgttcagttg ctcctcttcg aaaatactct tcagagaaag tatctgtacg tctgtattag 180
tacaaaccat tccttcccta tgtctcaatg cctgacattc agtgcctgac agaatcagca 240

-continued

```
tttggcatgt ccttggatat ggcatcaatt tgatgctttg aactgaaagt tctcataatg    300

catctcaaag tatcttctta aaaaatataa aaatgtaggc caacttgtgc tctcttgtaa    360

ggcttgcaaa gtggtaatta aataagcaga ctataactca caagggaaaa aaagtgcatt    420

tttaaataaa agaaaaaaac ggagacagtt aaaaggacaa ccaaaaagat aagcagatta    480

tttttggtta atcttgggga aaatatgaca cgatatttat ggtttctttt cttttctggt    540

ccattttatt ttacttaatg tactcactag tatcataata agcctatctc ctctcctgcc    600

ttctgatatt ttagcattcc tagaaactag agccctgctg ataggctcat tcatatgagg    660

agaaatatgc ttgcctttca tgctaatgaa ttttttacaa aactgctctt aaatcatgaa    720

tatttcaatg agcacacaaa acaacaggtc tcagtgtgtt gtaaacacca tcaaaacctc    780

cacaccatta ggcttataat ctcacaagca ttctgccttt gtcagacact tcacagggtg    840

caactgggtt a                                                         851


<210> SEQ ID NO 441
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046251

<400> SEQUENCE: 441

cagcgtgggg aacgagaaac tctttgcctg tagggaccct tctagctgca aacttaaaaa     60

tgtatgtggc aagatgcaac ccaagcaccg agcaggattc cagacgagtt ataatc        116


<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2336897

<400> SEQUENCE: 442

cagagtcaag cggaacatcc tggccatggg                                      30


<210> SEQ ID NO 443
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3108574

<400> SEQUENCE: 443

gcctcagaaa accacggatg tgaacatgag tgtgtaaatg ctgatggctc ctacctttgc     60

cagtgccatg aaggatttgc tcttaacc                                        88


<210> SEQ ID NO 444
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: Affymetrix ID 3354771

<400> SEQUENCE: 444
taattatcgg actaccaggt tcctggctga ggaggggttt tataaattcc ataactggtt 60
tgatgaccga gcctggtacc ctttgggacg aatcattgga ggaacaatt 109

<210> SEQ ID NO 445
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3367705

<400> SEQUENCE: 445
ctctagaaat cactcttagt tacagagacc gtcgcttcaa ggctgcagtc aaagtagttg 60
gtgtcaagtt tgagattggt cggaagcta 89

<210> SEQ ID NO 446
<211> LENGTH: 237
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3791751

<400> SEQUENCE: 446
cagcgcctta ttttgtgatc acagagaatg caattaatac tttggctgcc ttggtatgta 60
gaccaaacct tctgccacag tgttttgcag tgctgttgtc cagggcagct ctgccaatct 120
tttcattcca acagaaacga tgccagactt ctcggtgcta agcaaagtat aatgaggcgg 180
aagaggtggc tggaaccctc agtgagggaa tgtgctcctg ggatgattct ctacaaa 237

<210> SEQ ID NO 447
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2514350

<400> SEQUENCE: 447
acagagagtc aggtatgcta tttgctatgg gaaagtgtat attcctgcca tggttcctgt 60
tgtgcagact atacccacta tttaagagga gagctg 96

<210> SEQ ID NO 448
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586107

<400> SEQUENCE: 448
ctgatcgcac ttgccagtct ggatacacaa aatgtcataa ttcaaatatt tgtattcctc 60
gcgtttattt gtgtgacgga gacaatgact gtggagataa cagtgatgaa aaccctactt 120
at 122

<210> SEQ ID NO 449
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3108602

<400> SEQUENCE: 449
gggaccacgg ttgtgaacat tcgtgtgtaa gcagtgaaga ttcgtttgtg tgccagtgct 60
ttgaaggtta tatactccgt gaagatg 87

<210> SEQ ID NO 450
<211> LENGTH: 700
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2980482

<400> SEQUENCE: 450
gtctccttcg catctctgtt ctctatcctc tttcttcccc cttttctatt tgtttttggt 60
ttattttccc atgtttcttt tcgcaaatac agcaagtgtg tatattgagt caaatctctt 120
cctcctttct tacacaaaat tagcacatta aatatatagt actgcacctt actttttctc 180
tcactatgtc ctagagattg ctctacgcgt tgtatggcgt ttttcatagt tattcactgt 240
gtgtggatac cacagtgtat tcaactgtca cctgatgaca gacatttgca ttctttgcaa 300
tcctttgtaa atacaaacaa tgctgcaatg tacatgtcat tccacatatt ctccaaggta 360
tagttaggac agatcccaga agtggaattt ctgggtcaat gggcaagtgc atttttgctg 420
attattatcc agtttccttc tgttgagttc cattttgcat taccaccagc agtgtttgag 480
aatgactgtt tctccataga actagaactt ttacagtgaa ttttatccta acttttcttc 540
aatctccttt tacttttact ttctatttta aagaatataa ttcagatttc tctagtggtc 600
atgagtctgt gtgtagtgtg agaatctaga gacaactgtt ctaaggcggc atgagaatgg 660
gcagctcagc tcagagttta gacctcatct gtttccagtg 700

<210> SEQ ID NO 451
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3126512

<400> SEQUENCE: 451
atcaagtagg gtttccaagg agtctggttg ggaaggtggt accattgcct tcaaaa 56

<210> SEQ ID NO 452
<211> LENGTH: 233
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Affymetrix ID 3913484

<400> SEQUENCE: 452
ctgtagccag tcattaatct gaaggtttaa tatatcattt tattgggatg agatcatagt     60
ctttacacaa atgctatgta aacaagttac tgaatatttt tcacctcgtg gagttgtaca    120
caacctttta tatatacaca ccctaccttc tctcaaatgc tgggcttaca ggtttattag    180
ctagggcctt ttgaggtatg ctgtcaggcg acagcccgat gagggtgctc gct           233

<210> SEQ ID NO 453
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763571

<400> SEQUENCE: 453
cctaccgtta tacctgtgat gcttttgctg ctcttgaaaa tggatacact ttgcgcaggt     60
caaacgaaac tgactttgag ctgtactttt gtggacgcaa gcaa                     104

<210> SEQ ID NO 454
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2980481

<400> SEQUENCE: 454
gagacttttg cagtttcggc tgattcagat agtcattgg                            39

<210> SEQ ID NO 455
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608604

<400> SEQUENCE: 455
ttgtgctatg aaatagcagg tcttgttcat tttttgtaac tatttttttg gtacccatta     60
accatcccca cctgtcccct gtcttggaga attgatgcct gagataaatg ggtagccaga    120
tgcacctgta ctc                                                       133

<210> SEQ ID NO 456
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586064

<400> SEQUENCE: 456
ttgtgtatta cactgtgcga ggggagggct ctaggtttgg tgctatcaaa cgtgcctaca 60
tccccaactt tgaatccggc cgcaataatc ttgtgcagga agttgacctg aaactgaaat 120
acgtaatgca gccagatgg 139

<210> SEQ ID NO 457
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3018621

<400> SEQUENCE: 457
tgaacttcca cctgtgagct tgttctcgg 29

<210> SEQ ID NO 458
<211> LENGTH: 1094
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3126626

<400> SEQUENCE: 458
acggccacct tgtatcttgt cactgctcac tgatatattt cctgcctctc cctaccacga 60
aatggaacca catttccaaa tccttaattg ctttcctcct atcaaagaaa agatgtgctg 120
ttggctctcc atgctcctgt cccctgatgc tagctctctg tgctccccct cccctgacac 180
tagctctctg tgctccccct ccccgacctg tgcttttgtc tccacctgtt cctgtctccc 240
acctctggcc cttctgctca ctcctcccca gctgtcactc cttgaagctg tgttggtgtc 300
cacactctct ctacctagca tactttcttc tcatcactga ccagggagct tcaaacctca 360
cctcaatggt agtgtgttcc tgtactctag cttgaggacc agtgcctggc tcttataagg 420
caccaaacaa aagaatgaat gagcgagtga atgaatggaa aagtgaataa agggatgtct 480
cctacctgaa gatggctcca cttagtcctc tggcaccacc cacattcttc ttatgggcac 540
gtgtcattgc attgtcatta ttgtttgcgc agtcgtctcc tgaactcacc cctgagcagg 600
gcgcagaact ttcctttccc attttggtga tccagctcct tctggagcat ctgggggtaa 660
aaactgtttg tagacacata agcttatagg ccctttgcag ttccgctagt ctgtgaagca 720
tgactagcaa ataacataaa atagtagctg acgcaatcat ttttggaagg aagcagatgt 780
tataagtaaa taataatata aaactctaat gtactaactg ggcaagttgc tcctatttga 840
aaagccagag aaaagtaaca gtttggattt tataaagtgg ccttcctttg gatgtgtttt 900
agacttttaa aatattttcg ttgaatggaa tgaggggtgc cataaagtct gtaagctttt 960
aatcagtgtc acctttcact gcttcaattt taatttatac tcctgggcca ccattggttt 1020
tctgcagatg aggctactcc aggaggttca tactggcaca tgaatgggta tccggtgatg 1080
catgccttcc agta 1094

<210> SEQ ID NO 459
<211> LENGTH: 49
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Affymetrix ID 2649002

<400> SEQUENCE: 459
gtatttgacc acctgctacg tggaagatat tatgctagac acaagttag 49

<210> SEQ ID NO 460
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763573

<400> SEQUENCE: 460
ccgtgtgatt tatgtcggta aaatcagacc tgacacaaca cggacagaac tgagggaccg 60
ttttgaagtt tttggtgaaa ttgaggagtg cacagtaaat ctgcgggatg atg 113

<210> SEQ ID NO 461
<211> LENGTH: 501
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3396651

<400> SEQUENCE: 461
tgagccacgc tgtttccaag gaattgtact aggtgctgca atgcaaaggg ttatgacaaa 60
actgtctgta aatgtaggat ctgaattggt ctttgatagt tttcctgatt tgagaaagaa 120
gtctctattt ggctaattta gggagctaag agaatggaca aggtctgctt atgtccttct 180
ggcagcctag catagctttt gcctccctca aatcagttat aagtcaaaac aaataaggca 240 catttttaa aaaaattccc ccctttaatt gaccaaagta aagccatgac atttcatttg 300
gtaacctgtt tagaattata aaaatcattt catttggccc agcccatact gcccaagaca 360
aaacttccag acaattctga tgccatccag ttttgttctt acaaactgca tattaaaaaa 420
aaaaaaaaaa aaaaatcttc aacgtcctaa atgtgatgtg ctcagtgcga agcatatcag 480
agctggacgt gacatttatg t 501

<210> SEQ ID NO 462
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3893026

<400> SEQUENCE: 462
gtcggggaga aatcaggctc tcgaagctca taa 33

<210> SEQ ID NO 463
<211> LENGTH: 157
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Affymetrix ID 3046250

<400> SEQUENCE: 463
ctcgatgctc gattttgagg aagtctggtt tctagaggat gtgcattaag tgacagtcag     60
ctcgttagag tcaatgtcca tttcgccttg gcctcttctc tcccccacta gtgtcacttt    120
acatgagcga agtgctggca cctgttggta agaatga                             157

<210> SEQ ID NO 464
<211> LENGTH: 246
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586114

<400> SEQUENCE: 464
tgtgcctttg ggaccctgca aagtgatggc aagaattgtg ccatttcaac agaaaatttc     60
ctcatctttg ccttgtctaa ttccttgaga agcttacact tggaccctga aaaccatagc    120
ccacctttcc aaacaataaa tgtggaaaga actgtcatgt ctctagacta tgacagtgta    180
agtgatagaa tctacttcac acaaaattta gcctctggag ttggacagat ttcctatgcc    240
accctg                                                               246

<210> SEQ ID NO 465
<211> LENGTH: 511
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573880

<400> SEQUENCE: 465
gtttctccca taggctgtgt ttacatggag ctatcggttt agccttttaa gcttcattag     60
cttgtctatt attgaaatag tttccaagaa attttagata ttatcataac atctgggtct    120
actcaaacac ttattgtttg aaagacttat gtcttggacc tatcaaaaac tgactttatt    180
tattgcttag tgaaaatact agtgggatca acaatgattt tcttgaatgg gcatgaatgg    240
agatgcccgc acagtaatgt agaaatgttt catacagcta ttaaaatgta actgacctcc    300
ttagaggcag attagtaact gttcctactt tgtatagcta agtgacagtc acttaactta    360
catgactttc ttttttcaca ttgggtctct ggtcctgtgt cttcacctca tttatagcac    420
gtctccttga tttttggtag tatcaacttc ccagtgatct gttcagttaa gttcttctcc    480
cgttaaccag gaagtgctta ttctctcatc a                                   511

<210> SEQ ID NO 466
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586101

<400> SEQUENCE: 466
ctcggattcc gagtttctct gtgtaaatga cagacctccg gacaggaggt gcattcccca 60
gtcttgggtc tgtgatggcg atgtggattg tactgacggc tacgatgaga atcagaattg 120
caccaggaga acttgctctg aaaatgaatt cacctgtggt tacggactgt gtatc 175

<210> SEQ ID NO 467
<211> LENGTH: 134
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3126515

<400> SEQUENCE: 467
acaagacctt gttttgggac tggtgtgtgt actgtattcc tgactgtctg caaggactca 60
aatccatctg cgtttcctgc accagtggag gctgtttatc agtgatggga tgggctccac 120
actccacggt ggct 134

<210> SEQ ID NO 468
<211> LENGTH: 250
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2608689

<400> SEQUENCE: 468
gtgggaattt ctgactgaga ccaacatctg atatttgttt gcatactgta ggtgtaaact 60
gctggaaaaa aactggtatt atttttaaaa agggttgcac agccaaatgt taaagctgaa 120
gaagtgacgt tattttagaa gtcttttttt tttttttttcc ttctctgcaa tcagatttct 180
cagcctggta cattatgaac agcttagtgc tgttgagtaa tttatatcag gatgattagg 240
aaagcttttc 250

<210> SEQ ID NO 469
<211> LENGTH: 390
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 4023359

<400> SEQUENCE: 469
aggctcgttt tctcaggtct ttctacactt cccaaatcac ctgcatgttc catgctttaa 60
agtaggaacg ctcagaaaac atgccacacg gggaaaccaa acgttagtac ggggaaaggt 120
cagtttagaa ttacagctaa gttcaaatgt taattttctg gaagttcgtg ttagttattt 180
gaaagcacaa aagaacagaa ggaagggcag agttctgatg aggaagttaa accatgcatg 240
tcagtagggt tcttttcctg ctcacagaag agggtgagca gtgagttgga gcagccgctg 300
caactcttgc atgtcgtgtg tctacacggt gggtcccagc tgaggcatga gaggcatctc 360
agtgggggtt ttatctccta tgcttcttgc 390

<210> SEQ ID NO 470
<211> LENGTH: 78

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3046202

<400> SEQUENCE: 470
gaggtgcttg aactcgcttt ctccatcttg tatgactcaa actgccaact gaacttcatc     60
gctcctgaca agcatgag                                                    78

<210> SEQ ID NO 471
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2586075

<400> SEQUENCE: 471
agtgcacaga gagcgagttt cgatgtgtca atcagcagtg cattccctcg cgatggatct     60
gtgaccatta caacgactg                                                   79

<210> SEQ ID NO 472
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046247

<400> SEQUENCE: 472
cagattaccc tgcttgctgc tagcagaaac ccaaacccac tgcagtctcc catcacattg     60
accattcatt tgtcagcagt gcccctgggt gggaatcagg ctgacagcct tccaaaacct    120
cccctcctgt ccctgcttcc cccacacccc tgcctcaagg gacatctgtg atgcactgga    180
aggtgaccta aacatttggc cagaacccta attctgatac ttctggttct gtgacccccca    240 ttaattccct tactttccaa acctccaatt cctcacctgt gaatgaggaa ggtgcacctg    300
ggctgcagca ttgctgtgaa gatgaagcaa gtgcttgagg ctctgtgaga tcctgctgtg    360
tggggtctgc tgtccagatc atgaagaact cttgcccctc aggaacttgt atgtagatgc    420

<210> SEQ ID NO 473
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608629

<400> SEQUENCE: 473
ttttatgacc ggatgaaggt ggcccagcaa gaaatcaaag caacagtgac agtgaacacc     60
agtgacttgg gaaataaaaa gaaagacgat gaggtagaca gggatgccc               109

<210> SEQ ID NO 474
<211> LENGTH: 496
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3126548

<400> SEQUENCE: 474
ctgtgctatc tctgtcctgt acatgttggc ctgcacccca aaaggtgacg aggagcagct 60
ggcactgccc agggccaaca gccccacggg gaaggagggg taccaggccg tccttcagga 120
gtgggaggag cagcaccgca actacgtgag cagcctgaag cggcagatcg cacagctcaa 180
ggaggagctg caggagagga gtgagcagct caggaatggg cagtaccaag ccagcgatgc 240
tgctggcctg ggtctggaca ggagcccccc agagaaaacc caggccgacc tcctggcctt 300
cctgcactcg caggtggaca aggcagaggt gaatgctggc gtcaagctgg ccacagagta 360
tgcagcagtg cctttcgata gctttactct acagaaggtg taccagctgg agactggcct 420
tacccgccac cccgaggaga agcctgtgag gaaggacaag cgggatgagt tggtggaagc 480
cattgaatca gccttg 496

<210> SEQ ID NO 475
<211> LENGTH: 745
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3046198

<400> SEQUENCE: 475
tggcatcttg ctcaccgccc tgattctgtt cctcggctcc actgcttcag gtcacttccc 60
atggctgcag tccactggtg ggacaagagc aaagcccact gccagtaaga aggccaaagg 120
gcccttccat cctagccctc tgcaggcatg cccttccttc ccttgggcag gaaagccagc 180
agccccagac tgcccaaaaa cttgcccacc agaccaaggg cagtgcccca aggcccctgt 240
ctggaggaaa tggcctagct atttgatgag aagaccaaac cccacatcct cctttcccct 300
ctctctagaa tcatctcgca ccaccagtta cacttgaatt aagatctgcg ctcaaatctc 360
ctcccacctc tctccctgct tttgccttgc tctgttcctc tttggtccca agagcagcag 420
ccgcagcctc ctcgtgatcc tccctagcat aaatttccca aacagtccac aggtcccatg 480
cccactttgc gtctgcactg tgatcgtgac aaatcttccc tcctcaccag ctagtctggg 540
gtttcctctc cctgccccag gccagaactg ccttcttcat ttccacccac gctcccagcc 600
tcttagctga aagcacaaat ggtgaaatca gtagtctcgc tccatctcta atagactaaa 660
cctaaatgcc tctaggacgg actgttgcta tccaagcgtt tggtgttacc ttctcctggg 720
aggtcctgct gcaactcaag ttcca 745

<210> SEQ ID NO 476
<211> LENGTH: 1168
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3573882

<400> SEQUENCE: 476

-continued

```
gaggtaggta ccatggccat tcagcacagc cttgatttcc tcccaaagta ggtgagctat     60

agtgaagaat aggtgcaaac aaacaagctt acttccattg caaaatagaa gaagaggaag    120

ttagagataa ttctgatcaa tcattttgga ggctttgtta taaggcaacc cccggtatat    180

catggaattt ccattgacat ttgaatttgg acttggatct tcccttggtc ccattagctg    240

aggtttagta atctaaagtc cctatagtat atgattataa tgctatttta aaaaatatat    300

atataaaata tttttttctt tttaaaatag acactatagt tttacccata agtaatattt    360

aaagattata gctcccaaaa gaatggacca accactttcg tatcataatt tctttttggt    420

aaatatgaga ctattatgaa atcatagtat atgattgtat ttaaaggtac aatcaaagga    480

tcttttgtcc attccattaa taactgaata aaaaataaat aaaatggata gaaaaaaact    540

aaagttgaaa atacattctt aaactagttg tctgaattga gaaaagagtg agaactaggt    600

gtgcaagaac caaacgtatt ttattttatt ttttaaatgg gagcaacata tcagtcgtgt    660

caccagctgg tatattgtgt aaatattaaa gctccattgg gactgatttt tcatggcaac    720

atcagctttc taatgttcta aattctataa aaaccaccca caaagaaaca aagcaaattt    780

cattatctaa tgagttgctg gaaaatcata ttgagaataa ttatttcaga ttcctcagtt    840

gttaacttct acattcaagg cttatctctg cccccattga tttttaacct caaaatggtg    900

ttgagattta cgtggaaccc taaagcagta aaataaaaaa cctggttgca gcacattcac    960

actgttgtcc ttaaaattcc ccttttttct ctatgtacga taaagtaaca gtatgtcaga   1020

taagccggtg gggggatgag attaggctga ggcagtgcta gtcaactggg gaaaaggatg   1080

atggaaaaat cacccagttg tgctatattt ttaaagaagg aggtcgttta tgtgtgcaga   1140

caattctccc tgaggttagc ccaatgga                                      1168
```

<210> SEQ ID NO 477
<211> LENGTH: 109
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3088320

<400> SEQUENCE: 477

```
cgtgcgaaca aaccaacctg aaattctgca tgaactgccg gaacttgtcc accctttttg     60

ctagaggcac gataacattg ataagcgtgt tggccatgtt gagcttttc               109
```

<210> SEQ ID NO 478
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3095470

<400> SEQUENCE: 478

```
gagcccctcc tactggccaa cccagtctcc atccctcccc aaacataccc caggctctag     60

ccctgcttcg cagcaccct                                                 79
```

<210> SEQ ID NO 479
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3142384

<400> SEQUENCE: 479
gaatgcgtca tgaaaggcgt cacttccacg agagtttatg agagagcata 50

<210> SEQ ID NO 480
<211> LENGTH: 226
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2721315

<400> SEQUENCE: 480
actactaagc gaccaatttt gctgaagatt ttaagaggag atgacaattg tagacattat 60
atgttgcact gcatttcaag cccagaatat ctctagagaa aaaacaaatc tccctcaatc 120
tcctctttat gttattctcc aggaaggttc caaactttac cttctagcct cattcagcat 180
ctttcaagtc ctcatctcct tgctttccaa agctctaaat cacttc 226

<210> SEQ ID NO 481
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3933546

<400> SEQUENCE: 481
ccaagcaaac aatccagagc agctgtgcaa acaacggtgc ataaatgagg cctcctggac 60
catgaagcga gtcctgagct gcgtcccg 88

<210> SEQ ID NO 482
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608677

<400> SEQUENCE: 482
agttctgatt cacccacgaa ggttacattt atgctgaata catttgtaaa tactcagttt 60
tatactgtat gtatatgatt gctactctaa aggtttggat atatgtattg taattagaat 120
tgttggcatg atgacatttc atttgtgcca aaaatattaa aaatgccttt tttggaagga 180
ctaacagaaa gcacctgatt tgcacttgaa ccagattata gatttaaaag tatatgacat 240
gtattttgta tttaaaacta gaatagccag tatttatgtt ttttataaaa ctgtgcaata 300
cgaattatgc aatcacaata catttgtagc tcccgagtgt cctaaaggga gtgcacttct 360
ttgaagctgg tgtgttaata ctatgtaata aatggttaac tttcaaatga tgctgctgcc 420
aaaattatat taatagtgag tttcaggccc ctgggcattt tgtaccatgt aattatcctc 480
tggtgatgct gtttctcgtt agtggcagta gtgcctccgt ctcctagtga taatgctcca 540

```
agtctatgaa ctgttaaatc agcattcatt ttaagaaaag caactttagt ttcaaagata    600

cttttaagct tctaaattga tcatttaaac tatttcttta aataagagag ccaaattaga    660

ggctcatact ttagcttgtg aagaagataa tgaatttttt aaagggaact ttctatgcaa    720

tgttcaggat aaatgcatac tgctggccaa tcagtgtcat ctcctgggta aattttgatg    780

tcgcattata aagacatgca taattgatgg tttctagatt atctagtcca aacaatagag    840

tttatttttt cttcatctga accaacatgc tacagtagct aagaagtatt aaaactatat    900

acatccatat aaagatgaaa tatgaactat ctcattagaa gtcatagttg accacagaca    960

tgttattctt ctgaaagagc cacattttgg ttttatttct tgtcacatga tttcttttct   1020

tgatggatga aaaatatgaa aggaaacttt tatatctgtt gcctagtttt gtacatggat   1080

ctc                                                                 1083
```

```
<210> SEQ ID NO 483
<211> LENGTH: 256
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3893027

<400> SEQUENCE: 483

caaggacgcc cgaagcacag tggacggtca tgaaggagcg ggggtgtggc aggcgggtga     60

cgtccaggag agggagcgcc cctggctgcc cctcggccgc cgactggacg cgcgggcctt    120

gccagcgagc accctcatcg ggctgtcgcc tgacagcata cctcaaaagg ccctagctaa    180

taaacctgta agcccagcat ttgagagaag gtagggtgtg tatatataaa aggttgtgta    240

caactccacg aggtga                                                    256
```

```
<210> SEQ ID NO 484
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811420

<400> SEQUENCE: 484

gagtttgtga tgaatccttc cagtattttt ctgaaaacca gtgaactatt ttgtaggttt     60

ctgtgtcgtt agaaacatgc aaacctatcc actaaaacca ctccagttga tctattaagt    120

cattcgttag gtcttacctg gactctcttc actgtcacta tcatgatctg tccacatcac    180

tggccctttc tcctatcacc tagctctcct gtgagcccag cactgatata aagtggtttc    240

tagtcttctt ggactctcaa tttaacttgc ttcccatggg aatcttctaa ctgtttc       297
```

```
<210> SEQ ID NO 485
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608644

<400> SEQUENCE: 485
```

ttggctcggc ataacaaaga acttcagagc atgctgaaac ctggtggcca agtggacgga 60
gatgaagccc tggagtttta tgccaagcac acggcgcaga taga 104

<210> SEQ ID NO 486
<211> LENGTH: 156
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3811357

<400> SEQUENCE: 486
gaccttggac aatcatgaaa tatgcatctc actggatgca aagaaaatca gatggagcat 60
gaatggtact gtaccggttc atctggactg ccccagaaaa ataacttcaa gcaaacatcc 120
tatcaacaac aaggttgttc tgcataccaa gctgag 156

<210> SEQ ID NO 487
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2932274

<400> SEQUENCE: 487
atggcccaga tctttacacg atatcctcct ccgactcatc gtgagaaaac ctgcaa 56

<210> SEQ ID NO 488
<211> LENGTH: 358
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3811424

<400> SEQUENCE: 488
ttgggtttcg taaatgcagg gatacaaaag ctattggatc ttgagatagc tttgtatttt 60
gtagagaatc atcccaggag cacattccct cactgagggt tccagccacc tcttccgcct 120
cattatactt tgcttagcac cgagaagtct ggcatcgttt ctgttggaat gaaaagattg 180
gcagagctgc cctggacaac agcactgcaa aacactgtgg cagaaggttt ggtctacata 240
ccaaggcagc caaagtatta attgcattct ctgtgatcac aaaataaggc gctgaattat 300
tctcttcatg ttttaagaat gacaggcttt tgctctgcca gctccaagca tagtgcat 358

<210> SEQ ID NO 489
<211> LENGTH: 113
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3354786

<400> SEQUENCE: 489
cgaaggtcat gtcctggtgg gattatggct atcagattac agctatggca aaccgaacaa 60
ttttagtgga caataacaca tggaataata cccatatttc tcgagtaggg cag 113

<210> SEQ ID NO 490
<211> LENGTH: 234
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2740186

<400> SEQUENCE: 490
agccctgtca gcagagtcag ttttaacaac tgagaagagt ggcatgaaat ttagtacctg 60
ctttggacat gagcataccc attctcttgc tagttttgtt tttgcctgaa aattcactcc 120
aagtgtgagg tgtaccagta actcaatcac gtatagacat ttttttttta actgaaaatc 180
tccttttcca gaaggtttat taatacgctt tgaaacttag aatgccgaac tgcc 234

<210> SEQ ID NO 491
<211> LENGTH: 367
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586104

<400> SEQUENCE: 491
gtctggatca atgtacacac ttttcatagc agcttctgaa agagcctgtt tcttgttact 60
gttatgatat aggctgtgtc tttatcagtt gcaactatac tttctcttgc cttaggctaa 120
ttccagggtc ccctgggttt gggagcctat gacaccttca ttagttaaat aggaacatgt 180
ggggttaggg ttagagcatc tgaatcagtg atggctaatt tgaagtagaa gagtgactta 240
ttttaattca gtatttattg aacagtggtg ttctaggaac ttttgggctg tgtcagtgaa 300
taagacaaca atccctaccc acatggagct aatattctaa agaggggaga caggcaacca 360
atcagta 367

<210> SEQ ID NO 492
<211> LENGTH: 142
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3046236

<400> SEQUENCE: 492
gcagcgagga aaggacgcat tgatcttgaa gttgtagaga taatgtctca gcaccctgct 60
tggggtgcca tccttttagt ggcatggcaa aaccaagcac aaaatatttt ttattgtcct 120
ttccagaata gatccctttc tc 142

<210> SEQ ID NO 493
<211> LENGTH: 222
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3126509

<400> SEQUENCE: 493
tgtgcacctt tatcgcaagt atctccacag caacctcata gtggtacgga cgcctgtgcg 60
aggactcttc cacctctggc atgagaagcg ctgcatggac gagctgaccc ccgagcagta 120
caagatgtgc atgcagtcca aggccatgaa cgaggcatcc cacggccagc tgggcatgct 180
ggtgttcagg cacgagatag aggctcacct tcgcaaacag aa 222

<210> SEQ ID NO 494
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2608546

<400> SEQUENCE: 494
ggagggacag caacaaagag attcgcagca agagtgtgag ggaattggct caggatgcta 60
aagaagggca gaaggaggac cgagacgttc tcagctacta ca 102

<210> SEQ ID NO 495
<211> LENGTH: 64
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3108613

<400> SEQUENCE: 495
agactccgat ggaagacagg actctccagc aggggaactg ccaaaaacgg tccaacagcc 60
aaca 64

<210> SEQ ID NO 496
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2997541

<400> SEQUENCE: 496
tatgaaccaa atgaacctgc gcatacacaa cgcatac 37

<210> SEQ ID NO 497
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3088362

<400> SEQUENCE: 497
ttcaagtgtt caagcttttc caggtaccac aacgccagcc tcacccaatc cctctatgcc 60
cacaatccct acccgtcctg g 81

<210> SEQ ID NO 498
<211> LENGTH: 30

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3662157

<400> SEQUENCE: 498
tttttcaata cgatactgag ccatttgctg 30

<210> SEQ ID NO 499
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586125

<400> SEQUENCE: 499
atgacccatt caaaagggca ggatcagatc ttac 34

<210> SEQ ID NO 500
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608612

<400> SEQUENCE: 500
ggggcttcca atctagttat cgacctcatc atgaacgcat ccagtgaccg agtgttccat 60
gaaagcattc tcctggccat tgcc 84

<210> SEQ ID NO 501
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608627

<400> SEQUENCE: 501
gtagctgaag ttgcatgtcg acgatggaa 29

<210> SEQ ID NO 502
<211> LENGTH: 367
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586096

<400> SEQUENCE: 502
acccttcaat cagtggctgc gatcacaact gcacagacac cttaaccagt ttctattgtt 60
cctgtcgtcc tggttacaag ctcatgtctg acaagcggac ttgtgttgat attgatgaat 120
gcacagagat gccttttgtc tgtagccaga agtgtgagaa tgtaataggc tcctacatct 180
gtaagtgtgc cccaggctac ctccgagaac cagatggaaa gacctgccgg caaaacagta 240
acatcgaacc ctatctcatt tttagcaacc gttactattt gagaaattta actatagatg    300
gctattttta ctccctcatc ttggaaggac tggacaatgt tgtggcatta gattttgacc    360
gagtaga                                                              367

<210> SEQ ID NO 503
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811405

<400> SEQUENCE: 503
ccacgtccct caacagagaa aggtgagagt ctgttatttg ttaggtttcc ttgtccatat     60
ttcttggtgg gtcccacaaa agtctcatga atctctacaa gtgggaaaat aaattgccca    120
tttcttggca caccgaactt tccatgtcat attttaaaac tgtaagtcca tactttacat    180
agctaaagac caatgggcca aagcatggtg ggtcacacct ataatctcag cattttggga    240
ggccgatgtg gtaggattaa ttgagcc                                        267

<210> SEQ ID NO 504
<211> LENGTH: 228
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3862194

<400> SEQUENCE: 504
atctgtctgg tacaaaatgc ttcccccacc gactttgggg tgttgtgtag atccatgggt     60
acgtctctcc atccctccac tctccatcct tttatccgtc tatccagatc tctagctatc    120
ttctcatgta tccattgctc caaatagtgc aaacatccag gtcttcatct ctttcagcac    180
ctgcctcttt gatttagctc catgaactta tcttgtttgg ggtctcca                 228

<210> SEQ ID NO 505
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3126514

<400> SEQUENCE: 505
atttgggatg acgtgtcagt atcggtcaga cttcatcaat atag                      44

<210> SEQ ID NO 506
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3992437

<400> SEQUENCE: 506
ctgtcagtgg ggctatccaa ttgcttccct ct 32

<210> SEQ ID NO 507
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2702151

<400> SEQUENCE: 507
caggcctgct ttgctcgttt gtcaaagagg gatggctttg cagatggcta agtttccttc 60
aggctctgac atctgcctca tgactttggc actcttgtca tgaagatgaa gtgacagttc 120
ttttaaagtg ggaagccaga cacagggttt ctagtttgcc tgagatttcc atatagggat 180
ggctggtacc caggttacct tttggaatga tagattctct gccagggaat tctttttgga 240
agagaaaaga aaataataag agtgcgtgga attttttctt aaggacataa ctaactaact 300
aactaactgt gaaatacatt agtatattta ccatgacaga ttcgcatata aaaaactggc 360
tgttcccaca gctaagccat aatatttata tttggttttg atttgcaagt aagtttttaa 420
aagtgaattt gtgaagcctt aaccttagtg cggagtgttc taaaacccag tgagaaatgg 480
tatcttcagt agttaatctc cattgattga ttgatgatag aatatgtttg gattgcaatt 540
taaatctcag acttttgatc actactattt ctgttgagta ttcagtgcag cttagctgcc 600
aatataattt ttatttagat gattattgcc taatttatgg ccacatatat tttacatgtg 660
tatgttttac atatatggaa aatacacata agccttacag tgaaagatca gataaaatct 720
attgtaagat tgaatgcaca aaatgctttt attactctaa gcaaataaat caatcaaatc 780
acatttccca ttagacagca cctcagctcc tctatacata cagcagttcg ctggattgaa 840
tacaca 846

<210> SEQ ID NO 508
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2649018

<400> SEQUENCE: 508
catatgtcta agaatccatg gaaggatatt aaccgcttta atatcagata ataagttcct 60
aaacccaaag attccgtttc agtgggcctg ggatggtttt gagtgattct gagcaacatg 120
gtccga 126

<210> SEQ ID NO 509
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2908192

<400> SEQUENCE: 509
atgcggatca aacctcacca aggccagcac ataggagaga tgagcttcct acagcacaac 60
aa 62

<210> SEQ ID NO 510
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3573883

<400> SEQUENCE: 510
agggaagcta ctgtctacgt taagataaag ggtattgcct tggctctatt tggcatggat 60
ggagcccagt tggaaaattc ccaaatatta caacaagtcc ttgaacccag gccatgtggt 120
tagacgttgg tgttaaggtt agaccttatg ttagagtcat ttctgatgtt ccagcttcta 180
gccatgtagt gctctcagtc ttcatacccc agaaattatt ggtatatttg tagataccga 240
gaatgatccc tcagtctgag aggttagaat gatcatctgt aatctgaggg ttaatttcta 300
ggcaggtgga gagagtggta aaaaagaaat gaaattgaca agctaggaaa gaggaggcag 360
aaagatttgg aaaattcaca gagtttcacc cttaagctgt agaga 405

<210> SEQ ID NO 511
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608610

<400> SEQUENCE: 511
ggggaggttc cggatccagc tctatgagca 30

<210> SEQ ID NO 512
<211> LENGTH: 1687
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3126563

<400> SEQUENCE: 512
cacctgtgta gttgcttctg ttgtaagtgg tgaactttta tccaaactgc tgacgtcaaa 60
tatgtaccct cagctcaaac cactcctctg agatgcacac tcctgaccat cttcatggca 120
tattccacca gcaccctcaa ttcatgatgt ccccagctga gttctgatat tctgtctcca 180
agtcaccatt ccagtccttc tccttccatc ctgaagcagc ctagagggag agacagggaa 240
ggaaaattaa gtttcagcac aaggttgaga agggtcttga gacagatggg cttgtggagc 300
aataagtggg ctctcatcca gccctcaagg gaaggaatgt aggaatcagt cccaaaaagt 360
gatgcttgag cagaattctt ggagcatgtg taggaatttt ctgggcagaa tgagaggagc 420
tgcacagtgt cctttaacct caaggatctt tttctctgta ctgagtcttc agctcatttg 480
atttaagatg aaaaccaccc ttcctgatgt tattcatacc ctgtaaagaa atctacagac 540
ttcctcaaaa gaacaaatca ttgtacatta atgggagctg gggcttccca gcatgcaaag 600
ggtcatctag aacctgcaga tggccctagt gtagtccgtg ggccatctgc agctatcttc 660
tggggcactt gagagccatt gggccccagg ccccactcca gacctacaga gcagaatcat 720
ttgaggagcc tagctgttgt ggtgccccag gaggaccaca aaatgatgca gacttcactt 780
gcatatggtg aaccttacca gtaaggtccc tatatatctt gttcatttaa gtttggtatc 840
ttcagttctt ttcactgttc ctgcacatca cttagtgcac agtcttcagc aggctgatga 900
ctgagaactt gcgtttatgt gctttggtac catcacacta ttgattgaca gtgaacatcc 960
tgtcattaag cccacgtatt tctgatacat atcgtacatt ctttagctgt ggtgcaggca 1020
tcctatttag ttactgaagc agttagcttc ttgtactcca gagtgccaca tagacatttt 1080
acttactgaa aatatttgga aataatttca aattacagat gttctttgac ttaatgatgc 1140
tgttatatct ggataagcct attgtaagtc aaaaatattg taagtcaaaa agcatttaat 1200
accctgttaa acccaatgta aagtagaaaa attgtaattt gaaccactgt agtggggtat 1260
ggtctgtata agaaagttgc aaaaataaga atagtacaaa gaacttatgt gttctttact 1320
tagattgacc tgttgttaac attttacatc atttcccttt ttttaaattt ttttttcatt 1380
agagacaggg tctgtctttg tcccccaggc cagagtgcag tggtgcagtg gcacagtggt 1440
gcgatcttgg ctcactgcag cctctgcctt ccaggctcat gagatcctcc caccctagcc 1500
tcctaagtag ctgggacagc aggtgtgtac cactacatct gcctaaattt tttgtatctt 1560
ttgtagagac tgagttttgc catggtgccc acgctggtct caaactcctg ggctcaagtg 1620
atccacctgc cttgaagtcc tggaatgctg ggattacagg catgggccac tataccctgc 1680
tcatttg 1687

<210> SEQ ID NO 513
<211> LENGTH: 614
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2897465

<400> SEQUENCE: 513
cagagctctt gatatcttga atgtcttttc tgtttggcct ggctcttaat ttgcttttgt 60
tttgcccagt atagactcgg aagtaacagt tatagctagt ggtcttgcat gattgcatga 120
gatgtttaat cacaaattaa acttgttctg agtccattca aatgtgtttt tttaaatgta 180
gattgaaatc tttgtatttg aagcatacat gttgaaaata caccttatca gtttttaagt 240
acagggtttt atagtgtaat atatacagag taagtgtttg tttttgtttt tcaactgagg 300
tcaaaatgga ttctgaatga ttttgcatat gggatgagga aatgcttgga tccttaagga 360
gtttacgaaa tctgctgttt tatcaaagtg aaaaaaaatt gcttattact cttcatttta 420
cactaaagct taatgtcact aagtttcatg tctgtacaga ttatttaaat catggaaatg 480
aaaaaaatgt tctctgcttg ctaccaaagg acaaactctt ggaaatgaac actttctgct 540
ttccttcctc caaagaatta ataggcaaca gtgggagaaa aaaaaggcat aatggcaaat 600
ccttcaagca ggga 614

<210> SEQ ID NO 514
<211> LENGTH: 320
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2649054

<400> SEQUENCE: 514
agggcactag ccgtggactg taatgtggtt cagtttggat aaataatgaa gttagaggca 60
acggaagttc ctggtgaatt agatatgagc gtgactgaaa gaaaagagtg aagaatgact 120
ccaaggtttt aggcctgagt caccaaaagg atggagttgc catcagttga tatgggattc 180
atagctgata tggaaccagc tgtggggaag ctcaggggtt tgagtttagt catcttgagt 240
ttgaaatgtt tattaggtgg ccaagtgaag atgctgagta gggagttaga caccaaagct 300
gaaactccat cttgggatga 320

<210> SEQ ID NO 515
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608569

<400> SEQUENCE: 515
gagggaaata acaagccaca aaagcat 27

<210> SEQ ID NO 516
<211> LENGTH: 347
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2897464

<400> SEQUENCE: 516
agcccgagcc aggagcacta gagagggagg gggaagagca gaagttagag aaaaaaagcc 60
accggaggaa aggaaaaaac atcggccaac ctagaaacgt tttcattcgt cattccaaga 120
gagagagagg aaagaaaaat acaactttca ttctttcttt gcacgttcat aaacattcta 180
catacgtatt ctcttttgtc tcttcattta taactgctgt gaattgtaca tttctgtgtt 240
ttttggaggt gcagttaaac ttttaagctt aagtgtgaca ggactgataa atagaagatc 300
aagagtagat ccgactttag aagcctactt tgtgaccaag gagctca 347

<210> SEQ ID NO 517
<211> LENGTH: 146
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2980483

<400> SEQUENCE: 517
tgagagaacc tactgattta ccttttaata gtggtcaggg catttccaga ggctgttgga 60
aagattggac gctgatggag cttggcatgt ctgtgggaag taataaagct cagatagaag 120
gaggatgttc atcttctccg ggaatc 146

<210> SEQ ID NO 518
<211> LENGTH: 140

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3791695

<400> SEQUENCE: 518
gcaggtgcac tgtcattttg gtaactcaac actgtctgca ttttattttg gtgcatgggc 60
ggggggctct ggcttcgatt tagtccttca gacacataca gtgaaataaa taggtactcg 120
acgatagtat gtgttgttgc 140

<210> SEQ ID NO 519
<211> LENGTH: 184
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3603305

<400> SEQUENCE: 519
ccctgaggaa tatgtcatag ttctgagctg ccagtggacc gcccttttcc cctaccaata 60
ttaggtgatc ccgttttccc catgacaatg ttgtagtgtc ccccaccccc accccccagg 120
ccttggtgcc tcttgtatcc ctagtgctcc atagtttggc atttgcacgg tttcgaagtc 180
atta 184

<210> SEQ ID NO 520
<211> LENGTH: 142
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2608568

<400> SEQUENCE: 520
gttcaactgc tggttaccag ccaagatgtg gacaactaca aacagatcaa acaagacttg 60
gatcaactga ggtccatcgt ggaaaagtca gagctttggg tgtacaaagg gcagggcccc 120
gatgagacta tggatggtgc at 142

<210> SEQ ID NO 521
<211> LENGTH: 455
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586115

<400> SEQUENCE: 521
cctaggcata ttgttgtaga tcccaagaac agatacctct tctgggctga ctatgggcag 60
agaccaaaga ttgagcgttc tttccttgac tgtaccaatc gaacagtgct tgtgtcagag 120
ggcattgtca caccacgggg cttggcagtg gaccgaagtg atggctacgt ttattgggtt 180
gatgattctt tagatataat tgcaaggatt cgtatcaatg gagagaactc tgaagtgatt 240
cgttatggca gtcgttaccc aactccttat ggcatcactg tttttgaaaa ttctatcata 300
tgggtagata ggaatttgaa aaagatcttc caagccagca aggaaccaga gaacacagag 360
ccacccacag tgataagaga caatatcaac tggctaagag atgtgaccat ctttgacaag 420
caagtccagc cccggtcacc agcagaggtc aacaa 455

<210> SEQ ID NO 522
<211> LENGTH: 2178
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3811408

<400> SEQUENCE: 522
tcacaggtat gtctcactcc aaagcctatg atctcatgca gtttggcatg gatactcttc 60
tatctttttg atttatgatt ttccttcatt taaaaaatct tttatttaga agtataataa 120
atataccaaa atgtaaataa aatataaatg tatatcccat tgggctattt taaagtaaac 180
actttgtagc catcatgcag gtaaaagaaa cagggcattg ccagccccca taaggccatg 240
tcccctgaca atcatagccc tgtatcttcc accaaaggta gaaattatgt taagttttat 300
ggtagccaat tccttacttt ccttacacat ttaccaccta agtatgtcac cctaaatgat 360
ataaattagt tgtgcttgtt atttaacttc atgtagatga aattgtagtg tatgtagttt 420
gtgttttggg cttcatttgc tcatagttac gtttgtgaga tttcatgaag ctaaagtttg 480
ttcattttcc ttgttgtatt ttattgtgaa agttcaccca ctgtatttat tcatcctgtt 540
gtttttgtta tgatatataa tgctgctgtg aacattattg tacctgttct ttggtgcctt 600
gtgcatatat ttctattggg aacacaccaa atagtgaaat tgttgtagat gtaatgccat 660
gtatgagagt tcctgttgtt ttgtatactc tccaaactta gaactgtcag tctctttaat 720
tttagccatt ctggcatgtt cacaggagta tcacattgtg ggtttaattt gcatttccct 780
gattacttat tactaataat cttttcatat gcttattttc ttttagaacg tgcctatgca 840
agtctcttgt ccatttttca actgttttct atttcttatg aatttgtagg agttctttgc 900
agcttctggc tatgcatcct tcattaattt tgtgtgttgc aaatatattc ttccattttg 960
tgacttgtct ttttagtctc aaaacagaat cttttgatga aaagaatttc ttaattttga 1020
tgtaacctca tttatcactc ttttccttca tggttggcac ttgttgtgtc ttgtttgaca 1080
atgttgccta tcccaaagtc atgaagattt tctcttatgt taacttctaa aagttgtatc 1140
atttgtcttt tatatttata tctacataat gcacctggaa ttgagttata tgaatgctgt 1200
gaatttggga ggggcgtgtt tccttttttt cccacatgga tatccaatca actcagccac 1260
atttactggg ggaagacatc ttttttttcta atgcgctgta gtgttaggtt tttcaaaact 1320
taggtgtctg tatatgtgtg ggtctgttta tgagtctgtc tattcttttc cactggtctg 1380
tttcctacac ttgtgccaat gccacactgt cttacttata gctctataag tcttggtatt 1440
gttaaggaaa aatatttgta acatttgtta aaaatggcag agaagacttt attcaaggag 1500
gggaacattg tgataggtag agggactgct gcaacgaggt cttgctgtgg tgaggagaga 1560
gattgggctg gagtccaact tctacaagga caagagggga tttatagtca agcagcaggg 1620
tggggtcagt ggatggaaga ggaaacatca gagacagggg tattcttgct agaccaactc 1680
aacagaattc ttgctgaagg caggccaggg tgataagata tcaagagtta ggggtgagga 1740
cagataccaa gggtggagaa ttttcactaa aactagtagg attcttgctt aaactggatt 1800
ctataagaca gaaaaggaag cccaaggtca gggtctagtg gaagagaagg ctccggggag 1860
cccgacctga gtttgatcta ggagagtctt tgtcaatatc ctgtagaata tgaccttcac 1920
ctcattttct tttcctcaag tgtatctgga ctgtatttgg ccttttgggc ttccaggtga 1980
cttttagagt aagtttatca agatctacaa aaatagctac tgagattttg atttgaatag 2040
tatttcttcc tgataatttc tgagtaaaat tcattttaag gaagtaggag gggcagtggc 2100
ctgatgaaaa gcaaaaatga agaaaagaat aaggaaagac acagttttgc catcaccagc 2160
cagtgtttag tgatctta 2178

<210> SEQ ID NO 523
<211> LENGTH: 134
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2466604

<400> SEQUENCE: 523
cccactaata cgaggccttc ttgcaagacc agccaaactg caggtgcagg atcagctgat 60
gaacgaggag ctgacggaaa ggctctttgt gctgtccaat tccagcacct tggatctggc 120
gtccatcaac ctgc 134

<210> SEQ ID NO 524
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586166

<400> SEQUENCE: 524
tatgcttgca caatgagttt tcatgtggca atggagagtg tatccctcgt gcttatgtct 60
gtgaccatga caatgattgc caagacggca gtgacgaaca tgcttgca 108

<210> SEQ ID NO 525
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3018611

<400> SEQUENCE: 525
gtgatcccgt tctttctgtt cctcgctctt cccctccgat cgtcctcgct taccgcgtgt 60
cctccctcct cgctg 75

<210> SEQ ID NO 526
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3693008

<400> SEQUENCE: 526
ttgggaactc tagtctcgcc tcgggttgca 30

<210> SEQ ID NO 527
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3862192

<400> SEQUENCE: 527
tcagcaatga ccatgctggg aaactgtgtg gggcctgtgg aaactttgac ggggaccaga 60
ccaatgattg gcatgactcc caggagaagc cagcgatgga gaaatggaga gcgcaggact 120
tctccc 126

<210> SEQ ID NO 528
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2649046

<400> SEQUENCE: 528
gaggtccagt ctggtcataa caaccaaact ctactggggt g 41

<210> SEQ ID NO 529
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2763600

<400> SEQUENCE: 529
tttaaaacga caatcagagg agagtg 26

<210> SEQ ID NO 530
<211> LENGTH: 516
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3546098

<400> SEQUENCE: 530
gctgaatggc catggtacct acctcccgca gcagctgaga atatatatac atatatttgt 60
atgtatgtat gtatgtgtgt atgtacgtat aatttcttca gctcagcatt cagagagaac 120
actgctatag agaccaagat taggaatgac ttgggccaca tagaaattgt aggaatgggg 180
aggaaaagac cagcaccacc agacccactg gttttccttt aataggtatc atggggtata 240
attaacccac tgaaaatata cataccacat acatggttca aaagtaatta tttccaaaag 300
aaacccctca caattacaaa tatttaagta tttttttttc tttcaatcac ccctttctcc 360
tctctaggag catatgacaa atatattgtt tttatatgtg tattctctat gccactttta 420
gttgagctcc ttcttctttt tctggccttg tgtatgtttc tatgtttccg tggctaacaa 480
atgtgaccca ctctctacag cttaagggtg aaactc 516

<210> SEQ ID NO 531
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3385513

<400> SEQUENCE: 531
aagtatgtct gcatcgatgt ctgtactgta aatttc 36

<210> SEQ ID NO 532
<211> LENGTH: 150
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586141

<400> SEQUENCE: 532
ttcatcttcg gcgttcacct gtggccatgg ggagtgcatt cctgcacact ggcgctgtga 60
caaacgcaac gactgtgtgg atggcagtga tgagcacaac tgccccaccc acgcacctgc 120
ttcctgcctt gacacccaat acacctgtga 150

<210> SEQ ID NO 533
<211> LENGTH: 320
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3046243

<400> SEQUENCE: 533
ccaagttgga ataggatcta ctctgtgtag acttgctgga agtgaaacac acagagcctg 60
cgggaagagt tgttctatga gtacttgagc ccccagcctg actaggttaa gtcttctatg 120
agtacatgaa cccctagcct gactaggtta agtcttctat gagtacatga acccctagcc 180
tgactaggtt aagtcttcta tgagtacttg agcccccagc ctgactaggt taagtcttct 240
atgagtactt gagcccccag cctgactagg ttaagtcttg gagcagatct tagactctgt 300
cttcggtaag tggccaagtc 320

<210> SEQ ID NO 534
<211> LENGTH: 133
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3046224

<400> SEQUENCE: 534
atgagagcac ttacaaccaa gcctagctcc ctggaccagt tcaagagcaa actgcagaac 60
ctgagctaca ctgagatcct gaaaatccgc cagtccgaga ggatgaacca ggaagatttc 120

```
cagtcccgcc cga                                                     133


<210> SEQ ID NO 535
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 4023361

<400> SEQUENCE: 535

aatattttca tgcaagtttc caaaccca                                      28


<210> SEQ ID NO 536
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3546096

<400> SEQUENCE: 536

catctgctgg gtcttcgaag tctcagtaaa tattgaataa gctccctgga gctctgctgt    60

tgctgcctaa gacgggtagc cagccccgac ttgcatgagc agtcttgttt ggatatctgc   120

acatgtttgc tttctattgg ttcagactca ccttggaaca gagctgggtc tgttaagtct   180

gagaccttgc ttctggtact atacacatag ggcattagga agtggcccaa tgttttgctc   240

atcctaaagt cactcaatga cttgcagcag ccttcagcct tccttcagtt gcgagaagtt   300

tgttttcaaa tcttcccaga ttggtagacc aagccctcag ggccttgttc ttcccagtta   360

gcaactttct agctctccca tcctagatcc tctcttttct tagagagcct caggacatga   420

ccaagattg                                                          429


<210> SEQ ID NO 537
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3046199

<400> SEQUENCE: 537

atctggacgg atggactgaa tgcgctactc gggaaggaca tgatgagcga cctgacgcgg    60

aatgacctgg acaccctgct cagcatggaa atcaagctcc gcctcctgga cctggaaaac   120

atccagatcc ctgacgcacc tccgccgatt cccaaggagc ccagcaacta tgacttcgtc   180

tatga                                                              185


<210> SEQ ID NO 538
<211> LENGTH: 544
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740233
```

<400> SEQUENCE: 538
ggaagctctc acatggcaat ctataggtgg atgcagaagt tgtcagtgtc tatataacag 60
gttgggaagg gtgatgagtg gtgactgctg agacctggag gggaagtagg aatatattta 120
aaatcctaaa tcttgacatc acaaaacaaa aaagtcctat acttcttttt ccccaccaca 180
gttgttaaat tttatatttg cttaatgaat tattcttgta aatagagatc agccatctag 240
agaaaagctc atagcattag gtttgacatt gtaaattttt attaaatgaa taaaataaaa 300
tattatttgt atatttaaat atacatgtta ttccaagaat taaaatatag aaatgggtat 360
atcaacccaa atgagcataa tttcattgta ttttgatggt gcagaatgta ttttggggtt 420
tgtattgctg attagtagtg agtcagtgga ggcagtatgc caataagaac gacaaagaaa 480
tatgtactgc tgcgggcaag ccacctgagt gttaaagaaa gatgactgag ctttggctga 540
tttc 544

<210> SEQ ID NO 539
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2980484

<400> SEQUENCE: 539
ttgtggcaag cgatagtcct ctacatcttt t 31

<210> SEQ ID NO 540
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2980450

<400> SEQUENCE: 540
tggctgcgtt ttgatcgtct acaacaaggt tacagtgccc tctggtggca gtcatcaaaa 60
tcgcttctag acttgttttt 80

<210> SEQ ID NO 541
<211> LENGTH: 124
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763628

<400> SEQUENCE: 541
tcacctctgg atggaatcaa cacacaaagc agataaaaag ctgaacatta aagaccacat 60
tgttaaagca gagagccaaa ttgttcctcc accattccct atcccagact tcacatctaa 120
caag 124

<210> SEQ ID NO 542
<211> LENGTH: 37
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Affymetrix ID 2649009

<400> SEQUENCE: 542
gagagcattc acacaggcca tctggtctag ccctcat 37

<210> SEQ ID NO 543
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791690

<400> SEQUENCE: 543
ggggaagtcc ctgcgatata taatggtctc aatttaaatt ctgtgctgtt tttattttag 60
ctgtgtaatt tggaaacttc aaataaaaag cctgaaagga aagttggact atttaagctt 120
acacagactc tattaatgct atatggttat tctacccctg actttggaag aaggagaaac 180
tggcatggga atacactttt ctaaaaaaaa tactatttaa aaatatgaaa gtttatttaa 240
catctaagga aaggtactta attagaggga cactcaacaa gaagaattga ggatctaagt 300
aaatagtccc catctgctcc tggtcctacc acctggcgat tacttcctct tcttctctga 360
tagattttag ccaaccaatt ttgttttatt tgtgcaagtt gagaggccac ctgtta 416

<210> SEQ ID NO 544
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2980485

<400> SEQUENCE: 544
cggaggagga tatcgtgtaa agatctgggc catgctgact gccaagggtg gctgtataag 60
aaaaaggaaa agggaagttt cctaagcaac aaatggaaaa agttctgggt gatactgaag 120
gggtcgtcac tgtactggta tagcaatca 149

<210> SEQ ID NO 545
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3811446

<400> SEQUENCE: 545
tgtaactttc aatggaaacc tttgagattt tttacttaaa gtgcattcga gtaaatttaa 60
tttccaggca gcttaataca ttctttttag ccgtgttact tgtagtgtgt atgccctgct 120
ttcactcagt gtgtacaggg aaacgcacct gatt 154

<210> SEQ ID NO 546
<211> LENGTH: 1832
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3811358

<400> SEQUENCE: 546
cctgtgctgc tatcctgcca aaatcatttt aatggagtca gtttgcagta tgctccacgt 60
ggtaagatcc tccaagctgc tttagaagta acaatgaaga acgtggacgt ttttaatata 120
aagcctgttt tgtcttttgt tgttgttcaa acgggattca cagagtattt gaaaaatgta 180
tatatattaa gaggtcacgg gggctaattg ctggctggct gccttttgct gtggggtttt 240
gttacctggt tttaataaca gtaaatgtgc ccagcctctt ggccccagaa ctgtacagta 300
ttgtggctgc acttgctcta agagtagttg atgttgcatt ttccttattg ttaaaaacat 360
gttagaagca atgaatgtat ataaaagcct caactagtca ttttttctc ctcttctttt 420 ttttcattat atctaattat tttgcagttg ggcaacagag aaccatccct attttgtatt 480
gaagagggat tcacatctgc atcttaactg ctctttatga atgaaaaaac agtcctctgt 540
atgtactcct ctttacactg gccagggtca gagttaaata gagtatatgc actttccaaa 600
ttggggacaa gggctctaaa aaaagcccca aaaggagaag aacatctgag aacctcctcg 660
gccctcccag tccctcgctg cacaaatact ccgcaagaga ggccagaatg acagctgaca 720
gggtctatgg ccatcgggtc gtctccgaag atttggcagg ggcagaaaac tctggcaggc 780
ttaagatttg gaataaagtc acagaattaa ggaagcacct caatttagtt caaacaagac 840
gccaacattc tctccacagc tcacttacct ctctgtgttc agatgtggcc ttccatttat 900
atgtgatctt tgttttatta gtaaatgctt atcatctaaa gatgtagctc tggcccagtg 960
ggaaaaatta ggaagtgatt ataaatcgag aggagttata ataatcaaga ttaaatgtaa 1020
ataatcaggg caatcccaac acatgtctag ctttcacctc caggatctat tgagtgaaca 1080
gaattgcaaa tagtctctat ttgtaattga acttatccta aaacaaatag tttataaatg 1140
tgaacttaaa ctctaattaa ttccaactgt acttttaagg cagtggctgt ttttagactt 1200
tcttatcact tatagttagt aatgtacacc tactctatca gagaaaaaca ggaaaggctc 1260
gaaatacaag ccattctaag gaaattaggg agtcagttga aattctattc tgatcttatt 1320
ctgtggtgtc ttttgcagcc cagacaaatg tggttacaca ctttttaaga aatacaattc 1380
tacattgtca agcttatgaa ggttccaatc agatctttat tgttattcaa tttggatctt 1440
tcagggattt ttttttaaa ttattatggg acaaaggaca tttgttggag gggtgggagg 1500
gaggaagaat ttttaaatgt aaaacattcc caagtttgga tcagggagtt ggaagttttc 1560
agaataacca gaactaaggg tatgaaggac ctgtattggg gtcgatgtga tgcctctgcg 1620
aagaaccttg tgtgacaaat gagaaacatt ttgaagtttg tggtacgacc tttagattcc 1680
agagacatca gcatggctca aagtgcagct ccgtttggca gtgcaatggt ataaatttca 1740
agctggatat gtctaatggg tatttaaaca ataaatgtgc agttttaact aacaggatat 1800
ttaatgacaa ccttctggtt ggtagggaca tc 1832

<210> SEQ ID NO 547
<211> LENGTH: 214
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:

<223> OTHER INFORMATION: Affymetrix ID 3573884

<400> SEQUENCE: 547
ccaggaagat cgatgtgcag cagcccagca gcttctggag cgtttctcct tgccgcccca 60
gtgccgagtt gtggctgacc gcatggacaa taacgccaac atagcttacg ggtagccctt 120
tgaacgtgtg tgcattgtgc agagacagaa aattgcttat ctgggaggaa agggcccctt 180
ctcctacaac cttcaagaag tccggcattg gctg 214

<210> SEQ ID NO 548
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2925965

<400> SEQUENCE: 548
agaaaagttg ggtagaagaa ccatgtgaga gcattaatga gccacagtgc 50

<210> SEQ ID NO 549
<211> LENGTH: 258
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2608614

<400> SEQUENCE: 549
agctcattct gagggcacaa aattctgttt tgaaaaatga gttctgctag tatcctgctg 60
tgatcatttg gtcataaatc agacttggtt ccagaacatg agttacattt gaaaactgat 120
aaaacactga gaatacgcaa aggaaactgg cctaagatct ggcacatagt gggcactcca 180
taaatgtttg ttgaataagt aaatgattgc atgaagttta tttacagttt ttatccaaga 240
ttgtagggga tctcatca 258

<210> SEQ ID NO 550
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3787876

<400> SEQUENCE: 550
cagttacaag aacatgggag aaattgagcc caccttttac gtcacccttt atggcactaa 60
tgcagattcc cag 73

<210> SEQ ID NO 551
<211> LENGTH: 218
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2331561

<400> SEQUENCE: 551
ctggggccat ttggtgcaga acaaccccca acccagtggc catcttcaca actgcagcac 60
agtgctggcc ctaatgccag gtgagcgtgc aaagtcctgt ttctttgtct ttacataggg 120
accgggcgat gcgctttaga gaaattccct attatttcac aggaaaggag gctgtgaaaa 180
ggagagggca ggttttggag ccaagtcgac ctggcatc 218

<210> SEQ ID NO 552
<211> LENGTH: 250
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2661102

<400> SEQUENCE: 552
taattcttag actgcctcct tgggaccctg ctttcctcag tttacctgtc ctctactgcc 60
aggtgtatag tcctccgtta cagctccaaa gccccttgga gggctgcact gctcctatat 120
atgaacccca acccccatcc aaggcccttc acttctacat agcactcctc ggtctgaaag 180
acccaaccgc tgttctggaa acccaactgc tgctctcaca cctctgggcc ctctctacca 240
tggaatatga 250

<210> SEQ ID NO 553
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586047

<400> SEQUENCE: 553
tgaaaaccca atgtactcag ccagagacag tgctgtcaaa gtggttcagc caatccag 58

<210> SEQ ID NO 554
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3787860

<400> SEQUENCE: 554
tgagcaactc cgttcctctg ctctgtttct ggagcctctg ctattgcttt gctgcgggga 60
gccc 64

<210> SEQ ID NO 555
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3791668

<400> SEQUENCE: 555
atgggtcctt cagcggagac tacaagac 28

<210> SEQ ID NO 556
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3126507

<400> SEQUENCE: 556
tattgcacag ctaataaaat atgatt 26

<210> SEQ ID NO 557
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2608643

<400> SEQUENCE: 557
gaaagcctac atgcaaggtg aagtggaatt tgaggatgga gaaaacggtg aggatggggc 60
ggcgtccccc aggaacgtgg ggcacaacat ctacatatta g 101

<210> SEQ ID NO 558
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3807530

<400> SEQUENCE: 558
tgcgctgttc cgctcagcct tagaacctct gaaggaaaga gttaatgatg ctctgaaaat 60
cagatgctgg ggaaaaccag ctccccccac agacctcatc catcccacag acaggcatct 120
gtctccccca aactcctagc ctcttcctgt ctgtccctct catttggctt ggcctcatct 180
gccttgccct acctgtgtgt aagtgtgcac gtgcgtgtac aaacctggtc tcccagctag 240
actgtgagcc ctgagaagtg agctactttg atgatgtttc atcacaatcc caacattact 300
tggcatgatg ctttgtccct ggtggatact caacaaaca 339

<210> SEQ ID NO 559
<211> LENGTH: 432
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763570

<400> SEQUENCE: 559
tttgtactat ctactcaggt gctgaaaatt gtggtaggta tgtatgtgga tattgtgtgt 60
ttccacatgt gttcatgatt tctgtatgtg tgttgtgtgt gcatgcagct ttatattttg 120
tgagtgcatg tattgtgtgt atctctgtgg atattgtgtg tgtctgtgtg tgttgtgtga 180
atattaaaca tgtatgtgtg tagtattgtg ctttgtgtgt gcgtgtgtta tgcagatgtg 240
tgtggctatc atgtgtcttt gtgtgtgtat gtatgcaggt attgtatgtg tctacatgtg 300
tttatgattc atgtgtgtgt gtgtgtgtgt gtgtttgtaa cctgattttg ccttccaggc 360
ctaccctgaa tcctttcacg aaccatagca ttgccatcat tgttttatgg aacagaatat 420
gcaagtctca tt 432

<210> SEQ ID NO 560
<211> LENGTH: 102
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2925993

<400> SEQUENCE: 560
ccctactgcg aaagtatgct gaagaaagaa atggtgtcaa tgtcgtcagt ggtcctgtgt 60
ttgactttga ttatgatgga cgttgtgatt ccttagagaa tc 102

<210> SEQ ID NO 561
<211> LENGTH: 147
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2908205

<400> SEQUENCE: 561
gaattctaca tactaaatct ctctcctttt ttaattttaa tatttgttat catttattta 60
ttggtgctac tgtttatccg taataattgt ggggaaaaga tattaacatc acgtctttgt 120
ctctagtgca gtttttcgag atattcc 147

<210> SEQ ID NO 562
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586123

<400> SEQUENCE: 562
gatggcacca acaggacagt atttgcttct atatctatgg tggggccttc tatgaacctg 60
gccttagatt ggatttcaag aaacctttat tctaccaatc 100

<210> SEQ ID NO 563
<211> LENGTH: 283
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3791749

<400> SEQUENCE: 563
ccaggtaaga cctaacgaat gacttaatag atcaactgga gtggttttag tggataggtt 60
tgcatgtttc taacgacaca gaaacctaca aaatagttca ctggttttca gaaaaatact 120
ggaaggattc atcacaaact cctagcccca gccaacccca gtgcaaaaaa aaaaaaaaaa 180
aaaaatcatg cccaatcctt caaaagattc atatgtgcag ggttattact ctagacatca 240
gcttgcctgg gaccatcctg gcctacccta ttgtcccaga ata 283

<210> SEQ ID NO 564
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586195

<400> SEQUENCE: 564
agggattcat cagtgagggc atttcacacc ctcatgtggc atttcacttg gtagtgtcca 60
gatcggattg ggttttttttt cctctggtta gtcacggtcc ttggaaagaa agatatgctg 120
gctcatgttg ttatg 135

<210> SEQ ID NO 565
<211> LENGTH: 103
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2763627

<400> SEQUENCE: 565
tcaaggagga gcaatcaggc tggtagggca gagaggagga aggagactca gtagtcaaat 60
ccctggtggc cgatgccctt ccctgcgcca aatcagcatg att 103

<210> SEQ ID NO 566
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2608559

<400> SEQUENCE: 566
ttcagaaaca tcctccggaa acagcagcca agaagggcca agtaatgtac cag 53

<210> SEQ ID NO 567
<211> LENGTH: 132
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3126535

<400> SEQUENCE: 567
ggctcatctt atttcgacca ttcggcccca tcatgaaagt gaaaaatgaa aagctcaaca 60
tggccaacac gcttatcaat gttatcgtgc ctctagcaaa aagggtggac aagttccggc 120
agttcatgca ga 132

<210> SEQ ID NO 568
<211> LENGTH: 179
<212> TYPE: DNA
<213> ORGANISM: Artificial Sequence -continued
<220> FEATURE:
<223> OTHER INFORMATION: Description of Artificial Sequence: Synthetic
      polynucleotide
<220> FEATURE:
<223> OTHER INFORMATION: Affymetrix ID 3791743

<400> SEQUENCE: 568
agactcatga gtggggctaa cgccagggtc ggaatgcttt ctcttggtta ggtcttccag     60
caaaaccaat caaccaatac acatggaaaa tgcatcatac aaacttttca gatcagagct    120
ggggctttgc cttgtgtcag ccgacgaaga actcccaagg ccgttctgga ttgaatctc     179

<210> SEQ ID NO 569
<211> LENGTH: 638
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3727623

<400> SEQUENCE: 569
ggtagccctc tcatcgtctt ttagttccaa caaagaaagg tgccatgtct ttactagact     60
gaggagccct ctcgcgggtc tcccatcccc tccctccttc actcctgcct cctcagcttt    120
gcttcatgtt cgagcttacc tactcttcca ggactctctg cttggattca ctaaaaaggg    180
ccctggtaaa atagtggatc tcagttttta agagtacaag ctcttgtttc tgtttagtcc    240
gtaagttacc atgctaatga ggtgcacaca ataacttagc actactccgc agctctagtc    300
ctttataagt tgctttcctc ttactttcag ttttggtgat aatcgtcttc aaattaaagt    360
gctgtttaga tttattagat cccatattta cttactgcta tctactaagt ttccttttaa    420
ttctaccaac cccagataag taagagtact attaatagaa cacagagtgt gtttttgcac    480
tgtctgtacc taaagcaata atcctattgt acgctagagc atgctgcctg agtattacta    540
gtggacgtag gatattttcc ctacctaaga atttcactgt cttttaaaaa acaaaaagta    600
aagtaatgca tttgagcatg gccagactat tccctagg                            638

<210> SEQ ID NO 570
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586057

<400> SEQUENCE: 570
gaacctaaaa tcgagtctgc ctggatgaat ggagaggacc gcaacatcct ggttttcgag     60
gaccttggtt ggccaactgg cctttctatc gattatttga acaatgaccg aatctactgg    120
agtgacttc                                                            129

<210> SEQ ID NO 571
<211> LENGTH: 191
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2763598

<400> SEQUENCE: 571
gtgttcaatc tgatggcagt agtcattgta ataagacttt tggctggcgg gtgttgccat 60
catacactaa agagatttca tgacttaaga catttcatgg actcacaagt actgaaacag 120
ggtatgagtg gtaatggagg agagaactgt gactcaggaa agaagactcc ttcggtcaag 180
gggccagact t 191

<210> SEQ ID NO 572
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2925966

<400> SEQUENCE: 572
tggattcagg gcagaatatt tacacacttg gggtggactt cttcctgt 48

<210> SEQ ID NO 573
<211> LENGTH: 416
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 4016044

<400> SEQUENCE: 573
atgacgtctc tgcaatgcac atgtgtgaaa atctgctact gaaacataga gcaagcaaac 60
actggcaggt gggtcaaaac gctactggta gcaggaggaa cgactaaagc aaagtattac 120
cataaggtta aaacatatgg cctgacaaat gcctgccagg gacactacac ataaggaatg 180
tcttcagtgt cccttcgtgg ggccctgcag ccacccctga attcccttgg acccctagga 240
tagaaggggt cctgtaaatt tctttgcatc cacaaaaacg cccccaattt ctgtttgctt 300
tttctccttt tatcctccac cctagccatg ttgtcaaatt ctcttatcat gtcctcattg 360
ctgaaattca tatcatgtat ggcttcctta tattgcttga ggtactgagc cagccc 416

<210> SEQ ID NO 574
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2980475

<400> SEQUENCE: 574
aaataaactt ggatcggctg taatccatca ggaatc 36

<210> SEQ ID NO 575
<211> LENGTH: 112
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2944441

<400> SEQUENCE: 575
tgtaaaagtt acacatcaca agagattgga cagtagctta gcgtaacata gctatagtga 60
aaatcatttt tataaaaaaa taatctagat gcggtcatca gaatttttgg tc 112

<210> SEQ ID NO 576
<211> LENGTH: 328
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2608634

<400> SEQUENCE: 576
ggagtagaat ccctccatga gtgtcagagg tgcagtgcca atgtgcttgt tcccgagctt 60
agctctggtg gtatgggcct gctccgcctt ccctctctcc ctgaccttcc ctccctcgcc 120
cacacaccca cttccttcca ctgtgaaagc ggagtaaggc tttaattgca caggttcatc 180
atttcttgtt tggaagtctt cagattttta gttttatacc ttagctttct gcagaattct 240
ccgttgaatc aatgccctgg gaaccccatg gacagaagca ccttttaatg aagtccttcc 300
aaaactcgtt cctcagtgca ttgctctg 328

<210> SEQ ID NO 577
<211> LENGTH: 1186
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2727646

<400> SEQUENCE: 577
ggcctcccta gccagcactt gtatatacgc atctataaat tgtccgtgtt catacatttg 60
aggggaaaac accataaggt ttcgtttctg tatacaaccc tggcattatg tccactgtgt 120
atagaagtag attaagagcc atataagttt gaaggaaaca gttaatacca ttttttaagg 180
aaacaatata accacaaagc acagtttgaa caaaatctcc tcttttagct gatgaactta 240
ttctgtagat tctgtggaac aagcctatca gcttcagaat ggcattgtac tcaatggatt 300
tgatgctgtt tgacaaagtt actgattcac tgcatggctc ccacaggagt gggaaaacac 360
tgccatctta gtttggattc ttatgtagca ggaaataaag tataggttta gcctccttcg 420
caggcatgtc ctggacaccg ggccagtatc tatatatgtg tatgtacgtt tgtatgtgtg 480
tagacaaata tttggagggg tatttttgcc ctgagtccaa gagggtcctt tagtacctga 540
aaagtaactt ggctttcatt attagtactg ctcttgtttc ttttcacata gctgtctaga 600
gtagcttacc agaagcttcc atagtggtgc agaggaagtg gaaggcatca gtccctatgt 660
atttgcagtt cacctgcact taaggcactc tgttatttag actcatctta ctgtacctgt 720
tccttagacc ttccataatg ctactgtctc actgaaacat ttaaatttta ccctttagac 780
tgtagcctgg atattattct tgtagtttac ctctttaaaa acaaaacaaa acaaaacaaa 840
aaactcccct tcctcactgc ccaatataaa aggcaaatgt gtacatggca gagtttgtgt 900
gttgtcttga aagattcagg tatgttgcct ttatggtttc ccccttctac atttcttaga 960
ctacatttag agaactgtgg ccgttatctg gaagtaacca tttgcactgg agttctatgc 1020
tctcgcacct ttccaaagtt aacagatttt ggggttgtgt tgtcacccaa gagattgttg 1080
tttgccatac tttgtctgaa aaattccttt gtgtttctat tgacttcaat gatagtaaga 1140
aaagtggttg ttagttatag atgtctaggt acttcagggg cacttc 1186

<210> SEQ ID NO 578
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2925978

<400> SEQUENCE: 578
aggaaatatt gtggaagtgg atttcatggc tct 33

<210> SEQ ID NO 579
<211> LENGTH: 247
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2608490

<400> SEQUENCE: 579
gcatgtttct gtagtggcat ctcaactatt gcaatggaaa atatgtcctt ggcaagactc 60
ttagaaacac agcctcaaag gtcattggat tgtgcaagct tcttgactat ttacaaggtc 120
acctacctga atgaatagaa atgctccctg cccttaagga atttgcaatt ttatgaagag 180
agatgagtga gaactacttt gtggattatt cttggagaat gttgaatccc agatgagctt 240
ttagtcc 247

<210> SEQ ID NO 580
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3992448

<400> SEQUENCE: 580
agcaagtgta ttgtcccgac tgtgccaaaa agct 34

<210> SEQ ID NO 581
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3985030

<400> SEQUENCE: 581
ggctggctca gtacctcaag caatataagg aagccataca tgatatgaat ttcagcaatg 60
aggacatgat aagagaattt gacaacatgg ctagggtgga g 101

<210> SEQ ID NO 582
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 3753968

<400> SEQUENCE: 582
aagagaagat gccaaggccc cctcctccac ccaccgctaa ctctcagccc cagtcaccct     60
cttggagctt ccctgctttg aattaaagac                                      90

<210> SEQ ID NO 583
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3573878

<400> SEQUENCE: 583
tgatgctaag agtcctgggt aaatgtggtg agaatgcacg cgtgcatatg ctacacatat     60
gtgcttctca gttgcagaaa atgaactgct ttgggagatt atc                      103

<210> SEQ ID NO 584
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586112

<400> SEQUENCE: 584
tgtactgggc tgactgggat acacatgcca aaatcgagag agccacattg ggaggaaact     60
tccgcgtacc cattgtgaac agcagtctgg tcatgcccag tgggctgact ctggactatg    120

<210> SEQ ID NO 585
<211> LENGTH: 211
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3354794

<400> SEQUENCE: 585
ggaggcaaaa gctatgctag gctgccagaa ggacataagc agaccttgtc cattctctta     60
gctccctaaa ttagccaaat agagacttct ttctcaaatc aggaaaacta tcaaagacca    120
attcagatcc tacatttaca gacagttttg tcataaccct ttgcattgca gcacctagta    180
caattccttg gaaacagcgt ggctcaataa a                                   211

<210> SEQ ID NO 586
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925981

<400> SEQUENCE: 586
ttgacaccgg ctcctaataa cggaactcat ggaagtctta accaccttct aaagaatcct 60
gtttatacgc caaagcatcc caaagaagtg cacccccctgg tacagtgccc cttcacaaga 120
aaccccagag ataaccttgg ctgctcatgt aacccttcg 159

<210> SEQ ID NO 587
<211> LENGTH: 907
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3787884

<400> SEQUENCE: 587
tccttccgac aggagctgac tcatgtcagg atggcaggcc tggtatcttg ctcgggccct 60
agctgttggg gttctcatgg gttgcactga ccatactgct tacgtcttag ccattccgtc 120
ctgctcccca gctcactctc tgaagcacac atcattggct ttcctatttt tctgttcatt 180
ttttaattga gcaaatgtct attgaacact taaaattaat tagaatgtgg taatggacat 240
attactgagc ctctccattt ggaacccagt ggagttggga tttctagacc ctctttctgt 300
ttggatggtg tatgtgtata tgcatgggga aaggcacctg gggcctgggg gaggctatag 360
gatataagca ttagggaccc tgaggcttta agtggtttct atttcttctt agttattatg 420
tgccaccttc ttagttatta tgtgccacct cccctatgag tgacgtgttt gatcactagc 480
agaatagcaa gcagagtatc attcatgctg gggccagaat gatggccggt tgccagatat 540
aactgctttg gagcaaatct cttctgttta gagagataga agttatgaca tatgtaatac 600
acatctgtgt acacagaaac cggcacctgc cagacagagc tggttctaag atttaataca 660
gtgctttttt tcctctttga aatattttac tttaatacca gtgccttttc ttgttgaact 720
tcttggaaaa gccaccaatt ctagatcttg atttgaatta atacacacaa tatctgagac 780
acttacactt ttcaaaagat ttgtgtatgc attgcctaat tagagtaggg ggagaagggc 840
aactattatt atccctattt tacaaaactg aggcttagtg aggttcagcc acatgcctag 900
acttata 907

<210> SEQ ID NO 588
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3791660

<400> SEQUENCE: 588
agttaggggt cggatgcatg agcagcaatc ggggcactcc tactt 45

<210> SEQ ID NO 589
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3569378

<400> SEQUENCE: 589
ttcaaggatg cactgtatag ccaggctgtg ggaggaggga ggaaagatga aaaaccactt 60
aaatgtgaag gaacaacag 79

<210> SEQ ID NO 590
<211> LENGTH: 175
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2932285

<400> SEQUENCE: 590
gctgacacag gatgagagca cagtaaaact taagctaaga tttccacatt aatatcttgc 60
ccccaaacac catgcagtgc taaaagtcac attcccatca tgcaagcaca ttaaaatata 120
tggcgattaa aactcctggt ttctatttta cggcatttgc tctttccacg aggca 175

<210> SEQ ID NO 591
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2586165

<400> SEQUENCE: 591
gtgaggtgag agcactttca gtttttcccg gtgatttgtg tctttggagt gcagctgttg 60
cttta 65

<210> SEQ ID NO 592
<211> LENGTH: 103
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3787881

<400> SEQUENCE: 592
gtaaccagga ctttctcaca cgttccaccc aggacacgtt gacatgatga tctcctagca 60
tgtgctgggg atggatctgg gtgccaggga catagcatga aca 103

<210> SEQ ID NO 593
<211> LENGTH: 103
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2925998

<400> SEQUENCE: 593
ctgcttctct taaaggagaa gtagctgtga acattgtctg gataccagat atttgaatct 60
ttcttactat tggtaataaa ccttgatggc attgggcaaa cag 103

<210> SEQ ID NO 594
<211> LENGTH: 129
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2925975

<400> SEQUENCE: 594
catggaacaa ggcagttgta agaaatacat atatctgaat aaatatttgg gggatgttaa     60
aaatattaaa gttatctatg gacctgcagc tcgattgaga ccctctgatg tcccagataa    120
atactattc                                                            129

<210> SEQ ID NO 595
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3126541

<400> SEQUENCE: 595
cgtgttctca ccaataagtg gtagctaaat gatgaaaaca catggacaca tagagggcaa     60
caacacacac tggtgcctac ctctgagggt ggaggatggg aggaaggaga ggaccaggaa    120
aaataatagg tactaggctt aatactgggg tgatgaaata atctgtacaa taaattcctg    180
gggcagaagt ttacctat                                                  198

<210> SEQ ID NO 596
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2782529

<400> SEQUENCE: 596
tcagattgtt acagtccctt ctttgagaca aacaaacaga agtgcacaaa tgcacttaag     60
agtttccaag ggagtgtgga tttcaaataa ataaaccaaa aattttaacc aaaaccaaat    120
tttcaaggat ttctcaatct tgtctgcaag ctgaaaaaca gacctagctg gaaagtgaaa    180
agtgctcact cagggtaaaa agaatggaaa caattaatgt gattagaaga ggggtttgac    240
cgtggtcttg atttttaaac gccacatgca ggtattagag aaga                     284

<210> SEQ ID NO 597
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2763596

<400> SEQUENCE: 597
acattaattg tttaacagag tcctctttgt cacatccatt gccttctccg ggtgtttga      60 ttgttgaaac tcatgctaaa ctaattga                                        88

<210> SEQ ID NO 598
<211> LENGTH: 1076

<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2649079

<400> SEQUENCE: 598
ggccttgtac aacttatcca gaatgtctat taggattcta atgttatgtc cacttacaag 60
tagagacagt aaaaggatga atacccaatc tttagtgaca atgcagctga tttatgaaag 120
agagggctac actgctatgg aaacttagct tcaaagaaaa tgcaatgtat ctgcaattag 180
gtgttcattt tttactacat tttattaaaa cctgctttat actttcaact gcttgtaggc 240
acaacttctg caagtttaaa tatttgagct ttacaaataa acatacacat gctcagtttt 300
ttaagtaaac ctgtaaaata cccaggaagg caaatgttca ttgtttaatt agcactggga 360
ttttataata taatgtttgg tatttttgag gcattgttaa catgaaagtc aaccactggc 420
tttgtgaaaa atgctatgtc actattcaga atatgctggg taaattgact tgcctagtga 480
aaagcaaaat gttaaagaaa gaacttctgg ttctataatc atattatatg cactaaacta 540
tatgcatgaa agttctttgc atggattaat ggggcttacc cttgttgcac tcgaaatctg 600
aggtgtatct agccctgcca ctattggcta cttaccctca ttaatatccc acttgagaaa 660
aattgtgaga ctatactgtg tcaatatctg taaaaagaga gaaaacatgt tttgtttttt 720
tttgaagggg gtggtgtggg agtggccctt taactctatt tggctatctg aggatgtaca 780
aaattctcat ttaattttct ggtcagcaag ttccccacac agaaatcact ctgaggttta 840
cagaagaact gtaatattat tttaaaatgc gatttttctg tcattagttc tagatatgta 900
cttcatggtt aaattctaaa tctgaaaatg ctagtgggag atatcaagaa attttctttt 960
tgattactag tacctgtatt ctaacagaga gtttgaattt tttgcccgtg ttatcagaat 1020
gatggaaatt gatcattttc agttgttcat tgtgtattca atccagcgaa ctgctg 1076

<210> SEQ ID NO 599
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2925973

<400> SEQUENCE: 599
agagggttga tggtatggtt ggtatgctga tggatggtct gaaagagctg aacttgcaca 60
gatgcctgaa cctcatcctt atttcag 87

<210> SEQ ID NO 600
<211> LENGTH: 268
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2925999

<400> SEQUENCE: 600
gttggggtag cccatgttat gtgactatct ttatgagaat tttaaagtgg ttctggatat 60
cttttaactt ggagtttcat ttcttttcat tgtaatcaaa aaaaaaatta acagaagcca 120
aaatacttct gagaccttgt ttcaatcttt gctgtatatc ccctcaaaat ccaagttatt 180
aatcttatgt gttttctttt taattttttg attggatttc tttagattta atggttcaaa 240
tgagttcaac tttgagggac gatctttg 268

<210> SEQ ID NO 601
<211> LENGTH: 1122
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 3126508

<400> SEQUENCE: 601
tttgcctgca aaagtaaccc agttgcaccc tgtgaagtgt ctgacaaagg cagaatgctt 60
gtgagattat aagcctaatg gtgtggaggt tttgatggtg tttacaacac actgagacct 120
gttgttttgt gtgctcattg aaatattcat gatttaagag cagttttgta aaaaattcat 180
tagcatgaaa ggcaagcata tttctcctca tatgaatgag cctatcagca gggctctagt 240
ttctaggaat gctaaaatat cagaaggcag gagaggagat aggcttatta tgatactagt 300
gagtacatta agtaaaataa aatggaccag aaaagaaaag aaaccataaa tatcgtgtca 360
tattttcccc aagattaacc aaaaataatc tgcttatctt tttggttgtc cttttaactg 420
tctccgtttt tttcttttat ttaaaaatgc actttttttc ccttgtgagt tatagtctgc 480
ttatttaatt accactttgc aagccttaca agagagcaca agttggccta catttttata 540 tttttaaga agatactttg agatgcatta tgagaacttt cagttcaaag catcaaattg 600
atgccatatc caaggacatg ccaaatgctg attctgtcag gcactgaatg tcaggcattg 660
agacataggg aaggaatggt ttgtactaat acagacgtac agatactttc tctgaagagt 720
attttcgaag aggagcaact gaacactgga ggaaaagaaa atgacacttt ctgctttaca 780
gaaaaggaaa ctcattcaga ctggtgatat cgtgatgtac ctaaaagtca gaaaccacat 840
tttctcctca gaagtaggga ccgctttctt acctgtttaa ataaaccaaa gtataccgtg 900
tgaaccaaac aatctctttt caaaacaggg tgctcctcct ggcttctggc ttccataaga 960
agaaatggag aaaaaaatat atatatatat attgtgaaag atcaatccat ctgccagaat 1020
ctagtgggat ggaagttttt gctacatgtt atccacccca ggccaggtgg aagtaactga 1080 attattttt aaattaagca gttctactcg atcaccaaga tg 1122

<210> SEQ ID NO 602
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 2586072

<400> SEQUENCE: 602
tcagtgtaca agtggacatt gtgtacacag tgaactgaaa tgcgatggat ccgctgactg 60
tttggatgcg tctgatgaag ctgattg 87

<210> SEQ ID NO 603
<211> LENGTH: 636
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2661165

<400> SEQUENCE: 603
acaggagatt tagtagggcg ctcccgacag cctggctggc agtcactaat ccagaagaat 60
gaatgaatgt tgtactaaat actccccaat gtttgttcta ataattctcc tcagagctgt 120
cataacaaca gcaagtgttt ttttaaataa tcaggtaaac attttctgaa ttaacctggt 180
aatcaaaccg actgtacttc aaactgatcc taaagaaagt acataaatgg aatagcagtt 240
aagtcacaaa tgccaaatga aagccaccaa ccagtcactg tatattctgc atcatttatt 300
aaatattttt atatatgcat ttacaaactt tactcatttc agaactctgc tttcaatgca 360
tttttaaact gttttttttt tttttgcaga gagattctct tgtaaaatga gatccatgta 420
caaaactagg caacagatat aaaagtttcc tttcatattt ttcatccatc aagaaaagaa 480
atcatgtgac aagaaataaa accaaaatgt ggctctttca gaagaataac atgtctgtgg 540
tcaactatga cttctaatga gatagttcat atttcatctt tatatggatg tatatagttt 600
taatacttct tagctactgt agcatgttgg ttcaga 636

<210> SEQ ID NO 604
<211> LENGTH: 94
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3018623

<400> SEQUENCE: 604
tgcctttggg atcagcaaca tcttctcagg attcttctct tgttttgtgg ccaccactgc 60
tctttcccgc acggccgtcc aggagagcac tgga 94

<210> SEQ ID NO 605
<211> LENGTH: 462
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2944443

<400> SEQUENCE: 605
ctgactcttt ggttgtgcct atacaatgaa aagtctacaa atgaaatgag agaagtcagg 60
atattttcct ttgttaaact aagtagctga ataattagaa ctacctagat aaaagactca 120
aaatgttttt gttatctggt tgcctggtta ggacatagcc aacatttcaa tggaatgtag 180
tatcttgtac aactgcatat aattttttaa aaaataaaca atgactttgt ttctttagat 240
acatcaaatg ctgcttgagt ggccaaaggg aaaatgccaa ctctttgaaa tgtagtatct 300
gtagcacttt tcttctttca gtagtttttc atgccccaaa tacaaacttt aaggagtaac 360
atctatcctc aaaacccaaa aatacccatt tgttttgagg ttcacagtcc accagtataa 420
gttttaaact gcgccaaaag gcttaggtag ggttcagcag tc 462

<210> SEQ ID NO 606

<211> LENGTH: 109
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3573881

<400> SEQUENCE: 606
gttcaataga acatgcaaga atttctggaa gaaaggctgt ggaagggcca atggagaaaa 60
tgaatggaca aagctcagga atcctacgct atgtagaatg tcttggtgt 109

<210> SEQ ID NO 607
<211> LENGTH: 140
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3573895

<400> SEQUENCE: 607
gtaactggat tagggacgag tacgccagct tttttttttt tttttttttt ttttttttaa 60
catcttaaat cctgaaaaaa aaaaaaaaaa aaaaaaaaag gcagcagctc cgaattgaat 120
gaattgatgg gcacactcca 140

<210> SEQ ID NO 608
<211> LENGTH: 211
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811395

<400> SEQUENCE: 608
tgactggagc agtctggttt cttccctttt tatcgagttc tgtcattgtg ttcctcaaac 60
tgtggtttgt tccagaaagg aagaggttgt cttcttcacc cgcctgccct aagttgcgtc 120
aagttccagt tccctgtatt aagtaaatta ctaaatgagt ggaatgaaca tcataatgtc 180
aagggtaggg cgttgacatt atgggacaat a 211

<210> SEQ ID NO 609
<211> LENGTH: 394
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3787879

<400> SEQUENCE: 609
tatcagctcc taacaccgtg cctggactcc ctgagcaggc tttttctaa acagaagcca 60 gggaagcctg cgagaccttt gtcaagaagg gagagtttcc ttaaccaagt ccttcagctg 120
acctctacag aggtcactgc cagccttggc atgggaggag gcagctgcct ccctctttgt 180
ccctcctctg gcattttctc cattataatt cctgccatgt ctggtttaca ttcgtcatct 240
atgacacagc ttggcagcag agggaagtga agtggaggct tggagccctc agctgaatga 300
ttctagtcta gaaacctgtg aactgggggt gctggcctgt ggtctagact gtgtatgttt 360
ttacttctct gggcccttgc aggtacaaac tata 394

<210> SEQ ID NO 610
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608590

<400> SEQUENCE: 610
aatttgtggt tgacgctggc cattaaccta tctctgaaag tcagttttga aattggccta 60
aagaacttct c 71

<210> SEQ ID NO 611
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2763629

<400> SEQUENCE: 611
tttaagagtg ataatgctga cagtcgtaag aggtgtaggc aagtaggaaa tacggaaaat 60
cagacagcag gcagtgctgc attccaaacc caatgtg 97

<210> SEQ ID NO 612
<211> LENGTH: 565
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3992441

<400> SEQUENCE: 612
aaagagtcct tgctaagtct gccaggctag gttttgcgca tggtaaccat ctctcatttt 60
cctgtcgtcg gtttcatcca caaaggcccc cagagaatgc ccttctcccc ctgctattgt 120
ggtcccaaag gcccccccaag agtttggatt cgtccccagg ccaggttagc ctttgcaata 180
cagaacactt cctgactgtt gactaacaat gctgagagtt cacaagcctg agacctgcca 240
gccaacaccg gcaggcactg ccactttgca gggggattct ggggggaggg gtgggaggag 300
ggtagaaaga agggggtggg ggagggtggg gaaggggtaa gggaggccga agagtgataa 360
cccgggattg taatacccca tagctgaagg ctagttcaga gatgcctgtt ggcagggttt 420
cttttttttt tggtttgctg tttatttgtt tttgcgatca gcaaagctaa tcacttcatt 480
cctcatctcg cggccgcgat ccacgtgccc tgggcccttt cccttgcctc caattttccc 540
atcttcccgg ggagccttga aatgt 565

<210> SEQ ID NO 613
<211> LENGTH: 406
<212> TYPE: DNA
<213> ORGANISM: Artificial Sequence
<220> FEATURE:
<223> OTHER INFORMATION: Description of Artificial Sequence: Synthetic polynucleotide
<220> FEATURE:

<223> OTHER INFORMATION: Affymetrix ID 3727625

<400> SEQUENCE: 613
cctttaatga tctggtggtc tcctcgtcaa tccatcagca atgcttctct catagtgtca 60
tagacttggg aaacccaacc agtaggatat ttctacaagg tgttcatttt gtcacaagct 120
gtagataaca gcaagagatg gggtgtatt ggaattgcaa tacattgttc aggtgaataa 180
taaaatcaaa aacttttgca atcttaagca gagataaata aaagatagca atatgagaca 240
caggtggacg tagagttggc ctttttacag gcaaagaggc gaattgtaga attgttagat 300
ggcaatagtc attaaaaaca tagaaaaatg atgtctttaa gtggagaatt gtggaaggat 360
tgtaacatgg accatccaaa tttatggccg tatcaaatgg tagctg 406

<210> SEQ ID NO 614
<211> LENGTH: 477
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2615655

<400> SEQUENCE: 614
cctctaattt ggtccctggc acatgcatac ttgtcaatgt ttttattctt ttacaagacc 60
tgcattttat ttgaattacc cgaatagcaa tatgtaaaat acaagtgaca aaatgtgatg 120
agagcttctt gaaccggtaa actagtacag gtctgagaaa gacatattag aagaatcatt 180
atacttcctt gaattatatt tattttcatg tttctctaat gcaaagaatg tttcatcaaa 240
tgtatatttt ctgttgctta ctgtttgctc tgagaagaag ctgctgtttc aaagatggac 300
ctctgagtag ctaattgatt caagtagttt ttttatgttg acacattatt actgctgtta 360
gcagtcgttt tcaccaggta cttacagagc agatttcata catcattcat tcaagggcta 420
aatttatatt ttttggaaat catggcaact acacaggatg ttgcttacca ggacgga 477

<210> SEQ ID NO 615
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Affymetrix ID 3603302

<400> SEQUENCE: 615
gaatgagaac aagatccact gcacgcaaac tcttcttgaa ggggacggcc ccaaaaccta 60
ctggacccgt gagct 75

<210> SEQ ID NO 616
<211> LENGTH: 103
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Affymetrix ID 2586098

<400> SEQUENCE: 616
tggattcttc tagaattggc gattagtggg gtagacgaag atgatggggg aaaggggatc 60
aaggacactg gtgatcttgt cgaaatggtt gacctggcat tta 103

<210> SEQ ID NO 617
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2925996

<400> SEQUENCE: 617
gttaatgtta cacagagcac ggatcacaga tgttgagcac atcactggac tcagcttcta 60
tcaacaaaga aaagagccag tttcagacat tttaaagttg aaaacacatt tgccaacctt 120
tagccaagaa gactg 135

<210> SEQ ID NO 618
<211> LENGTH: 160
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3791650

<400> SEQUENCE: 618
aagtgccatt atagctaatg gtggccaact ggagacttac tttaccttaa ccatgtaaag 60
tatccttacc gtatttttta tgtgtacagt gttgcagaat atcagccacc tcttaaaagt 120
atcaatctta aaaagagcca tggaaggtaa aagtatgaaa 160

<210> SEQ ID NO 619
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2925967

<400> SEQUENCE: 619
ctaaaaacat gagaccggta tatccaacaa aaactttccc caatcactac ag 52

<210> SEQ ID NO 620
<211> LENGTH: 175
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586147

<400> SEQUENCE: 620
ctcgcagcta acagggtgga aaatgttgaa agtttggctt ttgattggat ttcaaagaat 60
ctctattgga cagactctca ttacaagagt atcagtgtca tgaggctagc tgataaaacg 120
agacgcacag tagttcagta tttaaataac ccacggtcgg tggtagttca tcctt 175

<210> SEQ ID NO 621
<211> LENGTH: 392
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3992436

<400> SEQUENCE: 621
cttgcttatc atggtggggc taacgttgct ctgagctgct ttgagatctt agcatatata     60
tgtacacata tacatacacg tatatatgcg tacacatata tgctcgcaca cacgcacaca    120
ctcggagact aaagaacact ggcgagaaca gcctgtggca acagaatgaa gtgaacagta    180
tgtagcgctt tctcatttgg gcgtagtaag tgatgaaagc atgcttcttc ctcagggtgt    240
cattctgggc caggcagtcc ctgatttaat gtctaagtgc acgcagggta tagaggtggg    300
ggagtggggg attcaggcac tggatcctaa aataataatg ctggggtccc cacccatgac    360
agaaatcctg ggttggcaca agcacaagta ga                                  392

<210> SEQ ID NO 622
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740285

<400> SEQUENCE: 622
ttgaatatat ctatgagggc atgtattagt taatggaaaa aaaaatacaa cactaacaat     60
acatagctgc aatgtgtaca atggctgatt taattaaata                          100

<210> SEQ ID NO 623
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2740135

<400> SEQUENCE: 623
ctcggtttgg gaccttagtt cattgtagtg agttgtgggt gctgcagagg ctggagcaag     60
attatgacct agctcggggg cggagtggat tatcttgtga gtgttctggc tgccagccat    120
tgccctggtg gggaaaatca catctccata gagctctgaa atcacctgga ttgctgggga    180
gtggaaactg atcctctgct actgctt                                        207

<210> SEQ ID NO 624
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586097

<400> SEQUENCE: 624
cggcacaatg actgtggtga ctatagcgac gagaggggct gcttatacca gacttgccaa     60
cagaatcagt ttacctgtca gaacgggcgc tgcattagta aaaccttcgt ctgtgatgag    120
gataatgact gtggagacgg atctgatgag ctgatgcacc tgtgccacac cccagaaccc    180

-continued

```
acgtgtccac ctcacgagtt caagtgtgac aatgggcgct gcatc                  225


<210> SEQ ID NO 625
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3985031

<400> SEQUENCE: 625

gcaggcattt gtcaggccat atgttttaac cttatggtaa tactttgctt tagtcgttcc     60

tcctgctacc agtagcgttt tgacccacct gccagtgttt gcttgctcta tgtttc        116


<210> SEQ ID NO 626
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2954890

<400> SEQUENCE: 626

aaggactgtt ctgtcgatgg tgatggtgtg gtggcggcag cgtggtttct gtatcgatcg     60

ttctgtatca gtcttt                                                     76


<210> SEQ ID NO 627
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2586154

<400> SEQUENCE: 627

ttggcgaggc ctccattatc ttctccaatg gtcgggattt gttaattggt gatattcatg     60

gaaggagctt ccggatccta gtggagtctc agaatcgtgg agtggccgtg ggtgtggctt    120

tccactatca                                                           130


<210> SEQ ID NO 628
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 4013550

<400> SEQUENCE: 628

tcctgacaat aaattccatc cgttgttttt tttgtttgtt tgttttttct tttcctttaa     60

gtaagctctt tattcatctt atggtggagc aattttaaaa tttgaaatat tttaaattgt    120

ttttgaactt tttgtgtaaa atatatcaga tctcaacatt gttggtttct tttgtttttc    180

attttgtaca actttcttga atttagaaat tacatctttg cagttctgtt aggtgctctg    240

taattaacct gacttatatg tgaacaattt tcatgagaca gtcattttta actaatgcag    300

tgattctttc tcactactat ctgtattgtg gaatgcacaa aattgtgtag gtgctgaatg    360
```

c 361

<210> SEQ ID NO 629
<211> LENGTH: 504
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811377

<400> SEQUENCE: 629
agctcagtca tgtctagaat ataccaaatg ataagaagtc tgatacaaac aagaagtctt 60
gtcctattag agttcatagt aatagcattt gatctataat aacagaaaaa atattgcatg 120
gacatacatt aatctattcc tgagcttaac tccagatgag gaatcagttt ttatatctca 180
tttgtacagg gtggagagag atgggctttt ttctttcgat ttgtttttcc acgtctattt 240
agagcaacca aaataggaaa actgctgcac aggtcttaaa attcacttcc tccatccgct 300
ttccgaattc tgctccaggt ctgatgacta taacttttta tacatgtcat ttatttttat 360
ttttatttta gtctaaatgt ctcttcaaaa acaccaggga aaaacatttt tagcttcact 420
aagaaaacaa acatgtttaa acaaccccca aaatgttcag gtagagtcgg tgtttttggc 480
ttgtgtgtat tttaacggtg agcc 504

<210> SEQ ID NO 630
<211> LENGTH: 715
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3763258

<400> SEQUENCE: 630
aaggccaact ctacgtccac ctgtgtctca tattgctatc ttttatttat ctctgcttaa 60
gattgcaaaa gtttttgatt ttattattca cctgaacaat gtattgcaat tccaatacac 120
ccccatctct tgctgttatc tacagcttgt gacaaaatga acaccttgta gaaatatcct 180
actggttggg tttcccaagt ctatgacact atgagagaag cattgctgat ggattgacga 240
ggagaccacc agatcattaa aggattagat actctgaagg caggaaacta gaaaatccca 300
ttgatgaaag gatattttaa tctagcgtaa aatgtttctt tgtcgtaaca gcagaatttc 360
ttgacatttt acaacttaat gaaacaaaag aacaatcatc tttaaagtca aacatctatc 420
aaattataaa ccaaacacat agcaccgata tcaacctcat aaaacgtgcg ggcccgcagg 480
gtagaaaaga actgtctggg gcactggcag caacgtgcca ttccaggaac tcagaatttc 540
gaagtgaaca tttttgtggc agatgctttt cctaaaaaac actgtatcat ccaataaata 600
tttgactaaa atccattttg tgcttttggg tgacgttaac tgacttcttt ctgaggccta 660
ataagaaaca agaaagctcc ttgtgtattt tagagcagga ttcgtcatca caagc 715

<210> SEQ ID NO 631
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3753974

<400> SEQUENCE: 631
atgaagatct ccgtggctgc cattcccttc ttcctcctca tcaccatcgc cctagggacc 60
aagactga 68

<210> SEQ ID NO 632
<211> LENGTH: 144
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3088318

<400> SEQUENCE: 632
agtaggcacc gcatcttcaa ttcatcttct gatcccctgc accttggtag catgtctagc 60
acatgcaaaa ggctctcaaa acatcctctc caggtcacaa gtcttccgcc acccatccct 120
tcctacctcc acgagcaagg gaca 144

<210> SEQ ID NO 633
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2925979

<400> SEQUENCE: 633
gccctctttg ttggctatgg acctggattc aagcatggca ttgaggc 47

<210> SEQ ID NO 634
<211> LENGTH: 295
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811413

<400> SEQUENCE: 634
ttgccctgca tggaaacggt gcaccctctc ccgctacaca ctcagagatg agagatgagc 60
ctgtttgtga aaccaaactc aggattctgt ttttgtgtaa gaaccgtacc acatggctga 120
catatgttca gtccatggct ggcagaagcc tcctgaacac atccccccatc cagtacctcc 180 ccggcagtga cccatctcat atttgcatat gttcccctgt cacaagattg tggggagggt 240
gcagtttgca gctgactcct tacctagcta cagctccaac taagggcgtg cattc 295

<210> SEQ ID NO 635
<211> LENGTH: 343
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2980497

<400> SEQUENCE: 635

-continued tgtgctgaca ttctacctgg tgatctctct agtgatttag aagtctgcac agatgggaca 60
gggagagagc actcttaatt agcataggag atgtaggaat tcaagcagaa cctgtataaa 120
atgctggaat ccccagtttt atgtgatgaa ggagagaatc tcttcagttt tcaagatttt 180
ttaattgaaa gtttttaaac acaaaaatca cataaaactt gattcttgaa acatagcatc 240
ttcacatata gacttaaact accaggtaag tatttgtcat tcactggttt tcaccagaag 300
atgaatttgt atcataaaaa gttatcaaca tgggccgggt aca 343

<210> SEQ ID NO 636
<211> LENGTH: 414
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811431

<400> SEQUENCE: 636
ctgcacgtgt agaatcaaag gactgacagc aggtcgaatg tgaggaatga gggagggaaa 60
gaatcaggac tcaagtgcca tcctggctgc ctcaaaaaat gatactgtct tccagaggga 120
aaggaaagat aacaacagtt actgctttgt ggcgtacatg tgatgaattt cattttggac 180
attccagtag gatatccaag tggaaatgcc cagtaagcct tagacataag gatctggatc 240
tcaagagaaa aattgaggtt gaaccataat atgtctttcc cctcgaatca tgtaggtttc 300
tcttttgcct tctttcattg ccctaagtgg tcctaaatgc tactgctgat gctgtcttag 360
tttgcgactg ttgtttgcac cccacctttt cccaaaggta atctgtagac ttgc 414

<210> SEQ ID NO 637
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2608556

<400> SEQUENCE: 637
agcaatcctg ggaaaagtga ccctgtgttg ga 32

<210> SEQ ID NO 638
<211> LENGTH: 109
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3108611

<400> SEQUENCE: 638
tatcactatg tatgctgttg gggtaggaaa agccattgag gaggaactac aagagattgc 60
ctctgagccc acaaacaagc atctcttcta tgccgaagac ttcagcaca 109

<210> SEQ ID NO 639
<211> LENGTH: 83
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3160684

<400> SEQUENCE: 639
tgttgctgca ctggattcca acgtatccgg aaaaattggt ctgcgcgctg tcgtgtatta 60
tttctgtacc actctcattg ctg 83

<210> SEQ ID NO 640
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 4023355

<400> SEQUENCE: 640
ttcaggagca gcacctagac cagtcttccc tcaaccccag ctgataaggc tgtggctcat 60
ttgtgaacat acatttaagg ggaagcg 87

<210> SEQ ID NO 641
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3862191

<400> SEQUENCE: 641
gggatgtagt atggaaacca ggcttcttgg ggcaaaggca cctggatcct catgggatga 60
gggcagtcag ggtgggtgtt tagtctgcaa gcggaggtgc taaatgtctg tgtcttgca 119

<210> SEQ ID NO 642
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2997556

<400> SEQUENCE: 642
cagactggct gcagcgagtt ggattcgtgc agaacatctg ctgccagacc cataatcaac 60
tgca 64

<210> SEQ ID NO 643
<211> LENGTH: 142
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3787882

<400> SEQUENCE: 643
gcccatggag gaaagttact gctgaggacc cacccaatgg aaggattctt ctcagccttg 60
accctggagc actgggaaca actggtctcc tgtgatggct gggactcctc gcgggagggg 120
actgcgctgc tatagctctt gc 142

<210> SEQ ID NO 644
<211> LENGTH: 243
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2483130

<400> SEQUENCE: 644
ttccgccgga tgacaaagtt atttcggcca gtctgcattt cagggcctgc gactgcagca 60
gcactggcca caaaaccacc cccgggcaac actccactgg ttgccatgct gctggcagct 120
acaaccccgg tggttgcccc tgaggttcct tctgctggtt gtgtttcctg ctgaggctgt 180
tcattattga caataatctg ggctgttttc ggaaggcaga ggtatcctcc atagtggttg 240
aca 243

<210> SEQ ID NO 645
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 3811426

<400> SEQUENCE: 645
atgagcagcg gctttccctt tggcagtctg cgagccaaga cttctg 46

<210> SEQ ID NO 646
<211> LENGTH: 185
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3787871

<400> SEQUENCE: 646
cccatgtttg aaggggccga catccacaag aggctctctc cggacgatgc agattttgtg 60
gatgtcctcc acacctacac gcgttccttc ggcttgagca ttggtattca gatgcctgtg 120
ggccacattg acatctaccc caatgggggt gacttccagc caggctgtgg actcaacgat 180
gtctt 185

<210> SEQ ID NO 647
<211> LENGTH: 341
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2660997

<400> SEQUENCE: 647
acactcaggg tggattcatg atgccaaagg ataacagaca atggaaagca ttttacaact 60
gttcacagta ccagcaagtc aagcacgtca cctaacaaag gggctacatc acaagctcaa 120
aacttccgat aactttacat tcccctaagg tgagagggtg tatttaaata acatcaatcc 180
aaccaaagcc ttgctccaac ttccacatca actattttcc ttgggcgaaa cagagtattg 240
cattgcatta agtgtattta caaccaactg tctgtgtaaa tataagagat gctaacatac 300
tagtaacaga acgaaattag ccttgctgat tttgccctgc c 341

<210> SEQ ID NO 648
<211> LENGTH: 215
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3787872

<400> SEQUENCE: 648
atgagcgagc cgtccacctc tttgttgact ctctggtgaa tcaggacaag ccgagttttg 60
ccttccagtg cactgactcc aatcgcttca aaaaggggat ctgtctgagc tgccgcaaga 120
accgttgtaa tagcattggc tacaatgcca agaaaatgag gaacaagagg aacagcaaaa 180
tgtacctaaa aacccgggca ggcatgcctt tcaga 215

<210> SEQ ID NO 649
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2763609

<400> SEQUENCE: 649
cttgatcttt ctgaactaga tgtgaacgac ttggatacag acagctttct gggtggactc 60
aagtggtgca gtgaccaatc agaaataata tccaatcagt acaacaatga gccttcaa 118

<210> SEQ ID NO 650
<211> LENGTH: 251
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2980500

<400> SEQUENCE: 650
agtcctctac tcgagtcttc ctgggcctga tcacttttgc atacaccaca aagcttagac 60
tgctcagagc tagttttctt ctcacattat atagcactga gttcatacat ttgcccttag 120
gtgaaaatag ctttgtttct taacactttt cttcctagcc aacctggttc ctccctcctc 180
ccctttctac cccacaaata acggaaattt gactgtggcc aaatctcttt cctcgttgct 240
gtgcctcttt t 251

<210> SEQ ID NO 651
<211> LENGTH: 122
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2586129

<400> SEQUENCE: 651

```
tctgtgtact ggactgaccg tgctactcgt cgggttatgc gagccaacaa gtggcatgga     60

gggaaccagt cagttgtaat gtataatatt caatggcccc ttgggattgt tgcggttcat    120

cc                                                                   122


<210> SEQ ID NO 652
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 4023341

<400> SEQUENCE: 652

gggaggcaag gtcaaactaa gaatagaagc tcaagtacta tcacctgtcc taagcataaa     60

tctaaaaaac tttccacttt ccgactagcc ataagtacat ggtcccatc               109


<210> SEQ ID NO 653
<211> LENGTH: 942
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 2897466

<400> SEQUENCE: 653

accatggtcc ctagtagtca gttgaagtgg caatgtctaa acagaaatga acaaaactaa     60

tgctagcagg ttaaaatcaa tcaaaatgtt taaaaattga ttctgtcctc agcatgttat    120

ttcctcagct ctgataattt actggtcttg agtattttga gaatttgatg ttgaacgtta    180

taaagtcaaa gaactgcttg tttagatgag gtttattttt atttttgata ttattcattc    240

ttgtcacaca tcaagaagaa aacactagag tgctgctgga attccaaatc tgaagaattc    300

taacgactgc attctttgtt attaaaaagg gcacaatcct tcctttttat ttggcagttt    360

aatttcagta ggaagcatgt cacatgtgca ctgttggtta gaattatgca tctgtcatgc    420

ctgactgctg aaccctacct aagccttttg gcgcagttta aaacttatac tggtggactg    480

tgaacctcaa aacaaatggg tatttttggg ttttgaggat agatgttact ccttaaagtt    540

tgtatttggg gcatgaaaaa ctactgaaag aagaaaagtg ctacagatac tacatttcaa    600

agagttggca ttttcccttt ggccactcaa gcagcatttg atgtatctaa agaaacaaag    660

tcattgttta ttttttaaaa aattatatgc agttgtacaa gatactacat tccattgaaa    720

tgttggctat gtcctaacca ggcaaccaga taacaaaaac attttgagtc ttttatctag    780

gtagttctaa ttattcagct acttagttta acaaaggaaa atatcctgac ttctctcatt    840

tcatttgtag acttttcatt gtataggcac aaccaaagag tcagactggt ttaaaactcc    900

agaaggaaaa aaagtatccc acacagtgga tgttgtttct aa                      942


<210> SEQ ID NO 654
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Affymetrix ID 3791755
```

<400> SEQUENCE: 654
tttctcacag atacggacaa gctcaagaat cccactgtca ctggatgtat tcattaagaa 60
ggaatctggc agcagcacag gggacagata ctttggagaa caggccaatt atctgggtgt 120
cctttataat ttgaagtttc tgaattcact catagataag ctgcttgaag agggcctggc 180
aatgggaaca taatgcacag atggccactg aagaaacaag agggaggaag ggaggctgga 240
agagagaaga gaatttgctt gtggtttcat tcatggggac aaatctacaa gctg 294

<210> SEQ ID NO 655
<211> LENGTH: 189
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 3811429

<400> SEQUENCE: 655
ttgtacggaa tacttaaagg gcatcaccca tgactaaacc agtgctttta aaatatggag 60
aatatgggga aatttaatat gagttgggat acttgactct tttttaaaac ctctctacct 120
gtttggcaca acagggtatt gataaagagt gggctcattg ttatggcaaa ggattcactt 180
gcatctctg 189

<210> SEQ ID NO 656
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Affymetrix ID 2649081

<400> SEQUENCE: 656
acagggataa gtcagcgaaa agatgatata ttgaaaattc atgaaggcca acgagaagtt 60
agcctctatc gccctgaaaa tttaaaccaa ccccccaaaa gaccctccta atctattaat 120
tcctctgctt gggagtccca aggaagtgaa agagaatccc ttagagctct gataca 176

<210> SEQ ID NO 657
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2830194

<400> SEQUENCE: 657
atgaactccc tcgtggcggc cgaaggcctg g 31

<210> SEQ ID NO 658
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Affymetrix ID 2830301

-continued

```
<400> SEQUENCE: 658

ttatttcgtg tgtgtctctt ggctctgtag                                  30


<210> SEQ ID NO 659
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Affymetrix ID 2830378

<400> SEQUENCE: 659

tgcttgcacc cacagtccat agacatccaa ccgcccaatg catatccaac ctcagcaact     60

ttacaatccc caacgccagc ccacaacttg actttta                              97
```